US012760066B2

(12) United States Patent
Xu

(10) Patent No.: US 12,760,066 B2
(45) Date of Patent: Oct. 13, 2026

(54) BIVALENT ANTAGONISTS OF INHIBITORS OF APOPTOSIS PROTEINS

(71) Applicant: Hepagene Therapeutics (HK) Limited, Wan Chai (HK)

(72) Inventor: Xiaodong Xu, Doylestown, PA (US)

(73) Assignee: Hepagene Therapeutics (HK) Limited, Wan Chai (HK)

(*) Notice: Subject to any disclaimer, the term of this patent is extended or adjusted under 35 U.S.C. 154(b) by 1298 days.

(21) Appl. No.: 17/601,403

(22) PCT Filed: Apr. 1, 2020

(86) PCT No.: PCT/US2020/026220
§ 371 (c)(1),
(2) Date: Oct. 4, 2021

(87) PCT Pub. No.: WO2020/206000
PCT Pub. Date: Oct. 8, 2020

(65) Prior Publication Data
US 2022/0220152 A1 Jul. 14, 2022

Related U.S. Application Data

(60) Provisional application No. 62/831,155, filed on Apr. 8, 2019, provisional application No. 62/830,031, filed on Apr. 5, 2019.

(51) Int. Cl.
*C07K 5/083* (2006.01)
*A61K 38/00* (2006.01)

(52) U.S. Cl.
CPC ............ *C07K 5/0806* (2013.01); *A61K 38/00* (2013.01)

(58) Field of Classification Search
CPC ....... C07K 5/0806; A61K 38/00; A61P 31/00; A61P 35/00; A61P 31/12
See application file for complete search history.

(56) References Cited

U.S. PATENT DOCUMENTS 7,517,906 B2 4/2009 Condon et al.

FOREIGN PATENT DOCUMENTS

WO WO-2019/023275 A1 1/2019

OTHER PUBLICATIONS

He et al, Molecules, 2019, 24, 1855, 1-34 (Year: 2019).*
Lu et al, International Journal of Molecular Sciences, 2016, 17, 561, 1-22 (Year: 2016).*
Chen et al. Adv. Drug Deliv. Rev. 65:1357-1369, 2013 (Year: 2013).*
Verdine et al(Methods in Enzymology, 2012, vol. 503, 3-33) (Year: 2012).*
International Search Report and Written Opinion for PCT Appl. Ser. No. PCT/US2020/026220 dated Jun. 17, 2020 (12 pages).
Haiying et al. "Potent Bivalent Smac Mimetics: Effect of the Linker on Binding to Inhibitor of Apoptosis Proteins (IA Rs) and Anticancer Activity", Journal of Medicinal Chemistry, vol. 54, No. 9, May 12, 2011(May 12, 2011), pp. 3306-3318.
Hennessy et al. "Discovery of a novel class of dimeric Smac mimetics as potent IAP antagonists resulting in a clinical candidate for the treatment of cancer (AZD5582)", Journal of Medicinal Chemistry, vol. 56, No. 24, Dec. 13, 2013 (Dec. 13, 2013), pp. 9897-9919.

* cited by examiner

*Primary Examiner* — Sudhakar Katakam
(74) *Attorney, Agent, or Firm* — Foley & Lardner LLP

(57) ABSTRACT

The present technology is directed to compounds, compositions, and methods related to treatment of cancers and viral infections mediated by IAPs, e.g., compounds of Formula I (including Formulas IA, IB, IC, ID, IE, IF, and IG), a stereoisomer thereof, or a pharmaceutically acceptable salt of the compound or the stereoisomer of the compound. In particular, the present compounds and compositions may be used to treat IAP-mediated ovarian cancer and hepatitis B infection.

19 Claims, No Drawings

BIVALENT ANTAGONISTS OF INHIBITORS OF APOPTOSIS PROTEINS

CROSS-REFERENCE TO RELATED PATENT APPLICATIONS

This application is a U.S. National Phase Application under 35 U.S.C. § 371 of International Application No. PCT/US2020/026220, filed Apr. 1, 2020, which claims the benefit of and priority to U.S. of America Application No. 62/830,031, filed Apr. 5, 2019, and U.S. of America Application No. 62/831,155, filed Apr. 8, 2019, each of which is incorporated herein by reference in its entirety.

FIELD

The present technology is directed to compounds, compositions, and methods related to antagonizing inhibitor of apoptosis proteins (IAPs), including host cell IAPs (cIAPs). In particular, the present compounds and compositions may be used to treat various cancers, including. e.g., ovarian cancer and chronic hepatitis B infections.

BACKGROUND

Apoptosis, also referred as programmed cell death, is a critical and highly regulated cell process that occurs in multicellular organisms, and apoptosis dysfunction is a hallmark of human cancers. Inhibitors of apoptosis proteins (IAPs), such as cellular inhibitor of apoptosis protein 1 and 2 (cIAP1 and cIAP2) and X-linked inhibitor of apoptosis protein (XIAP), have been identified as attractive targets for a new class of cancer therapy.

In 2015, Pellegrinia etc. (PNAS, 2015, 112(18), 5803-5808) demonstrated that the clinical-stage drug birinapant, which antagonizes host cell inhibitor of apoptosis proteins (cIAPs), promotes the killing of HBV-infected hepatocytes in a mouse model of HBV. Therefore, antagonists of cIAPs may also be efficacious in the treatment of chronic HBV infection and may promote elimination of virus.

SUMMARY

In one aspect, the present technology provides a compound according to Formula I, a stereoisomer thereof; or a pharmaceutically acceptable salt of the compound or the stereoisomer of the compound:

wherein

X is O, $NR^6$ or $CH_2$;

q is 0, 1 or 2

$R^1$ and $R^2$ are at each occurrence independently selected from a substituted or unsubstituted $C_{1-6}$ alkyl, $C_{3-6}$ cycloalkyl, aryl, aralkyl, heterocyclyl, or heterocycylalkyl group;

$R^3$ and $R^4$ at each occurrence are independently H, an amino-protecting group, or a substituted or unsubstituted $C_{1-6}$ alkyl group;

$R^5$ at each occurrence is independently H, F, $NH_2$, OH, NH-(amino protecting group), or O-(hydroxyl protecting group);

$R^6$ is at each occurrence independently H, a substituted or unsubstituted $C_{1-6}$ alkyl, $C_{3-6}$ cycloalkyl group, or an amino-protecting group; and Linker is a divalent moiety selected from a bond, oxy moiety or an optionally substituted moiety selected from the group consisting of amino, alkylene, heteroalkylene, alkenylene, heteroalkenylene, alkynylene, heteroalkynylene, cycloalkylene, cycloalkylheteroalkylene, arylene, aralkylene, arylheteroalkylene, heterocyclylene, heterocyclylalkylene, heterocyclylheteroalkylene, heteroarylene, heteroarylalkylene, and heteroarylheteroalkylene.

In any embodiments of the compound of formula I, $R^1$ and $R^2$ are independently selected from a substituted or unsubstituted $C_{1-6}$ alkyl, $C_{3-6}$ cycloalkyl, aryl, aralkyl, heterocyclyl, or heterocycylalkyl group;

$R^3$ and $R^4$ are independently H, an amino-protecting group, or a substituted or unsubstituted $C_{1-6}$ alkyl group;

$R^5$ is H, F, $NH_2$, OH, NH-(amino protecting group), or O-(hydroxyl protecting group);

$R^6$ is H, a substituted or unsubstituted $C_{1-6}$ alkyl, $C_{3-6}$ cycloalkyl group, or an amino-protecting group; and Linker is divalent and selected from the group consisting of a bond, amino, oxy, alkylene, heteroalkylene, alkenylene, heteroalkenylene, alkynylene, heteroalkynylene, cycloalkylene, cycloalkylheteroalkylene, arylene, aralkylene, arylheteroalkylene, heterocyclylene, heterocyclylalkylene, heterocyclylheteroalkylene, heteroarylene, heteroarylalkylene, and heteroarylheteroalkylene.

In a related aspect, a composition is provided that includes the compound of any one of the embodiments described herein and a pharmaceutically acceptable carrier.

I

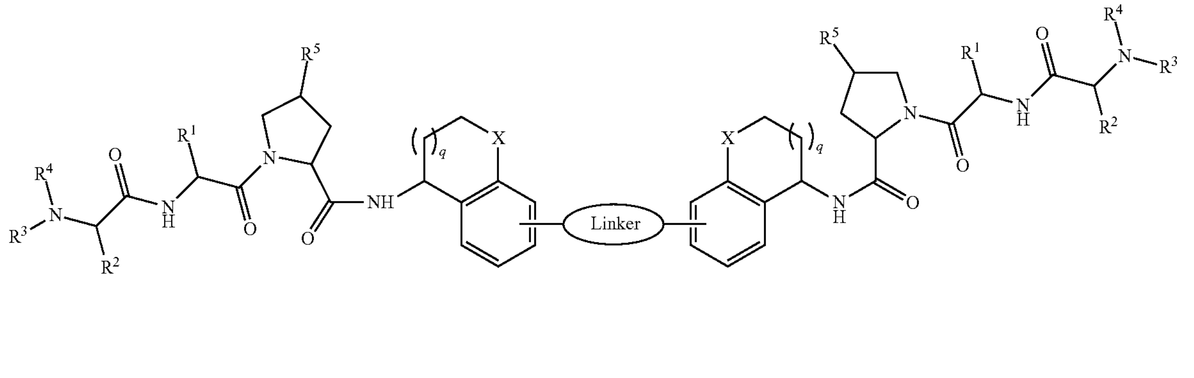

In another aspect, a pharmaceutical composition is provided, the pharmaceutical composition including an effective amount of the compound of any one of the herein described embodiments for treating a LAP-mediated disorder or condition, such as various cancers (e.g., ovarian, fallopian tube, peritoneal cancers) or viral infections (e.g., chronic hepatitis B infection).

In another aspect, a method is provided that includes administering an effective amount of a compound of any one of the embodiments described herein, or administering a pharmaceutical composition including an effective amount of a compound of any one of the embodiments described herein, to a subject suffering from a cIAP-mediated disorder condition.

DETAILED DESCRIPTION

In various aspects, the present technology provides compounds and methods for antagonizing the action of cIAP and the treatment of cIAP-mediated disorders and conditions. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In any embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups, oxo groups such as in carbonyls; carboxylates; esters; urethanes; oximes; hydroxylamines; alkoxyamines; aralkoxyamines; thiols; sulfides; sulfoxides; sulfines; sulfonyls, sulfonamides; amines; N-oxides; hydrazines; hydrazides; hydrazones; azides; amides; ureas; amidines, guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom of an acyclic group. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in any embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in any embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In any embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In any embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in any embodiments, from 2 to 8, 2 to 6, or 2 to 4 carbon atoms. In any embodiments, the alkenyl group has one, two, or three carbon-carbon double bonds. Examples include, but are not limited to vinyl, allyl, $-CH=CH(CH_3)$, $-CH=C(CH_3)_2$, $-C(CH_3)=CH_2$, $-C(CH_3)=CH(CH_3)$, $-C(CH_2CH_3)=CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In any embodiments the cycloalkenyl group may have one, two or three double bonds but does not include aromatic compounds. Cycloalkenyl groups have from 4 to 14 carbon atoms, or, in any embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in any embodiments, from 2 to 8, 2 to 6, or 2 to 4 carbon atoms. In any embodiments, the alkynyl group has one, two, or three carbon-carbon triple bonds. Examples include, but are not limited to $-C\equiv CH$, $-C\equiv CCH_3$, $-CH_2C\equiv CCH_3$, $-C\equiv CCH_2CH(CH_2CH_3)_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In any embodiments, aryl groups contain 6-14 carbons, and in others from 6 to 12 or even 6-10 carbon atoms in the ring portions of the groups. In any embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In any embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heteroalkyl groups are alkyl groups in which at least one carbon is replaced with a heteroatom selected from N, O or S. Thus, heteroalkyl groups may include straight chain and branched chain heteroalkyl groups having from 1 to 11 carbon atoms, and typically from 1 to 10 carbons or, in any embodiments, from 1 to 8, 1 to 6, or 1 to 4 carbon atoms. In any embodiments, the heteroalkyl group may have 1, 2, 3, 4, or 5 heteroatoms selected from N, O, or S. In any embodiments, the heteroalkyl group may include 1 or two heteroatoms, such as 1 or 2 oxygen atoms, 1 or 2 nitrogen atoms, one or two sulfur atoms, an oxygen and a nitrogen atom, an oxygen and sulfur atom, or a nitrogen and a sulfur atom. Heteroalkyl groups include for example, methoxy, ethoxy, methoxyethyl, methylthio, methylthiopropyl, ethyloxymethyl, and methylaminobutyl. Heteroalkyl groups may be substituted one or more times just as alkyl groups are with substituents such as those listed above. In any embodiments, a heteroalkyl group may be substituted with an oxo group, to form a ketone, an amide, a sulfone, a sulfoxide, or sulfonamide.

Heterocyclyl groups include aromatic (also referred to as heteroaryl) and non-aromatic ring compounds containing 3 or more ring members, of which one or more is a heteroatom such as, but not limited to, N, O, and S. In any embodiments, the heterocyclyl group contains 1, 2, 3 or 4 heteroatoms. In any embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Carbon-containing groups described herein having two or more points of attachment (i.e., divalent, trivalent, or polyvalent) within a compound of the present technology are designated by use of the suffix, "ene." For example, divalent alkyl groups are alkylene groups, divalent heteroalkyl groups are heteroalkylene, divalent aryl groups are arylene groups, divalent heteroaryl groups are divalent heteroarylene groups, and so forth. Such divalent groups may also be substituted with one or more substituents, e.g., with one or two substituents. In any embodiments, the substituent is an oxo group and may, for example provide a divalent group with one or two ketones, esters, or amides, depending on whether the carbon adjacent to a heteroatom is substituted with the oxo group. The heteroatom may also have chemically permissible substituents. For example, a sulfur atom may be substituted with one or two oxo groups to form a sulfoxide or a sulfone. However, substituted groups having a single point of attachment to the compound of the present technology are not referred to using the "ene" designation. Thus, e.g., chloroethyl is not referred to herein as chloroethylene. Cyclic groups that also have acyclic (i.e., linear or branched) portion(s) such as aralkylene, arylheteroalkylene, heterocyclylalkylene, etc., may have attachment points solely on the acyclic portions or on both the cyclic and acyclic portions. For example, a divalent heterocyclylheteroalkylene such as the following groups,

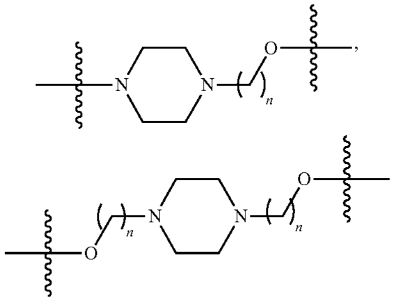

may have attachment points at each heteroalkylene portion of the group, or may have one attachment point on the heteroalkylene portion and another on the heterocyclyl portion. A divalent cyclic group substituted with acyclic groups but having both attachment points on the ring system is a substituted cyclic ene. For example, a 2-methyl phenyl group bearing attachment points at positions 1 and 4 is an arylene, not an aralkylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

As used herein, the term "protecting group" refers to a chemical group that exhibits the following characteristics: 1)

reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 3rd Ed. (John Wiley & Sons, Inc., New York), which is hereby incorporated by reference in its entirety and for any and all purposes as if fully set forth herein. Hydroxyl protecting groups include ethers, esters, and carbonates, among others. Hydroxyl protecting groups include but art not limited to: methoxymethyl ethers (MOM), methoxyethoxymethyl ethers (MEM), benzyloxymethyl ethers (BOM), tetrahydropyranyl ethers (THP), benzyl ethers (Bn), p-methoxybenzyl ethers, trimethylsilyl ethers (TMS), triethylsilyl ethers (TES), triisopropylsilyl ethers (TIPS), t-butyldimethylsilyl ethers (TBDMS), t-butyldiphenylsilyl ethers (TBDPS), o-nitrobenzyl ethers, p-nitrobenzyl ethers, trityl ethers, acetate, chloroacetate, dichloroacetate, trichloroacetate, trifluoroacetate, benzoate (Bz), methyl carbonate, allyl carbonate (alloc), dimethylthiocarbamate (DMTC), benzyl carbonate (Cbz), t-butyl carbonate (Boc), and 9-(fluorenylmethyl) carbonate (Fmoc). Amino protecting groups include, but are not limited to, urethanes, sulfonyl groups, silyl groups, and others. For example, amino protecting groups include mesitylenesulfonyl (Mts), benzyloxycarbonyl (Cbz or Z), t-butyloxycarbonyl (Boc), t-butyldimethylsilyl (TBS or TBDMS), 9-fluorenylmethyloxycarbonyl (Fmoc), allyloxycarbonyl (Alloc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α,α-dimethyldimethoxybenzyloxycarbonyl (DDZ), 5-bromo-7-nitroindolinyl, and the like. Amino protecting groups susceptible to acid-mediated removal include but are not limited to Boc and TBDMS. Amino protecting groups resistant to acid-mediated removal and susceptible to hydrogen-mediated removal include but are not limited to Alloc, Cbz, nitro, and 2-chlorobenzyloxycarbonyl. Amino groups susceptible to base-mediated removal, but resistant to acid-mediated removal include Fmoc.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —$COOR^{70}$ and —C(O)O-G groups. $R^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein.

The term "amide" (or "amido") includes C- and N-amide groups, i.e., —$C(O)NR^{71}R^{72}$, and —$NR^{71}C(O)R^{2}$ groups, respectively. $R^{7}$ and $R^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—$C(O)NH_2$) and formamide groups (—NHC(O)H). In any embodiments, the amide is —$NR^{71}C(O)$—($C_{1-5}$alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —$NR^{73}C(O)OR^{74}$ and —$OC(O)NR^{73}R^{74}$ groups, respectively. $R^{73}$ and $R^{74}$ are independently a substituted or unsubstituted alkyl, alkenyl, alkynyl, cycloalkyl, aryl, aralkyl, heterocyclylalkyl, or heterocyclyl group as defined herein. $R^{73}$ may also be H.

The term "amine" (or "amino") as used herein refers to —$NR^{75}R^{76}$ groups, wherein $R^{75}$ and $R^{76}$ are independently hydrogen, or a substituted or unsubstituted alkyl, alkenyl, alkynyl, cycloalkyl, aryl, aralkyl, heterocyclylalkyl or heterocyclyl group as defined herein. In any embodiments, the amine is alkylamino, dialkylamino, arylamino, or alkylarylamino. In other embodiments, the amine is $NH_2$, methylamino, dimethylamino, ethylamino, diethylamino, propylamino, isopropylamino, phenylamino, or benzylamino.

The term "sulfonamido" includes S- and N-sulfonamide groups, i.e., —$SO_2NR^{78}R^{79}$ and —$NR^{78}SO_2R^{79}$ groups, respectively. $R^{78}$ and $R^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—$SO_2NH_2$). In any embodiments herein, the sulfonamido is —$NHSO_2$— alkyl and is referred to as the "alkylsulfonylamino" group.

The term "thiol" refers to —SH groups, while "sulfides" include —$SR^{80}$ groups, "sulfoxides" include —$S(O)R^{81}$ groups, "sulfones" include —$SO_2R^{82}$ groups, and "sulfonyls" include —$SO_2OR^{83}$. $R^{80}$, $R^{81}$, $R^{82}$, and $R^{83}$ are each independently a substituted or unsubstituted alkyl, cycloalkyl, alkenyl, alkynyl, aryl aralkyl, heterocyclyl or heterocyclylalkyl group as defined herein. In any embodiments the sulfide is an alkylthio group, —S-alkyl.

The term "urea" refers to —$NR^{84}$—C(O)—$NR^{81}R^{86}$ groups. $R^{84}$, $R^{81}$, and $R^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —$C(NR^{87})NR^{88}R^{89}$ and —$NR^{87}C(NR^{88})R^{89}$, wherein $R^{17}$, $R^{B}$a, and $R^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —$NR^{90}C(NR^{91})NR^{92}R^{93}$, wherein $R^{90}$, $R^{91}$, $R^{92}$ and $R^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to $—C(R^{94})═C(R^{95})NR^{96}R^{97}$ and $—NR^{94}C(R^{91})═C(R^{96})R^{97}$, wherein $R^{94}$, $R^{95}$, $R^{96}$ and $R^{9'}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In any embodiments, the halogen is fluorine. In other embodiments, the halogen is chlorine or bromine.

The term "hydroxyl" as used herein can refer to —OH or its ionized form, —O—. A "hydroxyalkyl" group is a hydroxyl-substituted alkyl group, such as $HO—CH_2—$.

The term "imide" refers to $—C(O)NR^{98}C(O)R^{99}$, wherein $R^{98}$ and $R^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to $—CR^{100}(NR^{101})$ and $—N(CR^{100}R^{101})$ groups, wherein $R^{100}$ and $R^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that $R^{100}$ and $R^{101}$ are not both simultaneously hydrogen.

The term "nitro" as used herein refers to an $—NO_2$ group.

The term "trifluoromethyl" as used herein refers to $—CF_3$.

The term "trifluoromethoxy" as used herein refers to $—OCF_3$.

The term "azido" refers to $—N_3$.

The term "trialkyl ammonium" refers to a $—N(alkyl)_3$ group. A trialkylammonium group is positively charged and thus typically has an associated anion, such as halogen anion.

The term "isocyano" refers to —NC.

The term "isothiocyano" refers to —NCS.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, guanidines may exhibit the following isomeric forms in protic organic solution, also referred to as tautomers of each other:

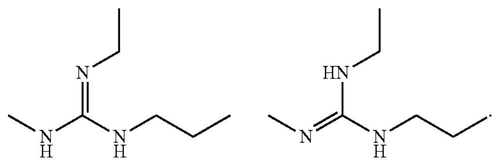

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

In one aspect, the present technology provides a compound of Formula I as described above. In any embodiments, the compound of Formula I is a compound of Formula IA, a stereoisomer thereof or a pharmaceutically acceptable salt of the compound or the stereoisomer of the compound:

IA

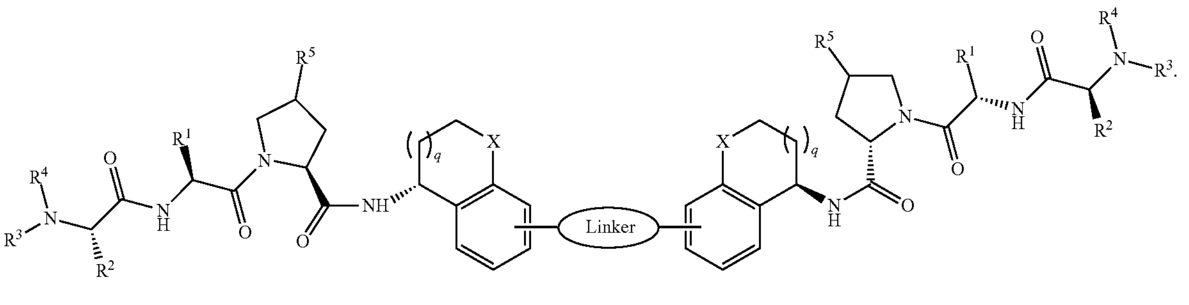

The variables Linker, X, q, $R^1$, $R^2$, $R^3$, $R^4$ and $R^5$ may be defined as having any of the values disclosed herein.

In any embodiments of compounds of Formulas I or IA, X may be O. In any other embodiments, X may be $CH_2$. In still others, X may be $NR^6$. In any embodiments, q may be 2. In any embodiments, q may be 1. In any embodiments, q may be 0. In any embodiments, the compound has the structure of any of Formulas IB, IC, ID, IE, IF, or IG, a stereoisomer thereof, or a pharmaceutically acceptable salt of the compound or the stereoisomer of the compound:

IB

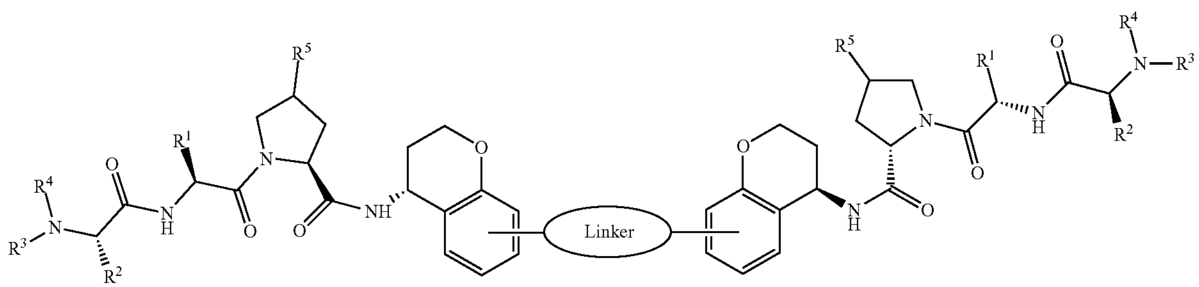

IC

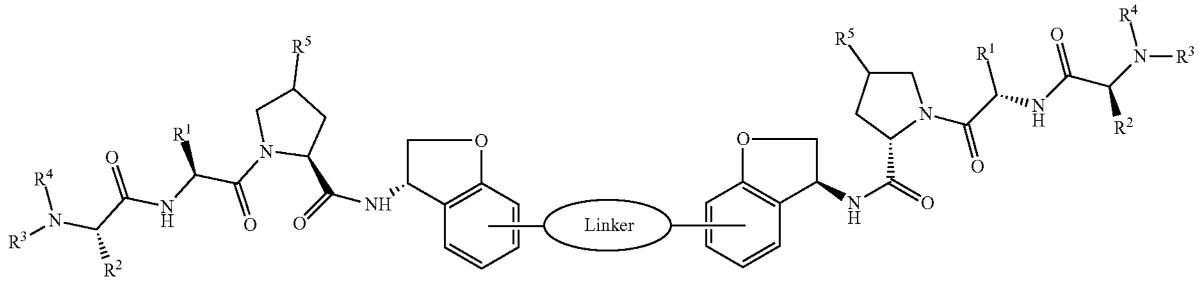

ID

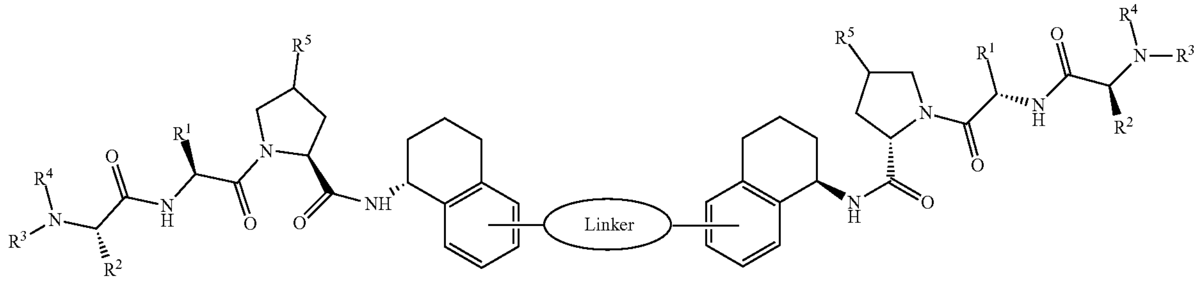

-continued

IE

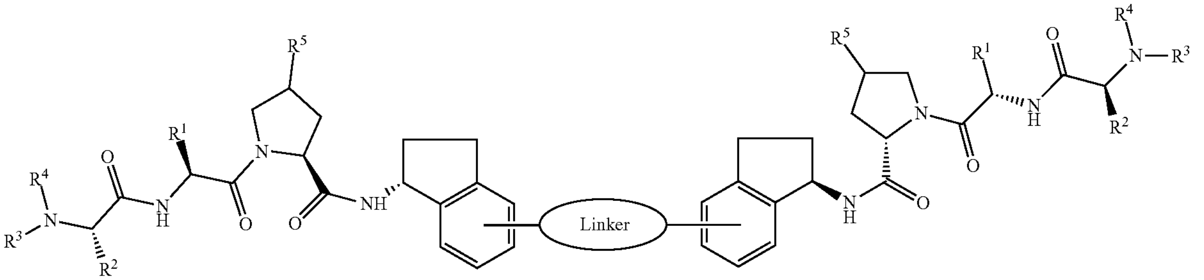

IF

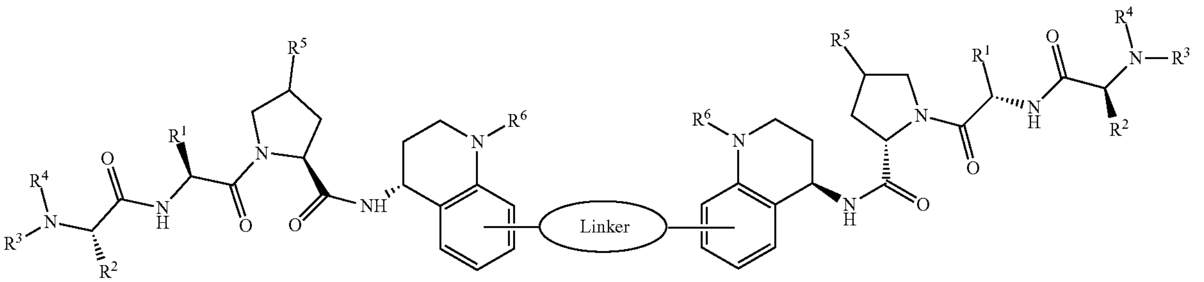

IG

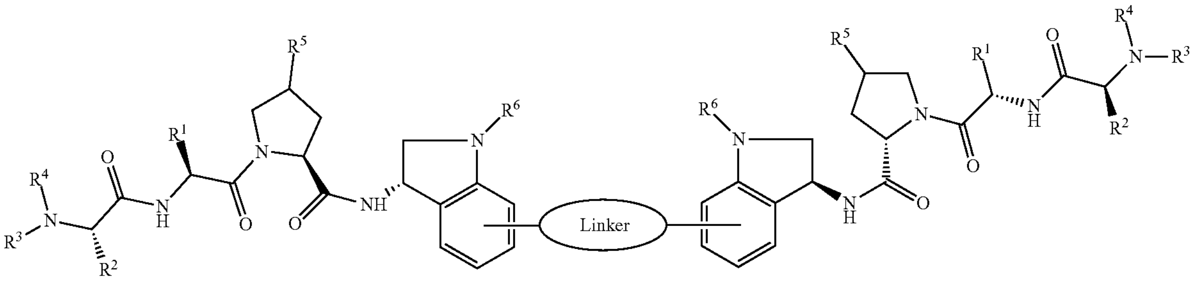

As noted above, in any embodiments of compounds of Formula I (including but not limited to compounds of Formula IA, IB, IC, ID, IE, IF, or IG), Linker is a divalent moiety selected from a bond, oxy moiety or an optionally substituted moiety selected from the group consisting of amino, alkylene, heteroalkylene, alkenylene, heteroalkenylene, alkynylene, heteroalkynylene, cycloalkylene, cycloalkylheteroalkylene, arylene, aralkylene, arylheteroalkylene, heterocyclylene, heterocyclylalkylene, heterocyclylheteroalkylene, heteroarylene, heteroarylalkylene, and heteroarylheteroalkylene. In any embodiments, Linker is an optionally substituted moiety selected from the group consisting of amino, alkylene, heteroalkylene, alkenylene, heteroalkenylene, alkynylene, heteroalkynylene, cycloalkylene, cycloalkylheteroalkylene, arylene, aralkylene, arylheteroalkylene, heterocyclylene, heterocyclylalkylene, In any embodiments, Linker is optionally substituted heterocyclylheteroalkylene, heteroarylene, heteroarylalkylene, or heteroarylheteroalkylene. In any embodiments Linker is optionally substituted with one, two, three or four oxo groups. In any embodiments Linker is optionally substituted on carbon or sulfur and comprises one or two carbonyl groups or one or two sulfonyl groups. In any embodiments, Linker may be selected from the group consisting of heteroalkylene, arylene, aralkylene, arylheteroalkylene, heterocyclylalkylene, and heterocyclylheteroalkylene. In any embodiments herein, Linker may be selected from a bond, amino or optionally substituted heteroalkylene. In any embodiments herein, Linker may be selected from the group consisting of $C_2$-$C_{12}$ polyalkylene oxide, phenylalkylene, phenyl heteroalkylene, piperazinylalkylene, and piperazinylheteroalkylene. For example, Linker may be selected from the group consisting of a bond,

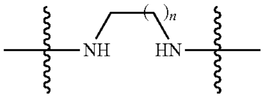

,

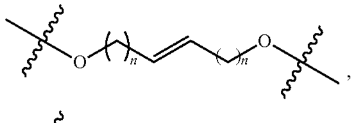

,

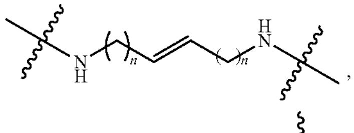

,

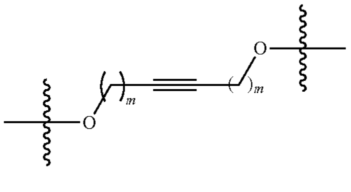

,

-continued
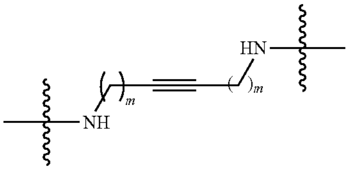
,
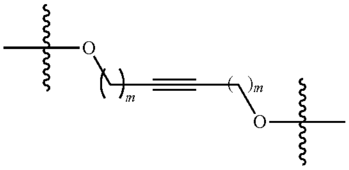
,
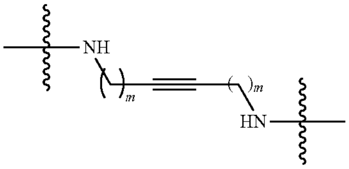
,
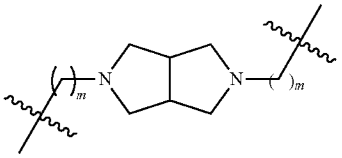
,
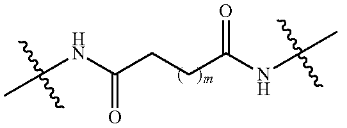
,
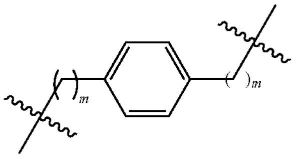
,
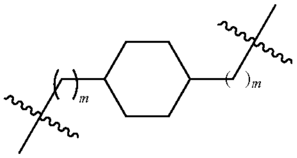
,
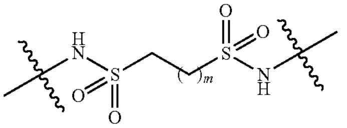
,
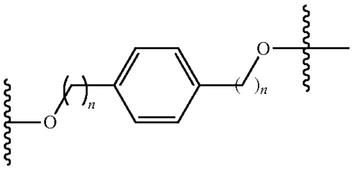
,
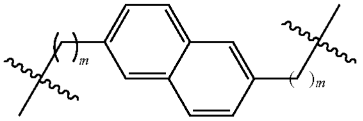
,
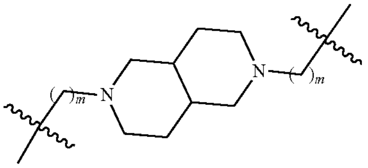
,
-continued
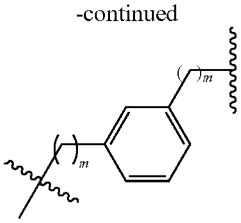
,
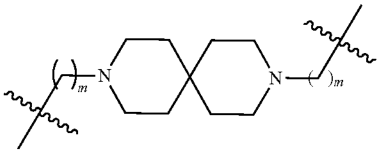
,
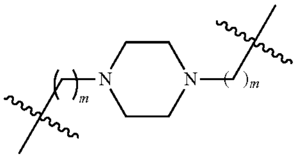
,
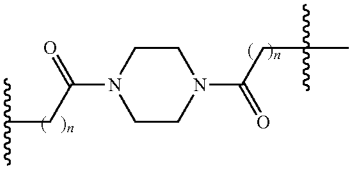
,
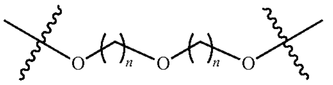
,
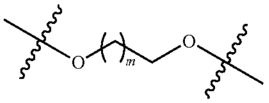
,
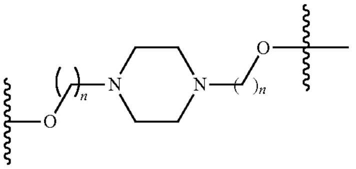
,
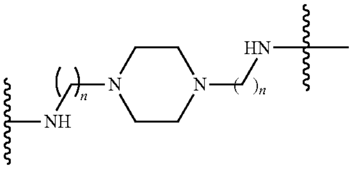
,
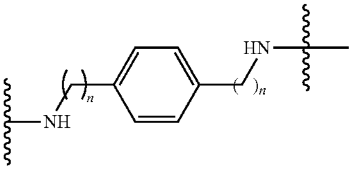
,
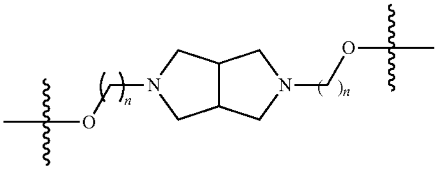
,
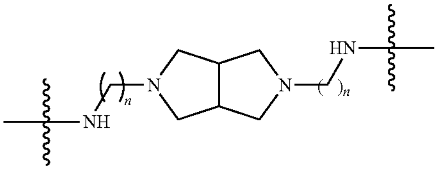
, -continued

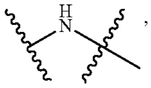,
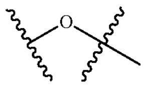,
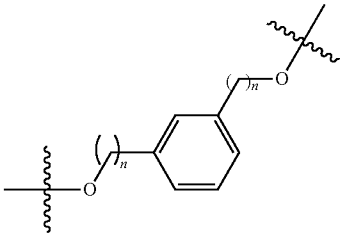,
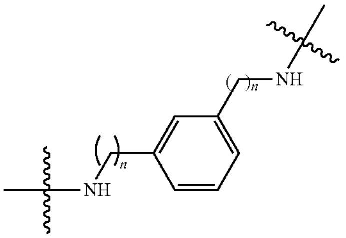,
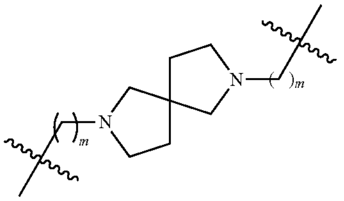,
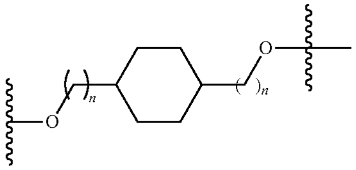,
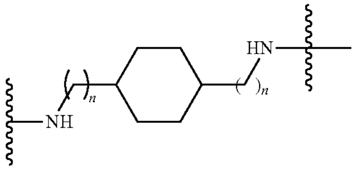,
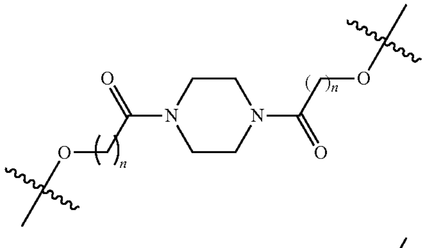,
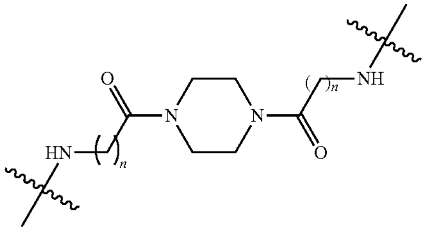,
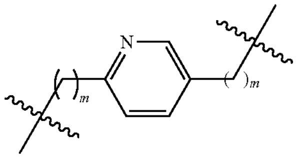, -continued

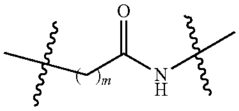,
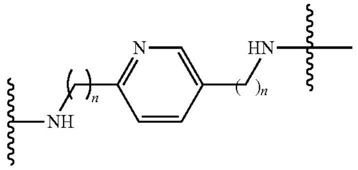, and
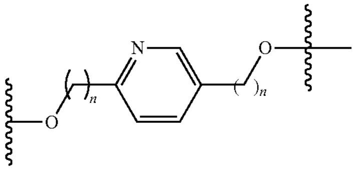

wherein m is 0, 1, 2, 3, 4, 5, or 6; and n is 1, 2, 3, 4, 5, 6.

Further, in any embodiments including such Linkers, n may also be 1, 2 or 3, and/or m may be 0, 1, 2, 3, or 4. In any embodiments, m may be 0 and/or n may be 1. In any embodiments, Linker may be a bond, —NH—, or —C(O)NH—.

In any embodiments, Linker may be

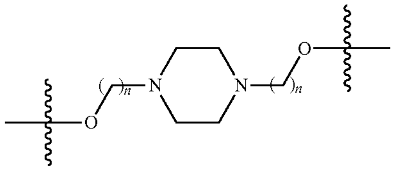

wherein n is 1, 2, 3, 4, 5, 6. For example, n may be 2 or may be 3.

In any embodiments, Linker may be

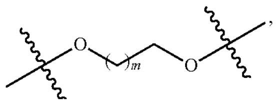, and m may be 0, 1, 2, 3, 4, 5, or 6. For example, m may be 1, 2, 3 or 4.

In any embodiments, Linker may be

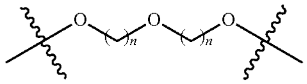

wherein n is n is 1, 2, 3, 4, 5, 6. For example, n may be 2 or 3.

In any embodiments, Linker may be

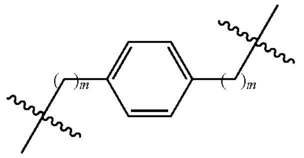

or

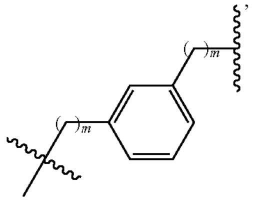

, and wherein m may be 0, 1, 2, 3, 4, 5, or 6. In any such embodiments, m may be 0 or 1.

In any embodiments of compounds of Formula I (including but not limited to compounds of Formula IA, IB, IC, ID, IE, IF, or IG), $R^1$ and $R^2$ may be independently a methyl, ethyl, n-propyl, i-propyl, n-butyl, s-butyl, i-butyl, t-butyl, cyclopropyl, cyclobutyl, cyclohexyl, or cyclopentyl group. In any embodiments, $R^3$ may be a methyl, ethyl, n-propyl, i-propyl, n-butyl, i-butyl, or t-butyl group. In any embodiments, $R^4$ may be H. In any embodiments, $R^4$ may be an amino-protecting group as defined herein, e.g., a urethane such as, but not limited to benzyloxycarbonyl, t-butyloxycarbonyl, fluorenyloxycarbonyl, or allyloxycarbonyl. In any embodiments herein, $R^6$ may be H. In any embodiments $R^6$ may be an amino-protecting group as defined herein, e.g., a urethane such as, but not limited to benzyloxycarbonyl, t-butyloxycarbonyl, fluorenyloxycarbonyl, or allyloxycarbonyl. In any embodiments of compounds of Formula I (including but not limited to compounds of Formula IA, IB, IC, ID, IE, IF, or IG), $R^2$ may be a methyl, ethyl, n-propyl, i-propyl, n-butyl, i-butyl, or t-butyl group In any embodiments $R^1$ may be cyclohexyl or isopropyl, and/or $R^2$ may methyl, and/or $R^3$ may be methyl, and/or $R^4$ may be H, and/or $R^3$ may be R In any embodiments, each occurrence of $R^1$ may be the same or different, each occurrence of $R^2$ may be the same or different, each occurrence of $R^3$ may be the same or different, each occurrence of $R^4$ may be the same or different, each occurrence of $R^5$ may be the same or different, and/or each occurrence of $R^6$ may be the same or different.

In an aspect of the present technology, a composition is provided that includes any one of the aspects and embodiments of compounds of Formula I (including but not limited to compounds of Formula IA, IB, IC, ID, IE, IF, or IG)) and a pharmaceutically acceptable carrier. In a related aspect, a pharmaceutical composition is provided which includes an effective amount of the compound of any one of the aspects and embodiments of compounds of Formula I (as well as but not limited to compounds of Formula IA, IB, IC, ID, IE, IF, or IG)) for treating a cancer or a viral infection mediated by an LAP, e.g., a cIAP. The cancer or viral infection mediated by an LAP may be ovarian cancer, fallopian tube cancer, peritoneal cancer, and hepatitis B infection.

In another aspect, a method is provided that includes administering an effective amount of a compound of any one of the aspects and embodiments of compounds of Formula I (including but not limited to compounds of Formula IA, IB, IC, ID, IE, IF, or IG) or administering a pharmaceutical composition comprising an effective amount of a compound of any one of the aspects and embodiments of compounds of Formulas I to a subject suffering from a cancer or a viral infection mediated by an IAP, e.g., a cIAP. The cancer or viral infection mediated by an IAP may be ovarian cancer, fallopian tube cancer, peritoneal cancer, and hepatitis B infection.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of a cancer or a viral infection mediated by an IAP. The cancer or viral infection mediated by an IAP may be ovarian cancer, fallopian tube cancer, peritoneal cancer, and hepatitis B infection. Another example of an effective amount includes amounts or dosages that are capable of reducing symptoms associated with viral infection, such as, for example, virus titer. As used herein, a "subject" or "patient" is a mammal, such as a cat, dog, rodent or primate. Typically, the subject is a human, and, preferably, a human suffering from or suspected of suffering from cancer or viral infection mediated by an IAP such as, but not limited to, ovarian cancer, fallopian tube cancer, peritoneal cancer, and hepatitis B infection. The term "subject" and "patient" can be used interchangeably.

Thus, the instant present technology provides pharmaceutical compositions and medicaments comprising any of the compounds disclosed herein (e.g., compounds of Formula I, including but not limited to compounds of Formula IA, IB, IC, ID, IE, IF, or IG) and a pharmaceutically acceptable carrier or one or more excipients or fillers. The compositions may be used in the methods and treatments described herein. Such compositions and medicaments include a therapeutically effective amount of any compound as described herein, including but not limited to a compound of Formula I (or of Formula IA, IB, IC, ID, IE, IF, or IG). The pharmaceutical composition may be packaged in unit dosage form.

The pharmaceutical compositions and medicaments may be prepared by mixing one or more compounds of the present technology, stereoisomers thereof and/or pharmaceutically acceptable salts thereof, with pharmaceutically acceptable carriers, excipients, binders, diluents or the like to prevent and treat disorders associated with the effects of increased plasma and/or hepatic lipid levels. The compounds and compositions described herein may be used to prepare formulations and medicaments that prevent or treat a cancers or viral infections associated with or mediated by IAPs, including but not limited to those described herein. Such compositions can be in the form of for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until for example, the desired therapeutic response is observed. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease in the symptoms of hyperlipidemia, such as, for example, a decrease in triglycerides in the blood stream. Effectiveness of the compositions and methods of the present technology may also be demonstrated by a decrease in the signs and symptoms of chronic liver disease, hypercholesteremia, obesity, metabolic syndrome, cardiovascular disease, gastrointestinal disease, atherosclerosis, renal disease, colorectal cancer, and stroke.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg Dosage of a compound of the present technology can also vary from 0.01 mg/kg to 100 mg/kg or, preferably, from 0.1 mg/kg to 10 mg/kg.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above nay also further each include or incorporate the variations of any or all other variations, aspects or aspects of the present technology.

EXAMPLES

General Synthetic and Analytical Details

All reagents and materials are or were purchased from commercial vendors.

Representative General Synthetic Schemes

The following compounds were or can be prepared as indicated in the following synthetic schemes using procedures known to those of ordinary skill in the art.

LIST OF ABBREVIATIONS

ACN acetonitrile
AcOH acetic acid
$Ad_2PBu$ butyldi-1-adamantylphosphine
t-Bu tert-butyl
t-BuXPhos 2-di-tert-butylphosphino-2',4',6'-triisopropylbiphenyl
CDI 1,1'-carbonyldiimidazole
DCM dichloromethane
DIAD diisopropyl azodicarboxylate
DMF dimethylformamide
DMA dimethylacetamide
DMAP 4-dimethylaminopyridine
DMP tert-2,2-dimethoxypropane
DMSO dimethyl sulfoxide
EDC 3-(ethyliminomethyleneamino)-N,N-dimethylpropan-1-amine
Et ethyl
HATU (1-[bis(dimethylamino)methylene]-1H-1,2,3-triazolo[4,5-b] pyridinium 3-oxid hexafluorophosphate)
LAH lithium aluminum hydride
Me methyl
MeCN acetonitrile
NCS N-chlorosuccinimide
PCC pyridinium chlorochromate
$Pd_2(dba)_3$ tris(dibenzylideneacetone)dipalladium
$Pd(dppf)Cl_2$ [1,1'-bis(diphenylphosphino)ferrocene]palladium(II) dichloride
PE petroleum ether
Ph phenyl
Py pyridine
Ruphos 2-dicyclohexylphosphino-2',6'-diisopropoxy-1,1'-biphenyl
STAB Sodium triacetoxyborohydride
TEA triethylamine
TFA trifluoroacetic acid
TFAA trifluoroacetic anhydride
THF tetrahydrofuran
TLC thin layer chromatography
TMS trimethylsilyl
TsCl p-toluenesulfonyl chloride
TsOH p-toluenesulfonic acid
Xantphos 4,5-bis(diphenylphosphino)-9,9-dimethylxanthene Example 1: Synthesis of Compound I
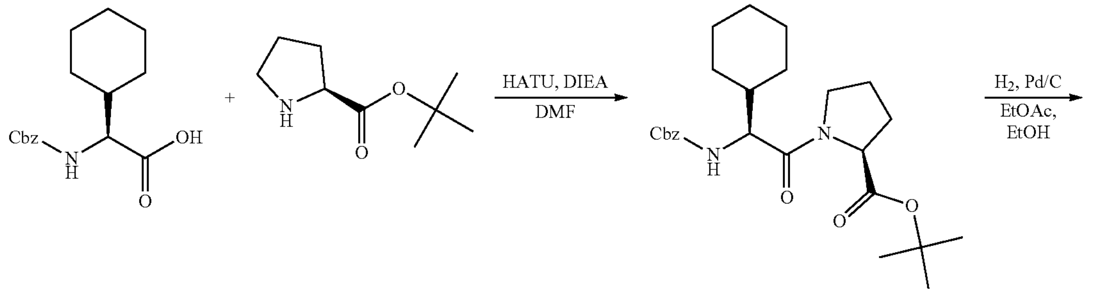
I-1
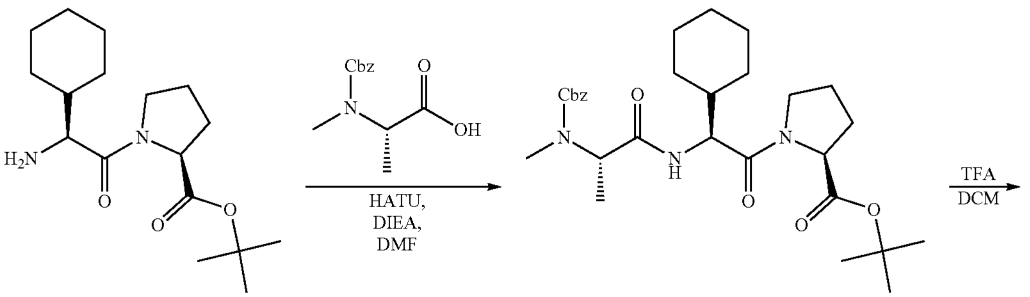
I-2
I-3
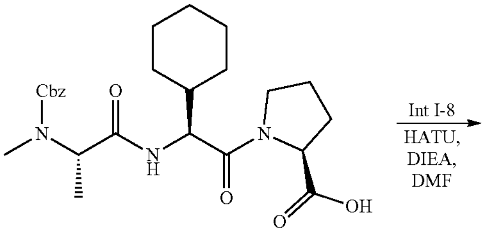
I-4
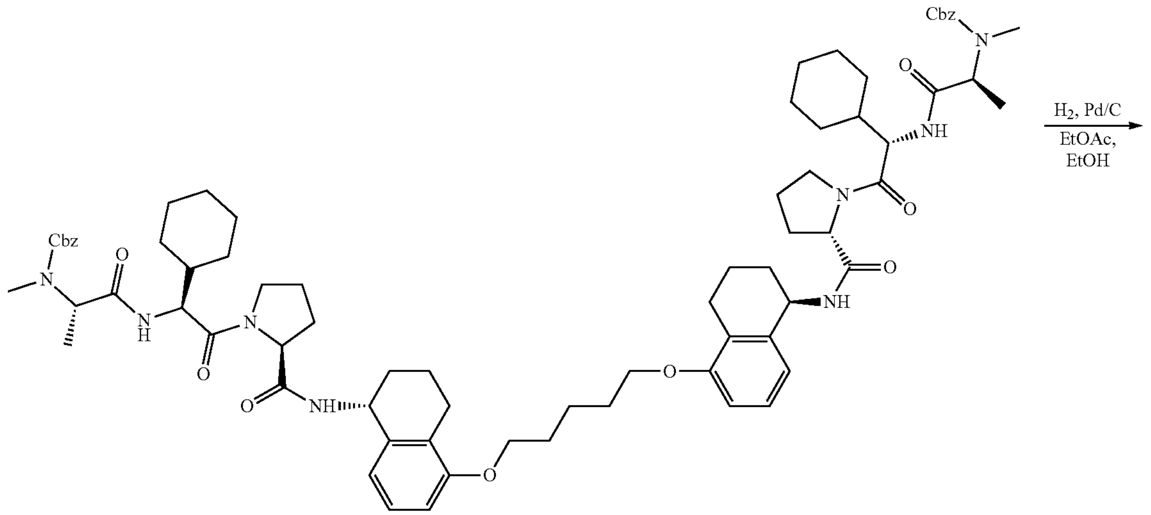
I-9

-continued

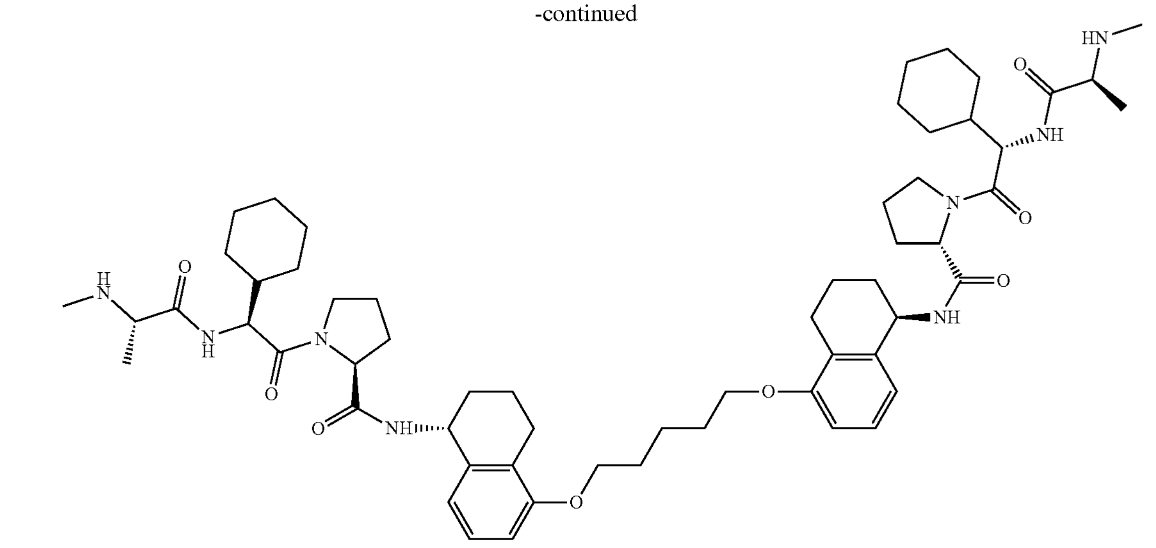

I

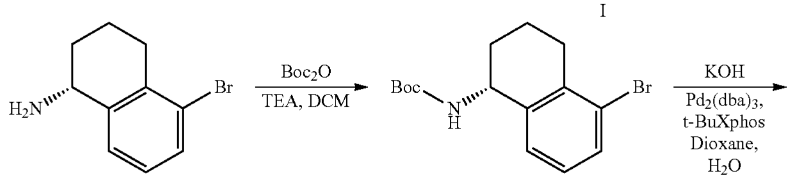

I-5

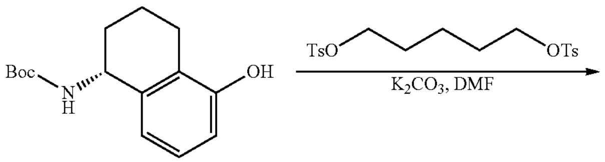

I-6

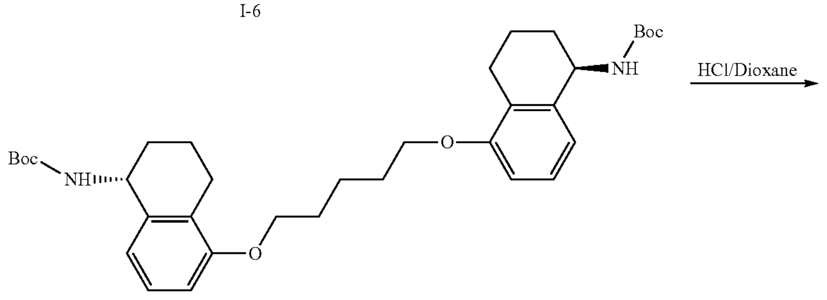

I-7

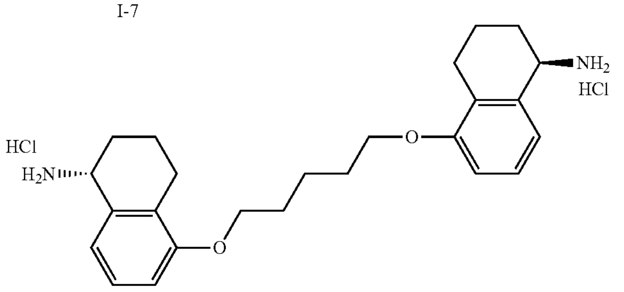

I-8 tert-Butyl (2S)-1-[(2S)-2-[[(benzyloxy)carbonyl] amino]-2-cyclohexylacetyl]pyrrolidine-2-carboxylate (Compound I-1)

To a solution of (S)-[[(benzyloxy)carbonyl]amino](cyclohexyl)acetic acid (10.0 g, 34.49 mmol) in DMF (120 mL) was added tert-butyl (2S)-pyrrolidine-2-carboxylate (6.6 g, 38.8 mmol) and DIEA (15.6 g, 121 mmol). Then HATU (29.1 g 76.5 mmol) was added to the mixture at 0° C. under $N_2$. The mixture was stirred at 0° C. for 2 h. After the reaction was completed, the mixture was purified by reverse phase flash column chromatography with $CH_3CN/H_2O$ (1/0, v/v) to afford the title compound (16.2 g 100%) as a light yellow oil LCMS (ESI, m/z): $[M+H]^+$=445.3.

tert-Butyl (2S)-1-[(2S)-2-amino-2-cyclohexylacetyl] pyrrolidine-2-carboxylate (Compound I-2)

To a solution of Compound I-1 (16.2 g 36.4 mmol) in EtOAc (200 mL) and EtOH (150 mL) was added Pd/C (8.0 g dry). The mixture was stirred at room temperature for 16 h under $H_2$. After the reaction was completed, the mixture was filtered. The filtrate was evaporated in vacuo to afford the title compound (10.3 g, crude) as a colorless oil. LCMS (ESI, m/z): $[M+H]^+$=311.2.

tert-Butyl (2S)-1-[(2S)-2-[(2S)-2-[[(benzyloxy)carbonyl](methyl)amino]propan amido]-2-cyclohexylacetyl]pyrrolidine-2-carboxylate (Compound I-3)

To a solution of Compound I-2 (10.3 g 33.2 mmol) in DMF (130 mL) was added (2S)-2-[[(benzyloxy)carbonyl](methyl)amino]propanoic acid (8.8 g 37.5 mmol) and DIEA (13.6 mL, 78.1 mmol). Then HATU (25.8 g, 68.0 mmol) was added to the mixture at 0° C. under $N_2$. The mixture was stirred at 0° C. for 2 h. After the reaction was completed, the mixture was purified by reverse phase flash column chromatography with $CH_3CN/H_2O$ (1/0, v/v) to afford the title compound (16.3 g 92%) as a light yellow oil. LCMS (ESI, m/z): $[M+H]^+$=530.3.

(2S)-1-[(2S)-2-[(2S)-2-[[(Benzyloxy)carbonyl](methyl)amino]propanamido]-2-cyclohexylacetyl] pyrrolidine-2-carboxylic Acid (Compound I-4)

To a solution of Compound I-3 (16.3 g 30.8 mmol) in DCM (150 mL) was added TFA (50 mL). The mixture was stirred at room temperature for 3 h. After the reaction was completed, the mixture was evaporated in vacuo. The residue was purified by reverse phase flash column chromatography with $CH_3CN/H_2O$ (60/40, v/v) to afford the title compound (13.2 g 90%) as a light yellow solid. LCMS (ESI, m/z): $[M+H]^+$=474.3.

tert-Butyl N-[(1R)-5-bromo-1,2,3,4-tetrahydronaphthalen-1-yl]carbamate (Compound I-5)

To a solution of (IR)-5-bromo-1,2,3,4-tetrahydronaphthalen-1-amine (5.0 g, 22.1 mmol) in DCM (100 mL) was added TEA (5.3 g, 52.4 mmol) and $Boc_2O$ (6.2 g, 28.4 mmol). The mixture was stirred at room temperature for 16 h. After the reaction was completed, the mixture was evaporated in vacuo. The residue was purified by flash column chromatography with petroleum ether/EtOAc (4/1, v/v) to afford the title compound (7.6 g, 100%) as a white solid. LCMS (ESI, m/z): $[M+H]^+$=326.1.

tert-ButylN-[(1R)-5-hydroxy-1,2,3,4-tetrahydronaphthalen-1-yl]carbamate (Compound I-6)

A mixture of Compound I-5 (5.2 g, 15.9 mmol), KOH (2.5 g, 44.6 mmol), $Pd_2(dba)_3$ (1.5 g, 1.70 mmol) and t-BuXPhos (1.4 g, 3.34 mmol) in dioxane (80 mL) and $H_2O$ (4 mL) was heated at 100° C. for 4 h. The mixture was diluted with $H_2O$ and extracted with DCM. The combined organic layers were washed with brine, dried over anhydrous sodium sulfate and filtered. The filtrate was concentrated under vacuum. The residue was purified by flash column chromatography with petroleum ether/EtOAc (75/25, v/v) and then purified by reverse phase flash column chromatography with $CH_3CN/H_2O$ (60/40, v/v) to afford the title compound (2.5 g, 59%) as a white solid. LCMS (ESI, m/z): $[M+H]^+$=264.2.

tert-Butyl N-[(1R)-5-[(5-[[(5R)-5-[(tert-butoxycarbonyl)amino]-5,6,7,8-tetrahydro naphthalen-1-yl]oxy]pentyl)oxy]-1,2,3,4-tetrahydronaphthalen-1-yl]carbamate (Compound I-7)

A mixture of Compound I-6 (502 mg, 1.90 mmol), 5-[(4-methylbenzenesulfonyl)oxy]pentyl 4-methylbenzenesulfonate (408 mg, 0.99 mmol) and $K_2CO_3$ (1.1 g 8.10 mmol) in DMF (15 mL) was heated at 65° C. for 16 h. After the reaction was completed, the reaction mixture was cooled to room temperature and then filtered. The filtrate was purified by reverse phase flash column chromatography with $CH_3CN/H_2O$ (1/0, v/v) to afford the title compound (520 mg, 45%) as an off-white solid. LCMS (ESI, m/z): $[M+H]^+$=595.4.

(1R)-5-[(5-[[(5R)-5-Amino-5,6,7,8-tetrahydronaphthalen-1-yl]oxy]pentyl)oxy]-1,2,3,4-tetrahydronaphthalen-1-amine Dihydrochloride (Compound I-8)

To a solution of Compound I-7 (520 mg 0.87 mmol) in dioxane (3 mL) was added HCl/dioxane (8.0 mL, 4 mol/L). The mixture was stirred at room temperature for 4 h. After the reaction was completed, the reaction mixture was evaporated in vacuo to afford the title compound (706 mg, crude) as a light yellow solid. LCMS (ESI, m/z): $[M+H]^+$=395.2.

Benzyl N-[(1S)-1-[[(1S)-2-[(2S)-2-[[(1R)-5-[(5-[[(5R)-5-[(2S)-1-[(2S)-2-[(2S)-2-[[(benzyloxy)carbonyl](methyl)amino]propanamido]-2-cyclohexylacetyl]pyrrolidine-2-amido]-5,6,7,8-tetrahydronaphthalen-1-yl]oxy]pentyl)oxy]-1,2,3,4-tetrahydronaphthalen-1-yl]carbamoyl]pyrrolidin-1-yl]-1-cyclohexyl-2-oxoethyl]carbamoyl]ethyl]-N-methylcarbamate (Compound I-9)

To a solution of Compound I-4 (706 mg 1.49 mmol) in DMF (15 mL) was added Compound I-8 (1.0 g 2.16 mmol) and DIEA (2.0 mL, 11.5 mmol). Then HATU (1.4 g 3.76 mmol) was added to the mixture at 0° C. under $N_2$. The mixture was stirred at 0° C. for 2 h. After the reaction was completed, the reaction mixture was purified by reverse phase flash column chromatography with $CH_3CN/H_2O$ (1/0, v/v) and then purified by flash column chromatography with DCM/MeOH (94/6, v/v) to afford the title compound (580 mg 29%) as an off-white solid. LCMS (ESI, m/z): $[M+H]^+$=1305.7.

(2S)-1-[(2S)-2-Cyclohexyl-2-[(2S)-2-(methylamino)propanamido]acetyl]-N-[(1R)-5-[2-[4-(2-[[(5R)-5-[(2S)-1-[(2S)-2-cyclohexyl-2-[(2S)-2-(methylamino)propanamido]acetyl]pyrrolidine-2-amido]-5,6,7,8-tetrahydronaphthalen-1-yl]oxy]ethyl)phenyl]ethoxy]-1,2,3,4-tetrahydronaphthalen-1-yl] pyrrolidine-2-carboxamide (Compound I)

To a solution of Compound I-9 (580 ng, 0.44 mmol) in EtOAc (15 mL) and EtOH (20 mL) was added Pd/C (370 mg, dry). The mixture was stirred at room temperature for 16 h under $H_2$. After the reaction was completed, the mixture was filtered. The filtrate was evaporated in vacuo. The residue was purified by Prep-HPLC with the following conditions: Column: XBridge Prep OBD C18 Colum, 30×150 mm, 5 um; Mobile Phase A: Water (10 mmol/L $NH_4HCO_3$), Mobile Phase B:ACN; Flow rate: 60 mL/min; Gradient: 49% B to 57% B in 7 min; 254 nm; RT: 8.5 min to afford the title compound (74.9 mg 16%) as a white solid. LCMS (ESI, m/z): $[M+H]^+$=1037.8. $^1$H NMR (400 MHz, DMSO-$d_6$, ppm): δ 8.06 (d, J=8.4 Hz, 2H), 7.84 (d, J=9.2 Hz, 2H), 7.13-7.02 (m, 2H), 6.88-6.75 (m, 4H), 4.93-4.81 (m, 2H), 4.48-4.37 (m, 2H), 4.33-4.26 (m, 2H), 4.03-3.89 (m, 4H), 3.76-3.66 (m, 2H), 3.65-3.55 (m, 2H), 2.98-2.88 (m, 2H), 2.61-2.53 (m, 3H), 2.16 (s, 6H), 2.09-1.90 (m, 6H), 1.88-1.53 (m, 3H), 1.19-0.85 (m, 16H).

Following the procedure described above for Example 1 and substituting the appropriate reagents, starting materials and purification methods known to those skilled in the art, the compounds listed below were prepared.

I-A

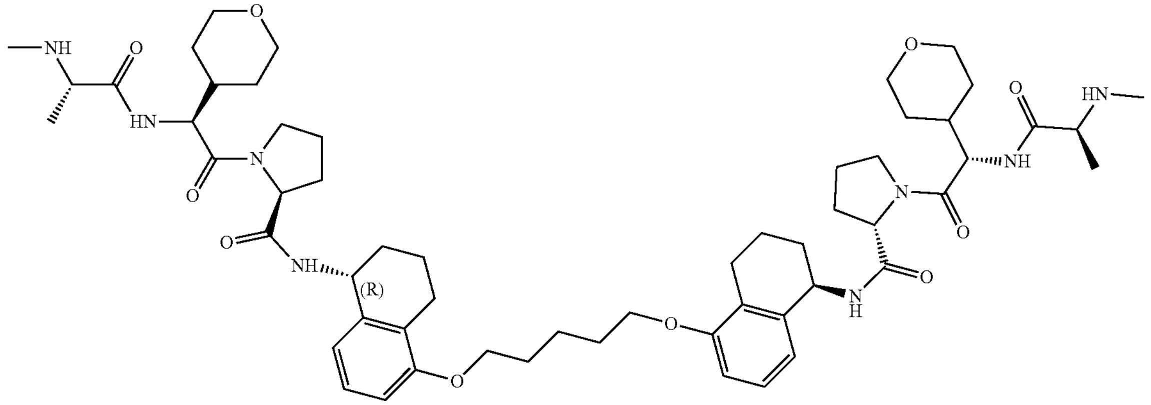

(S)-1-((S)-2-((S)-2-(methylamino)propanamido)-2-(tetrahydro-2H-pyran-4-yl)acetyl)-N—((R)-5-((5-(((R)-5-((S)-1-((S)-2-((S)-2-(methylamino)propanamido)-2-(tetrahydro-2H-pyran-4-yl)acetyl)pyrrolidine-2-carboxamido)-5,6,7,8-tetrahydronaphthalen-1-yl)oxy)pentyl)oxy)-1,2,3,4-tetrahydronaphthalen-1-yl)pyrrolidine-2-carboxamide (Compound I-A)

LCMS (ESI, m/z): $[M+H]^+$=1041.6. $^1$H NMR (300 MHz, DMSO-$d_6$): δ 8.22-8.09 (m, 2H), 8.01-7.89 (m, 2H), 7.18-7.03 (m, 2H), 6.91-6.77 (m, 4H), 4.99-4.80 (m, 2H), 4.60-4.45 (m, 2H), 4.40-4.27 (m, 2H), 4.07-3.94 (m, 4H), 3.93-3.53 (m, 8H), 3.30-3.18 (m, 4H), 3.05-2.91 (m, 2H), 2.69-2.55 (m, 4H), 2.25-2.14 (m, 6H), 2.12-1.89 (m, 8H), 1.89-1.53 (m, 22H), 1.39-1.19 (m, 4H), 1.17-1.05 (m, 6H).

I-B

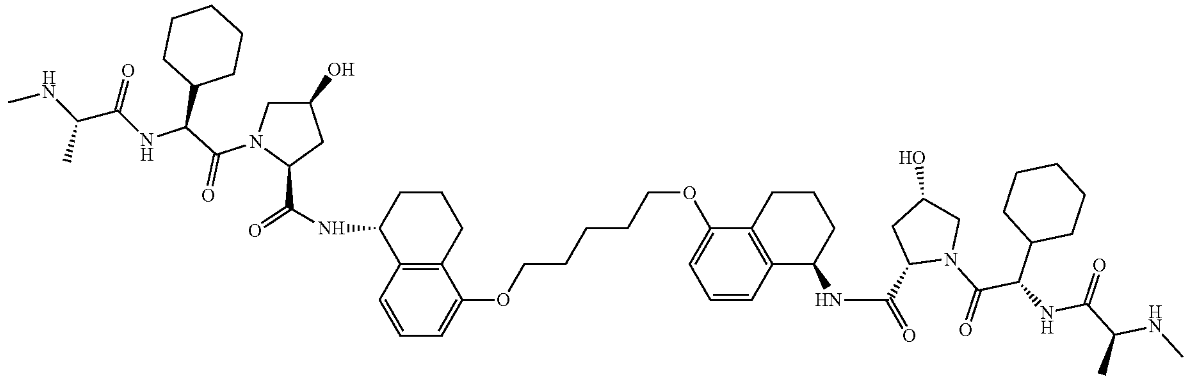

(2S,4S)-1-((S)-2-cyclohexyl-2-((S)-2-(methylamino) propanamido)acetyl)-N—((R)-5-((5-(((R)-5-((2S, 4S)-1-((S)-2-cyclohexyl-2-((S)-2-(methylamino) propanamido)acetyl)-4-hydroxypyrrolidine-2-carboxamido)-5,6,7,8-tetrahydronaphthalen-1-yl) oxy)pentyl)oxy)-1,2,3,4-tetrahydronaphthalen-1-yl)-4-hydroxypyrrolidine-2-carboxamide (Compound I-B)

LCMS (ESI, m/z): $[M+H]^+=1069.9$. $^1H$ NMR (300 MHz, DMSO-$d_6$): δ 8.30-8.14 (m, 2H), 7.99-7.86 (m, 2H), 7.15-7.01 (m, 2H), 6.95-6.85 (m, 2H), 6.84-6.77 (m, 2H), 5.47-5.35 (m, 2H), 4.98-4.81 (m, 2H), 4.42-4.30 (m, 4H), 4.28-4.18 (m, 2H), 4.07-3.96 (m, 4H), 3.95-3.83 (M, 2H), 3.50-3.40 (m, 4H), 3.05-2.94 (m, 2H), 2.68-2.56 (m, 4H), 2.37-2.24 (m, 2H), 2.23-2.13 (m, 6H), 1.90-1.55 (m, 28H), 1.18-0.90 (m, 16H).

I-C

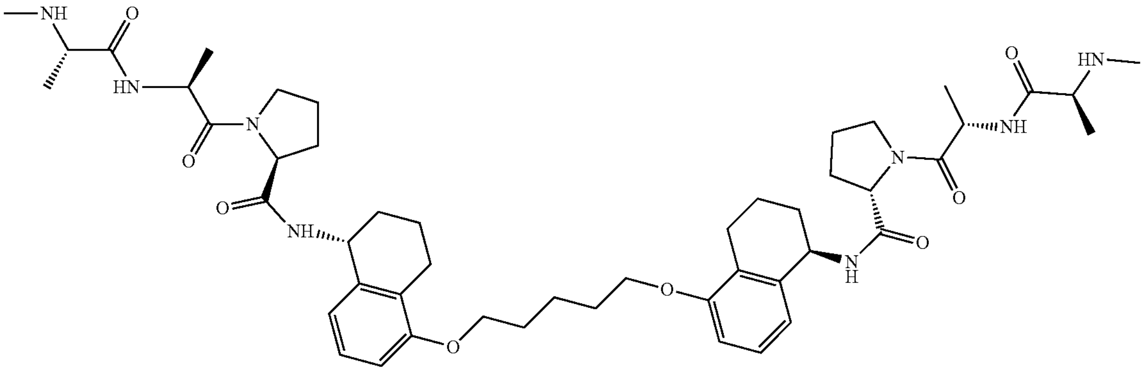

(2S)-1-[(2S)-2-[(2S)-2-(methylamino)propanamido] propanoyl]-N-[(1R)-5-[(5-[[(5R)-5-[(2S)-1-[(2S)-2-[(2S)-2-(methylamino)propanamido]propanoyl]pyrrolidine-2-amido]-5,6,7,8-tetrahydronaphthalen-1-yl] oxy]pentyl)oxy]-1,2,3,4-tetrahydronaphthalen-1-yl] pyrrolidine-2-carboxamide (Compound I-C)

LCMS (ESI, m/z): $[M+H]^+=901.5$. $^1H$ NMR (300 MHz, DMSO-$d_6$): δ 8.55-7.86 (m, 4H), 7.21-7.00 (m, 2H), 6.99-6.67 (m, 4H), 5.02-4.75 (m, 2H), 4.73-4.48 (m, 2H), 4.47-4.19 (m, 2H), 4.11-3.87 (m, 4H), 3.67-3.55 (m, 2H), 3.03-2.83 (m, 2H), 3.72-2.55 (m, 4H), 2.32-1.50 (m, 32H), 1.32-1.00 (m, 12H).

I-D

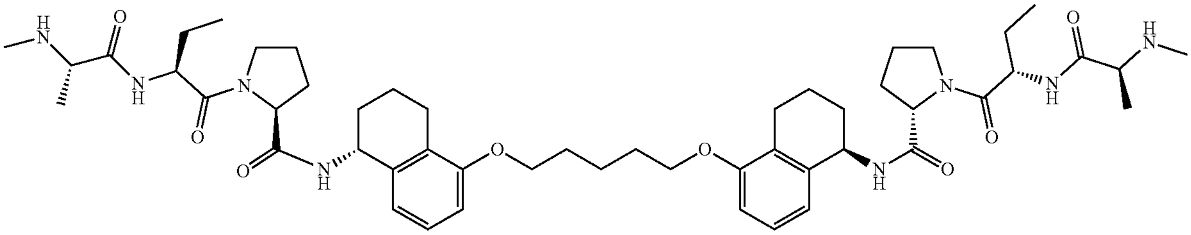

(2S)-1-[(2S)-2-[(2S)-2-(methylamino)propanamido]butanoyl]-N-[(1R)-5-[(5-[[(5R)-5-[(2S)-1-[(2S)-2-[(2S)-2-(methylamino)propanamido]butanoyl]pyrrolidine-2-amido]-5,6,7,8-tetrahydronaphthalen-1-yl]oxy]pentyl)oxy]-1,2,3,4-tetrahydronaphthalen-1-yl]pyrrolidine-2-carboxamide (Compound I-D)

LCMS (ESI, m/z): $[M+H]^+$=929.7. $^1H$ NMR (300 MHz, DMSO-$d_6$): δ 8.50-8.05 (m, 2H), 8.01-7.83 (m, 2H), 7.17-7.04 (m, 2H), 6.90-6.77 (m, 4H), 4.98-4.85 (m, 2H), 4.59-4.46 (m, 2H), 4.40-4.29 (m, 2H), 4.09-3.91 (m, 4H), 3.73-3.50 (m, 4H), 3.03-2.89 (m, 2H), 2.67-2.56 (m, 4H), 2.18 (s, 6H), 2.14-1.49 (m, 28H), 1.19-1.05 (m, 6H), 0.97-0.78 (m, 6H).

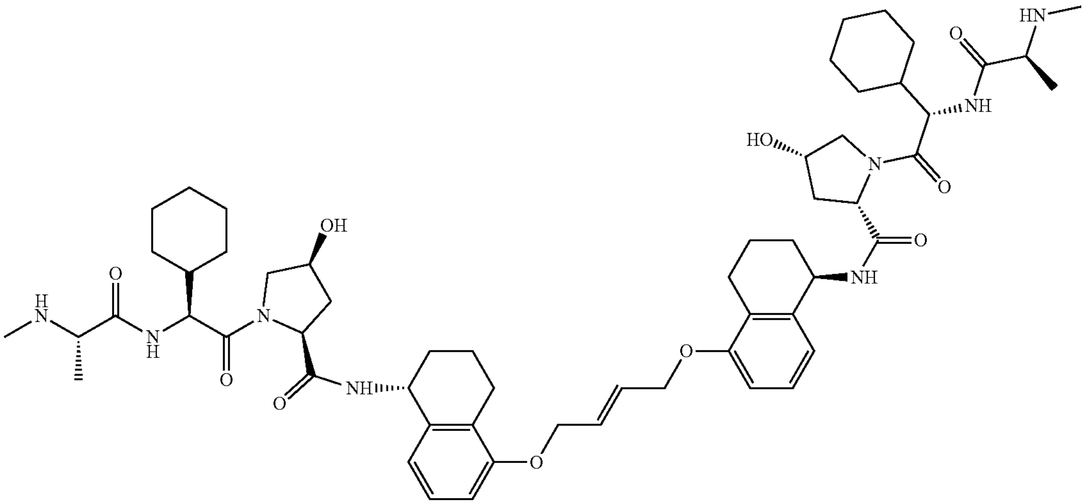

I-E (2S,4S)-1-[(2S)-2-cyclohexyl-2-[(2S)-2-(methylamino)propanamido]acetyl]-N-[(1R)-5-[[(2E)-4-[[(5R)-5-[(2S,4S)-1-[(2S)-2-cyclohexyl-2-[(2S)-2-(methylamino) propanamido]acetyl]-4-hydroxypyrrolidine-2-amido]-5,6,7,8-tetrahydronaphthalen-1-yl]oxy]but-2-en-1-yl]oxy]-1,2,3,4-tetrahydronaphthalen-1-yl]-4-hydroxypyrrolidine-2-carboxamide (Compound I-E)

LCMS (ESI, m/z): $[M+H]^+$=1053.6. $^1H$ NMR (300 MHz, DMSO-$d_6$): δ 8.28-8.17 (m, 2H), 8.01-7.86 (m, 2H), 7.15-7.02 (m, 2H), 6.96-6.88 (m, 2H), 6.87-6.79 (m, 2H), 6.10-6.03 (m, 2H), 5.52-5.42 (m, 2H), 4.98-4.85 (m, 2H), 4.65-4.55 (m, 4H), 4.45-4.28 (m, 4H), 4.27-4.18 (M, 2H), 3.93-3.85 (m, 2H), 3.53-3.43 (m, 2H), 3.07-2.96 (m, 2H), 2.67-2.57 (m, 4H), 2.36-2.25 (m, 2H), 2.18 (s, 6H), 1.93-1.53 (m, 24H), 1.22-0.95 (m, 16H).

I-F
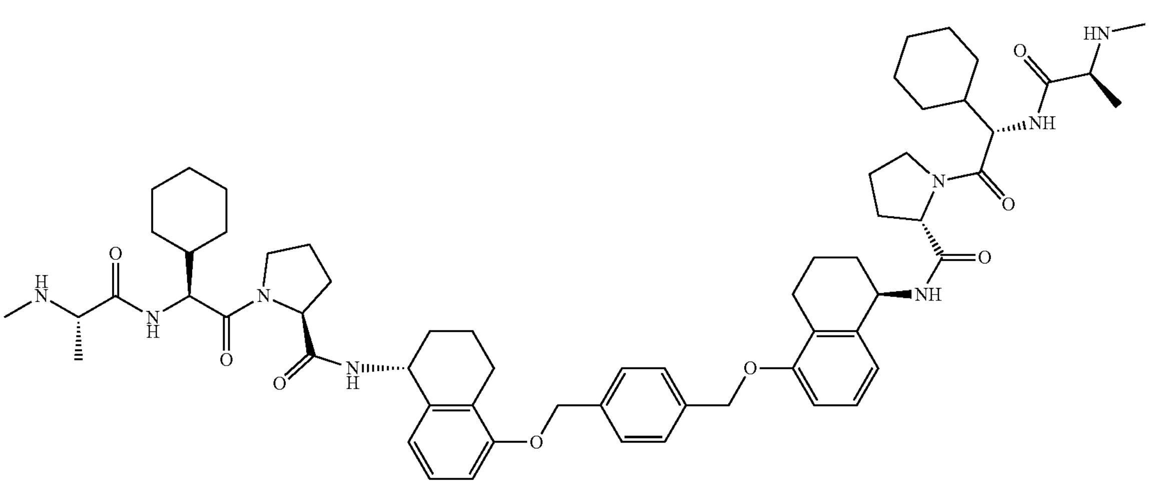
(2S)-1-[(2S)-2-cyclohexyl-2-[(2S)-2-(methylamino)propanamido]acetyl]-N-[(1R)-5-[[4-([[(5R)-5-[(2S)-1-[(2S)-2-cyclohexyl-2-[(2S)-2-(methylamino)propanamido]acetyl]pyrolidine-2-amido]-5,6,7,8-tetrahydronaphthalen-1-yl]oxy]methyl)phenyl]methoxy]-1,2,3,4-tetrahydronaphthalen-1-yl]pyrrolidine-2-carboxamide (Compound I-F)
LCMS (ESI, m/z): $[M+H]^+$=1071.7. $^1$H NMR (400 MHz, DMSO-$d_6$) δ 8.08 (d, J=8.8 Hz, 2H), 7.84 (d, J=8.8 Hz, 2H), 7.47 (s, 4H), 7.16-7.04 (m, 2H), 6.93-6.85 (m, 4H), 5.11 (s, 4H), 4.95-4.85 (m, 2H), 4.47-4.38 (m, 2H), 4.34-4.26 (m, 2H), 3.77-3.67 (m, 2H), 3.65-3.54 (m, 2H), 2.99-2.89 (m, 2H), 2.67-2.60 (m, 4H), 2.20-2.16 (m, 7H), 2.10-1.90 (m, 5H), 1.89-1.76 (m, 10H), 1.76-1.55 (m, 14H), 1.18-0.88 (m, 16H).
I-G
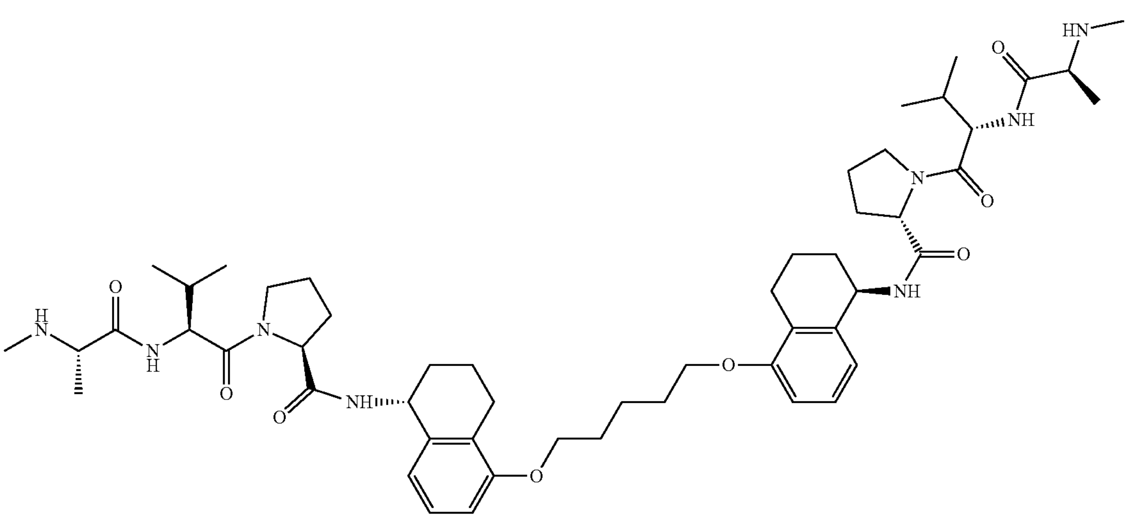

(2S)-1-[(2S)-3-methyl-2-[(2S)-2-(methylamino)propanamido]butanoyl]-N-[(1R)-5-[(5-[[(5R)-5-[(2S)-1-[(2S)-3-methyl-2-[(2S)-2-(methylamino)propanamido]butanoyl]pyrrolidine-2-amido]-5,6,7,8-tetrahydronaphthalen-1-yl]oxy]pentyl)oxy]-1,2,3,4-tetrahydronaphthalen-1-yl]pyrrolidine-2-carboxamide (Compound I-G)
LCMS (ESI, m/z): $[M+H]^+$=957.7. $^1$H NMR (300 MHz, DMSO-$d_6$): δ 8.20-8.09 (m, 2H), 8.02-7.78 (m, 2H), 7.17-7.00 (m, 2H), 6.93-6.74 (m, 4H), 4.98-4.81 (m, 2H), 4.51-4.40 (m, 2H), 4.38-4.27 (m, 2H), 4.04-3.95 (m, 4H), 3.74-3.60 (m, 6H), 3.10-2.98 (m, 2H), 2.67-2.55 (m, 4H), 2.18 (s, 6H), 2.10-1.59 (m, 24H), 1.19-1.08 (m, 6H), 0.99-0.78 (m, 12H).
Example 2: Synthesis of Compound II
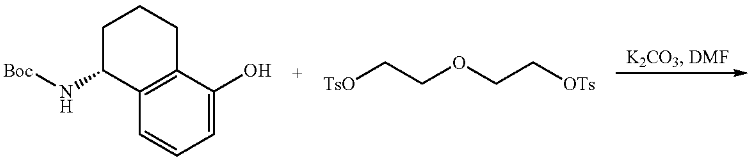
I-6
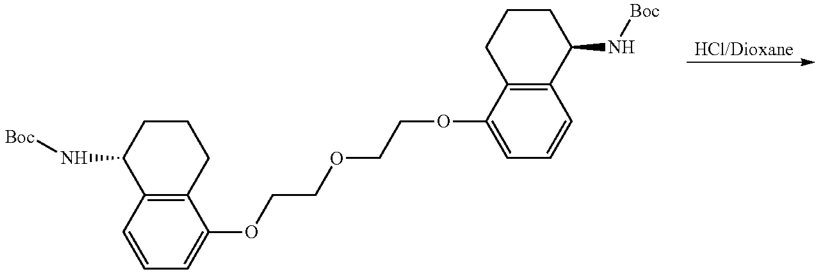
II-1
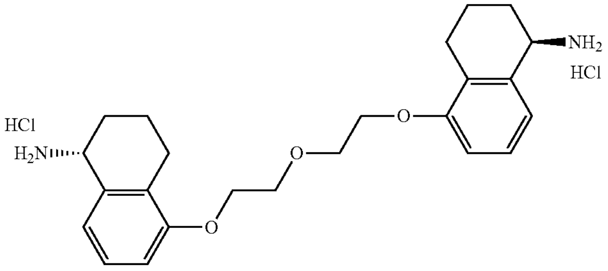
II-2
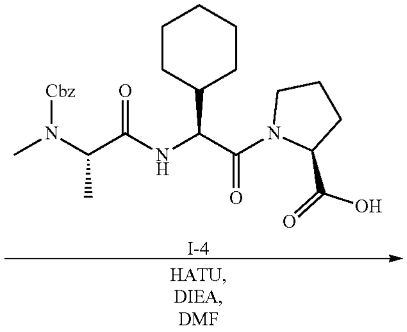
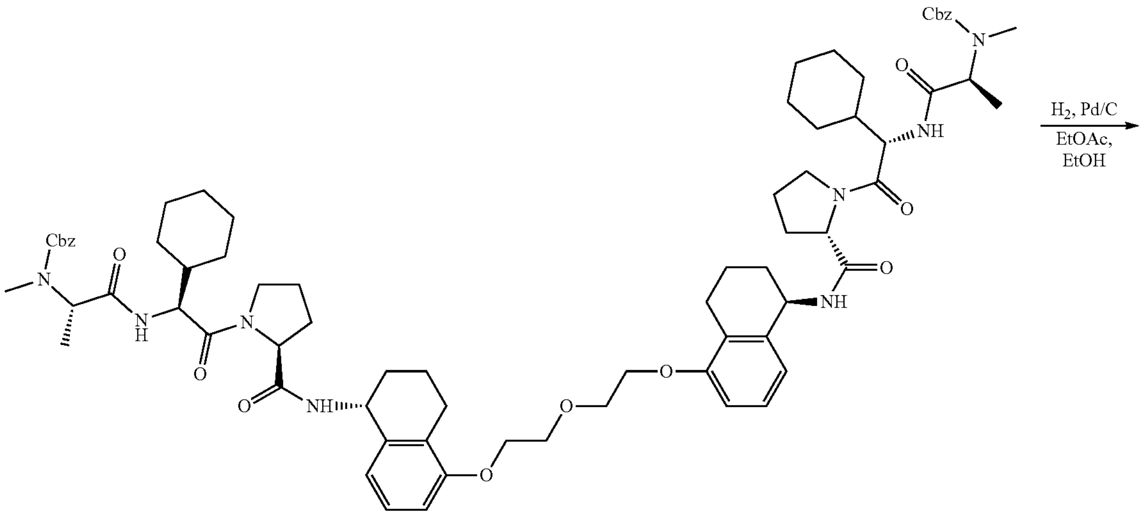
II-3

-continued

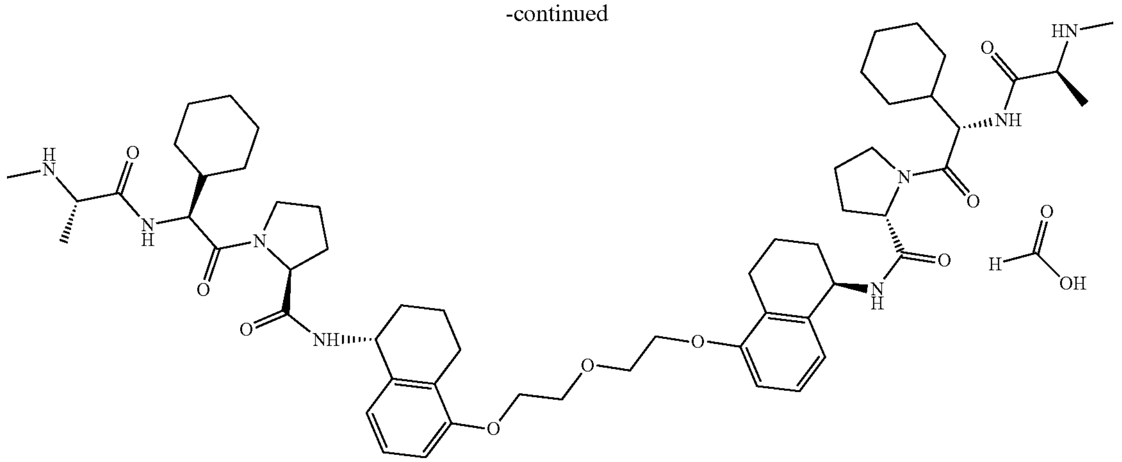

II tert-Butyl N-[(1R)-5-[2-(2-[[(5R)-5-[(tert-butoxycarbonyl)amino]-5,6,7,8-tetrahydro naphthalen-1-yl] oxy]ethoxy)ethoxy]-1,2,3,4-tetrahydronaphthalen-1-yl]carbamate (Compound II-1)

To a solution of Compound I-6 (500 mg 1.90 mmol) in DMF (15.0 mL) was added 2-[2-[(4-methylbenzenesulfonyl)oxy]ethoxy]ethyl-4-methylbenzene sulfonate (394 mg, 0.95 mmol) and $K_2CO_3$ (131 mg, 0.95 mmol). The resulting mixture was stirred at 65° C. for 48 h. The reaction was diluted with $H_2O$ and extracted with EtOAc. The combined organic layers were washed with brine, dried over anhydrous $Na_2SO_4$ and filtered. The filtrate was concentrated under vacuum. The residue was purified by flash column chromatography with petroleum ether/EtOAc (2/1, v/v) to afford the title compound (500 mg, 44%) as a white solid. LCMS (ESL, m/z): $[M+H]^+$=597.4.

(1R)-5-[2-(2-[[(5R)-5-Aino-5,6,7,8-tetrahydronaphthalen-1-yl]oxy]ethoxy)ethoxy]-1,2,3,4-tetrahydronaphthalen-1-amine Dihydrochloride (Compound II-2)

A mixture of Compound II-1 (450 mg, 0.75 mmol) in HCl/dioxane (20.0 mL, 4 mol/L) was stirred at room temperature for 2 h. After the reaction was completed, the resulting mixture was diluted with $H_2O$. The pH value of the mixture was adjusted to 7 with saturated $NaHCO_3$ (aq.). The mixture was extracted with EtOAc. The combined organic layers were washed with brine, dried over anhydrous $Na_2SO_4$ and filtered. The filtrate was concentrated under vacuum. The residue was purified by reverse phase flash column chromatography with 5-100% $CH_3CN$ in $H_2O$ to afford the title compound (130 mg, 44%) as a white solid. LCMS (ESI, m/z): $[M+H]^+$=397.2.

Benzyl N-[(1S)-1-[[(1S)-2-[(2S)-2-[[(1R)-5-[2-(2-[[(5R)-5-[(2S)-1-[(2S)-2-[(2S)-2-[[(benzyloxy)carbonyl](methyl)amino]propanamido]-2-cyclohexylacetyl]pyrrolidine-2-amido]-5,6,7,8-tetrahydronaphthalen-1-yl]oxy]ethoxy)ethoxy]-1,2,3,4-tetrahydronaphthalen-1-yl]carbamoyl]pyrrolidin-1-yl]-1-cyclohexyl-2-oxoethyl]carbamoyl]ethyl]-N-methylcarbamate (Compound II-3)

To a solution of Compound II-2 (100 mg, 0.25 mmol) in DMF (10 mL) was added Compound 1-4 (263 mg, 0.56 mmol) and DIEA (163 mg, 1.26 mmol). Then HATU (240 mg, 0.63 mmol) was added to the mixture at 0° C. The resulting mixture was stirred at 0° C. for 2 h. The reaction was diluted with $H_2O$ and extracted with EtOAc. The combined organic layers were washed with brine, dried over anhydrous $Na_2SO_4$ and filtered. The filtrate was concentrated under vacuum. The residue was purified by flash column chromatography with DCM/MeOH (10/1, v/v) to afford the title compound (250 mg, 76%) as a brown solid. LCMS (ESI, m/z): $[M+H]^+$=1307.7.

(2S)-1-[(2S)-2-Cyclohexyl-2-[(2S)-2-(methylamino)propanamido]acetyl]-N-[(1R)-5-[2-(2-[[(5R)-5-[(2S)-1-[(2S)-2-cyclohexyl-2-[(2S)-2-(methylamino)propanamido]acetyl]pyrrolidine-2-amido]-5,6,7,8-tetrahydronaphthalen-1-yl]oxy]ethoxy)ethoxy]-1,2,3,4-tetrahydronaphthalen-1-yl]pyrrolidine-2-carboxamide (Compound II)

To a solution of Compound II-3 (200 mg, 0.15 mmol) in EtOAc (8 mL) and EtOH (4 mL) was added Pd/C (68.0 mg, dry). The resulting mixture was stirred at room temperature for 16 h. After the reaction was completed, the reaction was filtered. The filtrate was concentrated under vacuum. The residue was purified by flash column chromatography with DCM/MeOH (10/1, v/v) and then purified by Prep-HPLC with the following conditions: Column: Xselect CSH OBD Column 30×150 mm, 5 um; Mobile Phase A: Water (0.1% Formic acid), Mobile Phase B: ACN; Flow rate: 60 mL/min; Gradient: 13% B to 34% B in 7 min; 254/220 nm; RT: 7.22 min to afford the title compound (19.1 mg, 12%) as a white solid. LCMS (ESI, m/z): $[M+H]^+$=1039.7. $^1H$ NMR (300 MHz, DMSO-$d_6$, ppm): δ 8.38-8.23 (m, 1H), 8.09 (d, J=8.7 Hz, 2H), 7.92 (d, J=9.0 Hz, 2H), 7.10-7.04 (m, 2H), 6.88-6.79 (m, 4H), 4.95-4.81 (m, 2H), 4.51-4.39 (m, 2H), 4.36-4.24 (m, 2H), 4.14-4.04 (m, 4H), 3.89-3.79 (m, 4H), 3.77-3.67 (m, 2H), 3.66-3.55 (m, 2H), 3.50-3.23 (m, 1H), 3.07-2.94 (m, 2H), 2.63-2.54 (m, 3H), 2.18 (s, 6H), 2.02-1.90 (m, 4H), 1.89-1.47 (m, 25H), 1.22-0.87 (m, 17H).

Following the procedure described above for Example 2 and substituting the appropriate reagents, starting materials and purification methods known to those skilled in the art, the compounds listed below were prepared.

II-A
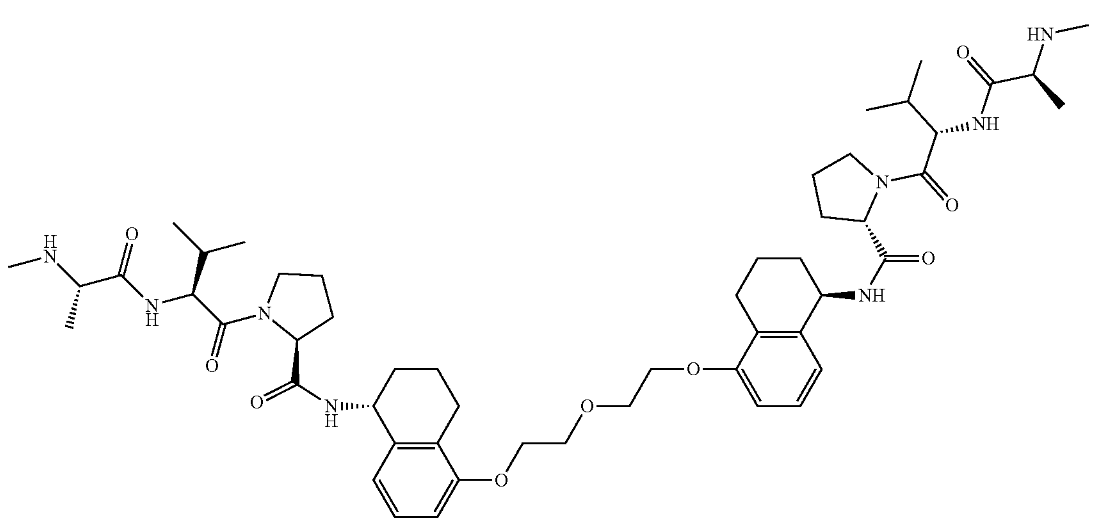
(2S)-1-[(2S)-3-Methyl-2-[(2S)-2-(methylamino)propanamido]butanoyl]-N-[(1R)-5-[2-(2-{[(5R)-5-[(2S)-1-[(2S)-3-methyl-2-[(2S)-2-(methylamino)propanamido]butanoyl]pyrrolidine-2-amido]-5,6,7,8-tetrahydronaphthalen-1-yl]oxy}ethoxy)ethoxy]-1,2,3,4-tetrahydronaphthalen-1-yl]pyrrolidine-2-carboxamide (Compound II-A)
LCMS (ESI, m/z): $[M+H]^+$=959.6. $^1$H NMR (300 MHz, DMSO-$d_6$, ppm): δ 8.38-8.13 (m, 2H), 7.91-7.87 (m, 2H), 7.13-7.04 (m, 2H), 6.89-6.79 (m, 4H), 4.95-4.80 (m, 2H), 4.45-4.28 (m, 4H), 4.12-4.07 (m, 4H), 3.87-3.80 (m, 4H), 3.69-3.51 (m, 4H), 2.97-2.92 (m, 2H), 2.58-2.50 (m, 4H), 2.16 (s, 6H), 2.02-1.57 (m, 20H), 1.17-1.04 (m, 6H), 0.97-0.75 (m, 12H).
II-B
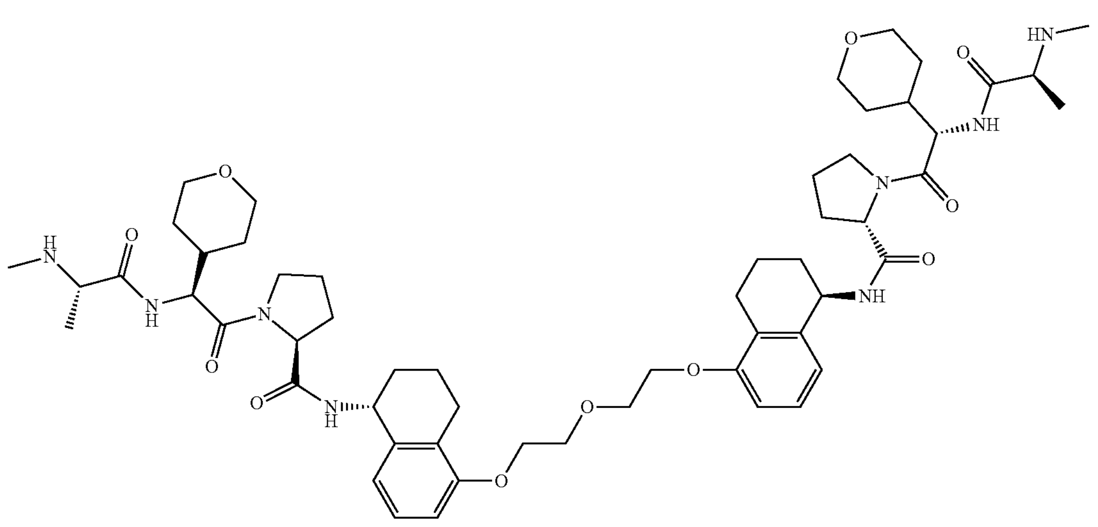

(2S)-1-[(2S)-2-[(2S)-2-(Methylamino)propanamido]-2-(oxan-4-yl)acetyl]-N-[(1R)-5-[2-(2-{[(5R)-5-[(2S)-1-[(2S)-2-[(2S)-2-(methylamino) propanamido]-2-(oxan-4-yl)acetyl]pyrrolidine-2-amido]-5,6,7,8-tetrahydronaphthalen-1-yl]oxy}ethoxy)ethoxy]-1,2,3,4-tetrahydronaphthalen-1-yl]pyrrolidine-2-carboxamide (Compound II-B)

LCMS (ESI, m/z): $[M+H]^+$=1043.5. $^1$H NMR (300 MHz, DMSO-$d_6$, ppm): δ 8.42-8.09 (m, 2H), 7.97-7.73 (m, 2H), 7.20-7.01 (m, 2H), 6.91-6.76 (m, 4H), 4.95-4.81 (m, 2H), 4.54-4.43 (m, 2H), 4.40-4.25 (m, 2H), 4.15-4.03 (m, 4H), 3.91-3.56 (m, 12H), 3.30-3.15 (m, 4H), 3.03-2.87 (m, 2H), 2.64-2.53 (m, 4H), 2.16 (s, 6H), 2.10-1.90 (m, 8H), 1.89-1.72 (m, 8H), 1.72-1.49 (m, 8H), 1.45-1.19 (m, 4H), 1.17-1.00 (m, 6H).

II-C

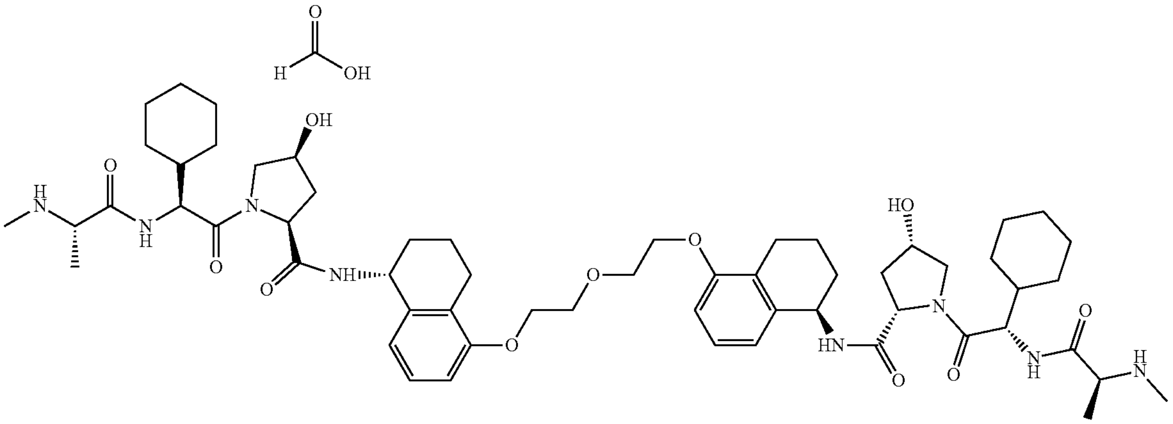

(2S,4S)-1-((S)-2-cyclohexyl-2-((S)-2-(methylamino) propanamido)acetyl)-N—((R)-5-(2-(2-(((R)-5-((2S, 4S)-1-((S)-2-cyclohexyl-2-((S)-2-(methylamino) propanamido)acetyl)-4-hydroxypyrrolidine-2-carboxamido)-5,6,7,8-tetrahydronaphthalen-1-yl) oxy)ethoxy) ethoxy)-1,2,3,4-tetrahydronaphthalen-1-yl)-4-hydroxypyrrolidine-2-carboxamide Formic Acid (Compound II-C)

LCMS (ESI, i/z): $[M+H]^+$=1071.7. $^1$H NMR (300 MHz, DMSO-$d_6$) δ 8.32-8.23 (m, 3H), 8.16-7.90 (m, 2H), 7.14-7.00 (m, 2H), 6.98-6.87 (m, 2H), 6.87-6.73 (m, 2H), 4.95-4.80 (m, 2H), 4.42-4.28 (m, 7H), 4.23-4.01 (m, 5H), 3.93-3.80 (m, 7H), 3.50-3.40 (m, 2H), 3.08-2.98 (m, 2H), 2.61-2.55 (m, 3H), 2.34-2.17 (m, 8H), 1.89-1.49 (m, 23H), 1.25-1.05 (m, 13H), 1.05-0.81 (m, 4H).

II-D

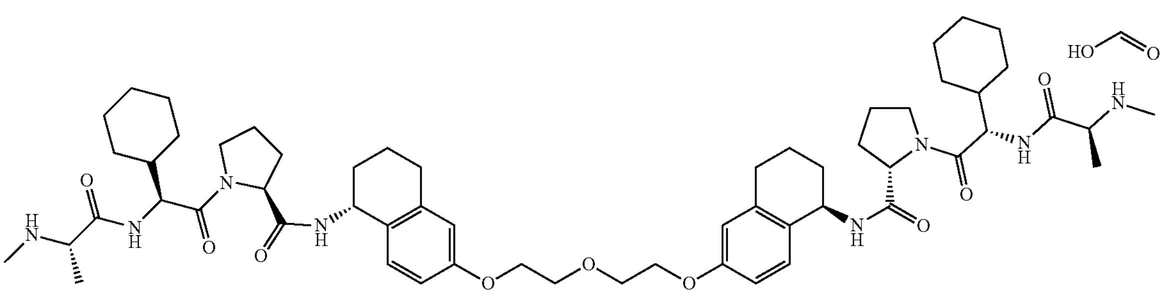

(2S)-1-[(2S)-2-cyclohexyl-2-[(2S)-2-(methylamino) propanamido]acetyl]-N-[(1R)-6-[2-(2-[[(5R)-5-[(2S)-1-1(2S)-2-cyclohexyl-2-[(2S)-2-(methylamino) propanamido]acetyl]pyrrolidine-2-amido]-5,6,7,8-tetrahydronaphthalen-2-yl]oxy]ethoxy)ethoxyl-1,2,3,4-tetrahydronaphthalen-1-yl]pyrrolidine-2-carboxamide Formic Acid (Compound II-D)

LCMS (ESI, m/z): $[M+H]^+$=1039.7. $^1H$ NMR (400 MHz, DMSO-$d_6$): δ 8.19 (s, 1H), 8.04 (d, J=8.4 Hz, 2H), 7.92 (d, 0.1=8.8 Hz, 2H), 7.14 (d, J=8.4 Hz, 2H), 6.70-6.64 (m, 4H), 4.90-4.80 (m, 2H), 4.50-4.40 (m, 2H), 4.39-4.21 (m, 2H), 4.08-4.03 (m, 4H), 3.79-3.68 (m, 6H), 3.65-3.55 (m, 2H), 3.10-2.95 (m, 2H), 2.73-2.62 (m, 4H), 2.19 (s, 6H), 2.10-1.93 (m, 4H), 1.90-1.55 (m, 26H), 1.27-1.09 (m, 11H), 1.08-0.88 (m, 5H).

II-E

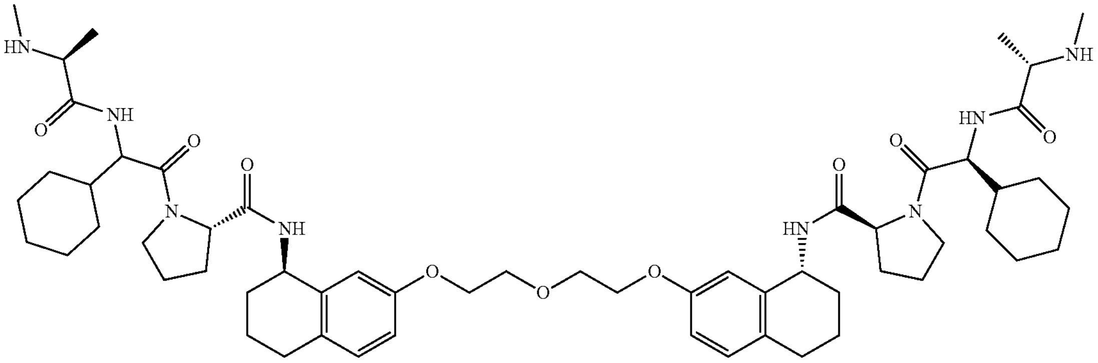

(2S)-1-[(2S)-2-cyclohexyl-2-[(2S)-2-(methylamino) propanamido]acetyl]-N-[(1R)-7-[2-(2-[[(8R)-8-[(2S)-1-[(2S)-2-cyclohexyl-2-[(2S)-2-(methylamino) propanamido]acetyl]pyrolidine-2-amido]-5,6,7,8-tetrahydronaphthalen-2-yl]oxy]ethoxy)ethoxy]-1,2,3,4-tetrahydronaphthalen-1-yl]pyrrolidine-2-carboxamide (Compound II-E)

LCMS (ESI, m/z): $[M+H]^+$=1039.7. $^1H$ NMR (300 MHz, DMSO-$d_6$) δ 8.27-8.18 (m, 2H), 7.87-7.69 (m, 2H), 7.00-6.93 (m, 2H), 6.87 (d, J=2.1 Hz, 2H), 6.77-6.67 (m, 2H), 4.97-4.85 (m, 2H), 4.54-4.38 (m, 2H), 4.33-4.16 (m, 4H), 4.08-3.96 (m, 2H), 3.87-3.70 (m, 6H), 3.67-3.55 (m, 2H), 3.01-2.89 (m, 2H), 2.74-2.61 (m, 4H), 2.17 (s, 6H), 2.13-1.94 (m, 4H), 1.92-1.51 (m, 25H), 1.32-0.80 (m, 17H).

II-F

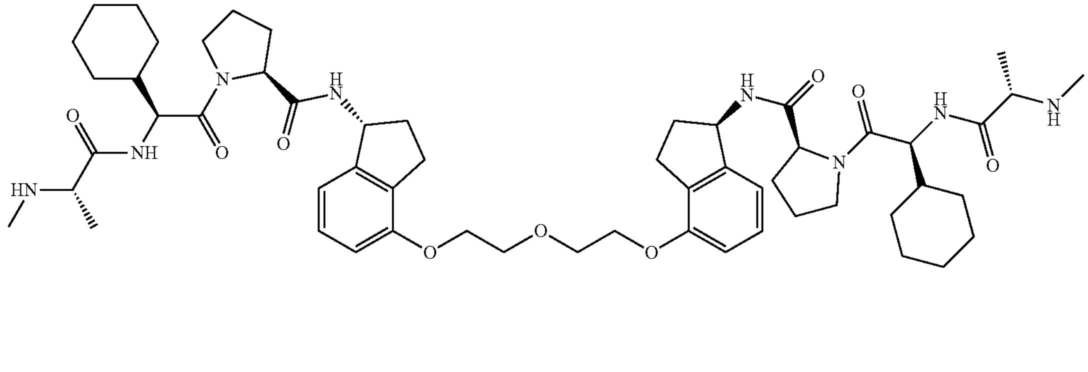

(2S)-1-[(2S)-2-cyclohexyl-2-[(2S)-2-(methylamino) propanamido]acetyl]-N-[(1R)-4-[2-(2-[[(1R)-1-[(2S)-1-[(2S)-2-cyclohexyl-2-[(2S)-2-(methylamino) propanamido]acetyl]pyrrolidine-2-amido]-2,3-dihydro-1H-inden-4-yl]oxy]ethoxy)ethoxy]-2,3-dihydro-1H-inden-1-yl]pyrrolidine-2-carboxamide (Compound II-F)
LCMS (ESI, m/z): $[M+H]^+=1011.7$. $^1H$ NMR (300 MHz, DMSO-$d_6$) δ 8.22-8.05 (m, 4H), 7.22-7.04 (m, 2H), 6.90-6.78 (m, 4H), 5.31-5.17 (m, 2H), 4.53-4.37 (m, 2H), 4.35-4.25 (m, 2H), 4.20-4.05 (m, 4H), 3.89-3.80 (m, 4H), 3.79-3.57 (m, 4H), 3.25-3.12 (m, 2H), 2.94-2.79 (m, 2H), 2.73-2.50 (m, 2H), 2.40-2.28 (m, 2H), 2.25 (s, 6H), 2.13-1.91 (m, 4H), 1.91-1.53 (m, 19H), 1.24-0.87 (m, 17H).
Example 3: Synthesis of Compound III
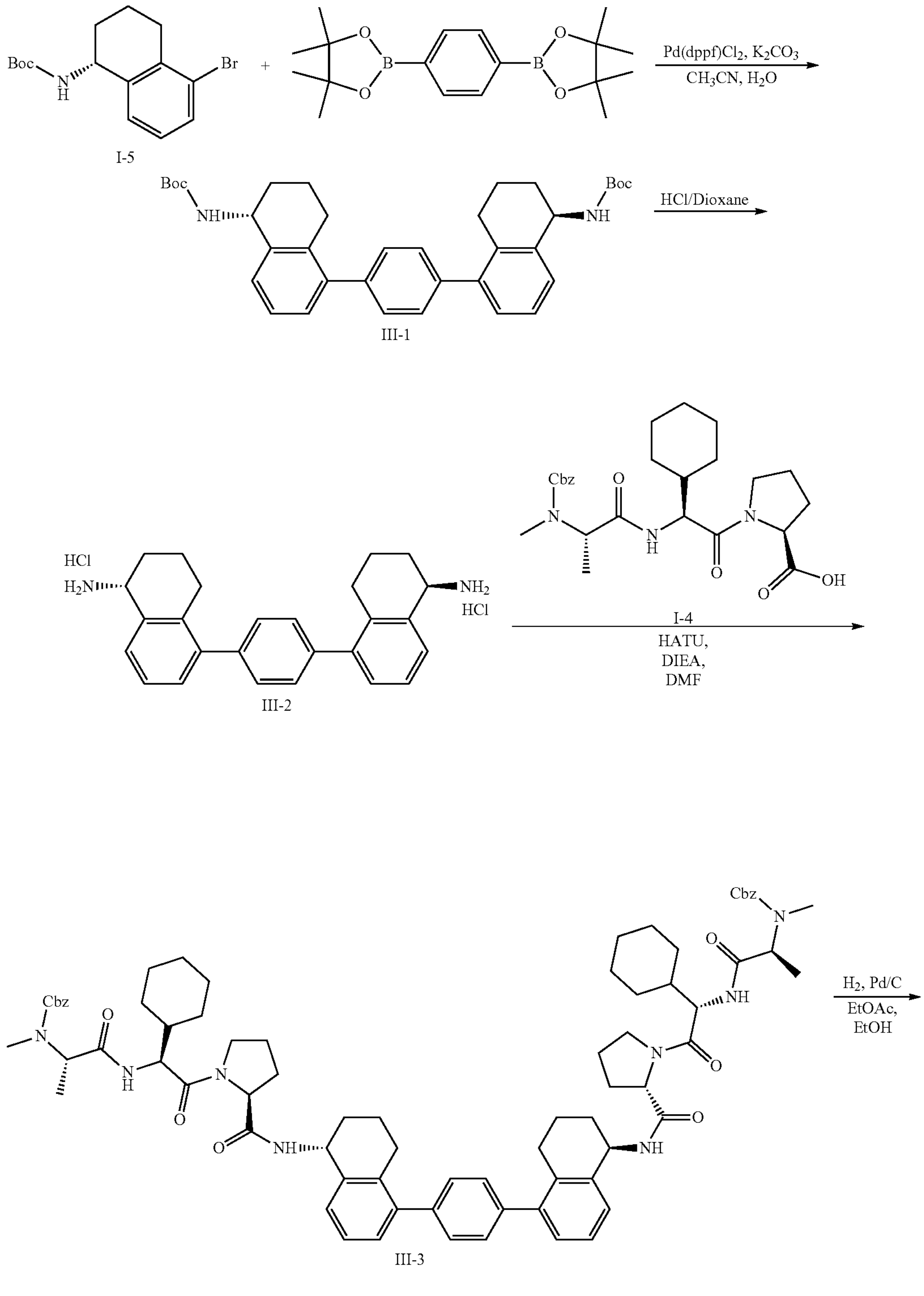

-continued

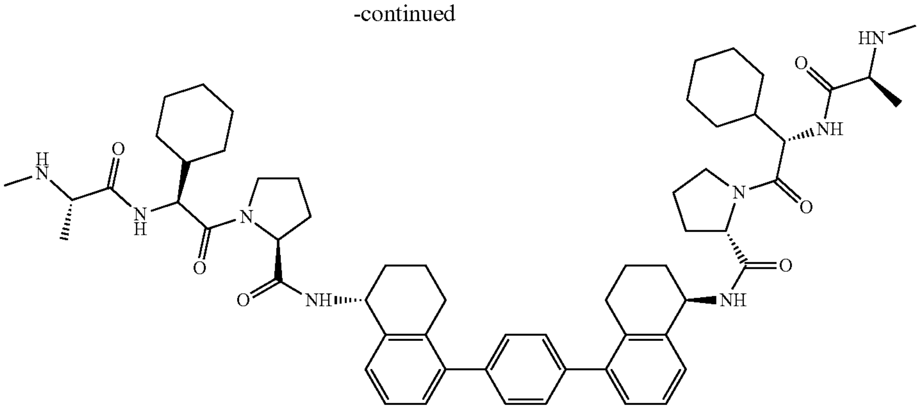

III tert-Butyl N-[(1R)-5-[4-[(5R)-5-[(tert-butoxycarbonyl)amino]-5,6,7,8-tetrahydro naphthalen-1-yl]phenyl]-1,2,3,4-tetrahydronaphthalen-1-yl]carbamate (Compound III-1)

To a solution of 4,4,5,5-tetramethyl-2-[4-(4,4,5,5-tetramethyl-1,3,2-dioxaborolan-2-yl)phenyl]-1,3,2-dioxaborolane (500 mg 1.52 mmol) in $CH_3CN$ (5 mL) and $H_2O$ (0.5 mL) was added Compound I-5 (988.5 mg 3.03 mmol), Pd(dppf) $Cl_2$ (111 mg 0.15 mmol) and $K_2CO_3$ (168 mg, 1.21 mmol). The mixture was stirred at 80° C. for 3 h under $N_2$. The resulting mixture was diluted with $H_2O$ and extracted with ethyl acetate. The combined organic layers were washed with brine, dried over anhydrous sodium sulfate and filtered. The filtrate was concentrated under vacuum. The residue was purified by flash column chromatography with ethyl acetate/petroleum ether (1/2, v/v) to afford the title compound (300 mg 35%) as a yellow solid. LCMS (ESI, m/z): $[M+H]^+$=569.3.

(1R,1'R)-5,5'-(1,4-Phenylene)bis(1,2,3,4-tetrahydronaphthalen-1-amine) Dihydrochloride (Compound III-2)

A mixture of Compound III-1 (200 mg 0.35 mmol) in HCl/dioxane (10.0 mL, 4 mol/L) was stirred at room temperature for 3 h. After the reaction was completed, the reaction mixture was concentrated under vacuum to afford the tide compound (150 mg, crude) as a white solid. LCMS (ESI, m/z): $[M+H]^+$=369.2

Benzyl N-[(1S)-1-{[(1S)-2-[(2S)-2-{1[(1R)-5-{4-[(5R)-5-[(2S)-1-[(2S)-2-[(2S)-2-{[(benzyloxy)carbonyl](methyl)amino}propanamido]-2-cyclohexylacetyl]pyrrolidine-2-amido]-5,6,7,8-tetrahydronaphthalen-1-yl]phenyl}-1,2,3,4-tetrahydronaphthalen-1-yl]carbamoyl}pyrrolidin-1-yl]-1-cyclohexyl-2-oxoethyl]carbamoyl}ethyl]-N-methylcarbamate (Compound III-3)

To a solution of Compound III-2 (150 mg 0.40 mmol) in DMF (5 mL) was added Compound I-4 (386 mg 0.81 mmol), DIEA (263 mg 2.04 mmol). Then HATU (310 mg 0.81 mmol) was added to the mixture at 0° C. under $N_2$. The resulting mixture was stirred at 0° C. for 3 h. After the reaction was completed, the mixture was diluted with $H_2O$ and extracted with ethyl acetate. The combined organic layers were washed with brine, dried over anhydrous sodium sulfate and filtered. The filtrate was concentrated under vacuum. The residue was purified by flash column chromatography twice with DCM/MeOH (10/1, v/v) to afford the title compound (220 mg 47%) as a yellow oil. LCMS (ESI, m/z): $[M+H]^+$=1279.7.

(2S)-1-[(2S)-2-Cyclohexyl-2-[(2S)-2-(methylamino) propanamido]acetyl]-N-[(1R)-5-[4-[(5R)-5-[(2S)-1-[(2S)-2-cyclohexyl-2-[(2S)-2-(methylamino)propanamido]acetyl]pyrrolidine-2-amido]-5,6,7,8-tetrahydronaphthalen-1-yl]phenyl]-1,2,3,4-tetrahydronaphthalen-1-yl]pyrrolidine-2-carboxamide (Compound III)

To a solution of Compound III-3 (200 mg, 0.16 mmol) in EtOH (5 mL) and EtOAc (10 mL) was added Pd/C (40.0 mg, dry). The mixture was stirred at room temperature for 16 h under $H_2$. After the reaction was completed, the mixture was filtered. The filtrate was evaporated in vacuo. The residue was purified by Prep-HPLC with the following conditions: Column: XBridge Prep OBD C18 Colum, 30×150 mm, 5 um; Mobile Phase A: Water (10 mmol/L $NH_4HCO_3$), Mobile Phase B ACN; Flow rate: 60 mL/min; Gradient: 39% B to 69% B in 7 min; 254 nm; RT: 6.08 min to afford the title compound (53.9 mg, 34%) as a white solid. LCMS (ESI, m/z): $[M+H]^+$=1011.7. $^1H$ NMR (300 MHz, DMSO-$d_6$, ppm): δ 8.27-8.19 (m, 2H), 7.92-7.88 (m, 2H), 7.34-7.29 (m, 6H), 7.25-7.19 (m, 2H), 7.13-7.09 (nm, 2H), 5.25-4.79 (m, 2H), 4.59-4.31 (m, 4H), 3.82-3.68 (m, 4H), 3.05-3.89 (m, 2H), 2.71-2.58 (m, 4H), 2.30-2.18 (m, 7H), 2.17-1.94 (m, 4H), 1.93-1.60 (m, 25H), 1.39-0.92 (m, 16H).

Following the procedure described above for Example 3 and substituting the appropriate reagents, starting materials and purification methods known to those skilled in the art, the compounds listed below were prepared.

III-A

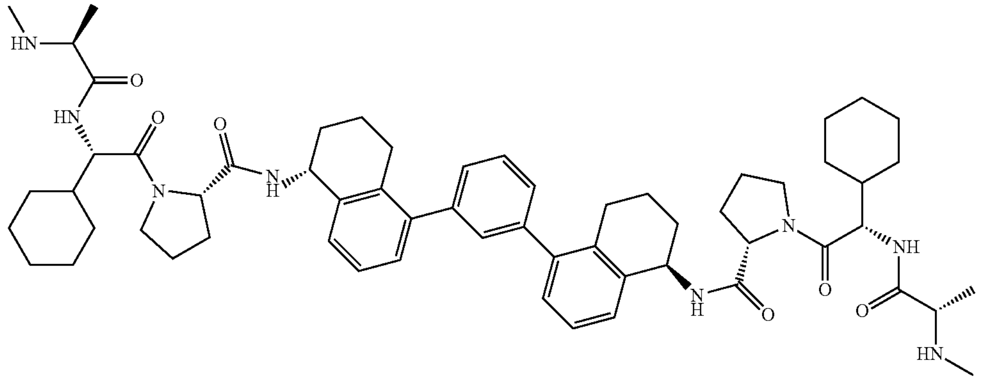

(2S)-1-[(2S)-2-Cyclohexyl-2-[(2S)-2-(methylamino) propanamido]acetyl]-N-[(1R)-5-(3-[(5R)-5-[(2S)-1-[(2S)-2-cyclohexyl-2-[(2S)-2-(methylamino)propanamido]acetyl]pyrolidine-2-amido]-5,6,7,8-tetrahydronaphthalen-1-yl]phenyl)-1,2,3,4-tetrahydronaphthalen-1-yl]pyrrolidine-2-carboxamide (Compound III-A)

LCMS (ESI, m/z): $[M+H]^+=1011.7$. $^1H$ NMR (300 MHz, DMSO-$d_6$, ppm): δ 8.55-8.12 (m, 2H), 7.93-7.72 (m, 2H), 7.64-7.46 (m, 1H), 7.37-7.08 (m, 9H), 5.10-4.93 (m, 2H), 4.54-4.39 (m, 2H), 4.38-4.28 (m, 2H), 3.81-3.55 (m, 4H), 3.03-2.89 (m, 2H), 2.70-2.55 (m, 4H), 2.17 (s, 6H), 2.11-1.93 (m, 6H), 1.92-1.52 ((m, 24H), 1.28-0.88 (m, 16H).

III-B

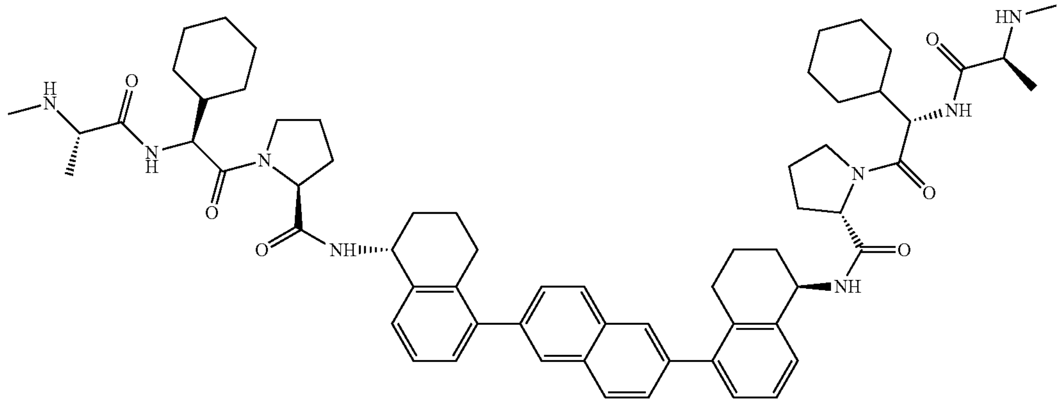

(2S)-1-[(2S)-2-Cyclohexyl-2-[(2S)-2-(methylamino) propanamido]acetyl]-N-[(1R)-5-{6-[(5R)-5-[(2S)-1-[(2S)-2-cyclohexyl-2-[(2S)-2-(methylamino)propanamido]acetyl]pyrrolidine-2-amido]-5,6,7,8-tetrahydronaphthalen-1-yl]naphthalen-2-yl}-1,2,3,4-tetrahydronaphthalen-1-yl]pyrrolidine-2-carboxamide (Compound III-B)

LCMS (ESI, m/z): $[M+H]^+=1062.6$; $^1H$ NMR (300 MHz, DMSO-$d_6$, ppm): δ 8.52-8.22 ((m, 2H), 8.00 (d, J=8.4 Hz, 2H), 7.90-7.84 (m, 4H), 7.52-7.42 (m, 2H), 7.39-7.29 (m, 2H), 7.29-7.21 (m, 2H), 7.20-7.12 (m, 2H), 5.08-4.95 (m, 2H), 4.54-4.28 (m, 4H), 3.81-3.55 (m, 4H), 3.01-2.88 (m, 2H), 2.71-2.55 (m, 4H), 2.18 (s, 6H), 2.12-1.93 (m, 6H), 1.92-1.55 (m, 24H), 1.26-0.84 (m, 16H).

III-C

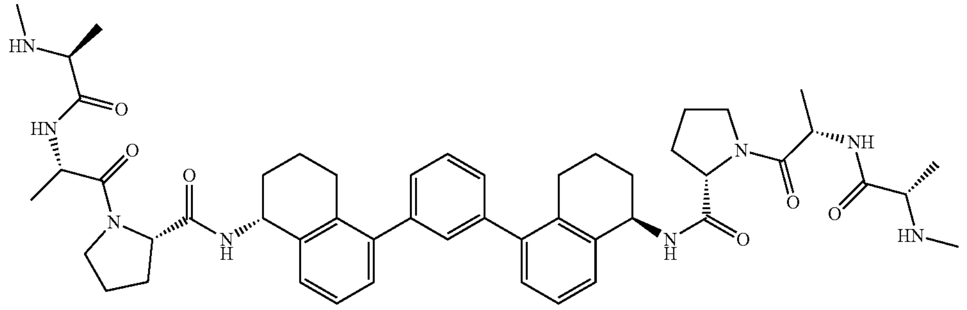

(2S)-1-[(2S)-2-[(2S)-2-(methylamino)propanamido]propanoyl]-N-[(1R)-5-[3-[(5R)-5-[(2S)-1-[(2S)-2-[(2S)-2-(methylamino)propanamido]propanoyl]pyrrolidine-2-amido]-5,6,7,8-tetrahydronaphthalen-1-yl]phenyl]-1,2,3,4-tetrahydronaphthalen-1-yl]pyrrolidine-2-carboxamide (Compound III-C)

LCMS (ESI, m/z): $[M+H]^+$=875.5. $^1H$ NMR (300 MHz, DMSO-$d_6$) δ 8.66-8.17 (m, 2H), 8.07-7.92 (m, 2H), 7.55-7.46 (m, 1H), 7.37-7.20 (m, 6H), 7.18-7.08 (m, 3H), 5.07-4.94 (m, 2H), 4.65-4.52 (m, 2H), 4.39-4.27 ((m, 2H), 3.72-3.50 (m, 4H), 3.00-2.87 (m, 2H), 2.70-2.55 (m, 4H), 2.19 (s, 6H), 2.13-1.57 (m, 18H), 1.27-1.17 (m, 6H), 1.14-1.05 (m, 6H).

III-D

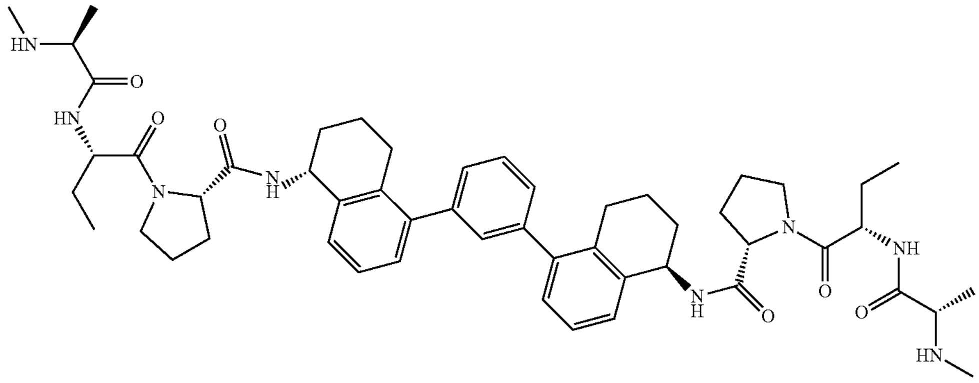

(2S)-1-[(2S)-2-[(2S)-2-(methylamino)propanamido]butanoyl]-N-[(1R)-5-[3-[(5R)-5-[(2S)-1-[(2S)-2-[(2S)-2-(methylamino)propanamido]butanoyl]pyrrolidine-2-amido]-5,6,7,8-tetrahydronaphthalen-1-yl]phenyl]-1,2,3,4-tetrahydronaphthalen-1-yl]pyrrolidine-2-carboxamide (Compound III-D)

LCMS (ESI, m/z): $[M+H]^+$=903.6. $^1H$ NMR (300 MHz, DMSO-$d_6$) δ 8.62-8.24 (m, 2H), 7.98-7.85 (m, 2H), 7.53-7.45 (m, 1H), 7.30-7.21 (m, 6H), 7.16-7.11 (m, 3H), 5.05-4.95 (m, 2H), 4.54-4.30 (m, 4H), 3.70-3.53 (m, 4H), 2.99-2.90 (m, 2H), 2.61-2.55 (m, 4H), 2.22-2.18 (m, 6H), 2.13-1.53 (m, 22H), 1.15-1.09 (m, 6H), 0.92-0.80 (m, 6H).

III-E

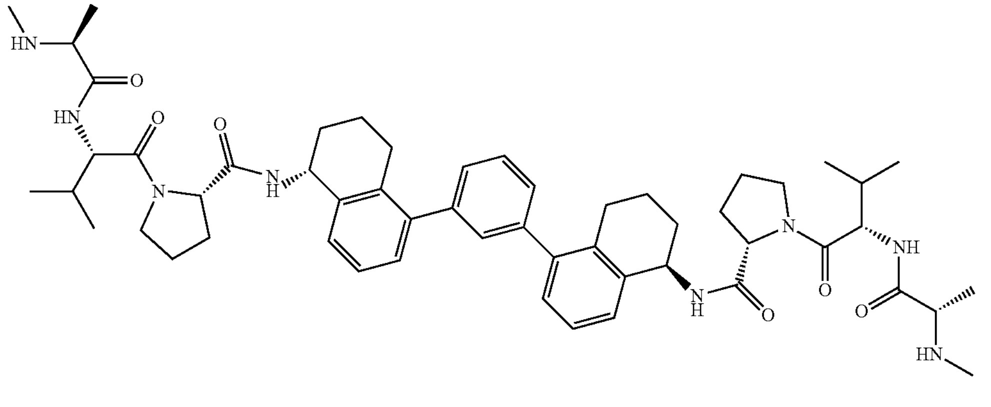

(2S)-1-[(2S)-3-methyl-2-[(2S)-2-(methylamino)propanamido]butanoyl]-N-[(1R)-5-[3-[(5R)-5-[(2S)-1-[(2S)-3-methyl-2-[(2S)-2-(methylamino)propanamido]butanoyl]pyrrolidine-2-amido]-5,6,7,8-tetrahydronaphthalen-1-yl]phenyl]-1,2,3,4-tetrahydronaphthalen-1-yl]pyrrolidine-2-carboxamide (Compound III-E)

LCMS (ESI, m/z): $[M+H]^+$=931.7. $^1H$ NMR (300 MHz, DMSO-$d_6$) δ 8.28 (d, J=8.7 Hz, 2H), 7.94 (d, J=9.0 Hz, 2H), 7.57-7.47 (m, 1H), 7.34-7.10 (m, 9H), 5.05-4.95 (m, 2H), 4.47-4.39 (m, 2H), 4.37-4.28 (m, 2H), 3.82-3.48 (m, 4H), 3.07-2.95 (m, 2H), 2.71-2.57 (m, 4H), 2.24-2.20 (m, 6H), 2.13-1.97 ((m, 6H), 1.97-1.53 (m, 14H), 1.18-1.11 (m, 6H), 0.97-0.87 (m, 12H).

III-F

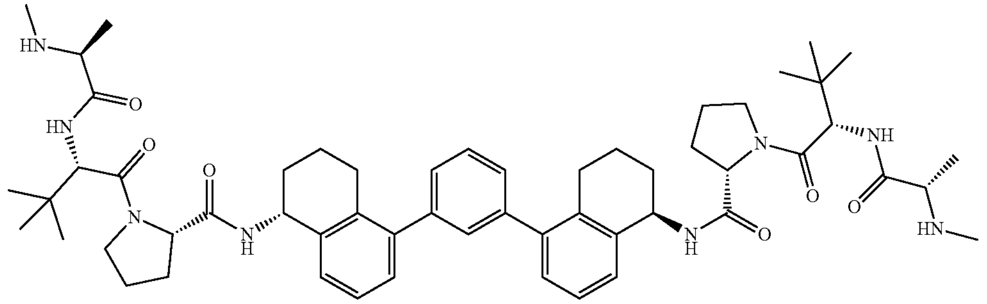

(2S)-1-[(2S)-3,3-dimethyl-2-[(2S)-2-(methylamino)propanamido]butanoyl]-N-[(1R)-5-[3-[(5R)-5-[(2S)-1-[(2S)-3,3-dimethyl-2-[(2S)-2-(methylamino)propanamido]butanoyl]pyrrolidine-2-amido]-5,6,7,8-tetrahydronaphthalen-1-yl]phenyl]-1,2,3,4-tetrahydronaphthalen-1-yl]pyrrolidine-2-carboxamide (Compound III-F)

LCMS (ESI, m/z): $[M+H]^+$=959.6. $^1H$ NMR (300 MHz, DMSO-$d_6$) δ 8.50-8.33 (m, 2H), 7.86 (d, J=9.6 Hz, 2H), 7.58-7.48 (m, 1H), 7.43-7.33 (m, 2H), 7.32-7.24 (m, 2H), 7.24-7.08 (m, 5H), 5.08-4.95 (m, 2H), 4.61-4.48 (m, 2H), 4.42-4.29 (m, 2H), 3.81-3.59 (m, 4H), 3.05-2.90 (m, 2H), 2.68-2.57 (m, 4H), 2.26-2.13 (m, 8H), 2.13-1.98 (m, 4H), 1.92-1.62 (m, 12H), 1.20-1.10 (m, 6H), 1.05 (s, 16H), 0.92 (s, 2H).

III-G

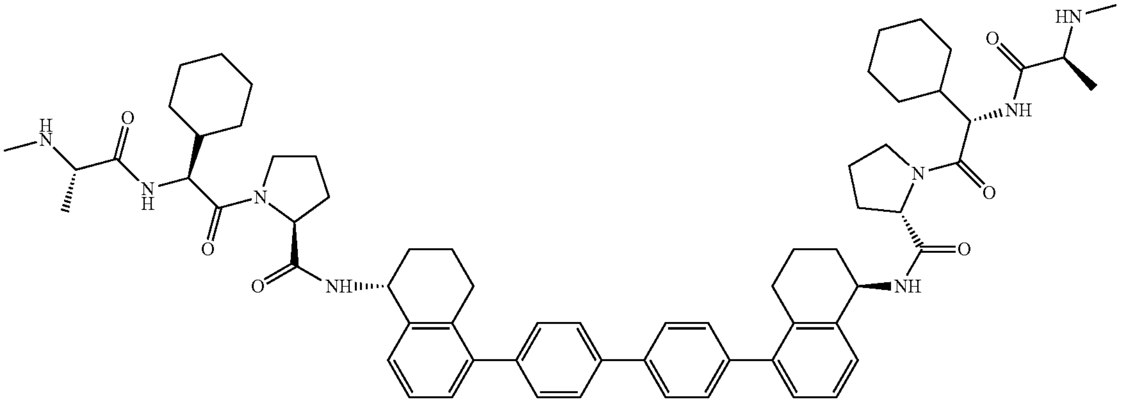

(S)-1-((S)-2-cyclohexyl-2-((S)-2-(methylamino)propanamido)acetyl)-N—((R)-5-(4'-((R)-5-((S)-1-((S)-2-cyclohexyl-2-((S)-2-(methylamino)propanamido)acetyl)pyrrolidine-2-carboxamido)-5,6,7,8-tetrahydronaphthalen-1-yl)-[1,1'-biphenyl]-4-yl)-1,2,3,4-tetrahydronaphthalen-1-yl)pyrrolidine-2-carboxamide (Compound III-G)

LCMS (ESL, m/z): $[M+H]^+$=1088.3. $^1$H NMR (300 MHz, DMSO-$d_6$) δ 8.26 (d, J=8.7 Hz, 2H), 7.89 (d, J=9.0 Hz, 2H), 7.78 (d, J=8.1 Hz, 4H), 7.40 (d, J=8.1 Hz, 4H), 7.33 (d, J=7.5 Hz, 2H), 7.26-7.21 (m, 2H), 7.12 (d, J=6.3 Hz, 2H), 5.10-4.95 (m, 2H), 4.51-4.39 (m, 2H), 4.39-4.29 (m, 2H), 3.81-3.70 (m, 2H), 3.70-3.56 (m, 2H), 2.99-2.90 (m, 2H), 2.71-2.55 (m, 4H), 2.18 (s, 6H), 2.10-1.93 (m, 4H), 1.92-1.54 (m, 25H), 1.28-0.87 (m, 17H).

III-H

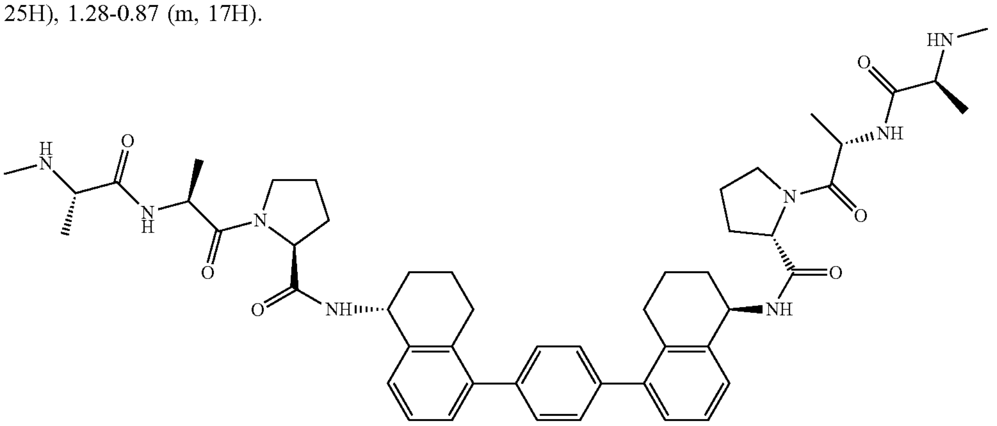

(2S)-1-[(2S)-2-[(2S)-2-(methylamino)propanamido]propanoyl]-N-[(1R)-5-[4-[(5R)-5-[(2S)-1-[(2S)-2-[(2S)-2-(methylamino)propanamido]propanoyl]pyrrolidine-2-amido]-5,6,7,8-tetrahydronaphthalen-1-yl]phenyl]-1,2,3,4-tetrahydronaphthalen-1-yl]pyrrolidine-2-carboxamide (Compound III-H)

LCMS (ESL, m/z): $[M+H]^+$=875.7. $^1$H NMR (300 MHz, DMSO-$d_6$): δ 8.32-8.16 (m, 2H), 8.09-7.91 (m, 2H), 7.41-7.21 (m, 8H), 7.19-7.05 (m, 2H), 5.09-4.96 (m, 2H), 4.67-4.52 (m, 2H), 4.49-4.29 (m, 2H), 3.73-3.56 (m, 4H), 3.04-2.89 (m, 2H), 2.76-2.57 (m, 4H), 2.27-2.18 (m, 6H), 2.15-1.57 (m, 16H), 1.32-1.19 (m, 6H), 1.18-1.06 (m, 6H).

III-I

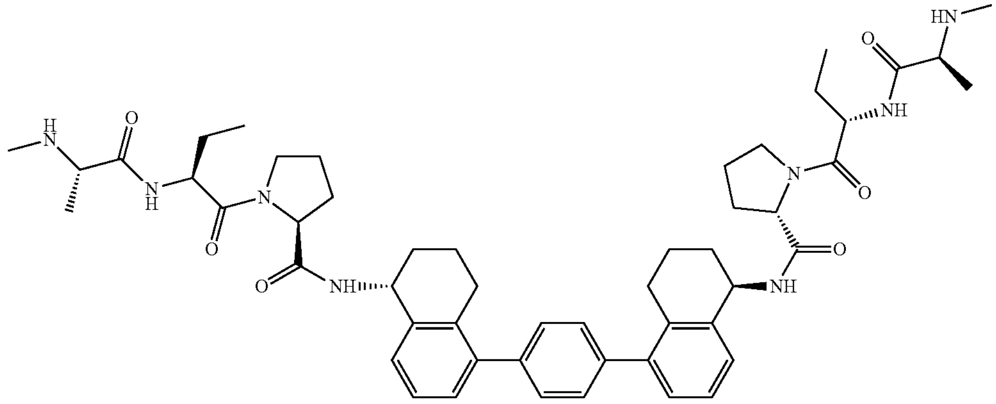

(2S)-1-[(2S)-2-[(2S)-2-(methylamino)propanamido]butanoyl]l-N-[(1R)-5-[4-[(5R)-5-[(2S)-1-[(2S)-2-[(2S)-2-(methylamino)propanamido]butanoyl]pyrrolidine-2-amido]-5,6,7,8-tetrahydronaphthalen-1-yl]phenyl]-1,2,3,4-tetrahydronaphthalen-1-yl]pyrrolidine-2-carboxamide (Compound III-I)

LCMS (ESL, m/z): $[M+H]^+$=903.8. $^1H$ NMR (300 MHz DMSO-$d_6$): δ 8.64-8.20 (m, 2H), 8.03-7.84 (m, 2H), 7.41-7.33 (m, 4H), 7.33-7.21 (m, 4H), 7.16-7.08 (m, 2H), 5.12-4.93 (m, 2H), 4.60-4.28 (m, 4H), 3.81-3.39 (m, 4H), 3.01-2.91 (m, 21H), 2.71-2.55 (m, 4H), 2.31-2.15 (m, 8H), 2.11-1.52 (m, 20H), 1.19-1.05 (m, 6H), 0.97-0.80 (m, 6H).

III-J

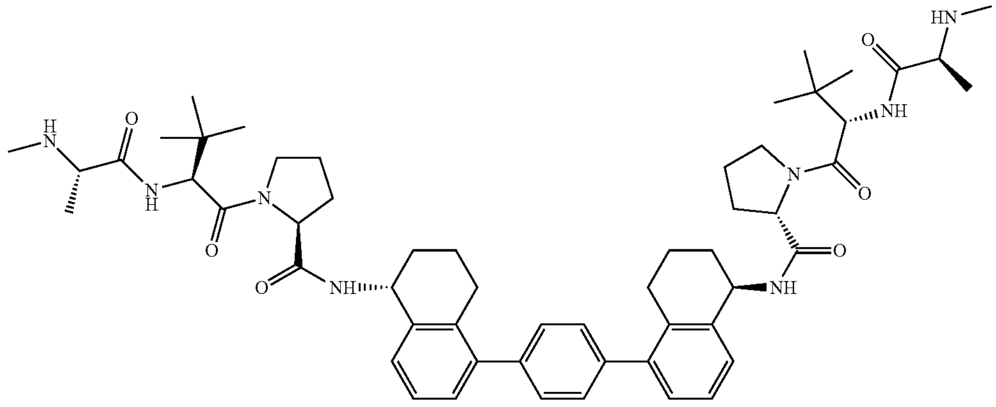

(2S)-1-[(2S)-3,3-dimethyl-2-[(2S)-2-(methylamino)propanamido]butanoyl]-N-[(1R)-5-[4-[(5R)-5-[(2S)-1-[(2S)-3,3-dimethyl-2-[(2S)-2-(methylamino)propanamido]butanoyl]pyrrolidine-2-amido]-5,6,7,8-tetrahydronaphthalen-1-yl]phenyl]-1,2,3,4-tetrahydronaphthalen-1-yl]pyrrolidine-2-carboxamide (Compound III-J)

$^1H$ NMR (300 MHz, DMSO-$d_6$): δ 8.50-8.35 (m, 2H), 7.93-7.83 (m, 2H), 7.43-7.35 (m, 6H), 7.24-7.10 (m, 4H), 5.12-4.91 (m, 2H), 4.66-4.51 (m, 2H), 4.45-4.29 (m, 2H), 3.81-3.59 (m, 4H), 3.06-2.90 (m, 2H), 2.77-2.58 (m, 4H), 2.26-2.00 (m, 12H), 1.94-1.65 (m, 12H), 1.19-1.09 (m, 6H), 1.08-0.90 (m, 18H).

III-K

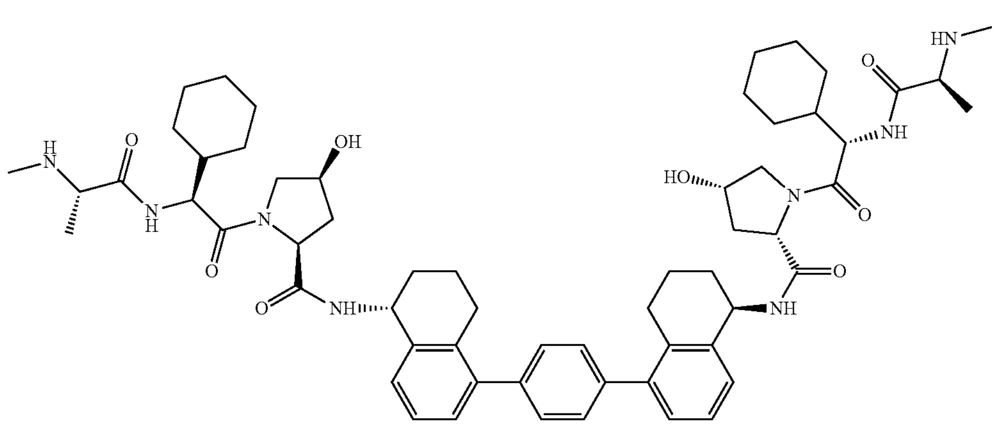

(2S,4S)-1-[(2S)-2-cyclohexyl-2-[(2S)-2-(methylamino)propanamido]acetyl]-N-[(1R)-5-[4-[(5R)-5-[(2S,4S)-1-[(2S)-2-cyclohexyl-2-[(2S)-2-(methylamino)propanamido]acetyl]-4-hydroxypyrrolidine-2-amido]-5,6,7,8-tetrahydronaphthalen-1-yl]phenyl]-1,2,3,4-tetrahydronaphthalen-1-yl]-4-hydroxypyrrolidine-2-carboxamide (Compound III-K)

LCMS (ESI, m/z): $[M+H]^+$=1043.9. $^1$H NMR (300 MHz, DMSO-$d_6$): δ 8.35-8.30 (m, 2H), 8.04-7.94 (m, 2H), 7.44-7.28 (m, 6H), 7.28-7.19 (m, 2H), 7.17-7.07 (m, 2H), 5.58-5.39 (m, 2H), 5.13-4.97 (m, 2H), 4.48-4.31 (m, 4H), 4.31-4.18 (m, 2H), 3.99-3.86 (m, 2H), 3.56-3.45 (m, 2H), 3.10-2.98 (m, 2H), 2.70-2.59 (m, 4H), 2.39-2.20 (m, 8H), 2.08-1.40 (m, 24H), 1.24-0.93 (m, 16H).

III-L

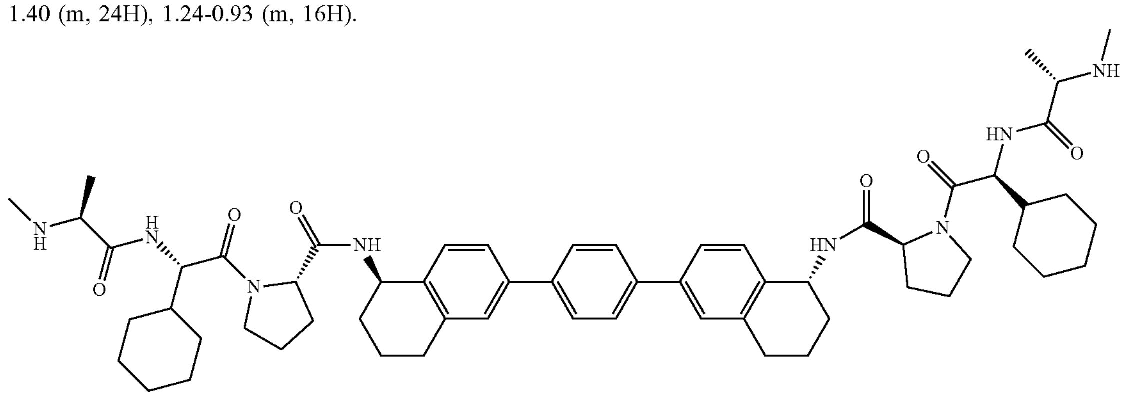

(2S)-1-[(2S)-2-cyclohexyl-2-[(2S)-2-(methylamino)propanamido]acetyl]-N-[(1R)-6-[4-[(5R)-5-[(2S)-1-[(2S)-2-cyclohexyl-2-[(2S)-2-(methylamino)propanamido]acetyl]pyrolidine-2-amido]-5,6,7,8-tetrahydronaphthalen-2-yl]phenyl]-1,2,3,4-tetrahydronaphthalen-1-yl]pyrrolidine-2-carboxamide (Compound III-L)

LCMS (ESI, m/z): $[M+H]^+$=1011.8. $^1$H NMR (300 MHz, DMSO-$d_6$) δ 8.50-8.15 (m, 2H), 7.93-7.84 (m, 2H), 7.80-7.69 (m, 4H), 7.54-7.41 (m, 4H), 7.40-7.29 (m, 2H), 5.02-4.91 (m, 2H), 4.52-4.40 (m, 2H), 4.40-4.28 (m, 2H), 3.81-3.70 (m, 2H), 3.70-3.56 (m, 2H), 3.02-2.90 (m, 2H), 2.86-2.79 (m, 4H), 2.17 (s, 6H), 2.13-1.52 (m, 30H), 1.28-0.90 (m, 16H).

III-M
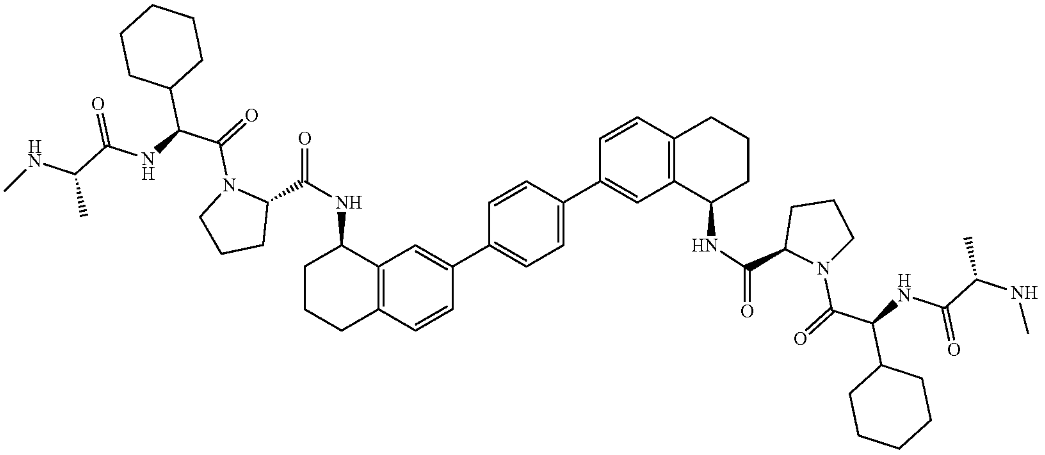
(2S)-1-[(2S)-2-cyclohexyl-2-[(2S)-2-(methylamino)propanamido]acetyl]-N-[(1R)-7-[4-[(8R)-8-[(2R)-1-[(2S)-2-cyclohexyl-2-[(2S)-2-(methylamino)propanamido]acetyl]pyrrolidine-2-amido]-5,6,7,8-tetrahydronaphthalen-2-yl]phenyl]-1,2,3,4-tetrahydronaphthalen-1-yl]pyrrolidine-2-carboxamide (Compound III-M)
LCMS (ESI, m/z): $[M+H]^+$=1011.6. $^1$H NMR (300 MHz, DMSO-$d_6$) δ 8.38-8.23 (m, 2H), 7.91-7.81 (m, 6H), 7.70-7.59 (m, 2H), 7.58-7.45 (m, 2H), 7.24-7.08 (m, 2H), 5.04-4.94 (m, 2H), 4.50-4.39 (m, 2H), 4.39-4.29 (m, 2H), 3.78-3.70 (m, 2H), 3.70-3.58 (m, 2H), 3.00-2.87 (m, 2H), 2.82-2.74 (m, 4H), 2.15 (s, 6H), 2.15-1.95 (m, 6H), 1.95-1.64 (m, 18H), 1.60-1.41 (m, 6H), 1.18-1.08 (m, 7H), 1.08-0.85 (m, 9H).
III-N
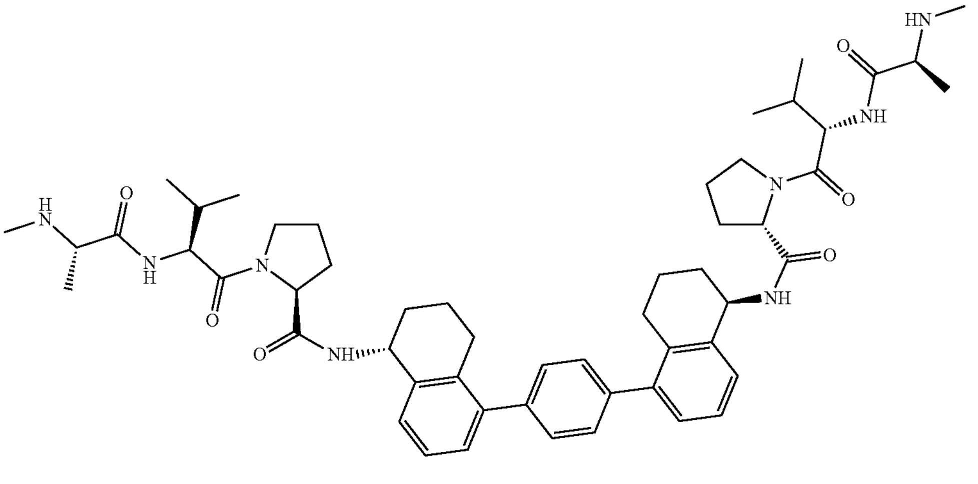

(2S)-1-[(2S)-3-methyl-2-[(2S)-2-(methylamino)propanamido]butanoyl]-N-[(1R)-5-[4-[(5R)-5-[(2S)-1-[(2S)-3-methyl-2-[(2S)-2-(methylamino)propanamido]butanoyl]pyrolidine-2-amido]-5,6,7,8-tetrahydronaphthalen-1-yl]phenyl]-1,2,3,4-tetrahydronaphthalen-1-yl]pyrrolidine-2-carboxamide (Compound I-N)
LCMS (ESI, m/z): $[M+H]^+$=931.7. $^1H$ NMR (300 MHz, DMSO-$d_6$): δ 8.60-8.26 (m, 2H), 7.97-7.76 (m, 2H), 7.44-7.31 (m, 6H), 7.28-7.19 (m, 2H), 7.16-7.08 (m, 2H), 5.09-4.97 (m, 2H), 4.56-4.40 (m, 2H), 4.39-4.28 (m, 2H), 3.79-3.50 (m, 4H), 3.03-2.91 (m, 2H), 2.69-2.54 (M, 4H), 2.26-1.96 (m, 14H), 1.95-1.76 (m, 8H), 1.76-1.58 (m, 4H), 1.19-1.04 (m, 6H), 1.00-0.78 (m, 12H).
Example 4: Synthesis of Compound IV
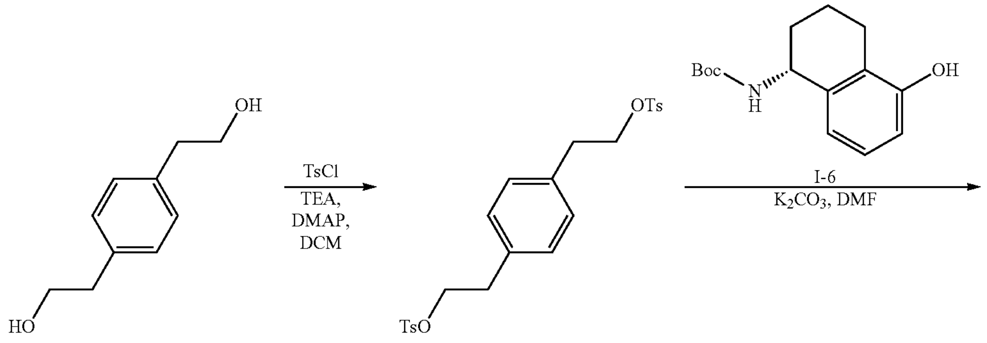
IV-1
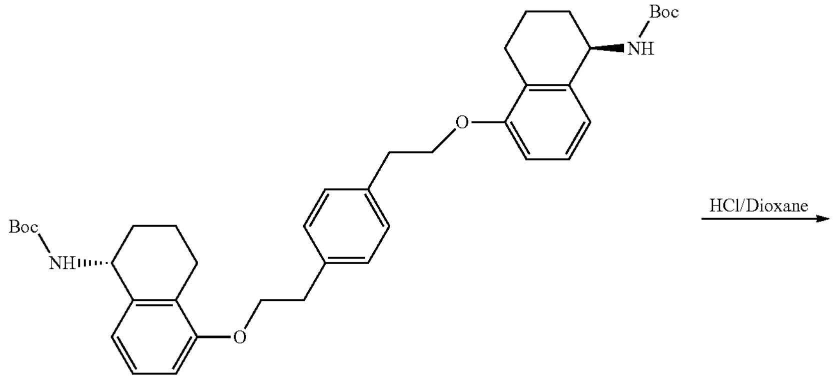
IV-2
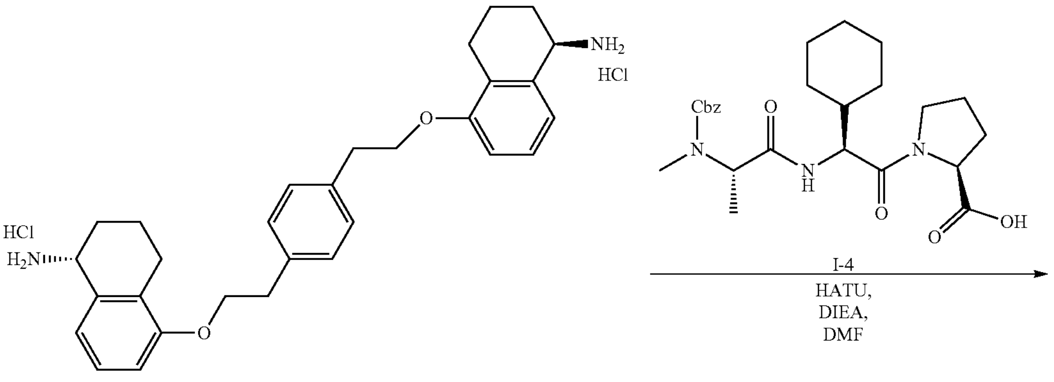
IV-3

-continued

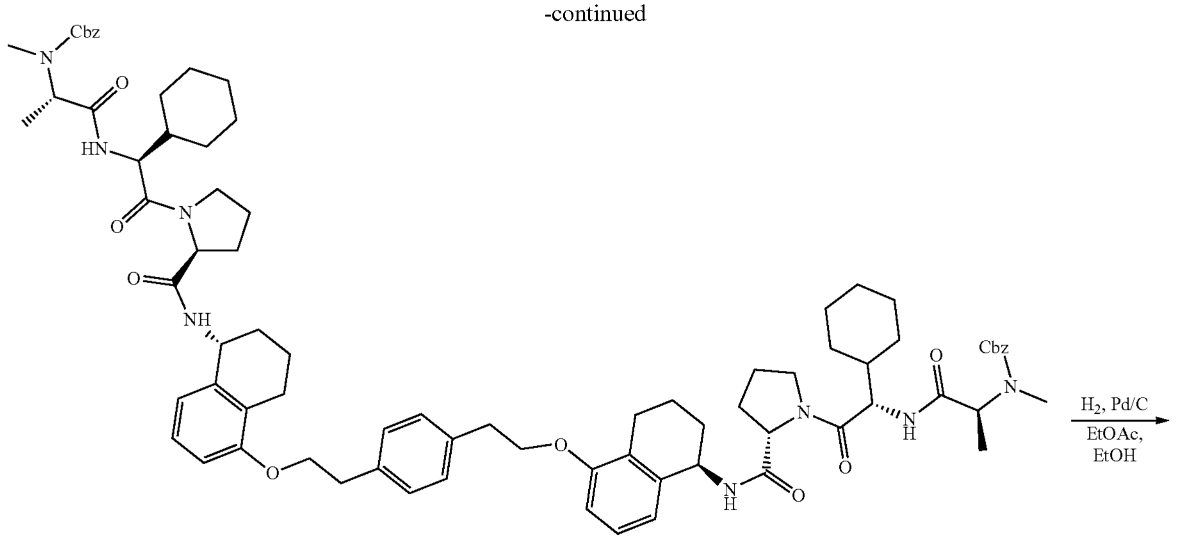

IV-4

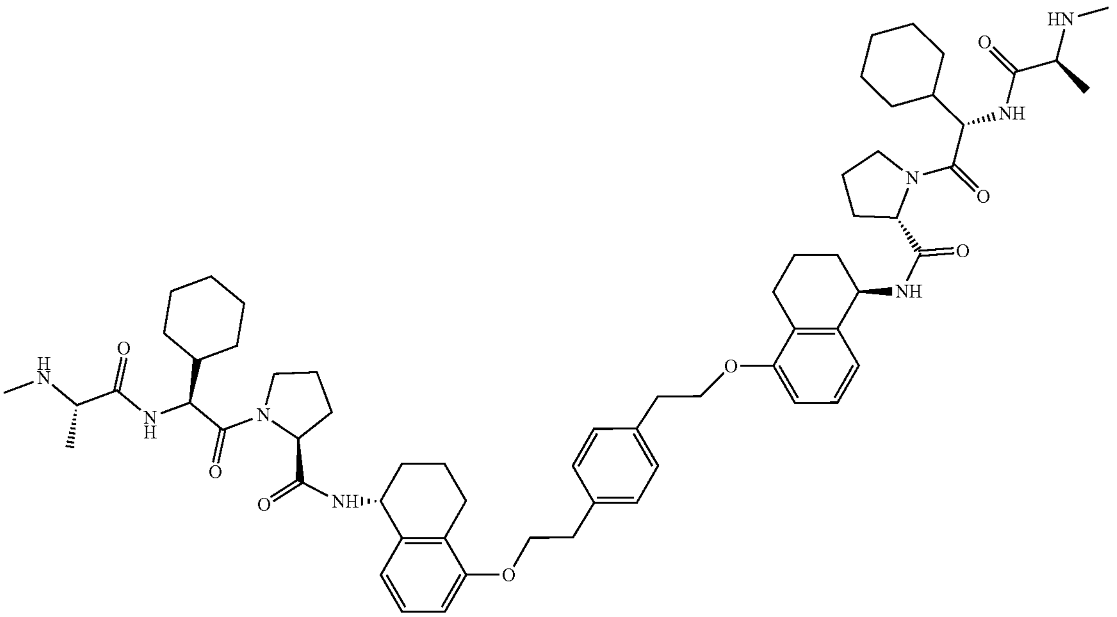

IV

2-(4-[2-[(4-Methylbenzenesulfonyl)oxy]ethyl]phenyl)ethyl 4-methylbenzenesulfonate (Compound IV-1)

To a solution of 2-[4-(2-hydroxyethyl)phenyl]ethanol (1.0 g 6.01 mmol) in DCM (50 mL) was added TEA (1.6 g 16.2 mmol), DMAP (177 mg 1.44 mmol) and TsCl (2.6 g 13.6 mmol). The mixture was stirred at room temperature for 16 h. After the reaction was completed, the mixture was evaporated in vacuo. The residue was purified by flash column chromatography with DCM/petroleum ether (100/0, v/v) to afford the title compound (2.0 g 70%) as a white solid. LCMS (ESI, m/z): $[M+H]^+$=475.1 tert-Butyl N-[1(1R)-5-[2-[4-(2-[[(5R)-5-[(tert-butoxycarbonyl)amino]-5,6,7,8-tetrahydronaphthalen-1-yl]oxy]ethyl)phenyl]ethoxy]-1,2,3,4-tetrahydronaphthalen-1-yl]carbamate (Compound IV-2)

A mixture of Compound IV-1 (346 mg, 0.72 mmol), Compound I-6 (318 mg 1.20 mmol) and $K_2CO_3$ (622 mg 4.49 mmol) in DMF (10 mL) was heated at 65° C. for 16 h After the reaction was completed, the reaction mixture was cooled to room temperature and then purified by reverse phase flash column chromatography with $CH_3CN/H_2O$ (100/0, v/v) to afford the title compound (135 mg 17%) as a white solid. LCMS (ESI, m/z): $[M+H]^+$=657.4.

(1R)-5-[2-[4-(2-[[(5R)-5-Amino-5,6,7,8-tetrahydronaphthalen-1-yl]oxy]ethyl) phenyl]ethoxy]-1,2,3,4-tetrahydronaphthalen-1-amine Dihydrochloride (Compound IV-3)

A mixture of Compound IV-2 (254 mg 0.38 mmol) in HCl/dioxane (10.0 mL, 4 mol/L) was stirred at room temperature for 4 h. After the reaction was completed, the mixture was evaporated in vacuo to afford the title compound (310 mg crude) as a yellow solid. LCMS (ESI, m/z): $[M+H]^+$=457.3.

Benzyl N-[1(1S)-1-[[(1S)-2-[(2S)-2-[[(1R)-5-[2-[4-(2-[[(5R)-5-[(2S)-1-[(2S)-2-[(2S)-2-[[(benzyloxy) carbonyl](methyl)amino]propanamido]-2-cyclohexylacetyl] pyrrolidine-2-amido]-5,6,7,8-tetrahydronaphthalen-1-yl]oxy]ethyl)phenyl] ethoxy]-1,2,3,4-tetrahydronaphthalen-1-yl] carbamoyl]pyrrolidin-yl]-1-cyclohexyl-2-oxoethyl] carbamoyl]ethyl]-N-methylcarbamate (Compound IV-4)

To a solution of Compound IV-3 (310 mg, 0.58 mmol) in DMF (10 mL) was added Compound I-4 (440 mg, 0.92 mmol) and DIEA (1.5 mL) at 0° C. under $N_2$. Then HATU (615 mg 1.61 mmol) was added to the mixture. The mixture was stirred at 0° C. for 2 h. After the reaction was completed, the mixture was purified by reverse phase flash column chromatography with $CH_3CN/H_2O$ (100/0, v/v) to afford the title compound (280 mg, 24%) as an off-white solid. LCMS (ESI, m/z): [M+H]+=1367.8.

(2S)-1-[(2S)-2-Cyclohexyl-2-[(2S)-2-(methylamino) propanamido]acetyl]-N-[(1R)-5-[2-[4-(2-[[(5R)-5-[(2S)-1-[(2S)-2-cyclohexyl-2-[(2S)-2-(methylamino) propanamido]acetyl]pyrrolidine-2-amido]-5,6,7,8-tetrahydronaphthalen-1-yl]oxy]ethyl) phenyl] ethoxy]-1,2,3,4-tetrahydronaphthalen-1-yl]pyrrolidine-2-carboxamide (Compound IV)

To a solution of Compound IV-4 (280 mg, 0.20 mmol) in EtOAc (10 mL) and EtOH (5 mL) was added Pd/C (191 mg, dry). The mixture was stirred at room temperature for 16 h under $H_2$. After the reaction was completed, the mixture was filtered. The filtrate was evaporated in vacuo. The residue was purified by Prep-HPLC with the following conditions: Column: XBridge Prep OBD C18 Colum, 30×150 mm, 5 um; Mobile Phase A: Water (10 mmol/L $NH_4HCO_3$), Mobile Phase B: ACN; Flow rate-60 mL/min; Gradient: 51% B to 81% B in 7 min; 254 nm; RT: 5.83 min to afford the title compound (83.5 mg, 37%) as a white solid.

LCMS (ESI, m/z): $[M+H]^+$=1099.7. $^1H$ NMR (300 MHz, DMSO-$d_6$, ppm): δ 8.46-8.02 (m, 2H), 7.94-7.68 (m, 2H), 7.26 (s, 4H), 7.09-7.04 (m, 2H), 6.86-6.79 (m, 4H), 4.93-4.79 (m, 2H), 4.49-4.37 (m, 2H), 4.31-4.27 (m, 2H), 4.15-4.06 (m, 4H), 3.78-3.66 (m, 2H), 3.65-3.54 (m, 2H), 3.03-2.95 (m, 6H), 2.16 (s, 6H), 2.09-1.89 (m, 4H), 1.88-1.50 (m, 25H), 1.15-0.94 (m, 17H).

Following the procedure described above for Example 4 and substituting the appropriate reagents, starting materials and purification methods known to those skilled in the art, the compounds listed below were prepared.

IV-A

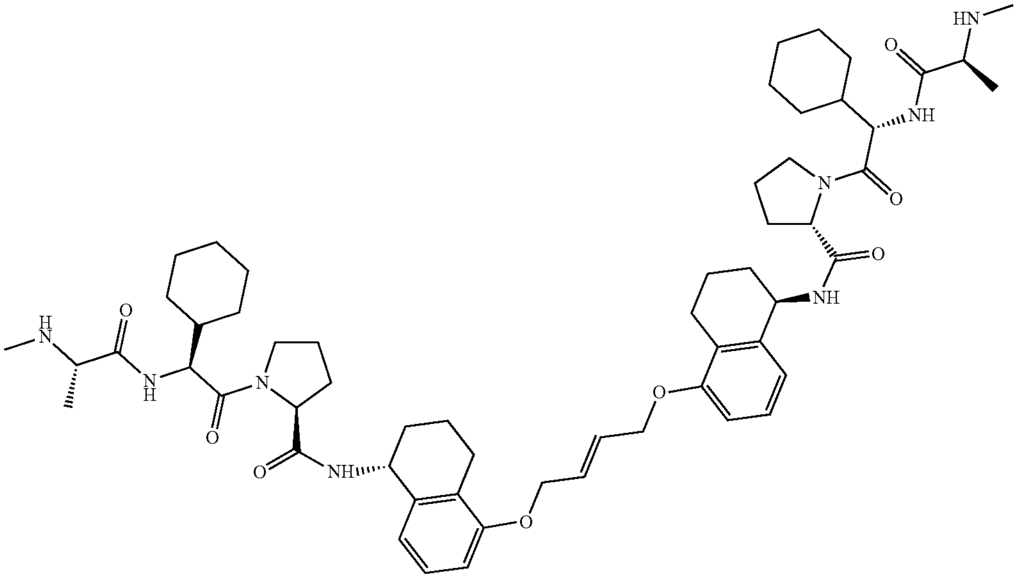

(2S)-1-[(2S)-2-Cyclohexyl-2-[(2S)-2-(methylamino)propanamido]acetyl]-N-[(1R)-5-[[(2E)-4-[[(5R)-5-[(2S)-1-[(2S)-2-cyclohexyl-2-[(2S)-2-(methylamino)propanamido]acetyl]pyrrolidine-2-amido]-5,6,7,8-tetrahydronaphthalen-1-yl]oxy]but-2-en-1-yl]oxy]-1,2,3,4-tetrahydronaphthalen-1-yl]pyrrolidine-2-carboxamide (Compound IV-A)

LCMS (ESI, m/z): $[M+H]^+$=1021.6. $^1H$ NMR (300 MHz, DMSO-$d_6$, ppm): δ 8.50-8.09 (m, 2H), 7.84-7.65 (m, 2H), 7.10-7.05 (m, 2H), 6.89-6.80 (m, 4H), 6.07 (s, 2H), 4.91-4.80 (m, 2H), 4.50 (s, 4H), 4.45-4.28 (m, 4H), 3.71-3.60 (m, 4H), 2.95-2.90 (m, 2H), 2.69-2.53 (m, 4H), 2.14 (s, 6H), 2.10-1.91 (m, 4H), 1.86-1.58 (m, 26H), 1.18-0.94 (m, 16H).

IV-B

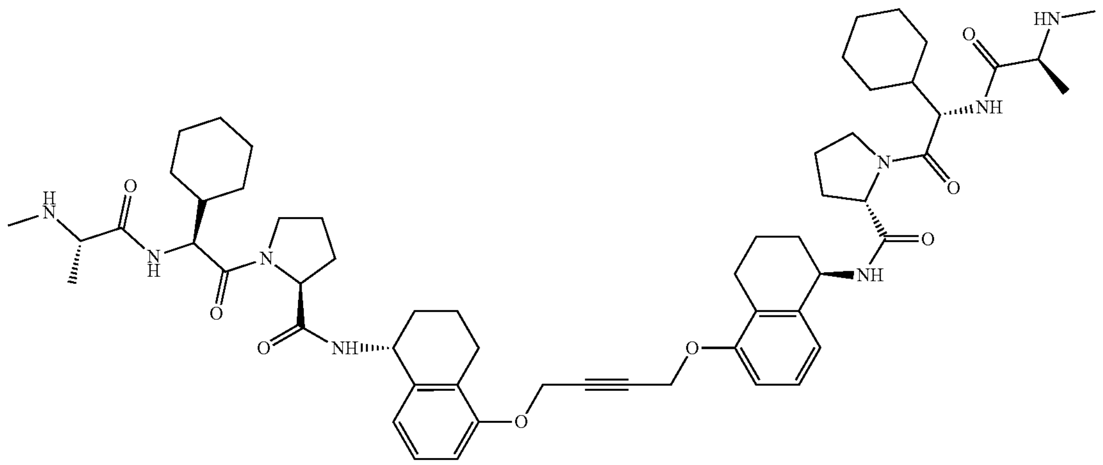

(S)-1-((S)-2-Cyclohexyl-2-((S)-2-(methylamino)propanamido)acetyl)-N—((R)-5-(4-((R)-5-((S)-1-((S)-2-cyclohexyl-2-((S)-2-(methylamino)propanamido)acetyl) pyrrolidine-2-carboxamido)-5,6,7,8-tetrahydronaphthalen-1-yloxy)but-2-ynyloxy)-1,2,3,4-tetrahydronaphthalen-1-yl)pyrrolidine-2-carboxamide (Compound IV-B)

LCMS (ESI, m/z): $[M+H]^+$=1019.6. $^1H$ NMR (300 MHz, DMSO-$d_6$, ppm): δ 8.50-8.11 (m, 2H), 7.88-7.65 (m, 2H), 7.11-7.06 (m, 2H), 6.93-6.84 (m, 4H), 4.91-4.86 (m, 6H), 4.46-4.40 (m, 2H), 4.32-4.28 (m, 2H), 3.77-3.70 (m, 2H), 3.67-3.57 (m, 2H), 2.96-2.91 (m, 2H), 2.56-2.50 (m, 4H), 2.17 (s, 6H), 2.06-1.96 (m, 4H), 1.85-1.59 (m, 26H), 1.19-0.95 (m, 16H).

Example 5: Synthesis of Compound V

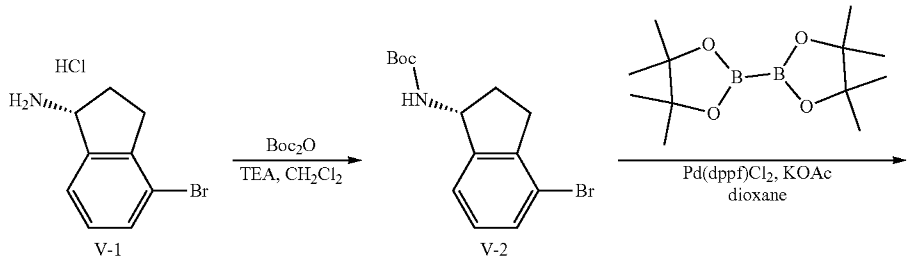

V-1 V-2

-continued
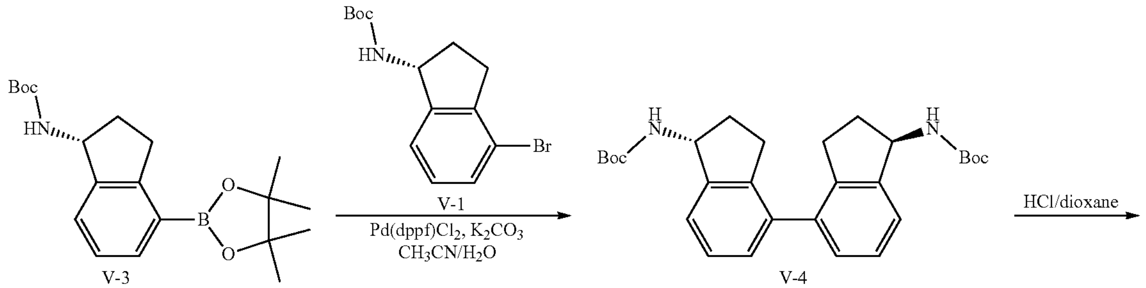
V-3 V-4
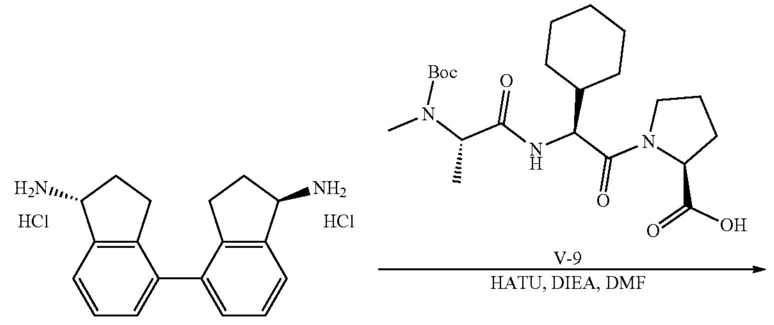
V-5
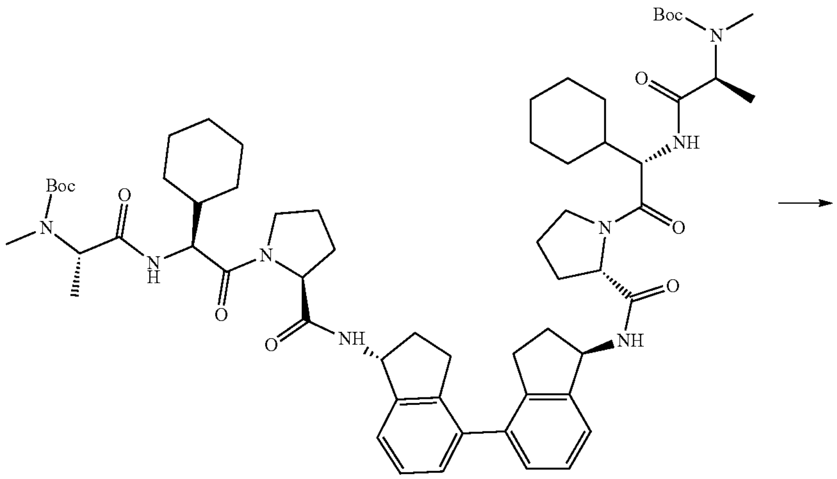
V-10
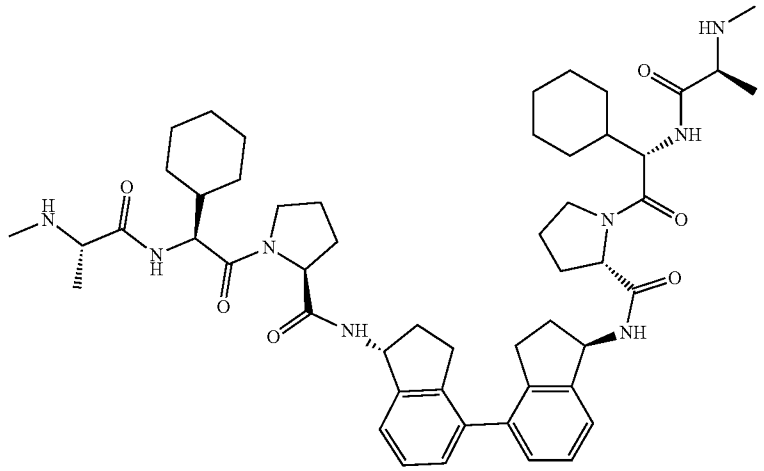
V

-continued

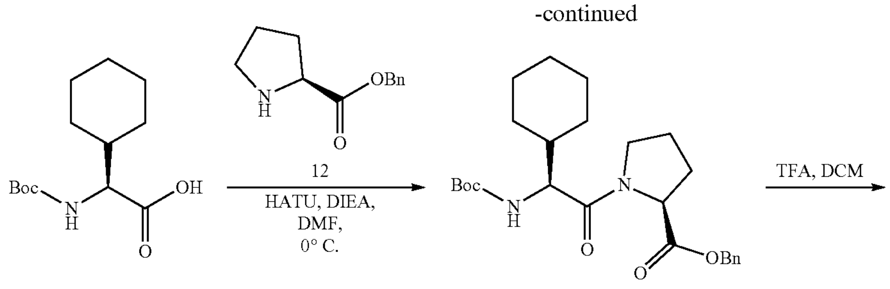

V-6

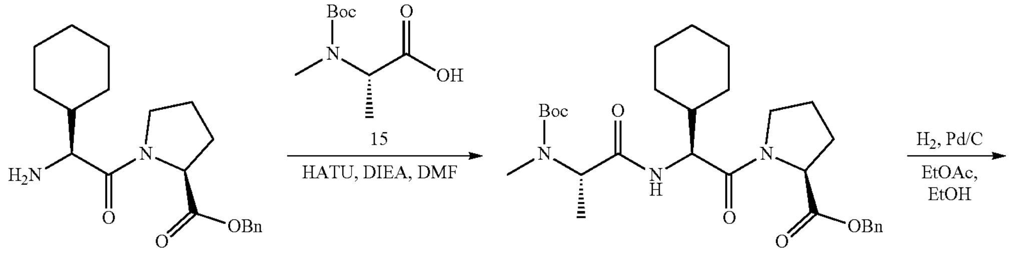

V-7

V-8

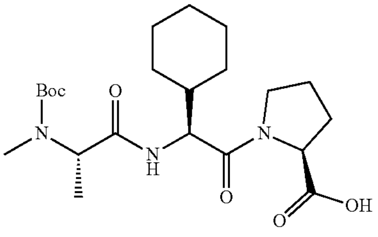

V-9 tert-Butyl (R)-(4-bromo-2,3-dihydro-1H-inden-1-yl) carbamate (Compound V-2)

To a solution of compound V-1 (4.7 g, 18.91 mmol) in $CH_2Cl_2$ (100.0 mL) was added TEA (5.4 g, 52.95 mmol) and $Boc_2O$ (5.4 g, 24.58 mmol). The resulting mixture was stirred at room temperature for 16 h. After the reaction was completed, the resulting mixture was concentrated under reduced pressure. The residue was purified by flash column chromatography with petroleum ether/ethyl acetate (93/7, v/v) to afford the title compound (5.4 g, 91%) as a light pink solid. LCMS (ESI, m/z): $[M+H]^+$=312.1.

tert-Butyl (R)-(4-(4,4,5,5-tetramethyl-1,3,2-dioxaborolan-2-yl)-2,3-dihydro-1H-inden-1-yl)carbamate (Compound V-3)

To a solution of compound V-2 (300.0 mg 0.96 mmol) in 1,4-dioxane (10.0 mL) was added 4,4,4',4',5,5,5',5'-octamethyl-2,2'-bi(1,3,2-dioxaborolane) (732.0 mg 2.88 mmol), KOAc (282.9 mg, 2.88 mmol) and Pd(dppf)$Cl_2$ (70.3 mg, 0.10 mmol) at room temperature. The resulting mixture was stirred at 80° C. for 16 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (89/11) to afford the title compound (450.0 mg crude) as a colorless oil. LCMS (ESI, m/z): $[M+H]^+$=360.2.

Di-tert-butyl ((1R,1'R)-2,2',3,3'-tetrahydro-1H,1'H-[4,4'-biindene]-1,1'-diyl) dicarbamate (Compound V-4)

To a solution of compound V-3 (400.0 mg, 1.11 mmol) in $CH_3CN/H_2O$ (10.0 mL/2.0 mL) was added tert-butyl (R)-(4-bromo-2,3-dihydro-1H-inden-1-yl)carbamate (347.6 mg 1.11 mmol), $K_2CO_3$ (461.6 mg, 3.34 mmol) and Pd(dppf)$Cl_2$ (81.5 mg, 0.11 mmol) at room temperature. The resulting mixture was stirred at 80° C. for 16 h under $N_2$. The resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (80/20, v/v) to afford the title compound (320.0 mg, 62%) as a white solid. LCMS (ESI, m/z): $[M+H]^+$=465.3.

(1R,1'R)-2,2',3,3'-tetrahydro-4,4'-bi(1H-indene)-1,1'-diamine dihydrochloride (Compound V-5)

A solution of compound V-4 (320.0 mg, 0.69 mmol) in HCl/1,4-dioxane (6.0 mL, 4 mol/L) was stirred at room temperature for 1 h. After the reaction was completed, the resulting mixture was concentrated under vacuum to afford the title compound (250.0 mg, crude) as a yellow solid. LCMS (ESI, m/z): $[M+H]^+$=265.2.

(S)-benzyl 1-((S)-2-(tert-butoxycarbonylamino)-2-cyclohexylacetyl) pyrrolidine-2-carboxylate (Compound V-6)

To a mixture of (S)-[(tert-butoxycarbonyl)amino](cyclohexyl)acetic acid (10.0 g 38.86 mmol), benzyl (2S)-pyrrolidine-2-carboxylate (7.9 g, 38.86 mmol) and DIEA (15.1 g 116.58 mmol) in DMF (25.0 mL) was added HATU (17.7 g 46.63 mmol) at 0° C. under $N_2$. The mixture was stirred at 0° C. for 2 h. The mixture was diluted with $H_2O$ and extracted with EtOAc. The combined organic layer was washed with brine, dried over $Na_2SO_4$ and filtered. The filtrate was evaporated in vacuo. The residue was purified by flash column chromatography with $CH_2Cl_2$/$CH_3OH$ (10/1, v/v) to afford the title compound (11.1 g, 64%) as a white solid. LCMS (ESL, m/z): $[M+H]^+$=445.3.

(S)-Benzyl 1-((S)-2-amino-2-cyclohexylacetyl)pyrrolidine-2-carboxylate (Compound V-7)

To a mixture of V-6 (11.1 g, 8.23 mmol) in $CH_2Cl_2$ (75.0 mL) was added TFA (15.0 mL). The mixture was stirred at room temperature for 2 h. After the reaction was completed, the mixture was evaporated in vacuo. The residue was purified by reverse phase flash column chromatography with $CH_3CN/H_2O$ (97/3, v/v) to afford the title compound (3.1 g, 36%) as a yellow green oil. LCMS (ESI, m/z): $[M+H]^+$=345.2.

(S)-Benzyl 1-((S)-2-((S)-2-(tert-butoxycarbonyl (methyl)amino)propanamido)-2-cyclohexylacetyl) pyrrolidine-2-carboxylate (Compound V-8)

To a mixture of compound V-7 (3.0 g, 8.82 mmol), (2S)-2-[(tert-butoxycarbonyl)methyl)amino]propanoic acid (1.8 g, 8.82 mmol) and DIEA (3.4 g, 26.47 mmol) in DMF (15.0 mL) was added HATU (4.0 g 10.59 mmol) at 0° C. under $N_2$. The mixture was stirred at 0° C. for 2 h. The mixture was diluted with $H_2O$ and extracted with EtOAc. The combined organic layer was washed with brine, dried over $Na_2SO_4$ and filtered. The filtrate was evaporated in vacuo. The mixture was purified by flash column chromatography with $CH_2Cl_2$/$CH_3OH$ (10/1, v/v) to afford the title compound (1.2 g, 25%) as a light green oil. LCMS (ESI, m/z): $[M+H]^+$=530.3.

(S)-1-((S)-2-((S)-2-(tert-butoxycarbonyl(methyl) amino)propanamido)-2-cyclohexylacetyl)pyrrolidine-2-carboxylic acid (Compound V-9)

To a solution of compound V-8 (1.2 g, 2.26 mmol) in EtOAc (15.0 mL) and EtOH (15.0 mL) was added Pd/C (240.0 mg, dry). The mixture was stirred at room temperature for 16 h under $H_2$. After the reaction was completed, the reaction mixture was filtered. The filtrate was concentrated under vacuum to afford the title compound (900.0 mg, crude) as a white solid. LCMS (ESI, m/z): $[M+H]^+$=440.3.

tert-Butyl ((S)-1-(((S)-2-((S)-2-(((1R,1'R)-1'-((S)-1-((S)-2-((S)-2-((tert-butoxy carbonyl)methyl)amino) propanamido)-2-cyclohexylacetyl)pyrrolidine-2-carboxamido)-2,2',3,3'-tetrahydro-1H,1'H-[4,4'-biinden]-1-yl)carbamoyl)pyrrolidin-1-yl)-1-cyclohexyl-2-oxoethyl)amino)-1-oxopropan-2-yl) (methyl)carbamate (Compound V-10)

To a solution of compound V-5 (250.0 mg, 0.74 mmol) in DMF (3.0 mL) was added V-9 (651.6 mg, 1.48 mmol) and DIEA (957.9 mg 7.41 mmol). Then HATU (986.3 mg, 2.59 mmol) was added to the mixture at 0° C. under $N_2$. The resulting mixture was stirred at 0° C. for 2 h. After the reaction was completed, the mixture was purified by reverse phase flash column chromatography with $CH_3CN/H_2O$ (80/20, v/v) to afford the title compound (600.0 mg, 73%) as a yellow solid. LCMS (ESI, m/z): $[M+H]^+$=1107.7.

(2S)-1-[(2S)-2-cyclohexyl-2-[(2S)-2-(methylamino) propanamido]acetyl]-N-[(1R,1'R)-1'-[(2S)-1-[(2S)-2-cyclohexyl-2-[(2S)-2-(methylamino)propanamido] acetyl]pyrrolidine-2-amido]-1H,1'H,2H,2'H,3H,3'H-[4,4'-biinden]-1-yl]pyrrolidine-2-carboxamide (Compound V)

To a solution of compound V-10 (550.0 mg, 0.49 mmol) in $CH_2CL$ (10.0 mL) was added TFA (6.0 mL). The mixture was stirred at room temperature for 2 h. After the reaction was completed, the pH value of the mixture was adjusted to 8 with $NaHCO_3$ solution. The mixture was diluted with $H_2O$ and extracted with $CH_2Cl_2$. The combined organic layer was washed with brine, dried over $Na_2SO_4$ and filtered. The filtrate was evaporated in vacuo. The residue was purified by Prep-HPLC with the following conditions: Column: Column: YMC-Actus Triart C18, 20×250 mm, 5 um, 12 nm; Mobile Phase A: Water (10 mmol/L $NH_4HCO_3$), Mobile Phase B:ACN; Flow rate: 60 mL/min; Gradient: 40% B to 70% B in 7 min; 254 nm; RT1: 6.25 min to afford the title compound (166.1 mg, 36%) as a white solid. LCMS (ESI, m/z): $[M+H]^+$=907.5. $^1H$ NMR (300 MHz, DMSO-$d_6$) δ 8.55-8.17 (m, 2H), 8.00-7.72 (m, 2H), 7.37-7.21 (m, 4H), 7.20-7.04 (m, 2H), 5.42-5.23 (m, 2H), 4.58-4.27 (m, 4H), 3.90-3.47 (m, 4H), 3.03-2.91 (m, 2H), 2.90-2.75 (m, 2H), 2.65-2.55 (m, 2H), 2.40-1.95 (m, 14H), 1.94-1.53 (m, 18H), 1.28-0.85 (m, 16H).

Following the procedure described above for Example 5 and substituting the appropriate reagents, starting materials and purification methods known to those skilled in the art, the compounds listed below were prepared.

V-A

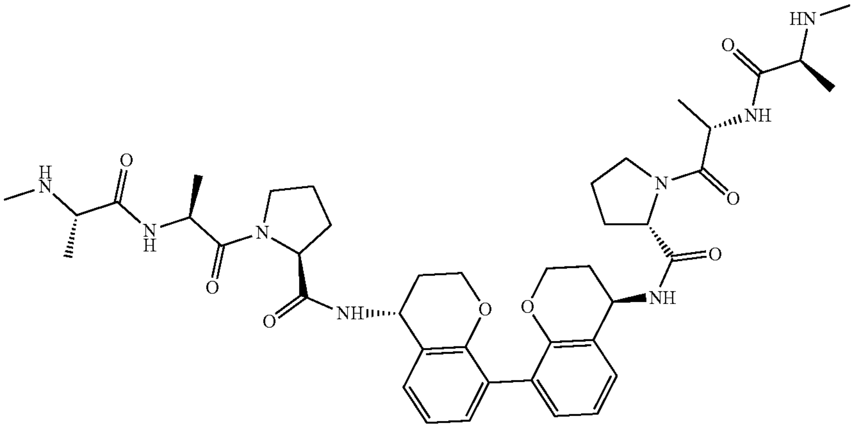

(2S)-1-[(2S)-2-[(2S)-2-(methylamino)propanamido]propanoyl]-N-[(4R)-8-[(4R)-4-[(2S)-1-[(2S)-2-[(2S)-2-(methylamino)propanamido]propanoyl]pyrrolidine-2-amido]-3,4-dihydro-2H-1-benzopyran-8-yl]-3,4-dihydro-2H-1-benzopyran-4-yl]pyrrolidine-2-carboxamide (Compound V-A)

LCMS (ESI, m/z): $[M+H]^+$=803.3. $^1H$ NMR (300 MHz, DMSO-$d_6$): δ 8.80-8.30 (m, 2H), 8.10-7.90 (m, 2H), 7.30-7.11 (m, 2H), 7.03-6.96 (m, 2H), 6.95-6.80 (m, 2H), 5.12-4.99 (m, 2H), 4.68-4.52 (m, 2H), 4.50-4.26 (m, 2H), 4.18-3.98 (m, 4H), 3.70-3.52 (m, 4H), 3.01-2.88 (m, 2H), 2.22-2.19 (m, 6H), 2.13-1.80 (m, 12H), 1.32-1.17 (m, 6H), 1.16-1.02 (m, 6H).

V-B

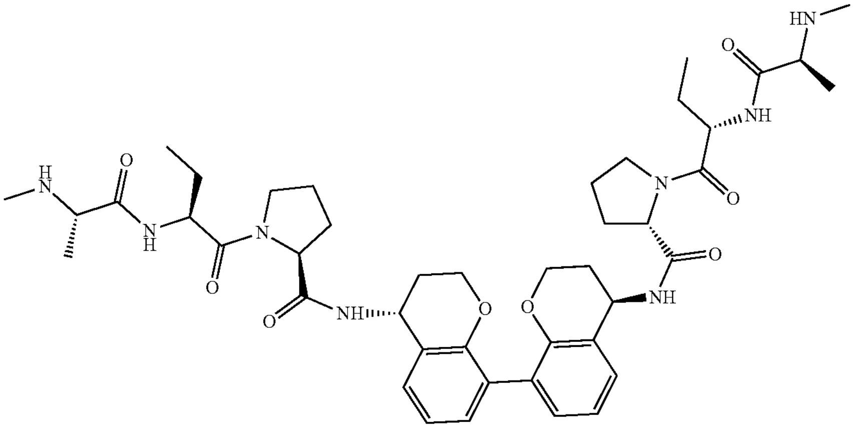

(2S)-1-[(2S)-2-[(2S)-2-(methylamino)propanamido]butanoyl]-N-[1(4R)-8-[(4R)-4-[(2S)-1-[(2S)-2-[(2S)-2-(methylamino)propanamido]butanoyl]pyrrolidine-2-amido]-3,4-dihydro-2H-1-benzopyran-8-yl]-3,4-dihydro-2H-1-benzopyran-4-yl]pyrrolidine-2-carboxamide (Compound V-B)

LCMS (ESI, m/z): $[M+H]^+$=831.4. $^1H$ NMR (300 MHz, DMSO-$d_6$): δ 8.83-8.35 (m, 2H), 8.10-7.80 (m, 2H), 7.41-7.12 (m, 2H), 7.02-6.96 (m, 2H), 6.95-6.80 (m, 2H), 5.15-4.92 (m, 2H), 4.59-4.25 (m, 4H), 4.18-3.85 (m, 4H), 3.78-3.48 (m, 4H), 3.03-2.90 (m, 2H), 2.25-2.18 (m, 6H), 2.16-1.92 (m, 6H), 1.91-1.70 (m, 8H), 1.68-1.48 (m, 2H), 1.18-1.02 (m, 6H), 0.96-0.78 (m, 6H).

V-C

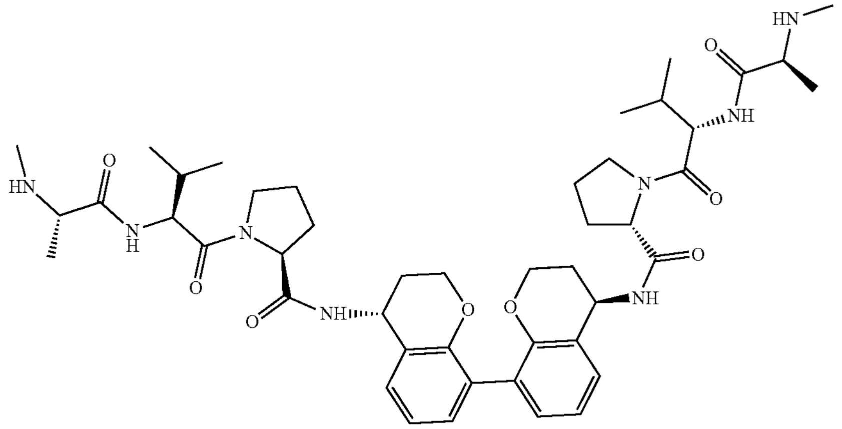

(2S)-1-[(2S)-3-methyl-2-[(2S)-2-(methylamino)propanamido]butanoyl]-N-[(4R)-8-[(4R)-4-[(2S)-1-[(2S)-3-methyl-2-[(2S)-2-(methylamino)propanamido]butanoyl]pyrrolidine-2-amido]-3,4-dihydro-2H-1-benzopyran-8-yl]-3,4-dihydro-2H-1-benzopyran-4-yl]pyrrolidine-2-carboxamide (Compound V-C)

LCMS (ESI, m/z): $[M+H]^+$=859.4. $^1H$ NMR (300 MHz, DMSO-$d_6$): δ 8.52-8.37 (m, 2H), 7.97-7.88 (m, 2H), 7.25-7.12 (m, 2H), 7.08-6.96 (m, 2H), 6.95-6.80 (m, 2H), 5.12-4.94 (m, 2H), 4.57-4.40 (m, 2H), 4.39-4.24 (m, 2H), 4.18-4.05 (m, 4H), 3.79-3.56 (m, 4H), 3.04-2.91 (m, 2H), 2.24-2.17 (m, 6H), 2.15-1.75 (m, 16H), 1.21-1.09 (m, 6H), 1.00-0.80 (m, 12H).

V-D

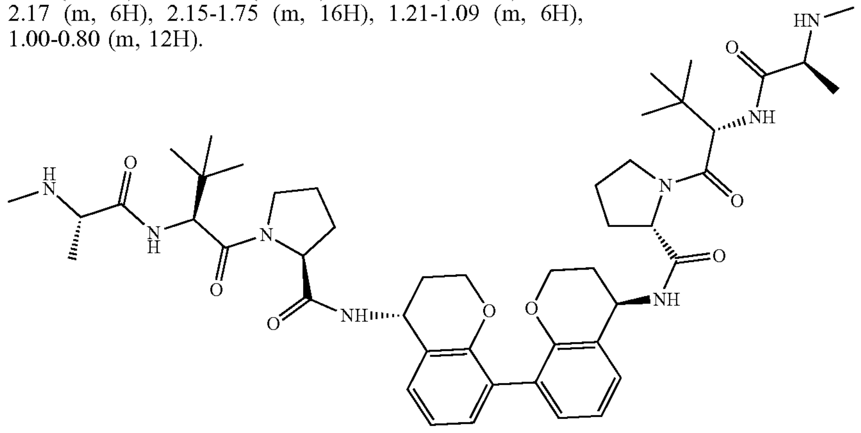

(2S)-1-[(2S)-3,3-dimethyl-2-[(2S)-2-(methylamino) propanamido]butanoyl]-N-[(4R)-8-[(4R)-4-[(2S)-1-(2S)-3,3-dimethyl-2-[(2S)-2-(methylamino)propanamido]butanoyl]pyrrolidine-2-amido]-3,4-dihydro-2H-1-benzopyran-8-yl-3,4-dihydro-2H-1-benzopyran-4-yl]pyrrolidine-2-carboxamide (Compound V-D)

LCMS (ESI, m/z): $[M+H]^+$=887.4. $^1H$ NMR (300 MHz, DMSO-$d_6$): δ 8.70-8.42 (m, 2H), 7.96-7.70 (m, 2H), 7.25-7.20 (m, 2H), 7.05-6.93 (m, 2H), 6.87-6.78 (m, 2H), 5.14-4.82 (m, 2H), 4.67-4.50 (m, 2H), 4.45-4.26 (m, 2H), 4.19-4.10 (m, 4H), 3.81-3.60 (m, 4H), 3.07-2.85 (m, 2H), 2.38-2.15 (m, 8H), 2.14-1.94 (m, 6H), 1.93-1.71 (m, 6H), 1.23-1.09 (m, 6H), 1.08-0.97 (m, 16H), 0.95-0.92 (m, 2H).

V-E

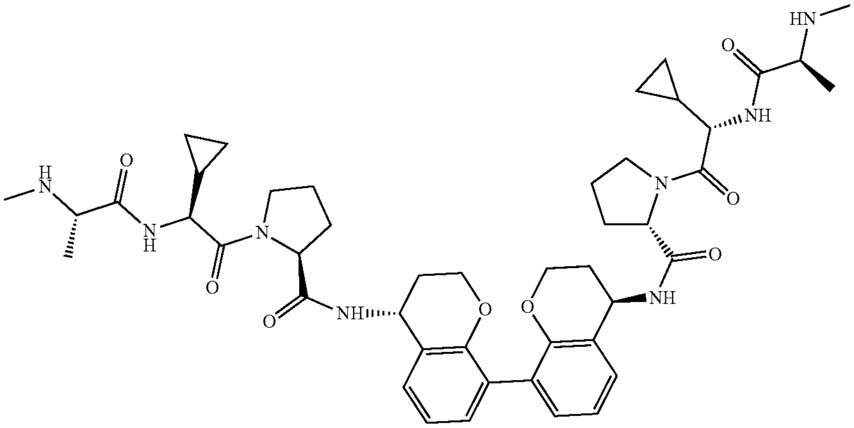

(2S)-1-[(2S)-2-cyclopropyl-2-[(2S)-2-(methylamino)propanamido]acetyl]-N-[(4R)-8-[(4R)-4-[(2S)-1-[(2S)-2-cyclopropyl-2-[(2S)-2-(methylamino)propanamido]acetyl]pyrrolidine-2-amido]-3,4-dihydro-2H-1-benzopyran-8-yl]-3,4-dihydro-2H-1-benzopyran-4-yl]pyrrolidine-2-carboxamide (Compound V-E)

LCMS (ESI, m/z): $[M+H]^+$=855.4. $^1H$ NMR (300 MHz, DMSO-$d_6$): δ 8.80-8.28 (m, 2H), 8.06-7.80 (m, 2H), 7.38-7.12 (m, 2H), 7.05-6.96 (m, 2H), 6.95-6.80 (m, 2H), 5.12-4.94 (m, 2H), 4.57-4.36 (m, 2H), 4.31-4.25 (m, 2H), 4.20-4.00 (m, 4H), 3.72-3.56 (m, 4H), 3.05-2.94 (m, 2H), 2.24-2.19 (m 6H), 2.13-1.95 (m 6H), 1.93-1.78 (m, 6H), 1.25-1.05 (m, 8H), 0.57-0.25 (m, 8H).

V-F

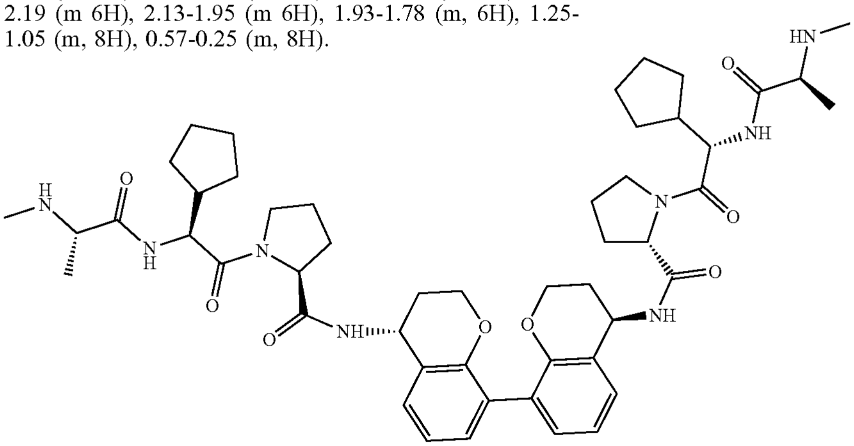

(2S)-1-[(2S)-2-cyclopentyl-2-[(2S)-2-(methylamino)propanamido]acetyl]-N-[(4R)-8-[(4R)-4-[(2S)-1-[(2S)-2-cyclopentyl-2-[(2S)-2-(methylamino)propanamido]acetyl]pyrrolidine-2-amido]-3,4-dihydro-2H-1-benzopyran-8-yl]-3,4-dihydro-2H-1-benzopyran-4-yl]pyrrolidine-2-carboxamide (Compound V-F)

LCMS (ESI, m/z): $[M+H]^+$=911.5. $^1H$ NMR (300 MHz, DMSO-$d_6$): δ 8.75-8.26 (m, 2H), 8.08-7.80 (m, 2H), 7.52-7.14 (m, 2H), 7.08-6.96 (m, 2H), 6.95-6.80 (m, 2H), 5.12-4.90 (m, 2H), 4.63-4.45 (m, 2H), 4.37-4.31 (m, 2H), 4.21-3.96 (m, 4H), 3.80-3.58 (m, 4H), 3.05-2.90 (m, 2H), 2.35-1.95 (m, 16H), 1.94-1.76 (m, 6H), 1.75-1.45 (m, 12H), 1.39-1.21 (m, 4H) 1.19-1.00 (m, 6H).

V-G

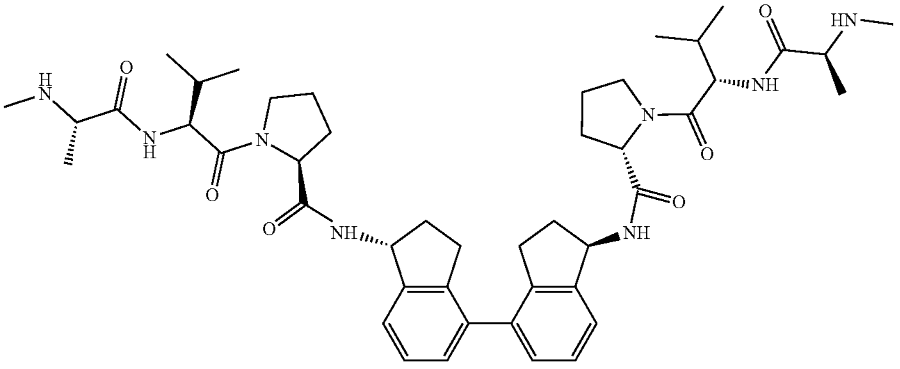

(2S)-1-[(2S)-3-methyl-2-[(2S)-2-(methylamino)propanamido]butanoyl]-N-[(1R,1'R)-1'-[(2S)-1-[(2S)-3-methyl-2-[(2S)-2-(methylamino)propanamido]butanoyl]pyrrolidine-2-amido]-1H,1'H,2H,2'H,3H,3'H-[4,4'-biinden]-1-yl]pyrrolidine-2-carboxamide (Compound V-G)

LCMS (ESI, m/z): $[M+H]^+$=827.4. $^1H$ NMR (300 MHz, DMSO-$d_6$): δ 8.38-8.20 (m, 2H), 8.01-7.85 (m, 2H), 7.33-7.21 (m, 4H), 7.20-7.03 (m, 2H), 5.43-5.25 (m, 2H), 4.52-4.41 (m, 2H), 4.39-4.23 (m, 2H), 3.80-3.58 (m, 4H), 3.05-2.92 (m, 2H), 2.90-2.71 (m, 2H), 2.64-2.55 (m, 2H), 2.44-2.16 (m, 10H), 2.15-1.95 (m, 6H), 1.93-1.66 (m, 6H), 1.18-1.05 (m, 6H), 1.02-0.82 (m, 12H).

V-H

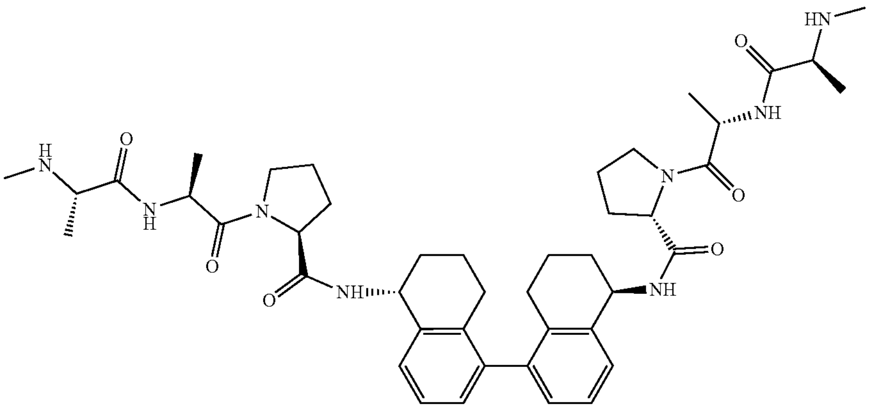

(2S)-1-[(2S)-2-[(2S)-2-(methylamino)propanamido]propanoyl]-N-[(5R,5'R)-5'-[(2S)-1-[(2S)-2-[(2S)-2-(methylamino)propanamido]propanoyl]pyrrolidine-2-amido]-5H,5'H,6H,6'H,7H,7'H,8H,8'H-[1,1'-binaphthalen]-5-yl]pyrrolidine-2-carboxamide (Compound V-H)

LCMS (ESI, m/z): $[M+H]^+$=799.6. $^1H$ NMR (300 MHz, DMSO-$d_6$) δ 8.64-8.15 (m, 2H), 8.10-7.91 (m, 2H), 7.36-7.15 (m, 4H), 6.97-6.82 (m, 2H), 5.05-4.93 (m, 2H), 4.68-4.52 (m, 2H), 4.43-4.28 (m, 2H), 3.72-3.47 (m, 4H), 3.01-2.89 (m, 2H), 2.38-2.25 (m, 3H), 2.26-2.17 (m, 7H), 2.17-1.53 (m, 18H), 1.29-1.18 (m, 6H), 1.16-1.05 (n, 6H).

V-I

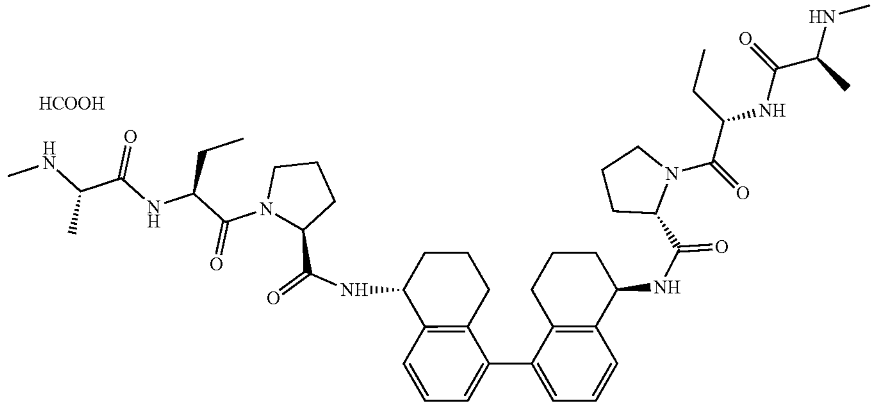

(2S)-1-[(2S)-2-[(2S)-2-(methylamino)propanamido] butanoyl]-N-[1(5R,5'R)-5'-[(2S)-1-[(2S)-2-[(2S)-2-(methylamino)propanamido]butanoyl]pyrrolidine-2-amido]-5H,5'H,6H,6'H,7H,7'H,8H,8'H-[1,1'-binaphthalen]-5-yl]pyrrolidine-2-carboxamide; Bis (Formic Acid) (Compound V-1)

LCMS (ESI, mm/z): $[M+H]^+$=827.5. $^{1}$H NMR (300 MHz, DMSO-$d_6$) δ 8.33-8.19 (m, 3H), 8.19-7.95 (m, 2H), 7.32-7.15 (m, 41H), 6.96-6.81 (m, 2H), 5.03-4.97 (m, 2H), 4.60-4.47 (m, 2H), 4.42-4.30 (m, 2H), 3.77-3.55 (m, 4H), 3.21-3.08 (m, 2H), 2.35-2.20 (m, 9H), 2.16-1.95 (m, 5H), 1.95-1.51 (m, 16H), 1.22-1.06 (m, 6H), 0.97-0.80 (m, 6H).

V-J

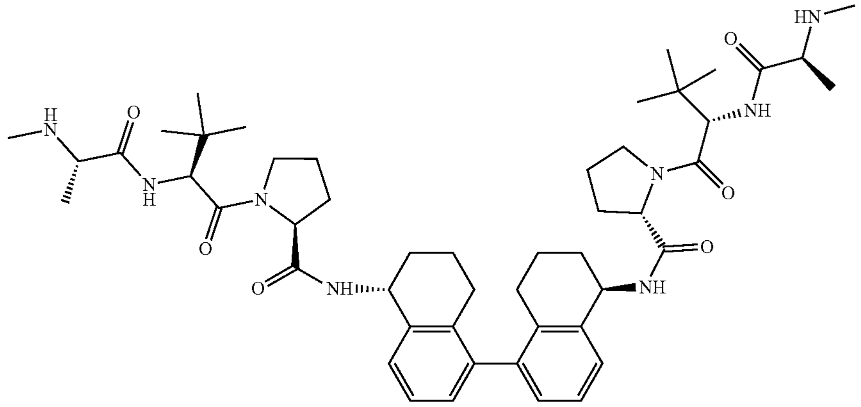

(2S)-1-[(2S)-3,3-dimethyl-2-[(2S)-2-(methylamino) propanamido]butanoyl]-N-[(5R,5'R)-5'-[(2S)-[(2S)-3,3-dimethyl-2-[(2S)-2-(methylamino)propanamido] butanoyl]pyrolidine-2-amido]-5H,5' H,6H,6'H,7H, 7'H,8H,8' H-[1,1'-binaphthalen]-5-yl]pyrrolidine-2-carboxamide (Compound V-J)

LCMS (ESL, m/z): $[M+H]^+$=883.6. $^{1}$H NMR (300 MHz, DMSO-$d_6$): δ: 8.42-8.35 (m, 2H), 7.89-7.80 (m, 2H), 7.39-7.35 (m, 2H), 7.18-7.13 (m, 2H), 6.92-6.84 (m, 2H), 5.02-4.95 (m, 2H), 4.60-4.53 (m, 2H), 4.37-4.33 (mi, 2H), 3.80-3.65 (mi, 4H), 3.03-2.96 (mi, 2H), 2.42-1.98 (m, 16H), 1.85-1.64 (m, 12H), 1.17-0.93 (m, 24H).

V-K

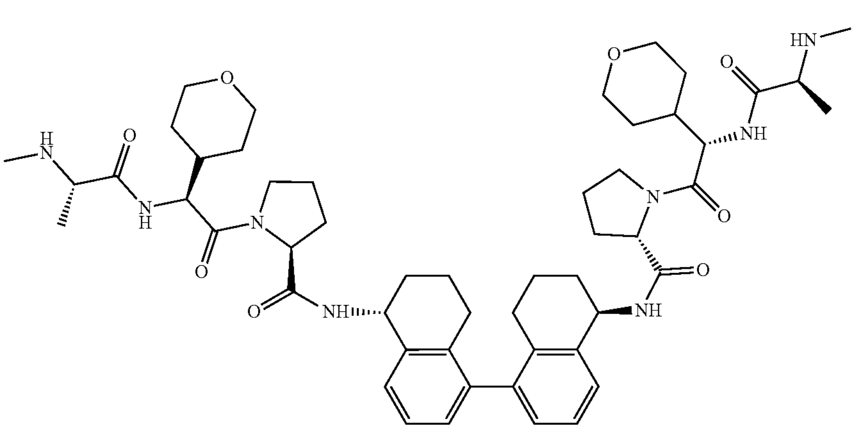

(S)-1-((S)-2-((S)-2-(methylamino)propanamido)-2-(tetrahydro-2H-pyran-4-yl)acetyl)-N-((5R,5'R)-5'-((S)-1-((S)-2-((S)-2-(methylamino)propanamido)-2-(tetrahydro-2H-pyran-4-yl)acetyl)pyrrolidine-2-carboxamido)-5,5',6,6',7,7',8,8'-octahydro-[1,1'-binaphthalen]-5-yl)pyrrolidine-2-carboxamide (Compound V-K)

LCMS (ESL, m/z): $[M+H]^+$=939.6. $^1$H NMR (300 MHz, DMSO-$d_6$) δ 8.56-8.25 (m, 2H), 8.03-7.93 (m, 2H), 7.36-7.25 (m, 21H), 7.25-7.12 (m, 2H), 6.95-6.81 (m, 2H), 5.05-4.89 (m, 2H), 4.61-4.44 (m, 2H), 4.40-4.26 (nm, 2H), 3.97-3.56 (nm, 8H), 3.30-3.18 (m, 4H), 3.03-2.90 (m, 2H), 2.38-1.92 (m, 18H), 1.90-1.69 (m, 10H), 1.68-1.50 (m, 6H), 1.42-1.18 (m, 4H), 1.18-1.05 (m, 6H).

V-L

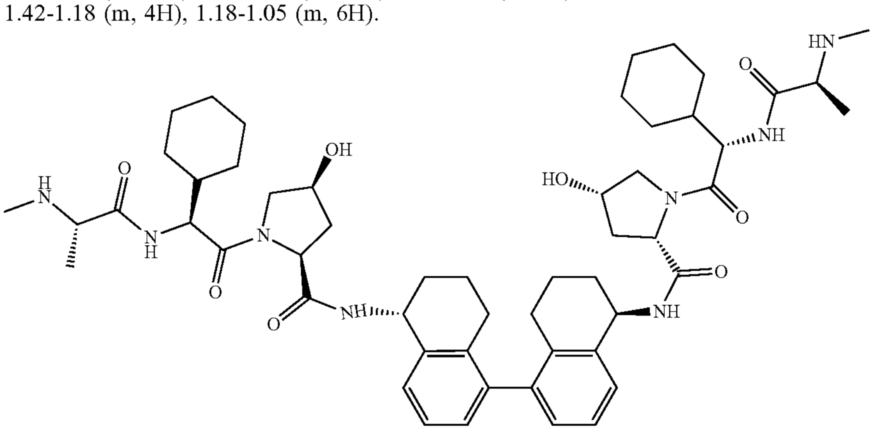

(2S,4S)-1-[(2S)-2-cyclohexyl-2-[(2S)-2-(methylamino)propanamido]acetyl]-N-[(5R,5'R)-5'-[(2S,4S)-1-[(2S)-2-cyclohexyl-2-[(2S)-2-(methylamino)propanamido]acetyl]-4-hydroxypyrrolidine-2-amido]-5H,5'H,6H,6'H,7H,7'H,8H,8'H-[1,1'-binaphthalen]-5-yl]-4-hydroxypyrrolidine-2-carboxamide (Compound V-L)

LCMS (ESI, m/z): $[M+H]^+$=967.7. $^1$H NMR (300 MHz, DMSO-$d_6$): δ 8.49-8.33 (m, 2H), 8.01-7.88 (m, 2H), 7.41-7.30 (m, 2H), 7.28-7.15 (m, 2H), 6.96-6.77 (m, 2H), 5.59-5.45 (m, 2H), 5.13-4.92 (m, 2H), 4.49-4.30 (m, 4H), 4.29-4.15 (m, 2H), 3.99-3.85 (m, 2H), 3.55-3.43 (m, 2H), 3.03-2.91 (m, 2H), 2.38-2.28 (m, 4H), 2.23-2.11 (m, 8H), 1.98-1.47 (m, 24H), 1.24-0.96 (m, 16H).

V-M

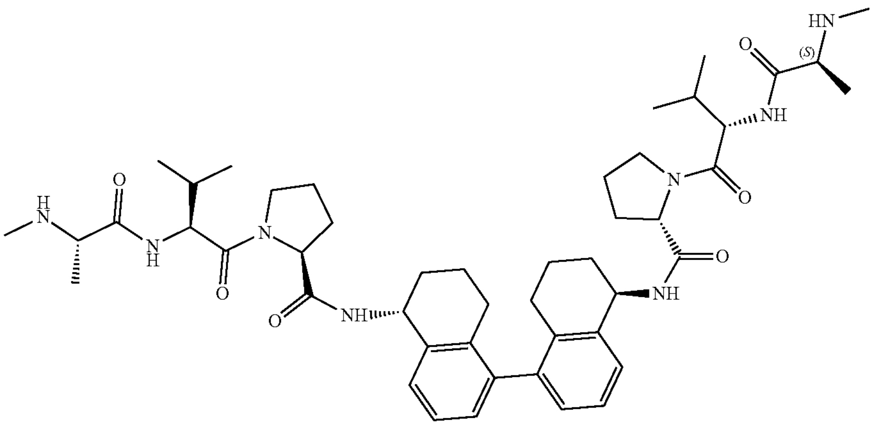

(2S)-1-[(2S)-3-methyl-2-[(2S)-2-(methylamino)propanamido]butanoyl]-N-[(5R,5'R)-5'-[(2S)-1-[(2S)-3-methy-2-[(2S)-2-(methylamino)propanamido]butanoyl]pyrolidine-2-amido]-5H,5'H,6H,6'H,7H,7'H,8H,8'H-[1,1'-binaphthalen]-5-yl]pyrrolidine-2-carboxamide (Compound V-M)

LCMS (ESI, m/z): $[M+H]^+$=855.7. $^1$H NMR (300 MHz, DMSO-$d_6$): δ 8.59-8.22 (m, 2H), 8.00-7.76 (m, 2H), 7.60-7.29 (m, 2H), 7.28-7.13 (m, 2H), 6.97-6.82 (m, 2H), 5.09-4.91 (m, 2H), 4.54-4.30 (m, 4H), 3.86-3.57 (m, 4H), 3.08-2.91 (m, 2H), 2.39-1.98 (m, 18H), 1.94-1.57 (m, 12H), 1.21-1.08 (m, 6H), 1.04-0.80 (m, 12H).

V-N

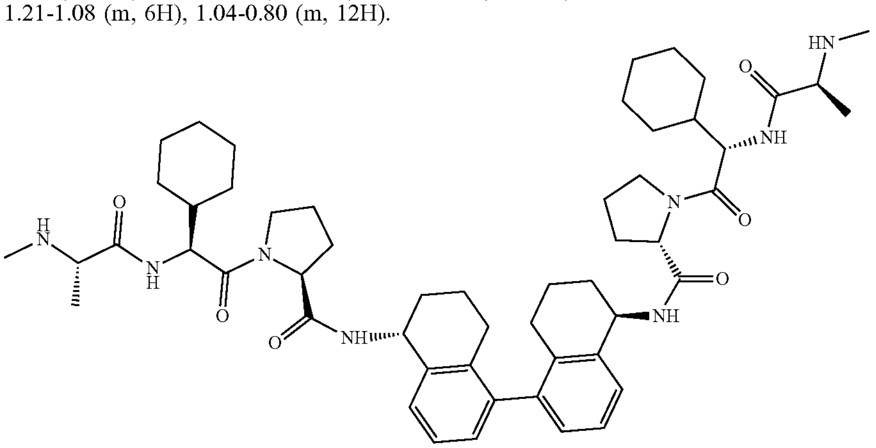

(2S)-1-[(2S)-2-cyclohexyl-2-[(2S)-2-(methylamino)propanamido]acetyl]-N-[(1R)-5-[(5R)-5-[(2S)-1-[(2S)-2-cyclohexyl-2-[(2S)-2-(methylamino)propanamido]acetyl]pyrolidine-2-amido]-5,6,7,8-tetrahydronaphthalen-1-yl]-1,2,3,4-tetrahydronaphthalen-1-yl]pyrrolidine-2-carboxamide (Compound V-N)

LCMS (ESI, m/z): $[M+H]^+$=935.8. $^1$H NMR (300 MHz, DMSO-$d_6$) δ 8.33-8.20 (m, 2H), 7.97-7.87 (m, 2H), 7.35-7.28 (m, 2H), 7.24-7.14 (m, 2H), 6.97-6.83 (m, 2H), 5.09-4.91 (m, 2H), 4.51-4.41 (m, 2H), 4.40-4.28 (nm, 2H), 3.83-3.70 (m, 2H), 3.68-3.58 (m, 2H), 3.04-2.90 (m, 2H), 2.40-2.31 (m, 1H), 2.27-2.13 (m, 8H), 2.11-1.96 (m, 6H), 1.91-1.53 (m, 25H), 1.25-0.92 (m, 16H).

V-O

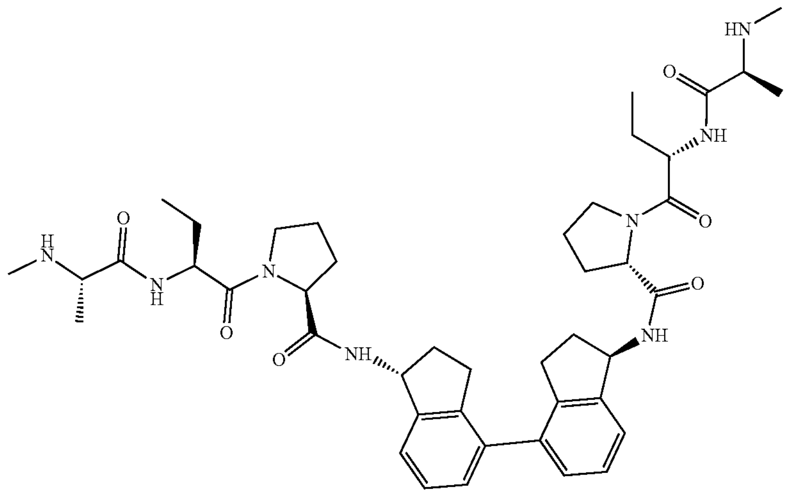

(2S,2'S)—N,N'-((1R,1'R)-2,2',3,3'-tetrahydro-1H, 1'H-[4,4'-biindene]-1,1'-diyl)bis(1-((S)-2-((S)-2-(methylamino)propanamido)butanoyl)pyrrolidine-2-carboxamide) (Compound V-O)

$[M+H]^+$=799.4. $^1$H NMR (300 MHz, DMSO-$d_6$): δ 8.34-8.17 (m, 2H), 8.08-7.93 (m, 2H), 7.45-7.21 (m, 4H), 7.19-7.08 (m, 2H), 5.42-5.27 (m, 2H), 4.61-4.50 (m, 2H), 4.38-4.30 (m, 2H), 3.78-3.56 (m, 4H), 3.02-2.92 (m, 2H), 2.90-2.77 (m, 2H), 2.62-2.56 (m, 2H), 2.38-2.28 (m, 2H), 2.25-2.17 (m, 7H), 2.16-1.98 (m, 5H), 1.93-1.69 (m, 8H), 1.66-1.50 (m, 2H), 1.16-1.07 (m, 6H), 0.96-0.82 (m, 6H).

V-P

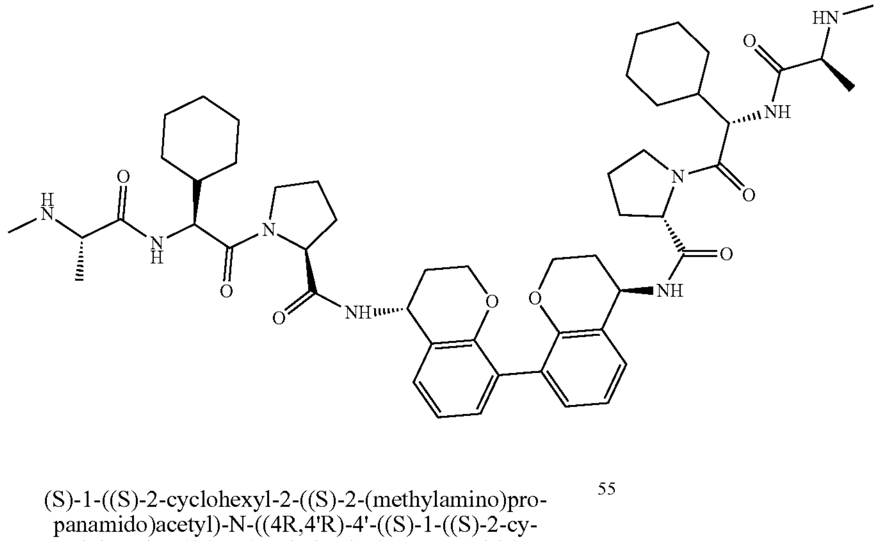

(S)-1-((S)-2-cyclohexyl-2-((S)-2-(methylamino)propanamido)acetyl)-N-((4R,4'R)-4'-((S)-1-((S)-2-cyclohexyl-2-((S)-2-(methylamino)propanamido) acetyl) pyrrolidine-2-carboxamido)-[8,8'-bichroman]-4-yl)pyrrolidine-2-carboxamide (Compound V-P)

LCMS (ESI, m/z): $[M+H]^+$=939.6. $^1$H NMR (300 MHz, DMSO-$d_6$): δ 8.74-8.33 (m, 2H), 7.98-7.73 (m, 2H), 7.55-7.12 (m, 2H), 7.08-6.98 (m, 2H), 6.97-6.82 (m, 2H), 5.13-4.92 (m, 2H), 4.56-4.25 (m, 4H), 4.21-3.99 (m, 4H), 3.83-3.58 (m, 4H), 3.06-2.91 (m, 2H), 2.28-2.15 (m, 6H), 2.14-1.96 (m, 6H), 1.96-1.40 (m, 20H), 1.29-0.89 (m, 16H).

V-Q
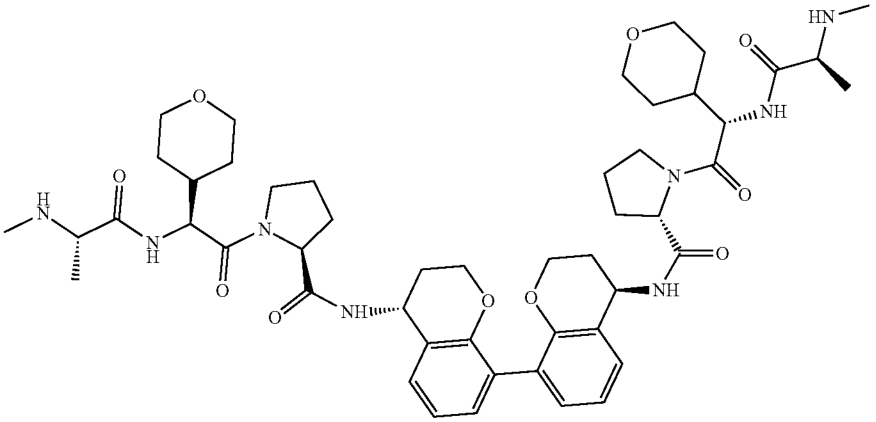
(S)-1-((S)-2-((S)-2-(methylamino)propanamido)-2-(tetrahydro-2H-pyran-4-yl)acetyl)-N-((4R,4'R)-4'-((S)-1-((S)-2-((S)-2-(methylamino)propanamido)-2-(tetrahydro-2H-pyran-4-yl)acetyl)pyrrolidine-2-carboxamido)-[8,8'-bichroman]-4-yl)pyrrolidine-2-carboxamide (Compound V-Q)
LCMS (ESI, m/z): $[M+H]^+$=943.5. $^1H$ NMR (300 MHz, DMSO-$d_6$): δ 8.78-8.33 (m, 2H), 8.07-7.75 (m, 2H), 7.59-7.10 (m, 2H), 7.07-6.98 (m, 2H), 6.94-6.83 (m, 2H), 5.10-4.89 (m, 2H), 4.60-4.42 (m, 2H), 4.39-4.27 (m, 2H), 4.22-4.00 (m, 4H), 3.93-3.63 (m, 8H), 3.25-3.17 ((m, 2H), 3.02-2.92 (m, 2H), 2.27-1.69 (m, 24H), 1.68-1.52 (m, 2H), 1.52-0.99 (m, 12H).
V-R
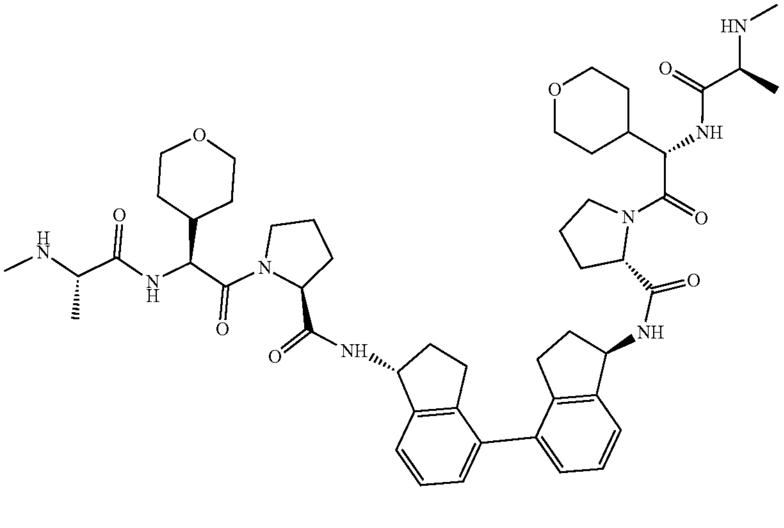

(S)-1-((S)-2-((S)-2-(methylamino)propanamido)-2-(tetrahydro-2H-pyran-4-yl)acetyl)-N-((1R,1'R)-1'-((S)-1-((S)-2-((S)-2-(methylamino)propanamido)-2-(tetrahydro-2H-pyran-4-yl)acetyl)pyrrolidine-2-carboxamido)-2,2',3,3'-tetrahydro-1H,1'H-[4,4'-biinden]-1-yl)pyrrolidine-2-carboxamide (Compound V-R)
LCMS (ESI, m/z): $[M+H]^+=911.6$. $^1H$ NMR (300 MHz, DMSO-$d_6$): δ 8.61-8.20 (m, 2H), 8.08-7.81 (m, 2H), 7.27-7.25 (m, 4H), 7.15-7.12 (m, 2H), 5.35-5.32 (m, 2H), 4.54-4.48 (m, 2H), 4.34-4.30 (m, 2H), 3.85-3.69 (m, 7H), 3.41-3.36 (m, 2H), 3.31-3.19 (m, 4H), 2.99-2.97 (m, 2H), 2.85-2.73 (m, 2H), 2.61-2.55 (m, 2H), 2.40-2.00 (m, 15H), 1.89-1.56 (m, 10H), 1.48-1.18 (m, 4H), 1.11 (d, J=6.6 Hz, 6H).
Example 6: Synthesis of Compound VI
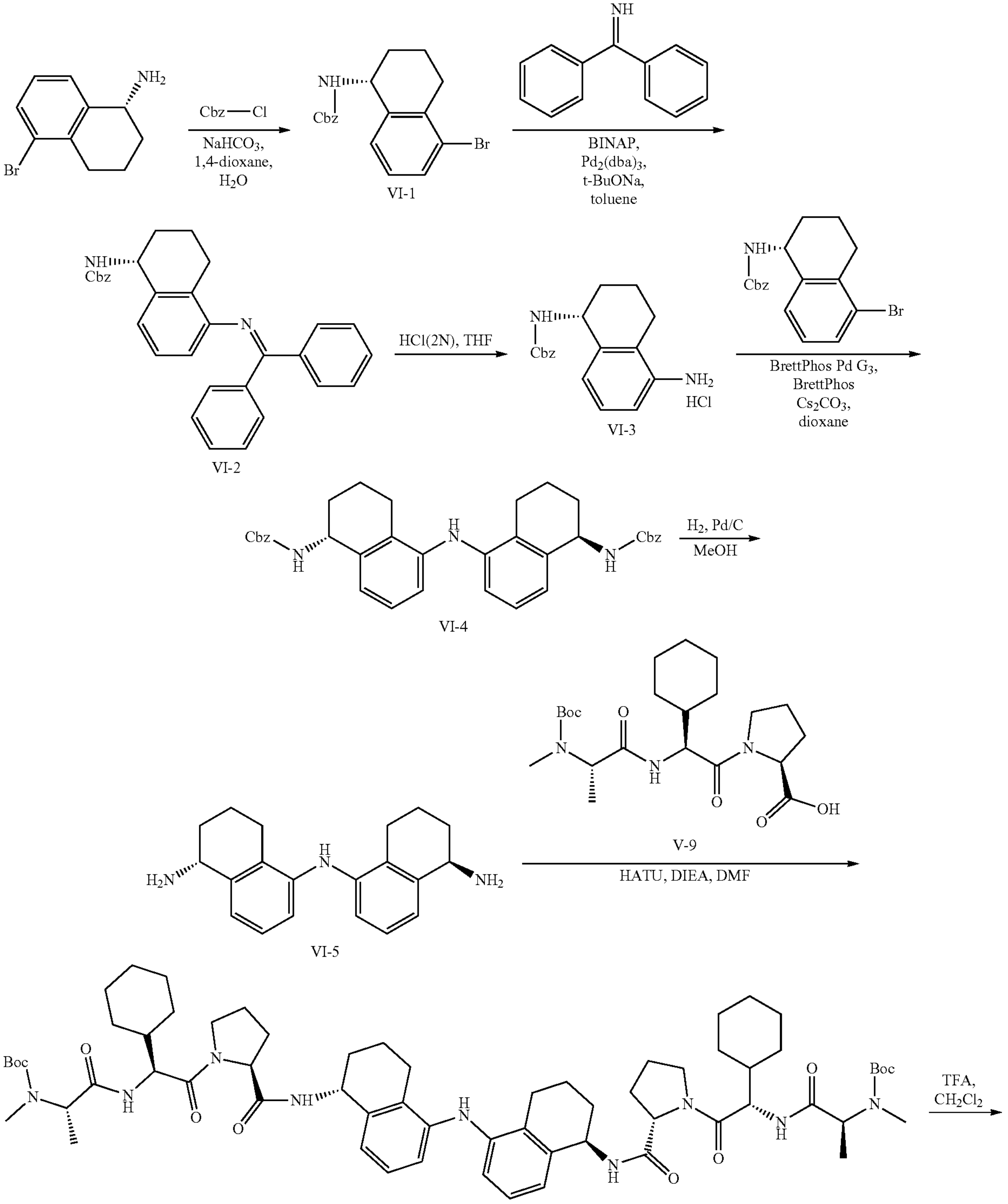

-continued

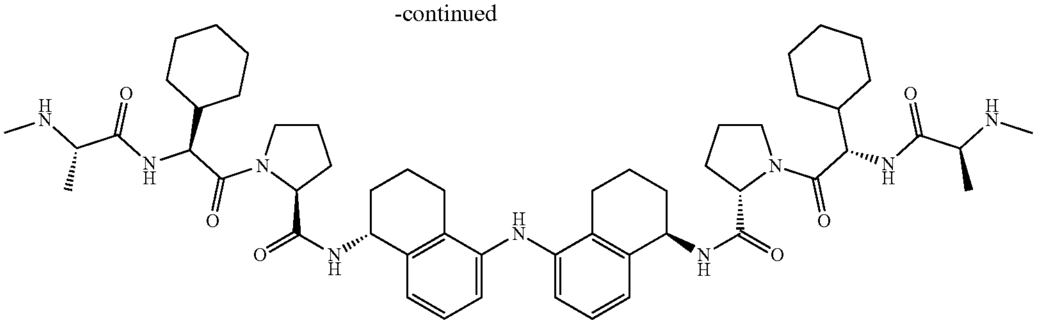

VI (R)-Benzyl 5-bromo-1,2,3,4-tetrahydronaphthalen-1-ylcarbamate (Compound VI-1)

To a solution of (R)-5-bromo-1,2,3,4-tetrahydronaphthalen-1-amine (500.0 mg 2.21 mmol) in dioxane/$H_2O$ (4.0/10.0 mL) was added $NaHCO_3$ (557.3 mg 6.63 mmol) and Cbz-Cl (452.7 n 2.65 mmol) at 0° C. under $N_2$. The resulting mixture was stirred at room temperature for 16 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with ethyl acetate/petroleum ether (1/10, v/v) to afford the title compound (570.0 mg 72%) as a white solid. LCMS (ESI, m/z): $[M+H]^+$=360.1.

(R)-Benzyl 5-(diphenylmethyleneamino)-1,2,3,4-tetrahydronaphthalen-1-ylcarbamate (Compound VI-2)

To a solution of compound VI-1 (500.0 mg, 1.39 mmol) in toluene (10.0 mL) was added diphenylmethanimine (264.1 mg, 1.46 mmol), $Pd_2(dba)_3$ (127.1 mg, 0.14 mmol), BINAP (172.8 mg, 0.28 mmol) and t-BuONa (200.1 mg, 2.08 mmol). The mixture was stirred at 80° C. for 16 h under $N_2$. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with ethyl acetate/petroleum ether (1/2, v/v) to afford the title compound (240.0 mg 38%) as a yellow solid. LCMS (ESI, m/z): $[M+H]^+$=461.2.

(R)-Benzyl 5-amino-1,2,3,4-tetrahydronaphthalen-1-ylcarbamate hydrochloride (Compound VI-3)

To a solution of compound VI-2 (315.0 mg, 0.98 mmol) in THF (5.0 mL) was added HCl (1 mL, 2 mol/L). The mixture was stirred at room temperature for 3 h. After the reaction was completed, the mixture was concentrated under vacuum to afford the title compound (160.0 mg, crude) as a yellow solid. LCMS (ESI, m/z): $[M+H]^+$=297.2.

Benzyl N-[(1R)-5-{[(5R)-5-{[(benzyloxy)carbonyl]amino}-5,6,7,8-tetrahydro naphthalen-1-yl]amino}-1,2,3,4-tetrahydronaphthalen-1-yl]carbamate (Compound VI-4)

To a solution of compound VI-3 (120.0 mg, crude) in dioxane (10.0 mL) was added (R)-benzyl 5-bromo-1,2,3,4-tetrahydronaphthalen-1-ylcarbamate (145.9 mg, 0.41 mmol), BrettPhos Pd G3 (36.7 mg 0.04 mmol), BrettPhos (43.5 mg 0.08 mmol) and $Cs_2CO_3$ (263.9 mg, 0.81 mmol). The mixture was stirred at 100° C. for 16 h under $N_2$. After the reaction was completed, the mixture was diluted with $H_2O$ and extracted with EtOAc. The combined organic layer was washed with brine, dried over anhydrous sodium sulfate and filtered. The filtrate was concentrated under vacuum. The residue was purified by reverse phase flash column chromatography with 5-100% $CH_3CN$ in $H_2O$ to afford the title compound (200.0 mg, 86%) as a yellow solid. LCMS (ESI, m/z): $[M+H]^+$=576.3.

(R)—N1-((R)-5-amino-5,6,7,8-tetrahydronaphthalen-1-yl)-5,6,7,8-tetrahydro naphthalene-1,5-diamine (Compound VI-5)

To a solution of compound VI-4 (200.0 mg, 0.35 mmol) in $CH_3OH$ (10.0 mL) was added Pd/C (40.0 mg, dry). The mixture was stirred at room temperature for 16 h under $H_2$. After the reaction was completed, the mixture was filtered. The filtrate was evaporated in vacuo to afford the title compound (50.0 mg, crude) as a yellow solid. LCMS (ESI, m/z): $[M+H]^+$=308.3.

tert-Butyl ((S)-1-(((S)-2-((S)-2-(((R)-5-(((R)-5-((S)-1-((S)-2-((S)-2-((tert-butoxy carbonyl)(methyl)amino)propanamido)-2-cyclohexylacetyl)pyrrolidine-2-carboxamido)-5,6,7,8-tetrahydronaphthalen-1-yl)amino)-1,2,3,4-tetrahydronaphthalen-1-yl)carbamoyl) pyrrolidin-1-yl)-1-cyclohexyl-2-oxoethyl)amino)-1-oxo propan-2-yl)(methyl)carbamate (Compound VI-6)

To a solution of compound VI-5 (40.0 mg, 0.13 mmol) in DMF (5.0 mL) was V-9 (114.4 mg, 0.26 mmol), DIEA (84.1 mg, 0.65 mmol) and HATU (123.7 mg, 0.33 mmol). The resulting mixture was stirred at 0° C. for 1 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with DCM/methanol (10/1, v/v) to afford the title compound (130.0 mg, 87%) as a yellow solid. LCMS (ESI, m/z): $[M+H]^+$=1150.7.

(S)-1-((S)-2-cyclohexyl-2-((S)-2-(methylamino)propanamido)acetyl)-N—((R)-5-(((R)-5-((S)-1-((S)-2-cyclohexyl-2-((S)-2-(methylamino)propanamido)acetyl)pyrrolidine-2-carboxamido)-5,6,7,8-tetrahydronaphthalen-1-yl)amino)-1,2,3,4-tetrahydro naphthalen-1-yl)pyrrolidine-2-carboxamide (Compound VI)

To a solution of VI-6 (130.0 mg, 0.11 mmol) in DCM (10.0 mL) was added TFA (2.0 mL). The mixture was stirred at room temperature for 1 h. After the reaction was completed, the mixture was diluted with $H_2O$. The pH value of the mixture was adjusted to 7 with saturated $NaHCO_3$ solution. The mixture was extracted with ethyl acetate. The combined organic layer was washed with brine, dried over anhydrous sodium sulfate and filtered. The filtrate was concentrated under vacuum. The residue was purified by Prep-HPLC with the following conditions: Column: XBridge Prep OBD C18 Colum, 30×150 mm, 5 um Mobile Phase A: Water (10 mmol/L $NH_4HCO_3$), Mobile Phase B:ACN; Flow rate: 60 mL/min; Gradient 39% B to 69% B in 7 min; 220 nm to afford the title compound (26.6 mg 25%) as a white solid. LCMS (ESI, m/z): $[M+H]^+$=950.6 $^1$H NMR (300 MHz, DMSO-$d_6$) δ 8.42-8.15 (m, 2H), 7.91-7.71 (m, 2H), 7.11-6.99 (m, 2H), 6.97-6.88 (m, 2H), 6.71-6.58 (s, 2H), 6.48 (s, 1H), 4.98-4.87 (m, 2H), 4.55-4.40 (m, 2H), 4.39-4.28 (m, 2H), 3.85-3.69 (m, 2H), 3.68-3.52 (m, 2H), 3.01-2.89 (m, 2H), 2.58-2.54 (m, 3H), 2.22-2.10 (m, 6H), 2.09-1.91 (m, 5H), 1.90-1.79 (m, 9H), 1.78-1.51 (m, 15H), 1.29-0.90 (m, 16H).

Following the procedure described above for Example 6 and substituting the appropriate reagents, starting materials and purification methods known to those skilled in the art, the compounds listed below were prepared.

VI-A

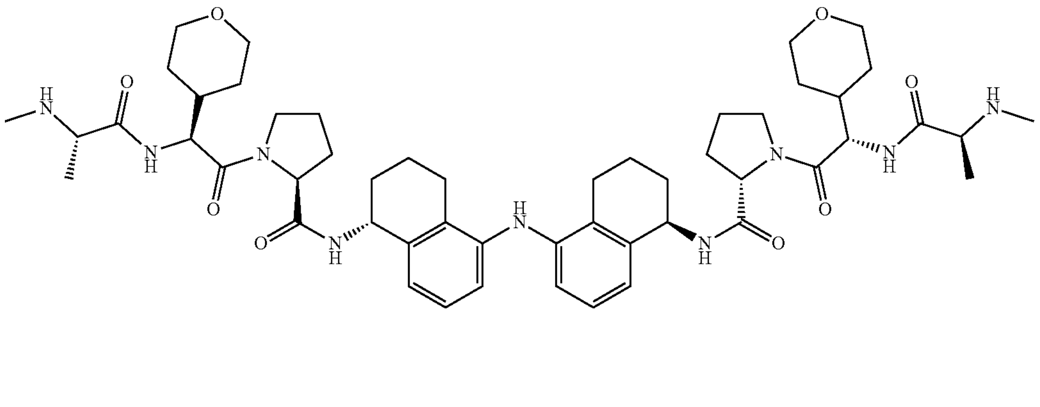

(S)-1-((S)-2-((S)-2-(methylamino)propanamido)-2-(tetrahydro-2H-pyran-4-yl)acetyl)-N—((R)-5-(((R)-5-((S)-1-((S)-2-((S)-2-(methylamino)propanamido)-2-(tetrahydro-2H-pyran-4-yl)acetyl)pyrrolidine-2-carboxamido)-5,6,7,8-tetrahydro naphthalen-1-yl) amino)-1,2,3,4-tetrahydronaphthalen-1-yl) pyrrolidine-2-carboxamide (Compound VI-A)

LCMS (ESI, m/z): $[M+H]^+$=954.0. $^1$H NMR (300 MHz, DMSO-$d_6$): δ 8.22 (d, J=8.7 Hz, 2H), 7.98 (d, J=8.7 Hz, 2H), 7.11-6.95 (m, 2H), 6.88 (d, J=7.5 Hz, 2H), 6.59 (d, J=7.5 Hz, 2H), 6.50 (s, 1H), 4.99-4.85 (m, 2H), 4.56-4.44 (m, 2H), 4.41-4.27 (m, 2H), 3.91-3.68 (m, 8H), 3.32-3.17 (m, 5H), 3.06-2.92 (m, 2H), 2.22-2.17 (m, 7H), 2.15-1.52 (m, 24H), 1.28-1.09 (m, 12H).

VI-B

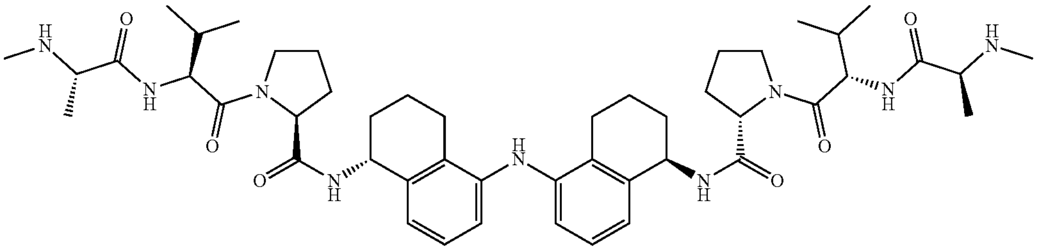

(S)-1-(methyl-L-alanyl-L-valyl)-N—((R)-5-(((R)-5-((S)-1-(methyl-L-alanyl-L-valyl)pyrolidine-2-carboxamido)-5,6,7,8-tetrahydronaphthalen-1-yl) amino)-1,2,3,4-tetrahydronaphthalen-1-yl) pyrrolidine-2-carboxamide (Compound VI-B)

LCMS (ESI, m/z): $[M+H]^+$=870.6. $^1$H NMR (300 MHz, DMSO-$d_6$): δ 8.23 (d, J=8.7 Hz, 2H), 7.95 (d, J=9.0 Hz, 2H), 7.07-6.86 (m, 4H), 6.64-6.54 (m, 2H), 6.50 (s, 1H), 5.00-4.90 (m, 2H), 4.50-4.28 (m, 4H), 3.79-3.56 (m, 4H), 3.10-2.96 (m, 3H), 2.60-2.54 (m, 3H), 2.23-2.16 (m, 7H), 2.14-1.94 (m, 6H), 1.91-1.51 ((m, 13H), 1.20-1.07 (m, 6H), 1.01-0.77 (n, 12H).

VI-C

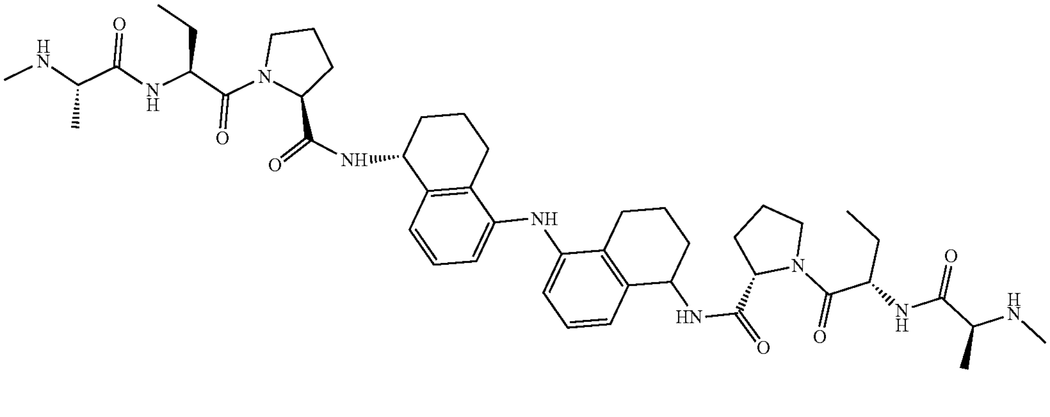

(2S,2'S)—N,N'-((1R,1'R)-azanediylbis(1,2,3,4-tetra-hydronaphthalene-5,1-diyl))bis(1-((S)-2-((S)-2-(methylamino)propanamido)butanoyl)pyrrolidine-2-carboxamide) (Compound VI-C)
LCMS (ESI, m/z): $[M+H]^+$=842.5. $^1H$ NMR (300 MHz, DMSO-$d_6$): δ 8.62-7.95 (m, 6H), 7.07-6.95 (m, 2H), 6.88-6.85 (m, 2H), 6.63-6.48 (m, 3H), 5.02-4.90 (m, 2H), 4.59-4.46 (m, 3H), 4.38-4.29 (m, 3H), 3.73-3.58 (m, 5H), 3.15-3.05 (m, 2H), 2.30-2.21 (m, 6H), 2.12-1.50 (m, 21H), 1.22-1.10 (m, 6H), 0.96-0.77 (m, 6H).
Example 7: Synthesis of Compound VII
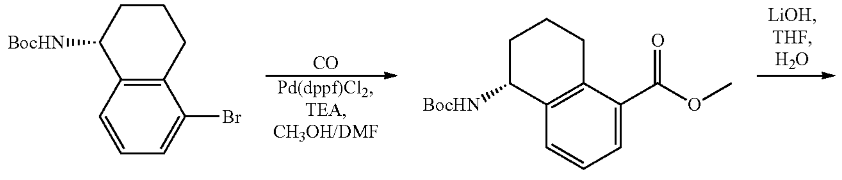
VII-1
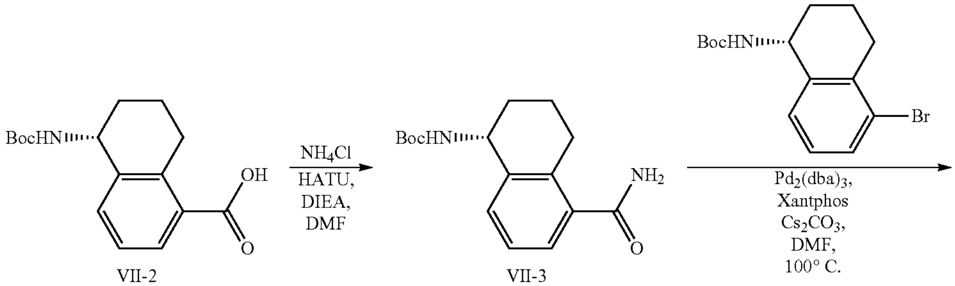
VII-2
VII-3
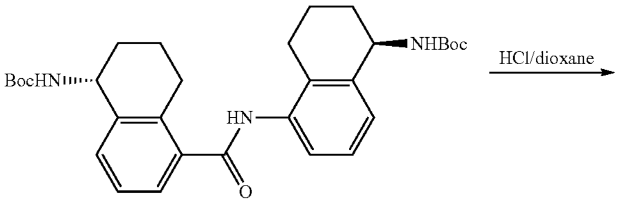
VII-4
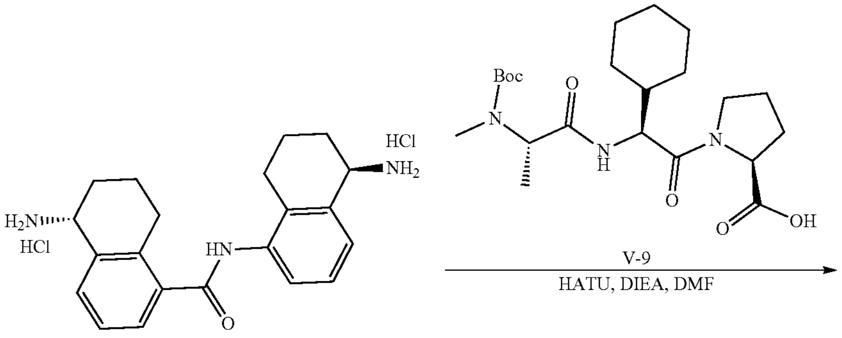
VII-5

-continued

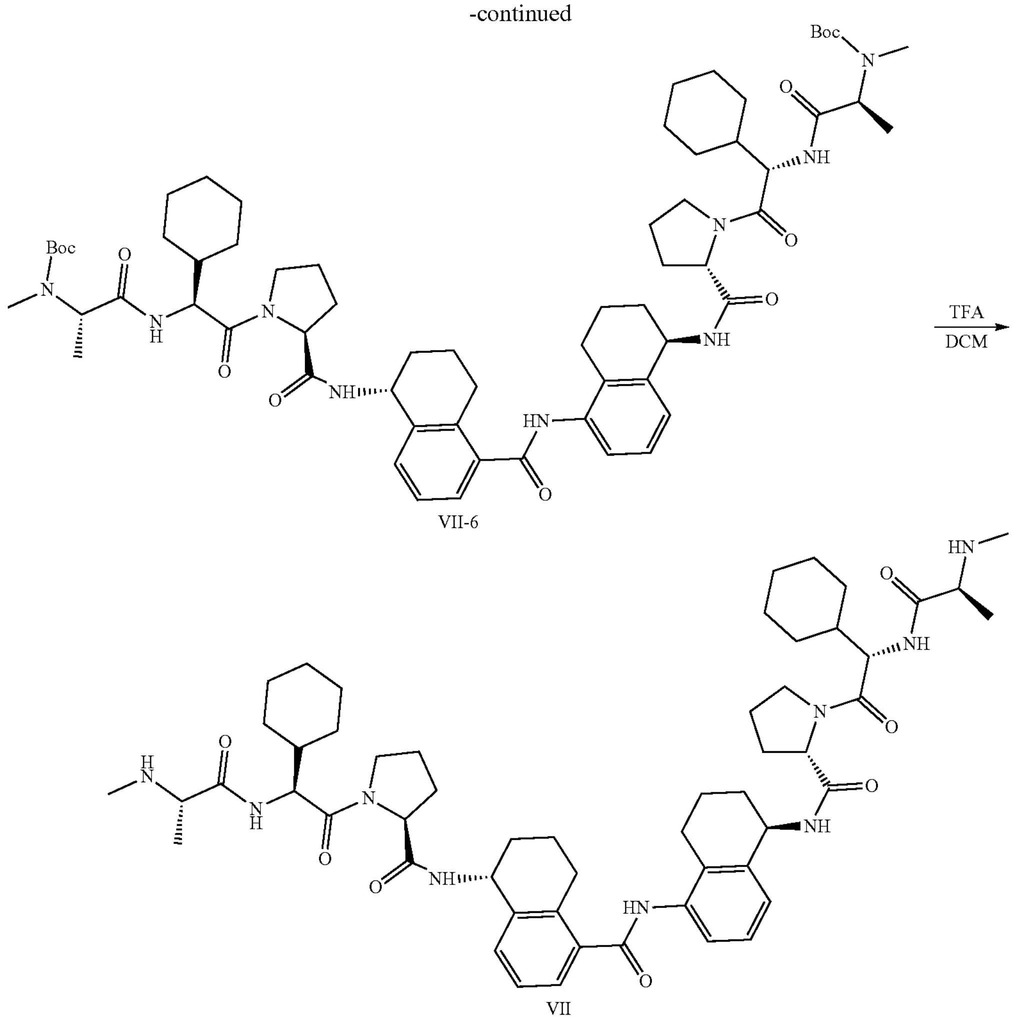

VII-6

VII (R)-Methyl 5-(tert-butoxycarbonylamino)-5,6,7,8-tetrahydronaphthalene-1-carboxylate (Compound VII-1)

To a solution of (R)-tert-butyl 5-bromo-1,2,3,4-tetrahydronaphthalen-1-ylcarbamate (500.0 mg, 1.53 mmol) in $CH_{30}H$ (20.0 mL) and DMF (6.0 mL) was added Pd(dppf) $Cl_2$ (112.1 mg, 0.15 mmol) and TEA (465.3 mg, 4.60 mmol). The resulting mixture was stirred at 80° C. for 16 h under CO. After the reaction was completed, the resulting mixture was diluted with $H_2O$ extracted with EtOAc. The combined organic layer was washed with brine, dried over anhydrous $Na_2SO_4$ and filtered. The filtrate was evaporated in vacuo. The residue was purified by flash column chromatography with petroleum ether/EtOAc (83/17, v/v) to afford the title compound (150.0 mg, 32%) as a light yellow solid. LCMS (ESI, m/z): $[M+H]^+$=306.2.

(R)-5-(tert-Butoxycarbonylamino)-5,6,7,8-tetrahydronaphthalene-1-carboxylic Acid (Compound VII-2)

To a solution of compound VII-1 (250.0 mg, 0.82 mmol) in THF (5.0 mL) and $H_2O$ (5.0 mL) was added LiOH (78.4 mg 3.28 mmol). The resulting mixture was stirred at 40° C. for 16 h. After the reaction was completed, the pH value of the mixture was adjusted to 4 with HCl (1 mol/L). The resulting mixture was extracted with EtOAc. The combined organic layer was washed with brine, dried over anhydrous $Na_2SO_4$ and filtered. The filtrate was concentrated under vacuum to afford the title compound (260.0 mg, crude) as a light yellow solid. LCMS (ESI, m/z): $[M+H]^+$=292.1.

(R)-tert-Butyl 5-carbamoyl-1,2,3,4-tetrahydronaphthalen-1-ylcarbamate (Compound VII-3)

To a solution of compound VII-2 (200.0 mg, 0.67 mmol) in DMF (8.0 ML) was added $NH_4Cl$ (146.9 mg, 2.75 mmol), DIEA (709.8 mg 5.49 mmol) and HATU (522.0 mg, 1.37 mmol) at 0° C. under $N_2$. The resulting mixture was stirred at room temperature for 2 h. After the reaction was completed, the reaction mixture was diluted with $H_2O$ and extracted with EtOAc. The combined organic layer was washed with brine, dried over anhydrous $Na_2SO_4$ and filtered. The filtrate was concentrated under vacuum. The residue was purified by flash column chromatography with petroleum ether/EtOAc (56/44, v/v) to afford the title compound (190.0 mg, 95%) as a white solid. LCMS (ESI, m/z): $[M+H]^+$=291.2.

tert-Butyl ((R)-5-(((R)-5-((tert-butoxycarbonyl)amino)-5,6,7,8-tetrahydro naphthalen-1-yl)carbamoyl)-1,2,3,4-tetrahydronaphthalen-1-yl)carbamate (Compound VII-4)

To a solution of compound VII-3 (150.0 mg, 0.52 mmol) in DMF (6.0 mL) was added (R)-tert-butyl 5-bromo-1,2,3,4-tetrahydronaphthalen-1-ylcarbamate (168.5 mg, 0.52 mmol), $Pd_2(dba)_3$ (47.3 mg, 0.05 mmol), XantPhos (59.8 mg, 0.10 mmol) and $Cs_2CO_3$ (336.6 mg, 1.03 mmol). The resulting mixture was stirred at 100° C. for 16 h under $N_2$. After the reaction was completed, the resulting mixture was diluted with $H_2O$ extracted with EtOAc. The combined organic layer was washed with brine, dried over anhydrous $Na_2SO_4$ and filtered. The filtrate was evaporated in vacuo. The residue was purified by flash column chromatography with petroleum ether/EtOAc (65/35, v/v) to afford the title compound (130.0 mg 47%) as a yellow solid. LCMS (ESI, m/z): $[M+H]^+$=536.3.

(R)-5-Amino-N—((R)-5-amino-5,6,7,8-tetrahydronaphthalen-1-yl)-5,6,7,8-tetrahydronaphthalene-1-carboxamide Dihydrochloride (Compound VII-5)

The solution of compound VII-4 (110.0 mg 0.21 mmol) in HCl/1,4-dioxane (5.0 mL, 4 mol/L) was stirred at room temperature for 2 h. After the reaction was completed, the resulting mixture was concentrated under vacuum to afford the tide compound (100.0 mg crude) as a white solid. LCMS (ESI, m/z): $[M+H]^+$=408.2.

tert-Butyl ((S)-1-(((S)-2-((S)-2-(((R)-5-((R)-5-((S)-1-((S)-2-((S)-2-((tert-butoxy carbonyl)methyl)amino)propanamido)-2-cyclohexylacetyl)pyrrolidine-2-carboxamido)-5,6,7,8-tetrahydronaphthalene-1-carboxamido)-1,2,3,4-tetrahydronaphthalen-1-yl)carbamoyl)pyrrolidin-1-yl)-1-cyclohexyl-2-oxoethyl)amino)-1-oxopropan-2-yl)methyl)carbamate (Compound VII-6)

To a solution of compound VII-5 (80.0 mg, crude) in DMF (5.0 mL) was added compound V-9 (230.6 mg, 0.53 mmol), DIEA (246.6 mg, 1.91 mmol) and HATU (453.4 mg 1.19 mmol) at 0° C. under $N_2$. The resulting mixture was stirred at 0° C. for 2 h. After the reaction was completed, the reaction was diluted with $H_2O$ extracted with EtOAc. The combined organic layer was washed with brine, dried over anhydrous $Na_2SO_4$ and filtered. The filtrate was concentrated under vacuum. The residue was purified by flash column chromatography with $CH_2Cl_2/CH_3OH$ (95/5, v/v) to afford the title compound (180.0 mg 64%) as a yellow solid. LCMS (ESI, m/z): $[M+H]^+$=1178.7.

(S)-1-((S)-2-Cyclohexyl-2-((S)-2-(methylamino)propanamido)acetyl)-N—((R)-5-(((R)-5-((S)-1-((S)-2-cyclohexyl-2-((S)-2-(methylamino)propanamido)acetyl)pyrrolidine-2-carboxamido)-5,6,7,8-tetrahydronaphthalen-1-yl)carbamoyl)-1,2,3,4-tetrahydro naphthalen-1-yl)pyrrolidine-2-carboxamide (Compound VII)

To a solution of compound VII-6 (130.0 mg 0.11 mmol) in $CH_2Cl_2$ (4.0 mL) was added TFA (2.0 mL). The resulting mixture was stirred at room temperature for 2 h. After the reaction was completed, the pH value of the mixture was adjusted to 7-8 with saturated $NaHCO_3$ solution. The resulting mixture was extracted with EtOAc. The combined organic layer was washed with brine, dried over anhydrous $Na_2SO_4$ and filtered. The filtrate was concentrated under vacuum. The residue was purified by Prep-HPLC with the following conditions: (Column: Xselect CSH OBD Column 30×150 mm, 5 um; Mobile Phase A: Water (0.05% FA), Mobile Phase B: ACN; Flow rate 60 mL/min; Gradient: 5% B to 35% B in 7 min; 254/220 nm) to afford the title compound (39.1 mg 36%) as a white solid. LCMS (ESI, m/z): $[M+H]^+$=978.7. $^1H$ NMR (300 MHz, DMSO-$d_6$) δ 9.63 (s, 1H), 8.51-8.18 (m, 2H), 7.92-7.70 (m, 2H), 7.50-7.09 (m, 6H), 5.04-4.89 (m, 2H), 4.52-4.26 (m, 4H), 3.81-3.54 (m, 4H), 3.01-2.81 (m, 4H), 2.76-2.64 (m, 2H), 2.24-2.12 (m, 6H), 2.11-1.93 (m, 6H), 1.92-1.50 (m, 24H), 1.24-0.89 (m, 16H).

Following the procedure described above for Example 7 and substituting the appropriate reagents, starting materials and purification methods known to those skilled in the art, the compounds listed below were prepared.

VII-A

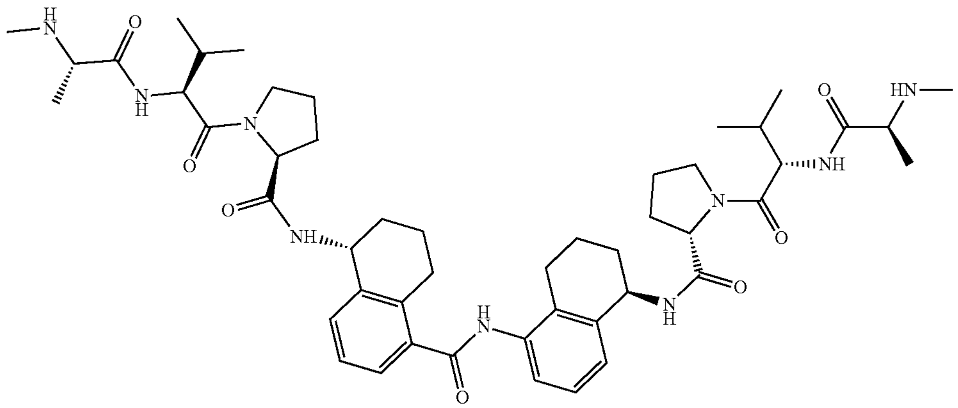

(2S)-1-[(2S)-3-methyl-2-[(2S)-2-(methylamino)propanamido]butanoyl]-N-[(1R)-5-[[(5R)-5-[(2S)-1-[(2S)-3-methyl-2-[(2S)-2-(methylamino)propanamido]butanoyl]pyrrolidine-2-amido]-5,6,7,8-tetrahydronaphthalen-1-yl]carbamoyl]-1,2,3,4-tetrahydro naphthalen-1-yl]pyrrolidine-2-carboxamide (Compound VI-A)

LCMS (ESI, m/z): $[M+H]^+$=898.6. $^1$H NMR (300 MHz, DMSO-$d_6$): δ 9.66 (s, 1H), 8.31-8.28 (m, 2H), 8.05-7.95 (m, 2H), 7.41-7.35 (m, 2H), 7.29-7.13 (m, 4H), 5.05-4.90 (m, 2H), 4.47-4.42 (m, 2H), 4.34-4.31 (m, 2H), 3.72-3.62 (m, 4H), 3.05-2.95 (m, 3H), 2.90-2.86 (m, 2H), 2.73-2.69 (m, 2H), 2.19 (s, 6H), 2.10-1.60 (m, 19H) 1.19-1.11 (m, 6H), 0.97-0.80 (m, 12H).

VII-B

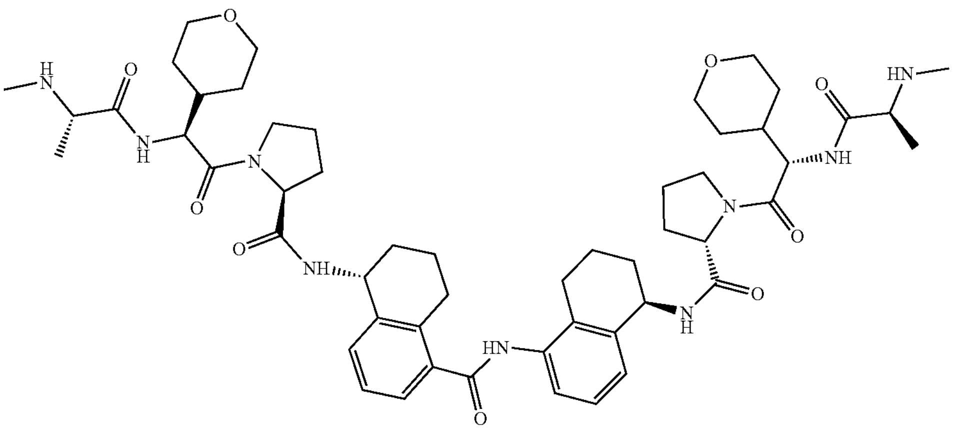

(2S)-1[(2S)-2-[(2S)-2-(methylamino)propanamido]-2-(oxan-4-yl)acetyl]-N-[(1R)-5-[[(5R)-5-[(2S)-1[(2S)-2-[(2S)-2-(methylamino)propanamido]-2-(oxan-4-yl)acetyl]pyrrolidine-2-amido]-5,6,7,8-tetrahydronaphthalen-1-yl]carbamoyl]-1,2,3,4-tetrahydro naphthalen-1-yl]pyrrolidine-2-carboxamide (Compound VII-B)

LCMS (ESI, m/z): $[M+H]^+$=982.5. $^1$H NMR (300 MHz, DMSO-$d_6$): δ 9.66 (s, 1H), 8.37-8.25 (m, 2H), 8.02-7.93 (m, 2H), 7.42-7.11 (m, 6H), 5.03-4.91 (m, 2H), 4.56-4.45 (m, 2H), 4.43-4.27 (m, 2H), 3.91-3.59 (m, 8H), 3.28-3.18 (m, 4H), 3.03-2.87 (m, 4H), 2.73-2.69 (m, 2H), 2.24-1.52 (m, 30H), 1.40-1.24 (m, 4H), 1.22-1.06 (m, 6H).

VII-C

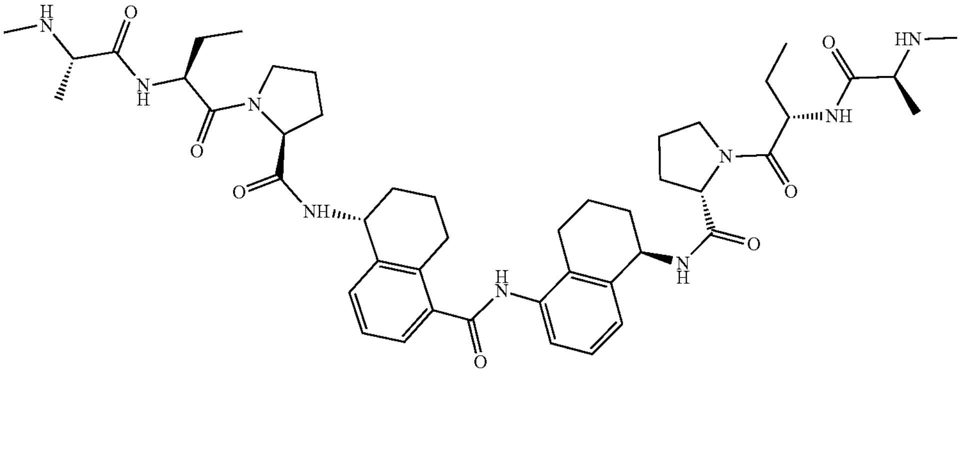

(2S)-1-[(2S)-2-[(2S)-2-(methylamino)propanamido] butanoyl]-N-[(1R)-5-[[(5R)-5-[(2S)-1-[(2S)-2-[(2S)-2-(methylamino)propanamido]butanoyl]pyrrolidine-2-amido]-5,6,7,8-tetrahydronaphthalen-1-yl] carbamoyl]-1,2,3,4-tetrahydronaphthalen-1-yl] pyrrolidine-2-carboxamide (Compound VII-C)

LCMS (ESI, m/z): $[M+H]^+$=870.5. $^1H$ NMR (300 MHz, DMSO-$d_6$): δ 9.67 (s, 1H), 8.30-8.20 (m, 2H), 8.03-7.93 (m, 2H), 7.41-7.03 (m, 6H), 5.05-4.93 (m, 2H), 4.58-4.48 (m, 2H), 4.40-4.26 (m, 2H), 3.73-3.57 (m, 3H), 3.02-2.83 (m, 4H), 2.76-2.67 (m, 2H), 2.26-2.15 (m, 6H), 2.13-1.49 (m, 23H), 1.19-1.06 (m, 6H), 0.96-0.76 (m, 6H).

VII-D

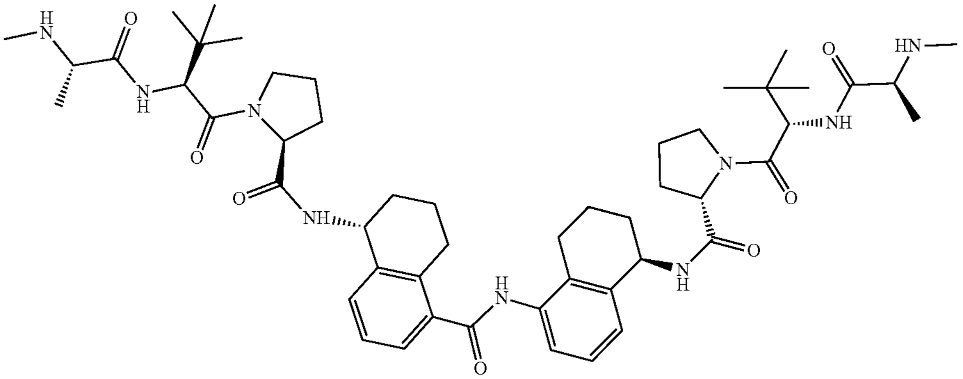

(S)-1-((S-3,3-dimethyl-2-((S)-2-(methylamino)propanamido)butanoyl)-N—((R)-5-(((R)-5-((S)—((S)-3,3-dimethyl-2-((S)-2-(methylamino)propanamido) butanoyl) pyrrolidine-2-carboxamido)-5,6,7,8-tetrahydronaphthalen-1-yl)carbamoyl)-1,2,3,4-tetrahydronaphthalen-1-yl)pyrrolidine-2-carboxamide (Compound VII-D)

LCMS (ESI, m/z): $[M+H]^+$=926.7. $^1H$ NMR (300 MHz, DMSO-$d_6$): δ 9.60 (s, 1H), 8.37-8.34 (m, 2H), 7.87-7.70 (m, 2H), 7.70-7.12 (m, 6H), 4.99-4.91 (m, 2H), 4.59-4.53 (m, 2H), 4.35-4.32 (m, 2H), 3.74-3.64 (m, 4H), 3.00-2.83 (m, 4H), 2.72-2.65 (m, 2H), 2.47-2.00 (m, 12H), 1.99-1.65 (m, 12H), 1.17-1.11 (m, 6H), 1.01-0.91 (m, 18H).

VII-E

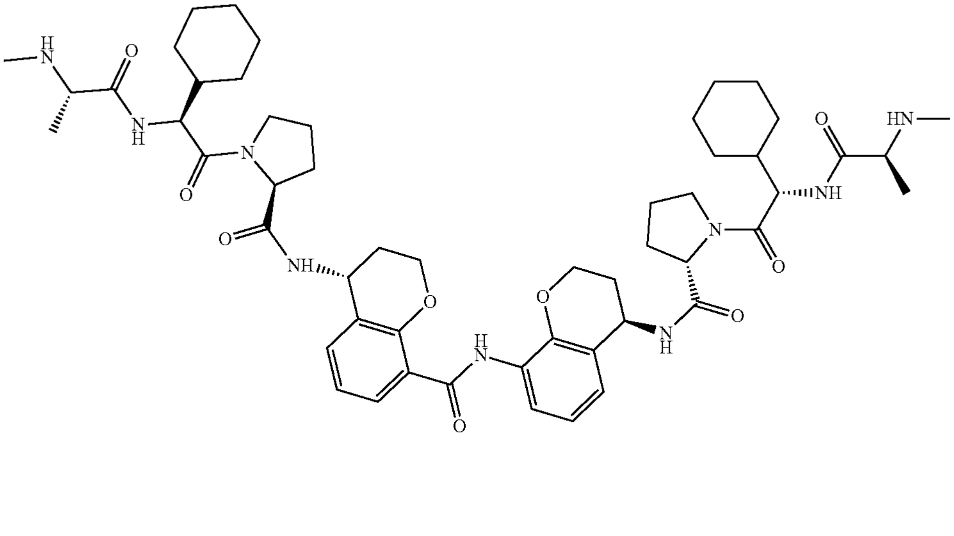

(2S)-1-[(2S)-2-cyclohexyl-2-[(2S)-2-(methylamino)propanamido]acetyl]-N-[(4R)-8-[[(4R)-4-[(2S)-1-[(2S)-2-cyclohexyl-2-[(2S)-2-(methylamino)propanamido]acetyl]pyrrolidine-2-amido]-3,4-dihydro-2H-1-benzopyran-8-yl]carbamoyl]-3,4-dihydro-2H-1-benzopyran-4-yl]pyrrolidine-2-carboxamide (Compound VII-E)

LCMS (ESI, m/z): $[M+H]^+=982.4$. $^1H$ NMR (300 MHz, DMSO-$d_6$): δ 10.60 (m, 1H), 8.78-8.42 (m, 1H), 8.39-8.30 (m, 2H), 8.04-7.95 (m, 1H), 7.94-7.68 (m, 2H), 7.52-7.44 (m, 1H), 7.17-6.84 (m, 3H), 5.29-4.89 (m, 2H), 4.66-4.22 (m, 8H), 3.84-3.45 (m, 4H), 3.06-2.88 (m, 2H), 2.34-1.44 (m, 32H), 1.34-0.84 (m, 16H).

VII-F

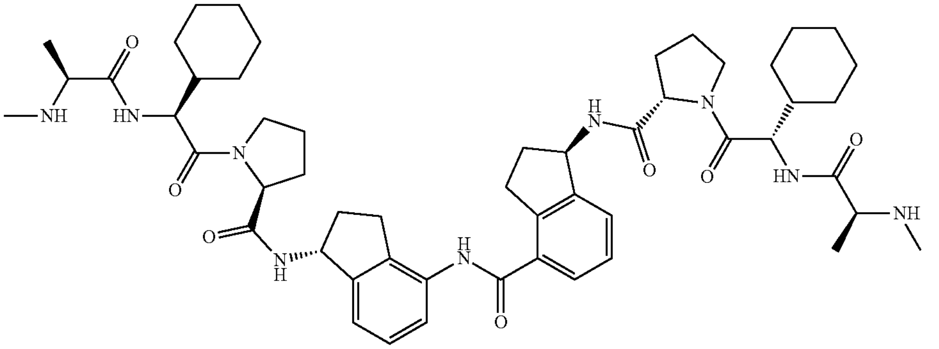

(2S)-1-[(2S)-2-cyclohexyl-2-[(2S)-2-(methylamino)propanamido]acetyl]-N-[(1R)-4-[[(1R)-1-[(2S)-[(2S)-2-cyclohexyl-2-[(2S)-2-(methylamino)propanamido]acetyl]pyrrolidine-2-amido]-2,3-dihydro-1H-inden-4-yl]carbamoyl]-2,3-dihydro-1H-inden-1-yl]pyrolidine-2-carboxamide (Compound VII-F)

LCMS (ESI, m/z): $[M+H]^+=950.5$. $^1H$ NMR (300 MHz, DMSO-$d_6$): δ 9.78 (s, 1H), 8.27-8.20 (m, 2H), 7.92-7.88 (m, 2H), 7.62-7.59 (m, 1H), 7.42-7.40 (m, 2H), 7.33-7.31 (m, 1H), 7.21-7.16 (m, 1H), 7.11-7.09 (m, 1H), 5.35-5.21 (m, 2H), 4.45-4.30 (m, 4H), 3.77-3.65 (m, 4H), 3.22-3.16 (m, 2H), 2.99-2.94 (m, 4H), 2.83-2.72 (m, 1H), 2.40-2.34 (m, 3H), 2.22-2.18 (m, 6H), 2.08-2.02 (m, 4H), 1.84-1.61 (m, 18H), 1.22-0.98 (m, 16H).

Example 8: Synthesis of Compound VIII

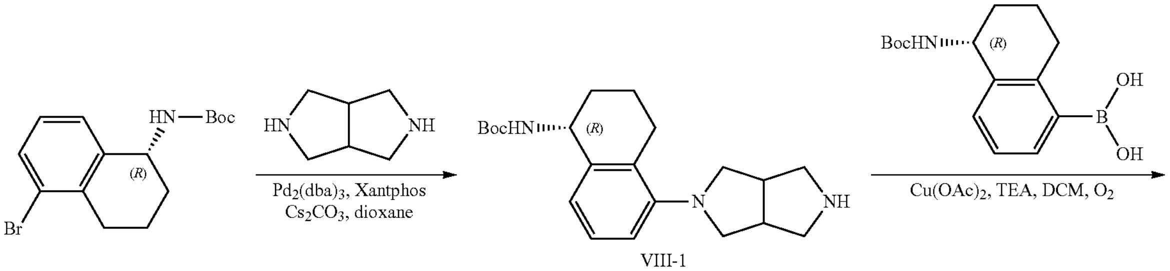

VIII-1

-continued

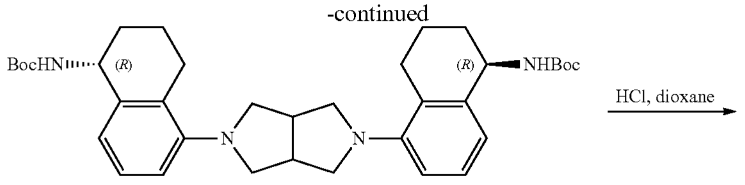

VIII-2

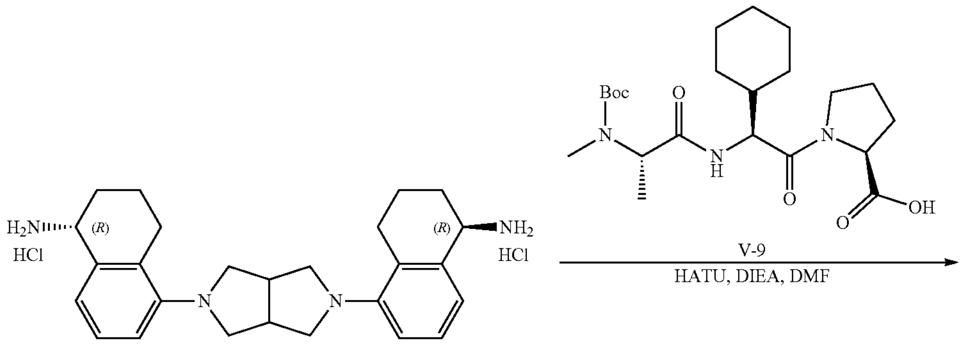

VIII-3

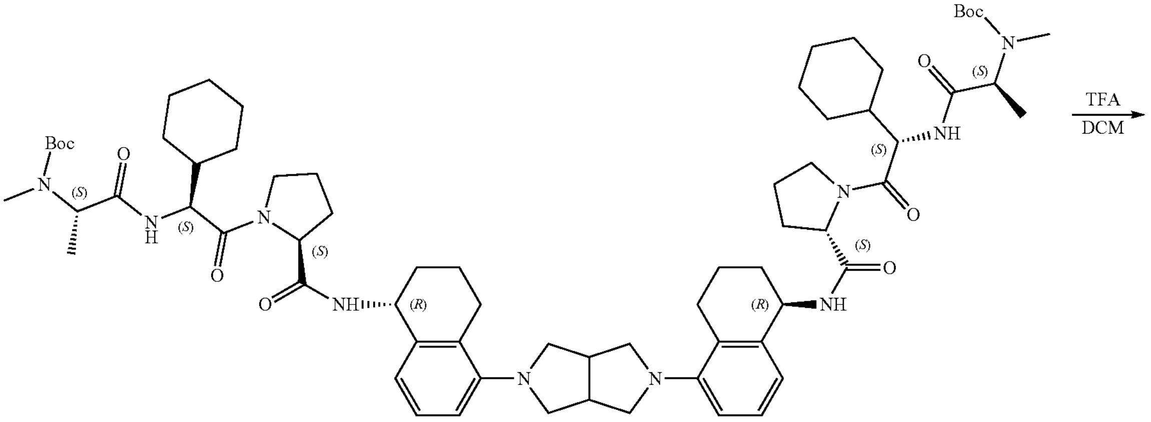

VIII-4

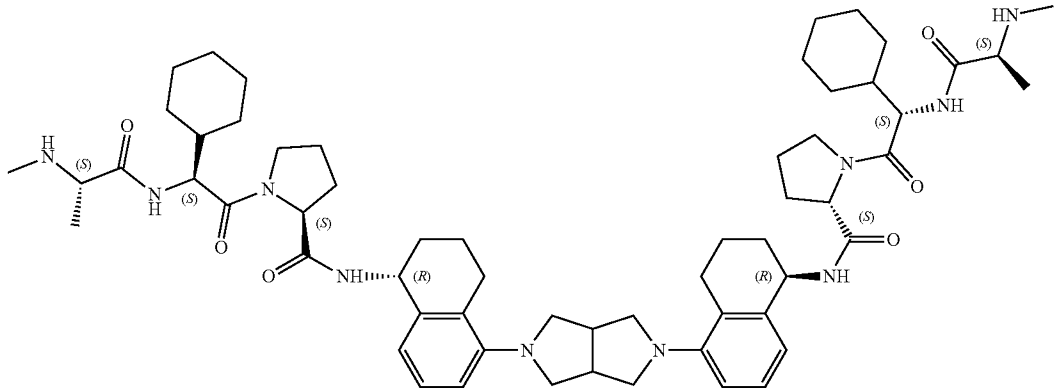

VIII tert-Butyl (R)-5-(hexahydropyrrolo[3,4-c]pyrrol-2 (1H)-yl)-1,2,3,4-tetrahydro naphthalen-1-ylcarbamate (Compound VIM-1)

To a solution of (R)-tert-butyl 5-bromo-1,2,3,4-tetrahydronaphthalen-1-ylcarbamate (500.0 mg, 1.53 mmol) in dioxane (10.0 mL) was added octahydropyrrolo[3,4-c]pyrrole (515.8 Mg 4.60 mmol) $Pd_2(dba)_3$ (140.4 Mg 0.15 mmol), XantPhos (177.4 mg, 0.31 mmol) and $Cs_2CO_3$ (1248.4 mg 3.83 mmol). The mixture was stirred at 100° C. for 16 h under $N_2$ atmosphere. After the reaction was completed, the mixture was diluted with $H_2O$ and extracted with EtOAc. The combined organic layer was washed with brine, dried over anhydrous sodium sulfate and filtered. The filtrate was concentrated under vacuum. The residue was purified by reverse phase flash column chromatography with 5-100% $CH_3CN$ in $H_2O$ to afford the title compound (280.0 mg 51%) as a yellow solid. LCMS (ESI, m/z): $[M+H]^+$=358.2.

tert-Butyl N-[(1R)-5-[5-[(5R)-5-[(tert-butoxycarbonyl)amino]-5,6,7,8-tetrahydro naphthalen-1-yl]-hexahydropyrrolo[3,4-c]pyrrol-2-yl]-1,2,3,4-tetrahydronaphthalen-1-yl]carbamate (Compound VIII-2)

To a solution of compound VIII-1 (200.0 mg, 0.55 mmol) in DCM (10.0 mL) was added (5R)-5-[(tert-butoxycarbonyl) amino]-5,6,7,8-tetrahydronaphthalen-1-ylboronic acid (244.3 mg, 0.84 mmol) $Cu(OAc)_2$ (203.2 mg, 1.12 mmol), TEA (226.4 mg 2.24 mmol) and 4 A MS (50.0 mg). The mixture was stirred at room temperature for 16 h under 02 atmosphere. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by reverse phase flash column chromatography with 5-100% $CH_3CN$ in $H_2O$ to afford the title compound (38.0 mg, 11%) as a yellow oil. LCMS (ESI, m/z): $[M+H]^+$=603.4.

(1R)-5-[5-[(5R)-5-amino-5,6,7,8-tetrahydronaphthalen-1-yl]-hexahydropyrrolo[3,4-c]pyrrol-2-yl]-1,2,3,4-tetrahydronaphthalen-1-amine Dihydrochloride (Compound VIII-3)

The solution of compound VII-2 (38.0 mg, 0.06 mmol) in HCl/dioxane (5.0 mL, 4 mol/L) was stirred at room temperature for 1 h. After the reaction as completed, the mixture was concentrated under vacuum to afford the title compound (40.0 mg, crude) as a white solid. LCMS (ESI, m/z): $[M+H]^+$=403.3.

tert-Butyl N-[(1S)-1-[[(1S)-2-[(2S)-2-[[(1R)-5-[5-[(5R)-5-[(2S)-1-[(2S)-2-[(2S)-2-[(tert-butoxycarbonyl)(methyl)amino]propanamido]-2-cyclohexylacetyl]pyrrolidine-2-amido]-5,6,7,8-tetrahydronaphthalen-1-yl]-hexahydropyrrolo[3,4-c]pyrol-2-yl]-1,2,3,4-tetrahydronaphthalen-1-yl]carbamoyl]pyrrolidin-1-yl]-1-cyclohexyl-2-oxoethyl]carbamoyl]ethyl]-N-methylcarbamate (Compound VIII-4)

To a solution of compound V-9 (40.0 mg, 0.09 mmol) in DMF (5.0 mL) was compound VIII-3 (95.2 mg 0.20 mmol), DIEA (58.8 mg, 0.46 mmol) and HATU (86.5 mg, 0.23 mmol). The resulting mixture was stirred at 0° C. for 1 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with DCM/methanol (10/1, v/v) to afford the title compound (100.0 mg 48%) as a yellow solid. LCMS (ESI, m/z): $[M+H]^+$=1245.8.

(2S)-1-[(2S)-2-cyclohexyl-2-[(2S)-2-(methylamino) propanamido]acetyl]-N-[(1R)-5-[5-[(5R)-5-[(2S)-1-[(2S)-2-cyclohexyl-2-[(2S)-2-(methylamino)propanamido]acetyl]pyrrolidine-2-amido]-5,6,7,8-tetrahydronaphthalen-1-yl]-hexahydropyrrolo[3,4-c]pyrrol-2-yl]-1,2,3,4-tetrahydronaphthalen-1-yl]pyrrolidine-2-carboxamide (Compound VIII)

To a solution of compound VIII-4 (60.0 mg 0.05 mmol) in DCM (1.0 mL) was added TFA (0.1 mL). The mixture was stirred at room temperature for 1 h. After the reaction was completed, the mixture was diluted with $H_2O$. The pH value of the mixture was adjusted to 7 with aq. $NaHCO_3$ and then extracted with ethyl acetate. The combined organic layer was washed with brine, dried over anhydrous sodium sulfate and filtered. The filtrate was concentrated under vacuum. The residue was purified by Prep-HPLC with the following conditions: Column: YMC-Actus Triart C18, 20×250 nm, 5 um, 12 nm; Mobile Phase A: Water (10 mmol/L $NH_4HCO_3$), Mobile Phase B:ACN; Flow rate: 60 mL/min; Gradient: 62% B to 92% B in 7 min; 220 nm, RT=5.27 min to afford the title compound (8.9 mg 18%) as a white solid. LCMS (ESI, m/z): $[M+H]^+$=1045.7. $^1H$ NMR (300 MHz, DMSO-$d_6$) δ 8.12-8.07 (m, 2H), 7.91-7.69 (m, 2H), 7.30-7.02 (m, 2H), 6.97-6.86 (m, 4H), 4.96-4.86 (m, 2H), 4.47-4.21 (m, 4H), 3.76-3.53 (m, 4H), 3.21-3.04 (m, 4H), 2.99-2.81 (m, 8H), 2.76-2.57 (m, 4H), 2.22-1.91 (m, 12H), 1.90-1.38 (m, 24H), 1.25-0.84 (m, 16H).

Following the procedure described above for Example 8 and substituting the appropriate reagents, starting materials and purification methods known to those skilled in the art, the compounds listed below were prepared.

VIII-A

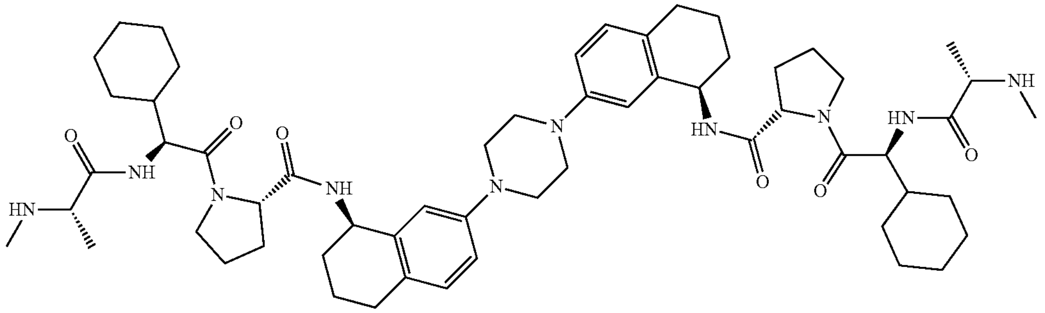

(2S)-1-[(2S)-2-cyclohexyl-2-[(2S)-2-(methylamino) propanamido]acetyl]-N-[(1R)-7-[4-[(8R)-8-[(2S)-1-[(2S)-2-cyclohexyl-2-[(2S)-2-(methylamino)propanamido]acetyl]pyrrolidine-2-amido]-5,6,7,8-tetrahydronaphthalen-2-yl]piperazin-1-yl]-1,2,3,4-tetrahydronaphthalen-1-yl]pyrrolidine-2-carboxamide (Compound-VIII-A)

LCMS (ESI, m/z): $[M+H]^+$=1019.8. $^1H$ NMR (300 MHz, DMSO-$d_6$) δ 8.26-8.10 (m, 2H), 7.90-7.78 (m, 2H), 7.03-6.78 (m, 6H), 5.00-4.76 (m, 2H), 4.53-4.35 (m, 2H), 4.35-4.21 (m, 2H), 4.07-3.50 (m, 4H), 3.31-3.18 (m, 7H), 2.99-2.95 (m, 2H), 2.73-2.64 (m, 4H), 2.28-2.17 (m, 7H), 2.17-1.99 (m, 4H), 1.84-1.50 (m, 25H), 1.20-0.93 (m, 17H).

VIII-B

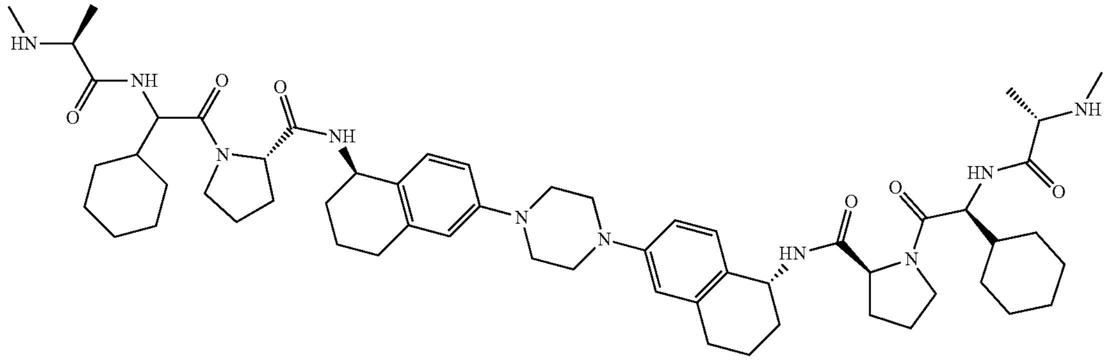

(2S)-1-[(2S)-2-cyclohexyl-2-[(2S)-2-(methylamino) propanamido]acetyl]-N-[1(1R)-6-[4-[(5R)-5-[(2S)-1-[(2S)-2-cyclohexyl-2-[(2S)-2-(methylamino)propanamido]acetyl]pyrrolidine-2-amido]-5,6,7,8-tetrahydronaphthalen-2-yl]piperazin-1-yl]-1,2,3,4-tetrahydronaphthalen-1-yl]pyrrolidine-2-carboxamide (Compound-VIII-B)

LCMS (ESI, m/z): $[M+H]^+$=1019.8. $^1H$ NMR (300 MHz, DMSO-$d_6$) δ 7.99 (d, J=9.0 Hz, 2H), 7.86 (d, J=9.0 Hz, 2H), 7.11 (d, J=8.4 Hz, 2H), 6.84-6.75 (m, 2H), 6.68 (s, 2H), 4.95-4.77 (m, 2H), 4.55-4.42 (m, 2H), 4.37-4.23 (m, 2H), 3.78-3.56 (m, 4H), 3.29-3.18 (m, 8H), 3.02-2.91 (m, 2H), 2.78-2.65 (m, 4H), 2.17 (s, 6H), 2.11-1.95 (m, 4H), 1.94-1.46 (m, 26H), 1.24-0.89 (m, 16H).

VIII-C

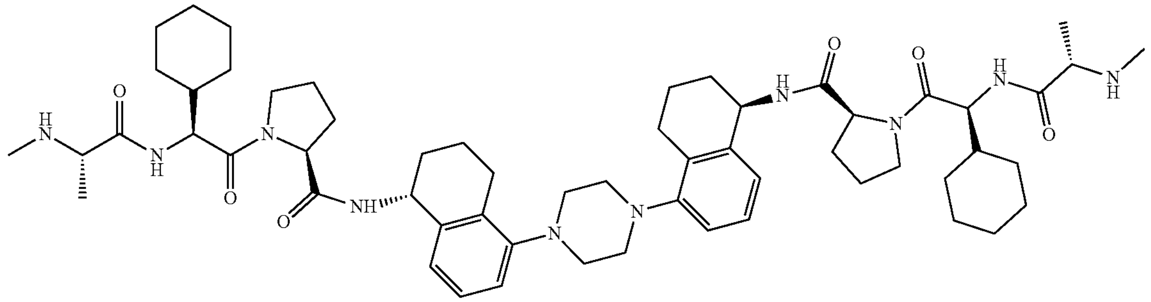

(2S,2'S)—N,N'-((1R,1'R)-piperazine-1,4-diylbis(1,2,3,4-tetrahydronaphthalene-5,1-diyl))bis(1-((S)-2-cyclohexyl-2-((S)-2-(methylamino)propanamido)acetyl)pyrrolidine-2-carboxamide) (Compound VIII-C)

LCMS (ESI, m/z): $[M+H]^+$=1019.8. $^1$H NMR (400 MHz, $CDCl_3$): δ 7.61 (s, 2H), 7.15-7.07 (m, 4H), 6.98-6.95 (m, 4H), 5.14 (s, 2H), 4.63-4.51 (m, 4H), 3.85-3.81 (m, 2H), 3.63-3.53 (m, 2H), 3.10-2.95 (m, 10H), 2.86-2.82 (m, 2H), 2.72-2.66 (m, 2H), 2.57-2.48 (m, 2H), 2.35 (s, 6H), 2.16-1.95 (m, 6H), 1.93-1.76 (m, 8H), 1.66-1.57 (m, 12H), 1.28-1.24

VIII-D

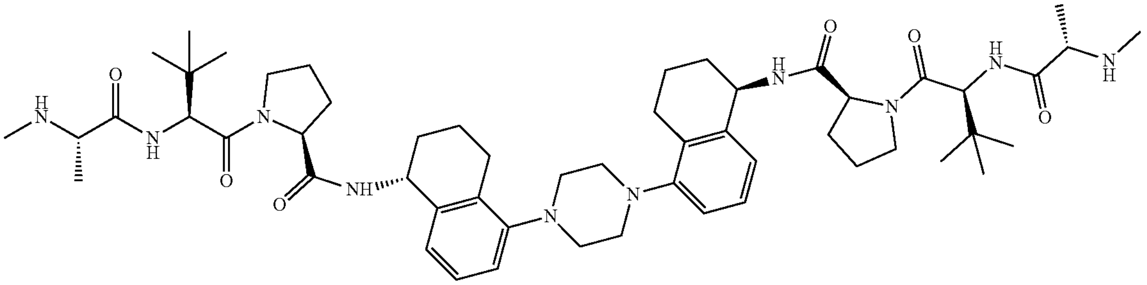

(2S,2'S)—N,N'-((1R,1'R)-piperazine-1,4-diylbis(1,2,3,4-tetrahydronaphthalene-5,1-diyl))bis(1-((S)-3,3-dimethyl-2-((S)-2-(methylamino)propanamido)butanoyl) pyrolidine-2-carboxamide) (Compound VIII-D)

LCMS (ESI, m/z): $[M+H]^+$=967.6. $^1$H NMR (400 MHz, $CDCl_3$): δ 7.76 (m, 2H), 7.20-6.94 (m, 8H), 5.21-5.07 (m, 2H), 4.63-4.57 (m, 2H), 4.42-4.40 (m, 1H), 3.63-4.40 (m, 4H), 3.01-2.83 (m, 10H), 2.80-2.70 (m, 4H), 2.48-2.32 (m, 8H), 2.18-1.93 (m, 8H), 1.78-1.53 (m, 6H), 1.32-1.30 (m, 3H), 1.21-0.99 (m, 18H), 0.89-0.82 (m, 6H).

VIII-E

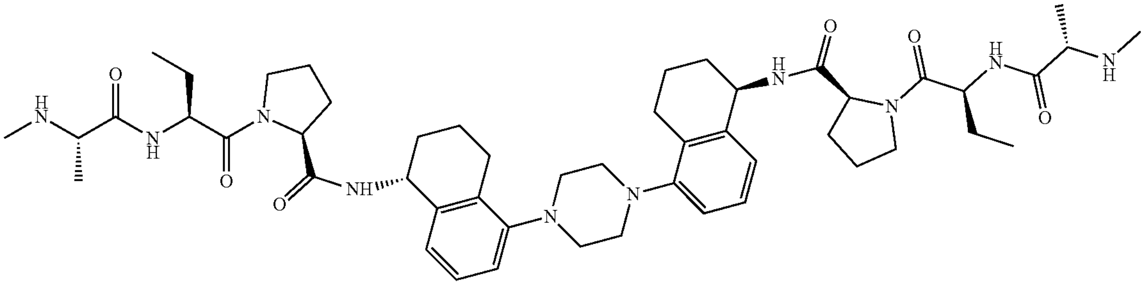

(2S,2'S)—N,N'-((1R,1'R)-piperazine-1,4-diylbis(1,2,3,4-tetrahydronaphthalene-5,1-diyl))bis(1-((S)-2-((S)-2-(methylamino)propanamido)butanoyl)pyrrolidine-2-carboxamide) (Compound VII-E)

LCMS (ESI, m/z): $[M+H]^+$=911.7.

VIII-F
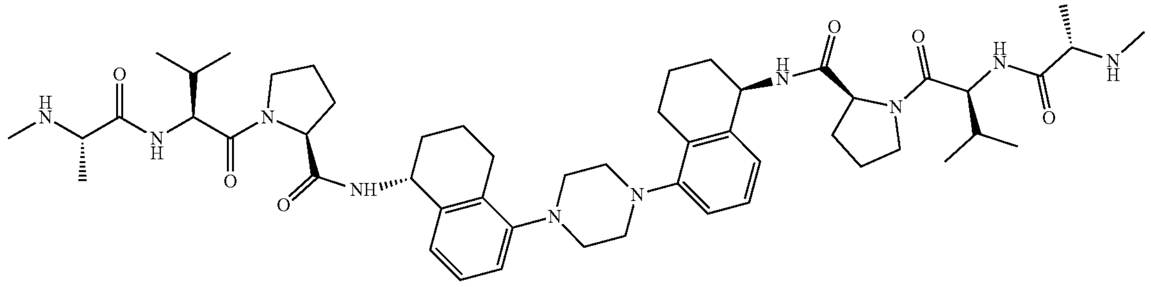
(2S,2'S)—N,N'-((1R,1'R)-piperazine-1,4-diylbis(1,2,3,4-tetrahydronaphthalene-5,1-diyl))bis(1-(methyl-L-alanyl-L-valyl)pyrrolidine-2-carboxamide) (Compound VII-F)
LCMS (ESI, m/z): $[M+H]^+$=939.5.
Example 9: Synthesis of Compound IX
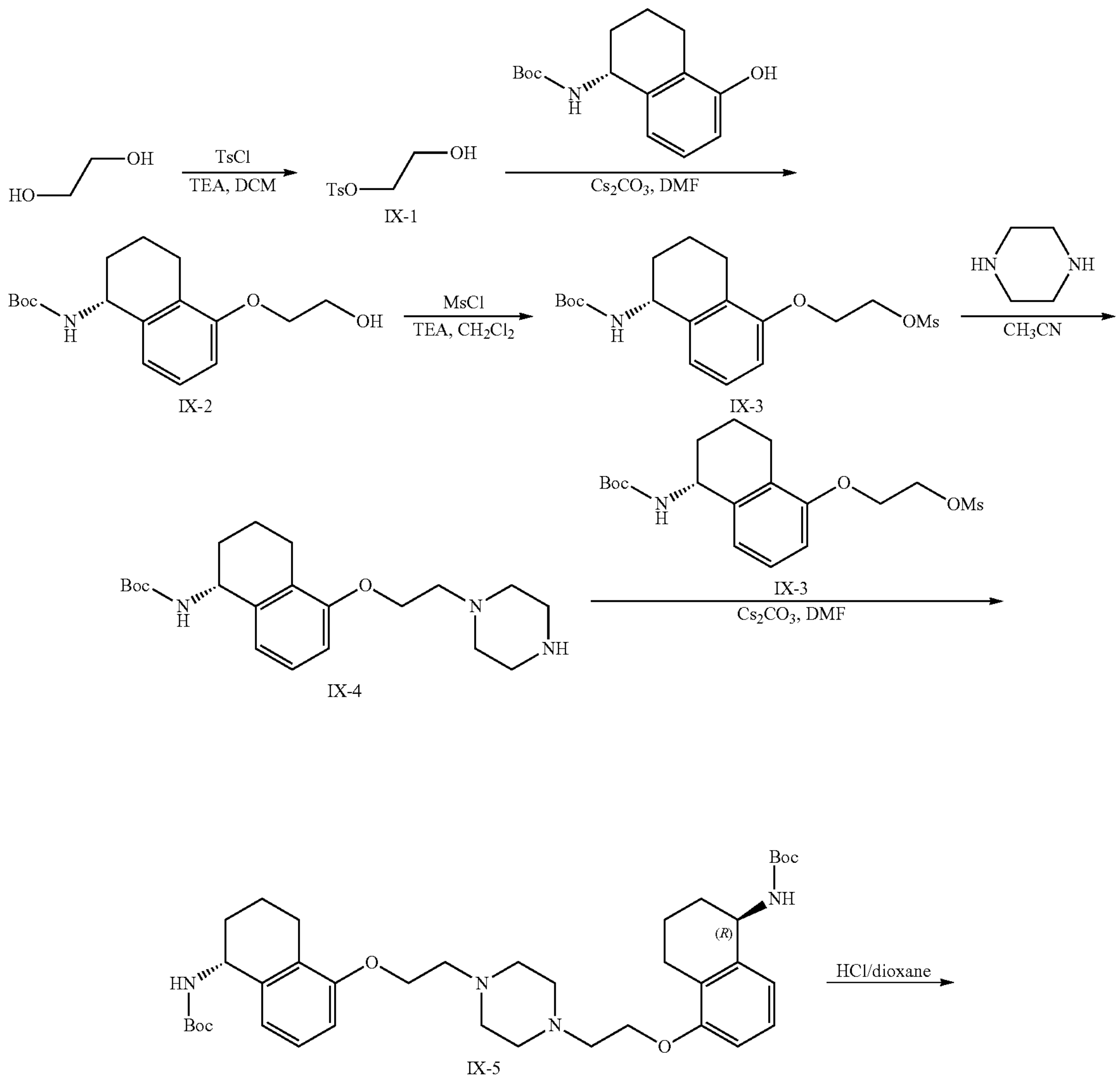

-continued

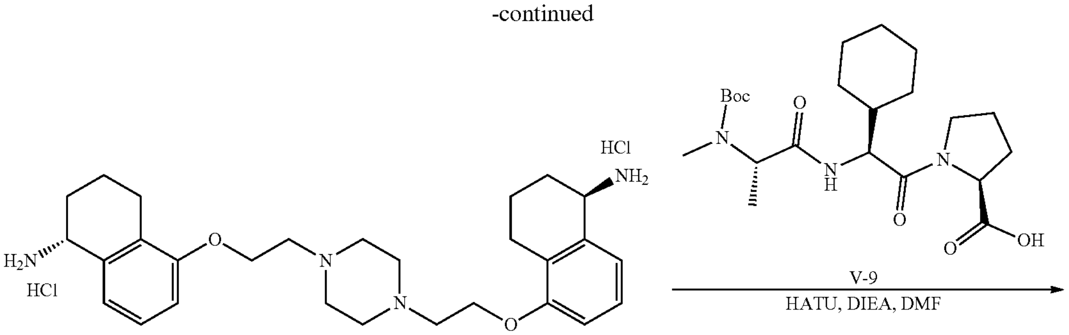

IX-6

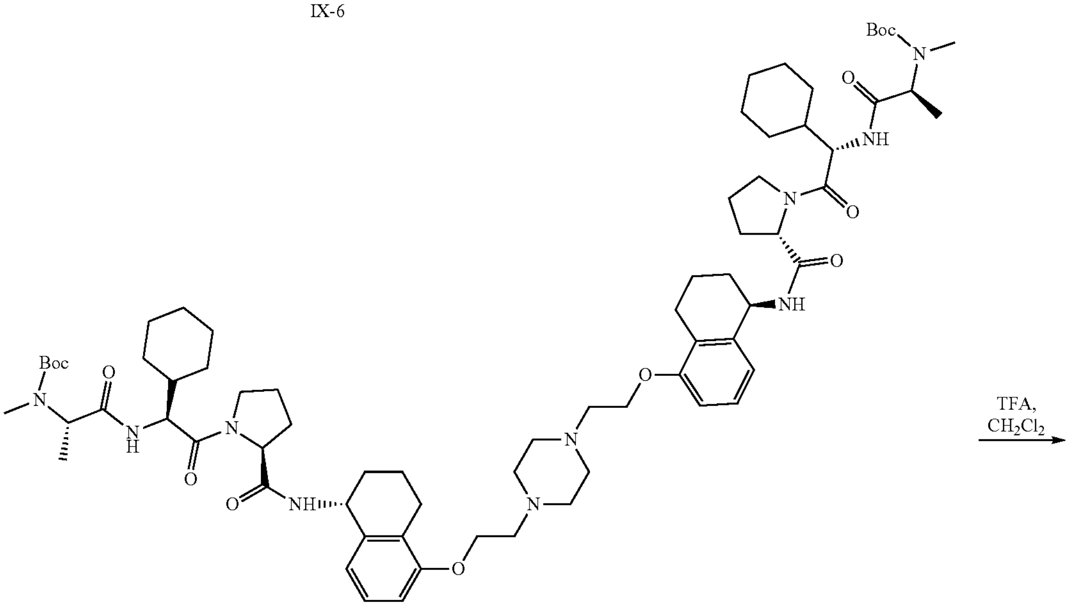

IX-7

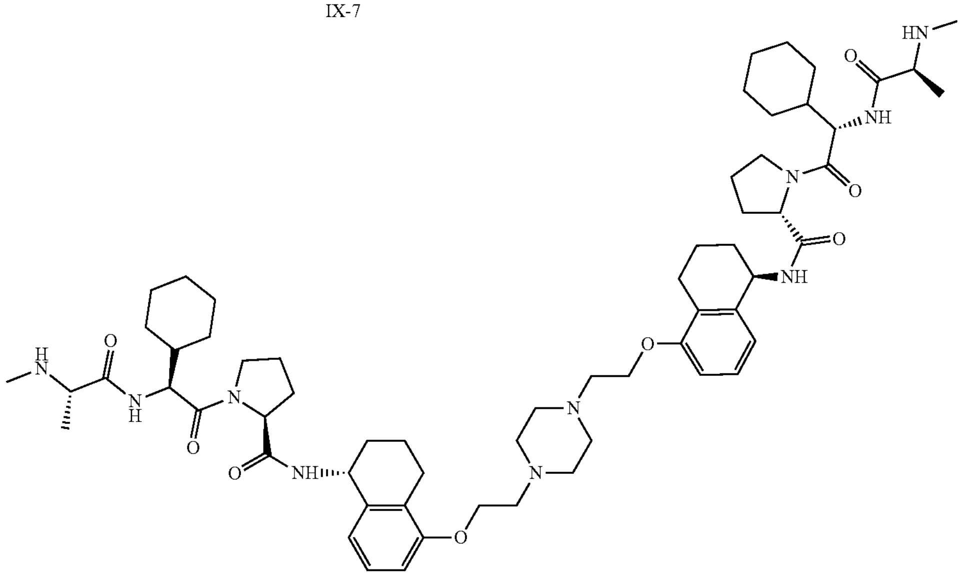

IX

2-[(4-methylbenzenesulfonyl)oxy]ethanol (Compound IX-1)

To a solution of ethylene glycol (65.1 g 1048.85 mmol) in DCM (500.0 mL) was added p-toluenesulfonyl chloride (20.0 g 104.89 mmol) and TEA (53.1 g 524.43 mmol). The mixture was stirred at room temperature for 16 h under $N_2$ atmosphere. After the reaction was completed, the mixture was diluted with $H_2O$ and extracted with DCM. The combined organic layer was washed with brine, dried over anhydrous sodium sulfate and filtered. The filtrate was concentrated under vacuum. The residue was purified by flash column chromatography with ethyl acetate/petroleum ether (1/1, v/v) to afford the title compound (10.0 g 44%) as a white solid. LCMS (ESI, m/z): $[M+H]^+$=217.0.

tert-Butyl N-[(1R)-5-(2-hydroxyethoxy)-1,2,3,4-tetrahydronaphthalen-1-yl]carbamate (Compound IX-2)

To a solution of (R)-tert-butyl 5-hydroxy-1,2,3,4-tetrahydronaphthalen-1-ylcarbamate (500.0 mg 1.90 mmol) in DMF (20.0 mL) was added compound LX-1 (615.9 mg 2.85 mmol) and $Cs_2CO_3$ (1.2 g, 3.80 mmol). The mixture was stirred at 80° C. for 16 h under $N_2$ atmosphere. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with ethyl acetate/petroleum ether (1/1, v/v) to afford the title compound (155.0 mg 27%) as a yellow solid. LCMS (ESI, m/z): $[M+H]^+$=308.2.

(R)-2-(5-(tert-Butoxycarbonylamino)-5,6,7,8-tetrahydronaphthalen-1-yloxy) ethyl methanesulfonate (Compound IX-3)

To a solution of compound IX-2 (300.0 mg, 0.98 mmol) in DCM (5.0 mL) was added MsCl (167.7 mg, 1.46 mmol) and TEA (197.5 mg 1.95 mmol). The mixture was stirred at room temperature for 3 h under $N_2$ atmosphere. After the reaction was completed, the mixture was diluted with $H_2O$ and extracted with DCM. The combined organic layer was washed with brine, dried over anhydrous sodium sulfate and filtered. The filtrate was concentrated under vacuum to afford the title compound (330.0 mg, crude) as a yellow oil. LCMS (ESI, m/z): [M+H]'°=386.2.

(R)-tert-Butyl 5-(2-(piperazin-1-yl)ethoxy)-1,2,3,4-tetrahydronaphthalen-1-yl carbamate (Compound IX-4)

To a solution of compound IX-3 (180.0 mg, 0.47 mmol) in $CH_3CN$ (6.0 mL) was added piperazine (402.2 mg 4.67 mmol). The mixture was stirred at 80° C. for 16 h. After the reaction was completed, the mixture was diluted with $H_2O$ and extracted with DCM. The combined organic layer was washed with brine, dried over anhydrous sodium sulfate and filtered. The filtrate was concentrated under vacuum to afford the title compound (120.0 mg, crude) as a yellow oil. LCMS (ESI, m/z): $[M+H]^+$=376.3.

tert-Butyl N-[(1R)-5-[2-[4-(2-[[(5R)-5-[(tert-butoxycarbonyl)amino]-5,6,7,8-tetrahydronaphthalen-1-yl]oxy]ethyl)piperazin-1-yl]ethoxy]-1,2,3,4-tetrahydro naphthalen-1-yl]carbamate (Compound IX-5)

To a solution of compound IX-4 (200.0 mg, 0.53 mmol) in DMF (10.0 mL) was added IX-3 (308.0 mg, 0.80 mmol) and $Cs_2CO_3$ (347.1 mg, 1.07 mmol). The mixture was stirred at 80° C. for 16 h. After the reaction was completed, the mixture was diluted with $H_2O$ and extracted with EtOAc. The combined organic layer was washed with brine, dried over anhydrous sodium sulfate and filtered. The filtrate was concentrated under vacuum purified by reverse phase flash column chromatography with 5-100% $CH_3CN$ in $H_2O$ to afford the title compound (100.0 mg, 28%) as a yellow solid. LCMS (ESI, m/z): $[M+H]^+$=665.4.

(1R)-5-[2-[4-(2-[[(5R)-5-amino-5,6,7,8-tetrahydronaphthalen-1-yl]oxy]ethyl) piperazin-1-yl]ethoxy]-1,2,3,4-tetrahydronaphthalen-1-amine dihydrochloride (Compound IX-6)

The solution of compound IX-5 (90.0 mg, 0.14 mmol) in HCl/dioxane (10.0 mL, 4 mol/L) was stirred at room temperature for 1 h. The mixture was concentrated under vacuum to afford the title compound (80.0 mg, crude) as a white solid. LCMS (ESI, m/z): $[M+H]^+$=465.3.

tert-Butyl N-[(1S)-1-{[(1S)-2-[(2S)-2-{[(1R)-5-(2-[4-(2-{[(5R)-5-[(2S)-1-[(2S)-2-[(2S)-2-{[(tert-butoxy)carbonyl](methyl)amino)propanamido]-2-cyclohexylacetyl]pyrrolidine-2-amido]-5,6,7,8-tetrahydronaphthalen-1-yl]oxy}ethyl)piperazin-1-yl]ethoxy}-1,2,3,4-tetrahydronaphthalen-1-yl]carbamoyl}pyrrolidin-1-yl]-1-cyclohexyl-2-oxoethyl]carbamoyl}ethyl]-N-methylcarbamate (Compound IX-7)

To a solution of compound IX-6 (70.0 mg, 0.13 mmol) in DMF (5.0 mL) was added V-9 (114.5 mg 0.26 mmol), DIEA (84.2 mg, 0.65 mmol) and HATU (123.8 n 0.32 mmol). The resulting mixture was stirred at 0° C. for 1 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with DCM/methanol (10/1, v/v) to afford the title compound (100.0 mg, 48%) as a yellow solid. LCMS (ESI, m/z): $[M+H]^+$=1307.8.

(2S)-1-[(2S)-2-cyclohexyl-2-[(2S)-2-(methylamino) propanamido]acetyl]-N-[(1R)-5-{2-[4-(2-{[(5R)-5-[(2S)-1-[(2S)-2-cyclohexyl-2-[(2S)-2-(methylamino) propanamido]acetyl]pyrolidine-2-amido]-5,6,7,8-tetrahydronaphthalen-1-yl]oxy}ethyl)piperazin-1-yl]ethoxy}-1,2,3,4-tetrahydronaphthalen-1-yl]pyrrolidine-2-carboxamide (Compound IX)

To a solution of compound IX-7 (90.0 mg, 0.07 mmol) in DCM (5.0 mL) was added TFA (1.0 mL). The mixture was stirred at room temperature for 1 h. After the reaction was completed, the mixture was diluted with $H_2O$. The pH value of the mixture was adjusted to 8 with aq. $NaHCO_3$ and then extracted with $CH_2Cl_2$. The combined organic layer was washed with brine, dried over anhydrous sodium sulfate and filtered. The filtrate was concentrated under vacuum. The residue was purified by Prep-HPLC with the following conditions: Column: XBridge Prep OBD C18 Colum, 30×150 mm, 5 um; Mobile Phase A: Water (10 mmol/L $NH_4HCO_3$), Mobile Phase B: ACN; Flow rate: 60 mL/min; Gradient: 39/o B to 69/o B in 7 min; 220 nm; RT1'6.08 to afford the title compound (17.4 mg, 23%) as a white solid. LCMS (ESI, m/z): $[M+H]^+$=1107.7. $^1H$ NMR (300 MHz, DMSO-$d_6$) δ 8.11-8.09 (m, 2H), 7.88-7.82 (m, 2H), 7.12-7.07 (m, 2H), 6.87-6.78 (m, 4H), 4.94-4.81 (m, 2H), 4.47-4.42 (m, 2H), 4.37-4.27 (m, 2H), 4.11-4.03 (m, 4H), 3.70-3.62 (m, 4H), 2.95-2.91 (m, 2H), 2.76-2.65 (m, 5H), 2.62-2.54 (m, 5H), 2.20-2.15 (m, 7H), 2.14-1.92 (m, 6H), 1.89-1.50 (m, 27H), 1.23-0.86 (m, 18H).

Example 10: Synthesis of Compound X

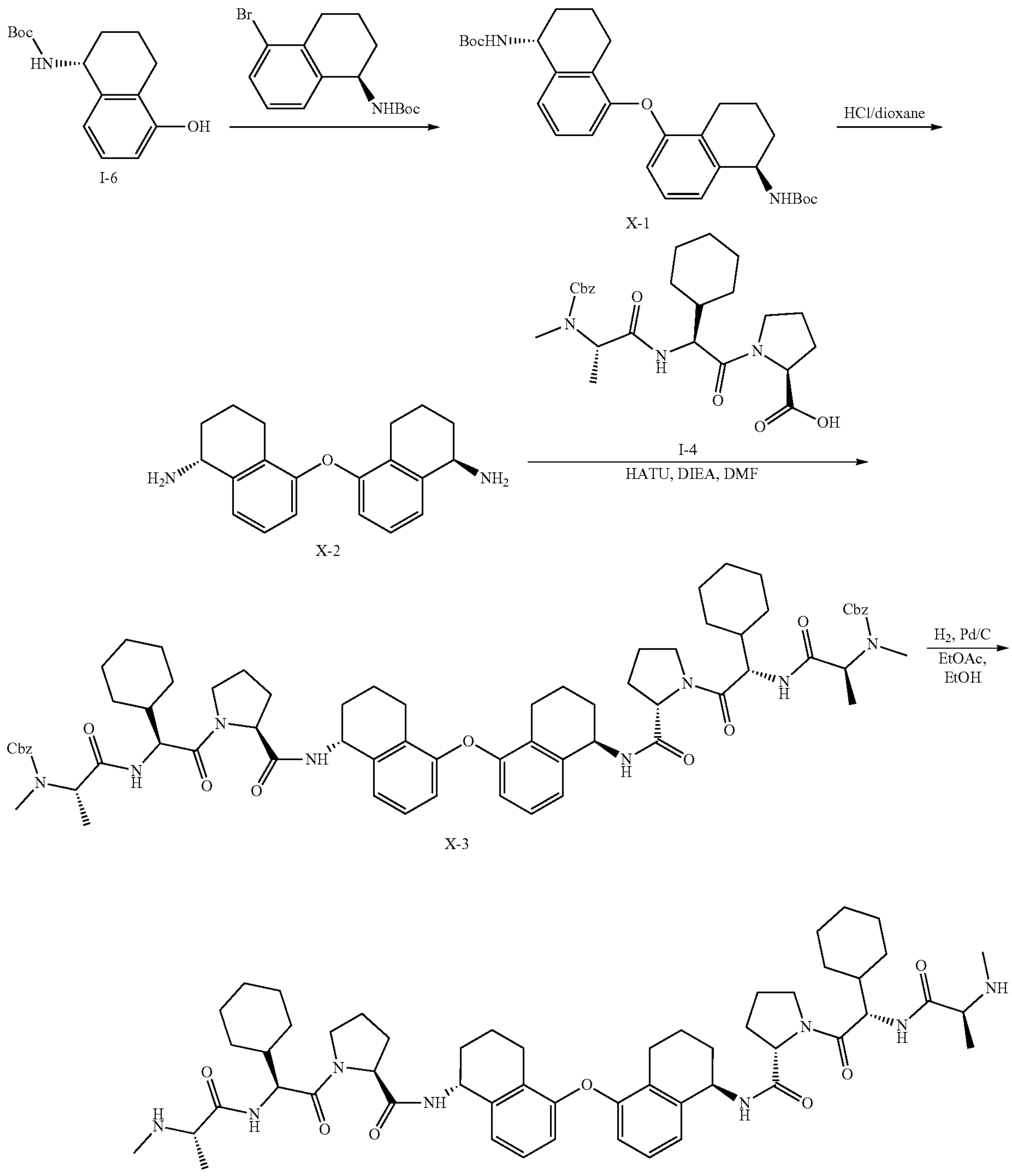

X tert-Butyl N-[(1R)-5-[[(5R)-5-[(tert-butoxycarbonyl) amino]-5,6,7,8-tetrahydro naphthalen-1-yl]oxy]-1,2, 3,4-tetrahydronaphthalen-1-yl]carbamate (Compound X-1)

To a solution of tert-butyl N-[(1R)-5-bromo-1,2,3,4-tetrahydronaphthalen-1-yl]carbamate (300.0 mg, 0.92 mmol) in dioxane (15.0 mL) was added I-6 (242.1 mg 0.92 mmol), $Pd_2$(dba) (168.4 mg 0.18 mmol), t-BuXPhos (156.2 mg 0.36 mmol) and $Cs_2CO_3$ (898.8 mg 2.75 mmol). The reaction mixture was stirred at 100° C. for 2 h under $N_2$. After the reaction was complete, the reaction mixture was cooled to room temperature and then filtered. The filtrate was concentrated under vacuum. The residue was purified by flash column chromatography with Petroleum ether/EtOAc (85/15, v/v) to afford the title compound (314.0 mg 67%) as a yellow solid. LCMS (ESI, m/z): $[M+H]^+$=509.3.

(1R)-5-[[(5R)-5-amino-5,6,7,8-tetrahydronaphthalen-1-yl]oxy]-1,2,3,4-tetrahydro naphthalen-1-amine dihydrochloride (Compound X-2)

A solution of compound X-1 (314.0 mg 0.62 mmol) in HCl/dioxane (15.0 mL, 4 mol/L) was stirred at room temperature for 2 h. After the reaction was complete, the reaction mixture was concentrated under vacuum to afford the title compound (310.0 mg crude) as a white solid. LCMS (ESI, m/z): $[M+H]^+$=309.2.

Benzyl N-[(1S)-1-[[(1S)-2-[(2S)-2-[[(1R)-5-[[(5R)-5-[(2S)-1-[(2S)-2-[(2S)-2-[[(benzyloxy)carbonyl](methyl)amino]propanamido]-2-cyclohexylacetyl]pyrrolidine-2-amido]-5,6,7,8-tetrahydronaphthalen-1-yl]oxy]-1,2,3,4-tetrahydronaphthalen-1-yl]carbamoyl]pyrrolidin-1-yl]-1-cyclohexyl-2-oxoethyl]carbamoyl]ethyl]-N-methylcarbamate (Compound X-3)

To a solution of compound X-2 (310.0 mg crude) in DMF (10.0 mL) was added DIEA (1039.2 mg 8.04 mmol), compound I-4 (999.5 mg 2.11 mmol) and HATU (1910.8 mg 5.03 mmol) at 0° C. under $N_2$. The reaction mixture was stirred at room temperature for 2 h under $N_2$. After the reaction was complete, the reaction mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with $CH_2Cl_2$/MeOH (96/4, v/v) and then purified by reverse phase flash column chromatography with ACN/

$H_2O$ (90/10, v/v) to afford the title compound (280.0 mg 23%) as a white solid. LCMS (ESI, m/z): $[M+H]^+$=1219.7

(2S)-1-[(2S)-2-cyclohexyl-2-[(2S)-2-(methylamino)propanamido]acetyl]-N-[(1R)-5-[[(5R)-5-[(2S)-1-[(2S)-2-cyclohexyl-2-[(2S)-2-(methylamino)propanamido]acetyl]pyrrolidine-2-amido]-5,6,7,8-tetrahydronaphthalen-1-yl]oxy]-1,2,3,4-tetrahydro naphthalen-1-yl]pyrrolidine-2-carboxamide (Compound X)

To a solution of compound X-3 (280.0 mg, 0.23 mmol) in EtOAc (10.0 mL) and EtOH (5.0 mL) was added Pd/C (300.0 mg, dry). The reaction mixture was stirred at room temperature for 16 h under $H_2$. After the reaction was complete, the resulting mixture was filtered. The filtrate was concentrated under reduced pressure. The residue was purified by Prep-HPLC with the following conditions: Column: XBridge Shield RP18 OBD Colum, 30×150 mm, 5 um; Mobile Phase A: Water (10 mmol/L $NH_4HCO_3$), Mobile Phase B: ACN; Flow rate: 60 mL/min; Gradient: 32% B to 82% B in 7 min; 220 nm; RT1: 5.45 to afford the title compound (136.6 mg, 63%) as a white solid. LCMS (ESI, m/z): $[M+H]^+$=951.6. $^1H$ NMR (300 MHz, DMSO-$d_6$) δ 8.52-8.12 (m, 2H), 7.93-7.70 (m, 2H), 7.40-7.06 (m, 4H), 6.58-6.55 (m, 2H), 5.07-4.95 (m, 2H), 4.50-4.41 (m, 2H), 4.34-4.29 (m, 2H), 3.81-3.70 (m, 2H), 3.65-3.57 (m, 2H), 2.95-2.91 (m, 2H), 2.70-2.60 (m, 4H), 2.16 (s, 6H), 2.10-1.93 (m, 6H), 1.93-1.49 (m, 24H), 1.28-0.89 (m, 16H).

Following the procedure described above for Example 10 and substituting the appropriate reagents, starting materials and purification methods known to those skilled in the art, the compounds listed below were prepared.

X-A

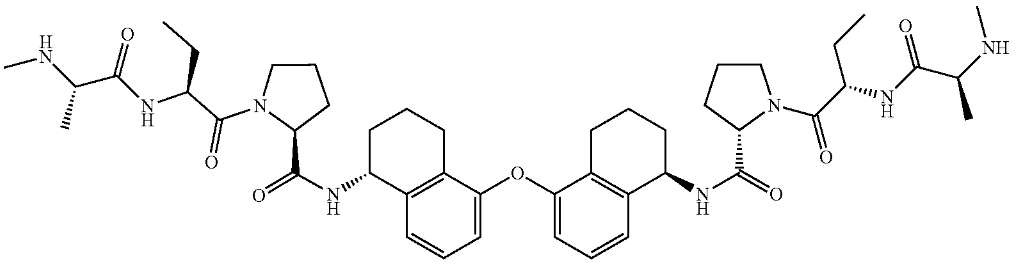

(2S)-1-[(2S)-3-methyl-2-[(2S)-2-(methylamino)propanamido]butanoyl]-N-[(1R)-5-[[(5R)-5-[(2S)-1-[(2S)-3-methyl-2-[(2S)-2-(methylamino)propanamido]butanoyl]pyrolidine-2-amido]-5,6,7,8-tetrahydronaphthalen-1-yl]carbamoyl]-1,2,3,4-tetrahydro naphthalen-1-yl]pyrrolidine-2-carboxamide (Compound X-A)

LCMS (ESI, m/z): $[M+H]^+$=843.5. $^1$H NMR (300 MHz, DMSO-$d_6$): δ 8.25 (d, J=8.7 Hz, 2H), 7.97 (d, J=8.1 Hz, 2H), 7.25-7.01 (m, 4H), 6.62-6.52 (m, 2H), 5.04-4.93 (m, 2H), 4.59-4.41 (m, 2H), 4.41-4.28 (m, 2H), 3.75-3.48 (m, 4H), 3.02-2.88 (m, 2H), 2.68-2.57 (m, 4H), 2.18 (s, 6H), 2.15-1.44 (m, 22H), 1.16-1.06 (m, 6H), 0.94-0.76 (m, 6H).

X-B

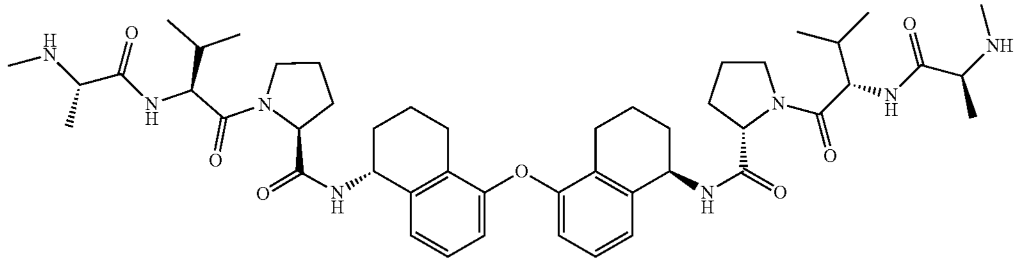

(S)-1-(Methyl-L-alanyl-L-valyl)-N—((R)-5-(((R)-5-((S)-1-(methyl-L-alanyl-L-valyl)pyrrolidine-2-carboxamido)-5,6,7,8-tetrahydronaphthalen-1-yl)oxy)-1,2,3,4-tetrahydronaphthalen-1-yl)pyrrolidine-2-carboxamide (Compound X-B)

LCMS (ESI, m/z): $[M+H]^+$=871.6. $^1$H NMR (300 MHz, DMSO-$d_6$): δ 8.30-8.25 (m, 2H), 7.95-7.92 (m, 2H), 7.11-7.04 (m, 4H), 6.58-6.55 (m, 2H), 5.03-4.95 (m, 2H), 4.47-4.42 (m, 2H), 4.34-4.30 (m, 2H), 3.77-3.62 (m, 4H), 3.06-2.92 (m, 2H), 2.67-2.60 (m, 4H), 2.22-2.18 (m, 6H), 2.09-1.96 (m, 7H), 1.88-1.78 (m, 9H), 1.72-1.62 (m, 4H), 1.16-1.10 (m, 6H), 0.95-0.80 (m, 12H).

X-C

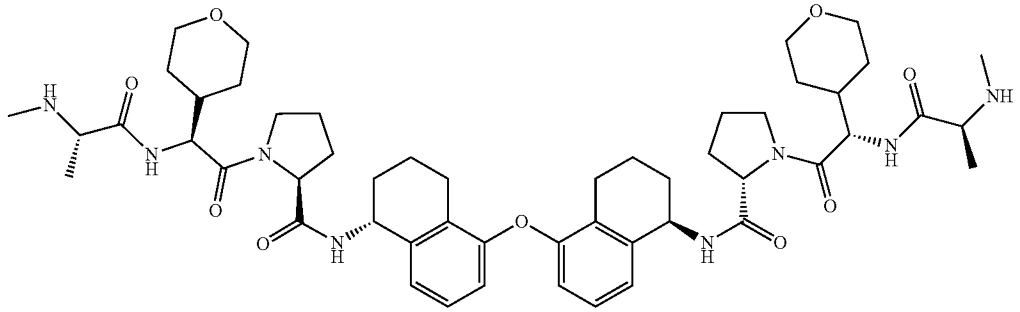

(S)-1-((S)-2-((S)-2-(methylamino)propanamido)-2-(tetrahydro-2H-pyran-4-yl)acetyl)-N—((R)-5-(((R)-5-((S)-1-((S)-2-((S)-2-(methylamino)propanamido)-2-(tetrahydro-2H-pyran-4-yl)acetyl)pyrrolidine-2-carboxamido)-5,6,7,8-tetrahydro naphthalen-1-yl)oxy)-1,2,3,4-tetrahydronaphthalen-1-yl)pyrrolidine-2-carboxamide (Compound X-C)

LCMS (ESI, m/z): $[M+H]^+$=955.6. $^1H$ NMR (300 MHz, DMSO-$d_6$): δ 8.53-8.01 (m, 5H), 7.40-7.00 (m, 4H), 6.61-6.54 (m, 2H), 5.06-4.90 (m, 2H), 4.56-4.46 (m, 3H), 4.37-4.26 (m, 3H), 3.89-3.57 (m, 1H), 3.34-3.13 (m, 6H), 2.68-2.59 (m, 3H), 2.30-2.21 (m, 6H), 2.14-1.51 (m, 20H), 1.42-1.21 (m, 4H), 1.21-1.06 (m, 6H).

Example 11: Biological Activity

Assay Protocol

IAPs are one main cause of cancer development and may result from overexpression of anti-apoptotic proteins. This protocol establishes three binding assays for XIAP Bir3 domain, cIAP1 and cIAP2 using FP (fluorescence polarization) technology. The fluorescence probe used is a synthetic peptide conjugated to 5-carboxyfluorescein (AbuRPFK-5FAM). The fluorescence polarization value (mP) was detected by Envision, which was used to reflect the binding degree of protein and fluorescent marker.

TABLE 1

Materials and instruments

| Number | Name | Vendor | Cat# |
|---|---|---|---|
| 1 | HEPES | Life Technologies | 15630-080 |
| 2 | NaCl | Sigma | S5886 |
| 3 | Triton X-100 | Sigma | T8787 |
| 4 | XIAP-BIR3 | Reaction Biology | APT-11-374 |
| 5 | cIAP1-BIR3 | Reaction Biology | APT-11-370 |
| 6 | cIAP2-BIR3 | Reaction Biology | APT-11-372 |
| 7 | AbuRPF-K(5-Fam)-$NH_2$(SM5F) | NJ Peptide | |
| 8 | DMSO | MP | 196055 |
| 9 | Topseal A | PerkinElmer | E5341 |
| 10 | ProxiPlate-384 F Plus | PerkinElmer | 6008260 |
| 11 | V96 MicroWell Plates | nunc | 249944 |
| 12 | 384-well plates | corning | 3657 |
| 13 | Envision | Perkin Elmer | 2104 |
| 14 | Centrifuge | Eppendorf | 5810R |

Procedure

Reaction Reagent

TABLE 2

1× reaction buffer(200 mL) pH 7.5

| Name | Stock | Volume | Final Conc. |
|---|---|---|---|
| HEPES | 1M (20×) | 10 μL | 50 mM |
| Triton X-100 | 100% (10000×) | 20 μL | 0.01% |
| NaCl | Powder | 2.34 g | 200 mM |
| ddH2O | | 190 mL | |

TABLE 3

Enzyme solution

| Name | Stock | Volume | 2.5× Conc. | Final Conc. |
|---|---|---|---|---|
| 2.5× XIAP-BIR3 solution (2353 μL) | | | | |
| XIAP-BIR3 | 181 μM (1810×) | 1.3 μL | 1.00 nM | 40 nM |
| 1× reaction buffer | | 2351.7 μL | | |
| 2.5× cIAP1-BIR3 solution (2466.7 μL) | | | | |
| cIAP1-BIR3 | 92.5 μM (2466.7×) | 1 μL | 37.5 nM | 15 nM |
| 1× reaction buffer | | 2465.7 μL | | |
| 2.5× cIAP2-BIR3 solution (2376 μL) | | | | |
| cIAP2-BIR3 | 52.8 μM (264×) | 9 μL | 200 nM | 80 nM |
| 1× reaction buffer | | 2367 μL | | |

TABLE 4

2× substrate SM5F (10 mL)

| Name | Stock | Volume | 2× Conc. | Final Conc. |
|---|---|---|---|---|
| SM5F | 10 μM (1000×) | 10 μL | 10 nM | 5 nM |
| 1× reaction buffer | | 9990 μL | | |

Test compounds: Stock Conc. = 10 mM.

Measurements a. Prepare 100 times of the final cpd concentration in appropriate tube and transfer 5 uL cpd to 45 μL 1× reaction buffer with 10% DMSO b. The final reference cpd concentration is 10000, 3333.3, 1111.1, 370.4, 123.4, 41.2, 13.7, 4.57, 1.52, 0.51, 0.17 and 0 nM. So the 100 times of the concentration is 1000, 333.3, 111.1, 37.04, 12.34, 4.12, 1.0.46, 0.15, 0.05, 0.017 and 0 μM. The final test cpds concentration is 3333.3, 1111.1, 370.4, 123.4, 41.2, 13.7, 4.57, 1.52, 0.51, 0.17, 0.057 and 0 nM. So the 100 times of the concentration is 333.3, 111.1, 37.04, 12.34, 4.12, 1.0.46, 0.15, 0.05, 0.017, 0.0057 and 0 Mm c. Add 8 μL/well each dose enzyme to 384 wen microplate (ProxiPlate-384 F Plus, 6008260) using multichannel pipette, prepared in Table 3.

d. Centrifuge at 1000 rpm e. Add 2 μL/well cpd to 384 well microplate (ProxiPlate-384 F Plus, 6008260) using multichannel pipette, prepared in step a).

f. Centrifuge at 1000 rpm RT, 15 min.

g Start the assay by adding 10 uL/well substrate (prepared in Table 4) to the same 384 wen microplate using multichannel pipette.

h. Centrifuge at 1000 rpm.

i. Cover the assay plate and incubate for 60 min at 25° C.

j. Read on Envision 2104 for mP and plot the $IC_{50}$s with mP values.

k. Data analysis: IC50s were determined based on a non-linear regression analysis of data collected.

Biological Data

Compounds of the present technology as described herein were or are tested according to the protocol above and show or are expected to show $IC_{50}$ values equal to or below 1 uM in one or more of the above assays. Certain compounds exhibit or are expected to exhibit $IC_{50}$s of 100 nM or less, and others exhibit or are expected to exhibit $IC_{50}$s of 10 nM or less in one or more of the above binding assays. Exemplary results are shown in Table 5 for selected compounds.

TABLE 5

| Compound | $IC_{50}$ (nm) XIAP-BIR3 binding assay | $IC_{50}$ (nm) cIAP1-BIR3 binding assay | $IC_{50}$ (nm) cIAP2-BIR3 binding assay |
|---|---|---|---|
| I | B | A | B |
| I-A | B | A | A |
| I-B | C | A | B |
| I-C | C | A | B |
| I-D | B | A | A |
| I-E | B | A | B |
| I-F | C | A | C |
| I-G | B | A | B |
| II | B | A | A |
| II-A | C | A | A |
| II-B | B | A | B |
| II-C | B | A | B |
| II-D | D | A | B |
| II-E | C | C | C |
| II-F | B | A | B |
| III | B | A | B |
| III-A | B | A | B |
| III-B | B | A | B |
| III-C | A | A | A |
| III-D | B | A | B |
| III-E | A | A | B |
| III-F | B | A | B |
| III-G | C | A | B |
| III-H | C | A | B |
| III-I | B | A | B |
| III-J | B | A | A |
| III-K | B | A | A |
| III-L | C | B | C |
| III-M | D | B | C |
| III-N | B | A | B |
| IV | C | B | B |
| IV-A | B | A | B |
| IV-B | B | A | B |
| V | B | A | B |
| V-A | C | A | B |
| V-B | B | A | B |
| V-C | B | A | B |
| V-D | B | A | B |
| V-E | B | A | B |
| V-F | B | A | B |
| V-G | B | A | B |
| V-H | C | A | B |
| V-I | B | A | A |
| V-J | B | A | B |
| V-K | B | A | B |
| V-L | B | A | B |
| V-M | B | A | A |
| V-N | A | A | A |
| V-O | B | A | B |
| V-P | B | A | B |
| V-Q | B | A | B |
| V-R | B | A | B |
| VI | B | A | B |
| VI-A | B | A | B |
| VI-B | B | A | B |
| VI-C | B | A | B |
| VII | B | A | A |
| VII-A | B | A | A |
| VII-B | B | A | B |
| VII-C | B | A | B |
| VIII | B | A | A |
| VIII-A | D | B | C |
| VIII-B | D | B | C |
| VIII-C | B | A | B |
| VIII-D | C | A | B |
| VIII-E | C | A | B |
| VIII-F | B | A | B |
| IX | C | A | B |
| X | B | A | B |
| X-A | B | A | B |

TABLE 5-continued

| Compound | $IC_{50}$ (nm) XIAP-BIR3 binding assay | $IC_{50}$ (nm) cIAP1-BIR3 binding assay | $IC_{50}$ (nm) cIAP2-BIR3 binding assay |
|---|---|---|---|
| X-B | B | A | B |
| X-C | B | A | B |

A: 1-10 nM
B: >10 nM-100 nM
C: >100 nM-1 μM
D: >1 μM

Equivalents

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

An publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound of Formula I, or a pharmaceutically acceptable salt of the compound:

I

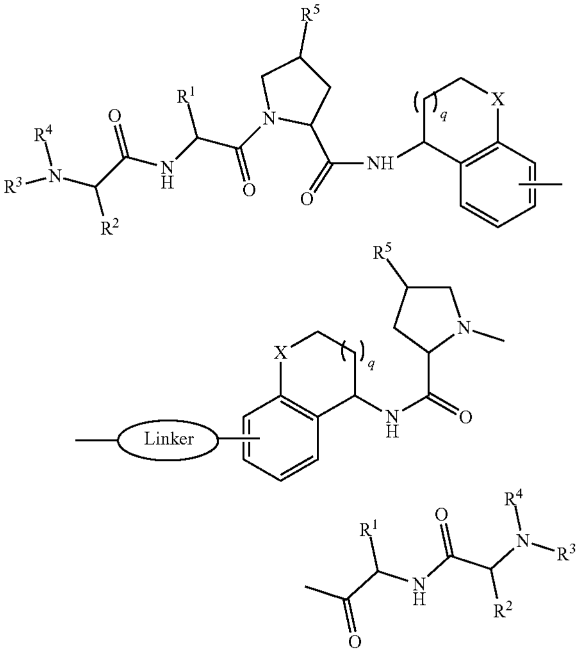

wherein

X is O or $CH_2$;

q is 0, 1

$R^1$ is selected from an unsubstituted $C_{1-6}$ alkyl, $C_{3-6}$ cycloalkyl, or heterocycylalkyl group;

$R^2$ is an unsubstituted $C_{1-6}$ alkyl;

$R^3$ and $R^4$ at each occurrence are independently H, an amino-protecting group, or an unsubstituted $C_{1-6}$ alkyl group;

$R^5$ at each occurrence is independently H, —OH, or O-(hydroxyl protecting group); and Linker is a divalent moiety selected from a bond, an oxy moiety, an amino moiety,

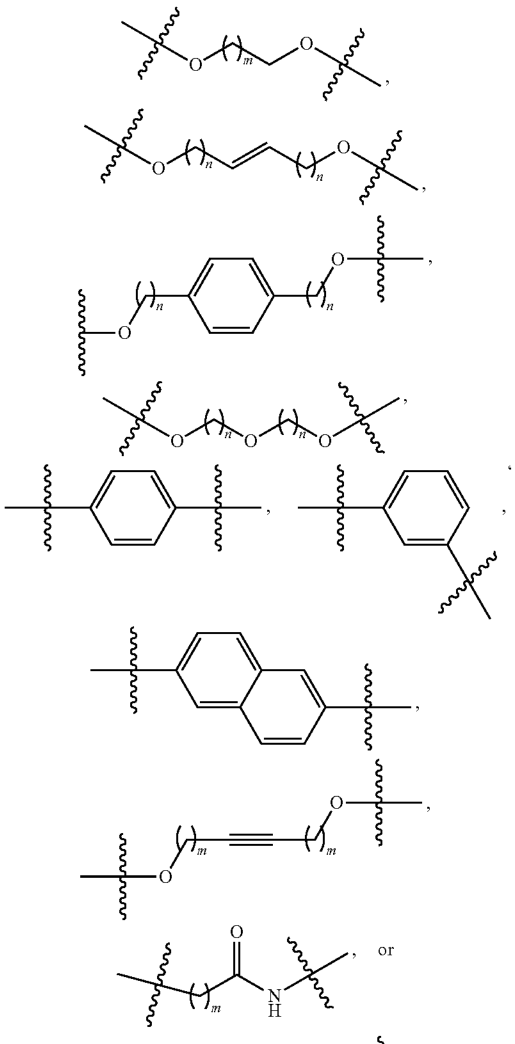

or

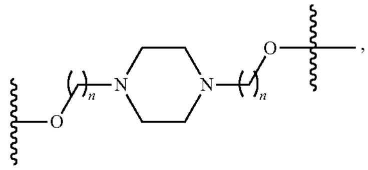

wherein:

m is 0, 1, 2, 3, or 4; and n is 1 or 2.

2. The compound of claim 1 wherein Linker is selected from the group consisting of

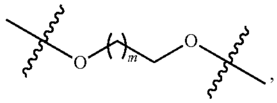

,

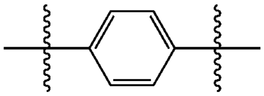

,

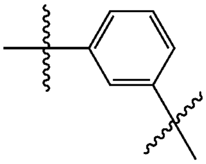

,

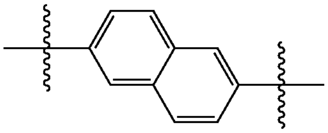

,

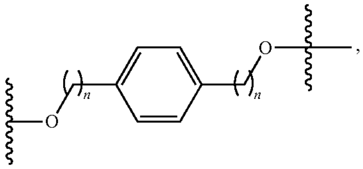

, and

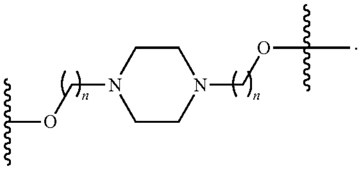

.

3. The compound of claim 1 wherein Linker is selected from the group consisting of

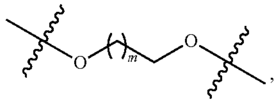

,

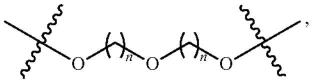

,

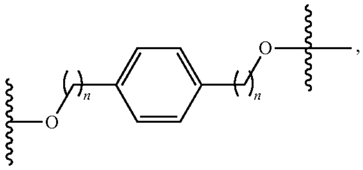

, and

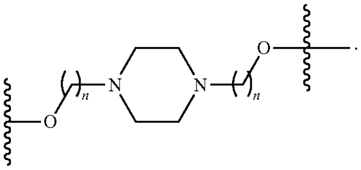

.

4. The compound of claim 1, wherein Linker is

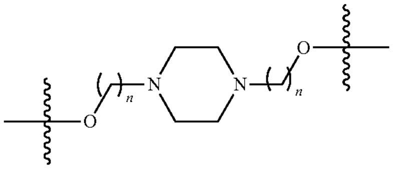

and n is 2.

5. The compound of claim 1, wherein Linker is a bond, —NH—, or —C(O)NH—.

6. The compound of claim 1 wherein Linker is

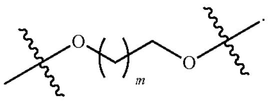

.

7. The compound of claim 6 wherein m is 4.

8. The compound of claim 1 wherein Linker is

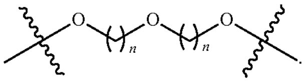

.

9. The compound of claim 8 wherein n is 2.

10. The compound of claim 1 wherein Linker is

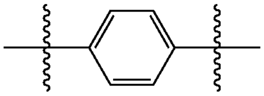

or

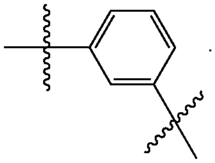

.

11. The compound of claim 1 wherein $R^1$ is selected from the group consisting of a methyl, ethyl, n-propyl, i-propyl, n-butyl, s-butyl, i-butyl, t-butyl, cyclopropyl, cyclobutyl, cyclohexyl, and cyclopentyl group, and $R^2$ is methyl.

12. The compound of claim 1 wherein $R^3$ is a methyl group.

13. The compound of claim 1 wherein $R^4$ is an amino-protecting group.

14. The compound of claim 1 wherein $R^4$ is H.

15. The compound of claim 1 wherein $R^5$ is H.

16. The compound of claim 1 wherein X is $CH_2$.

17. The compound of claim 1 having the structure of Formula IA, or a pharmaceutically acceptable salt of the compound:

IA
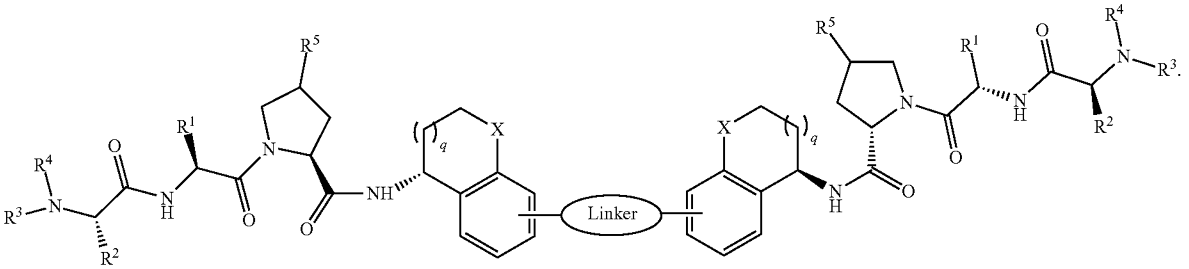
18. The compound of claim 1 wherein the compound is selected from the group consisting of:
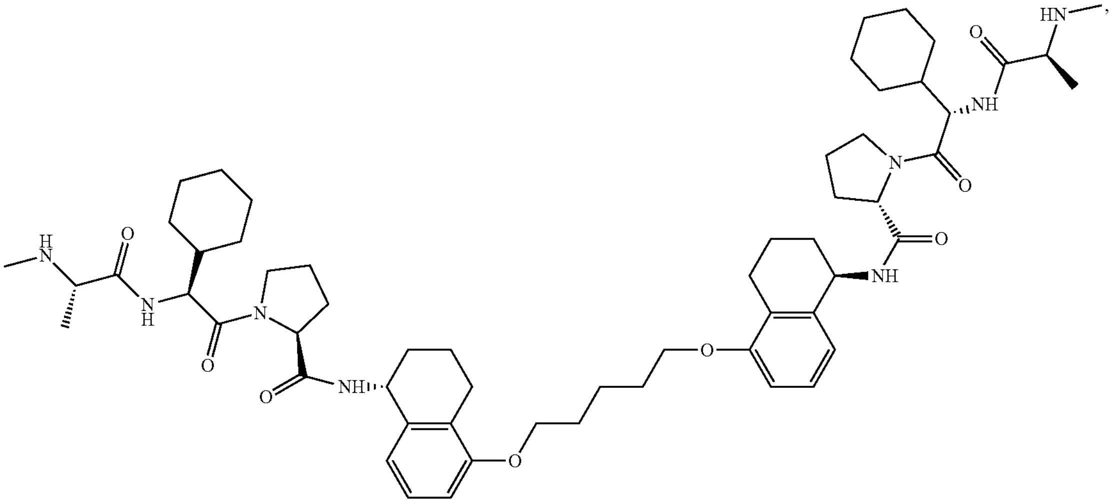
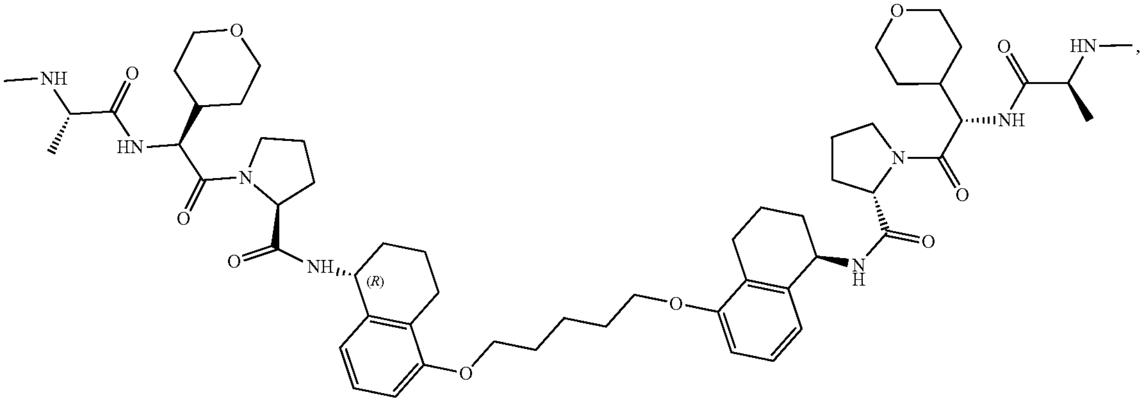

-continued
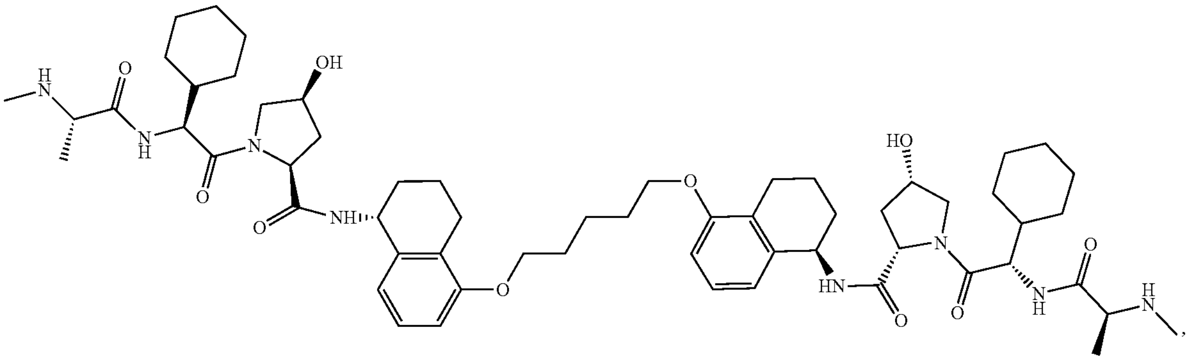
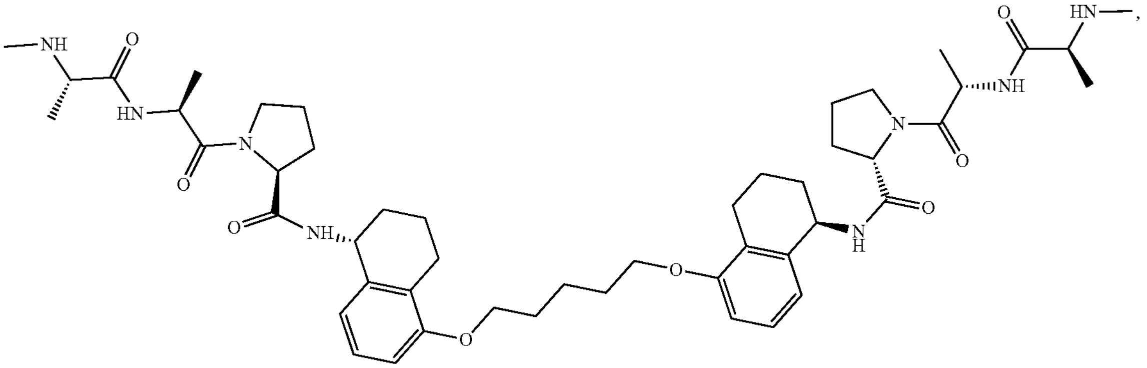
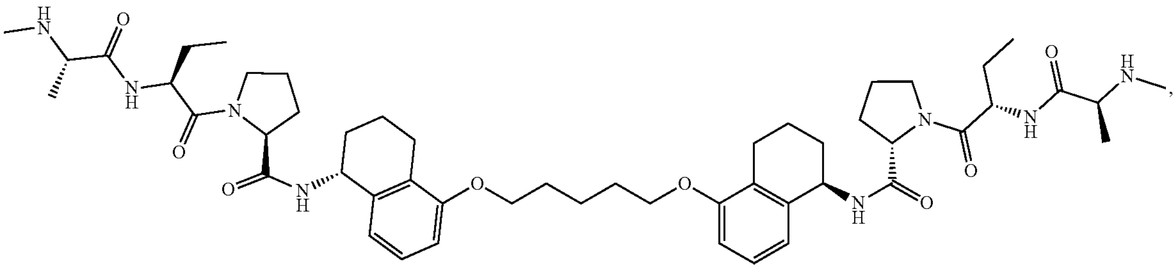
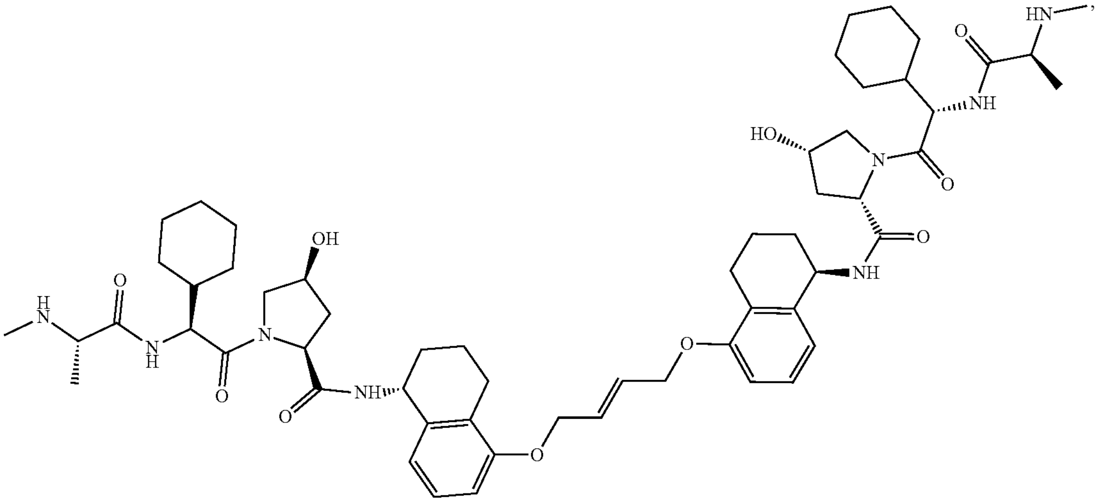

-continued
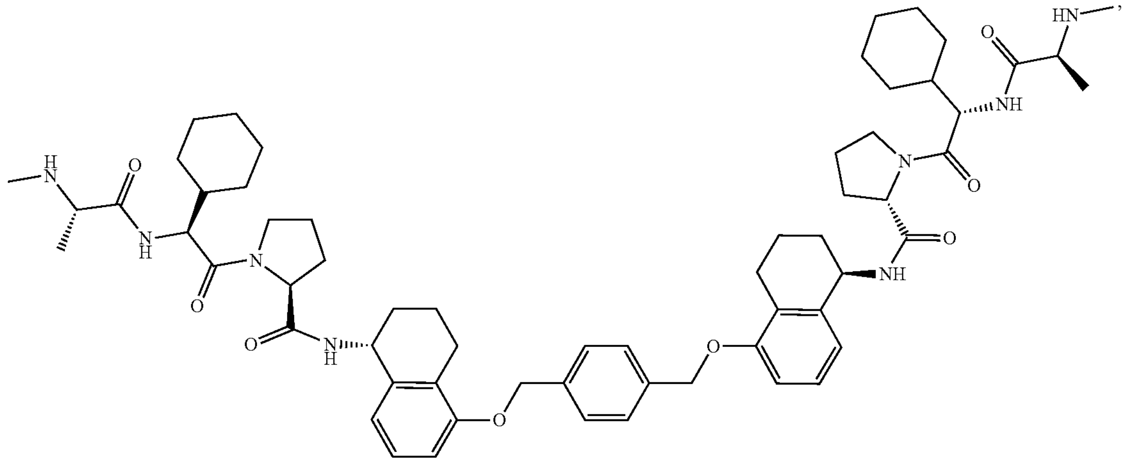
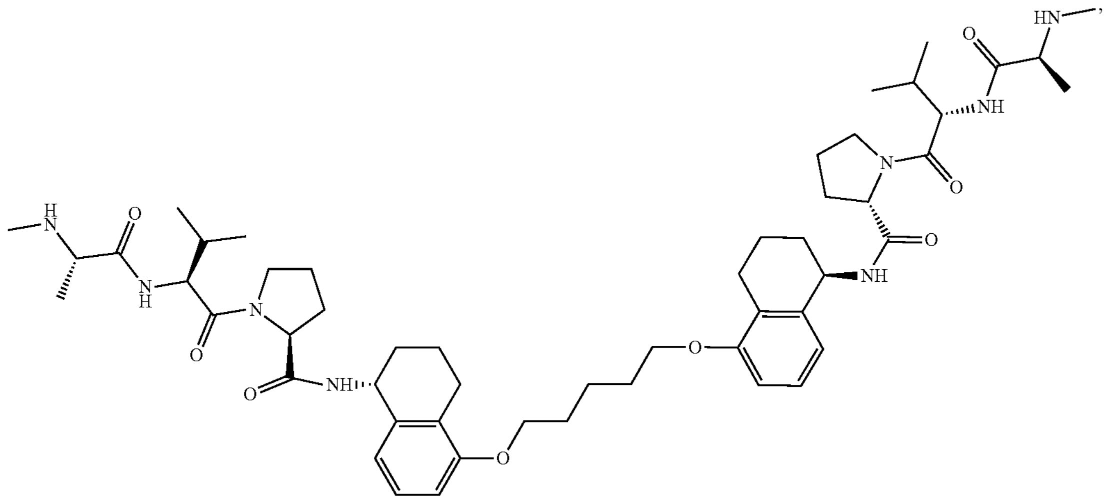
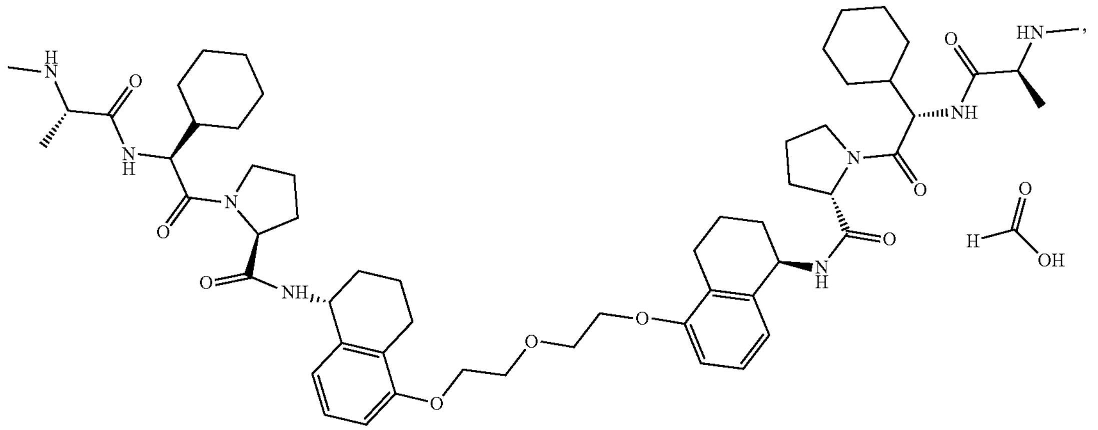

-continued
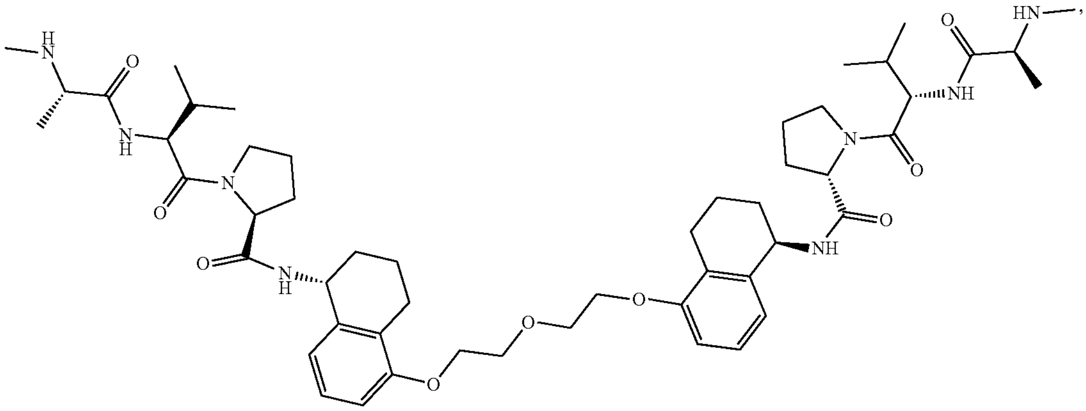
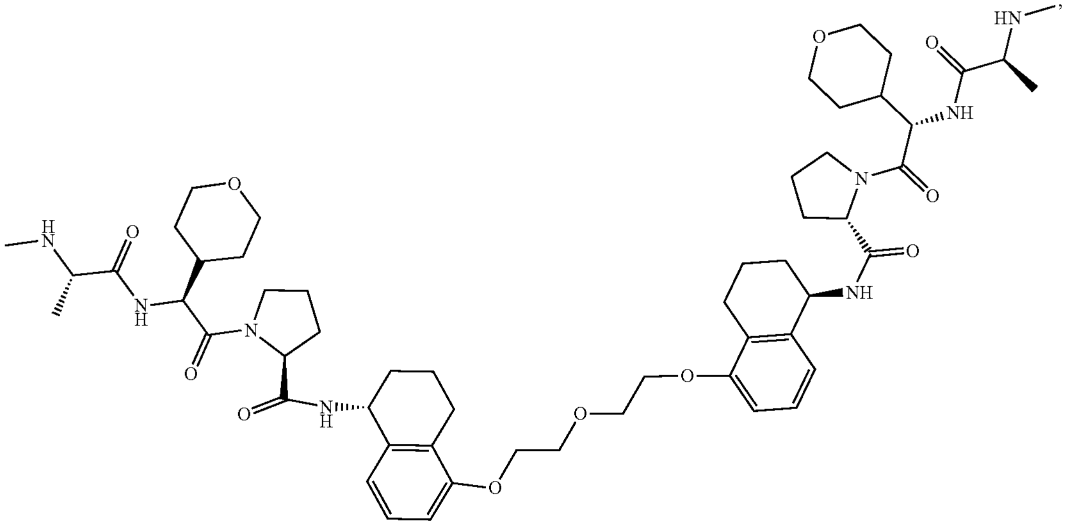
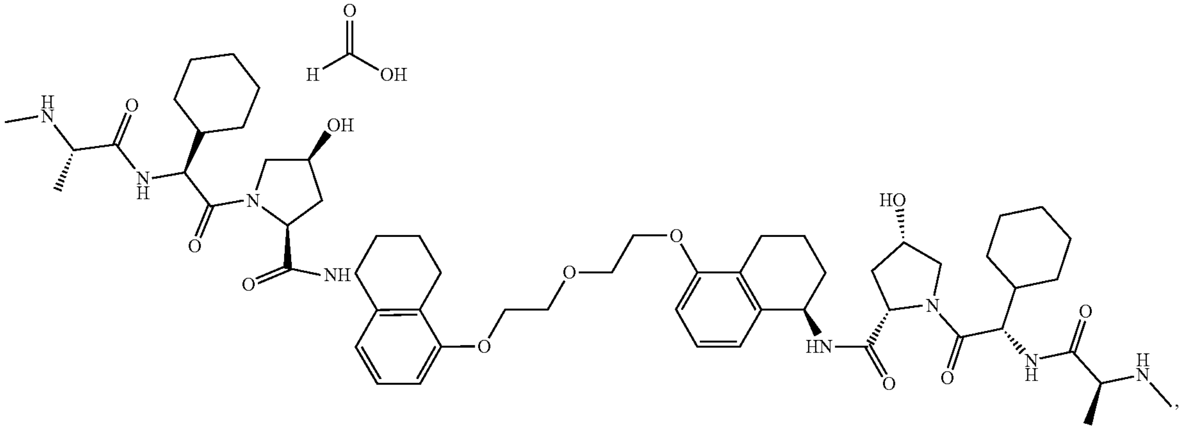
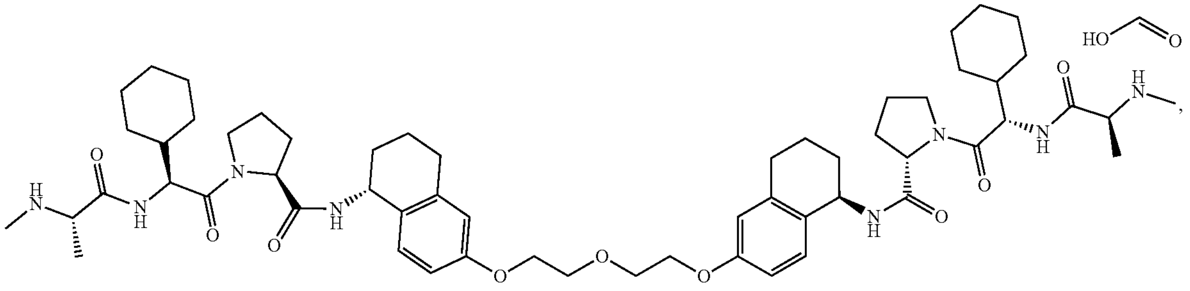

-continued
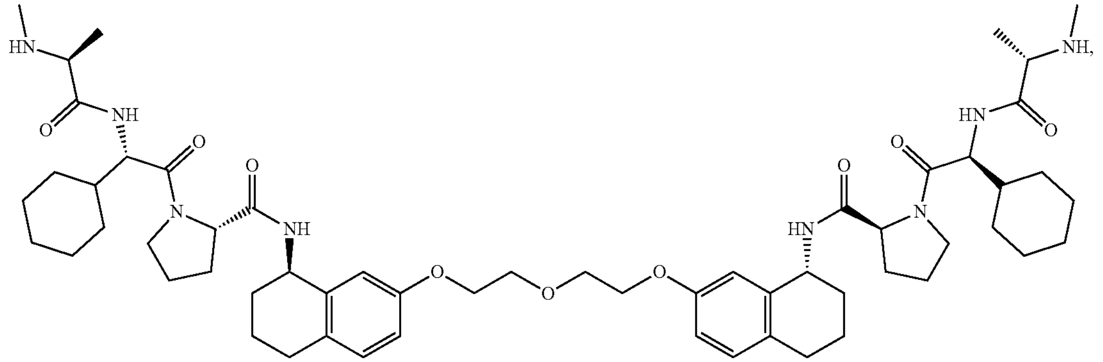
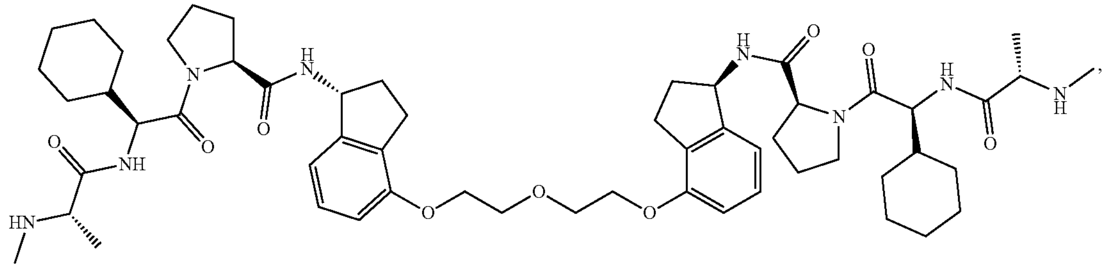
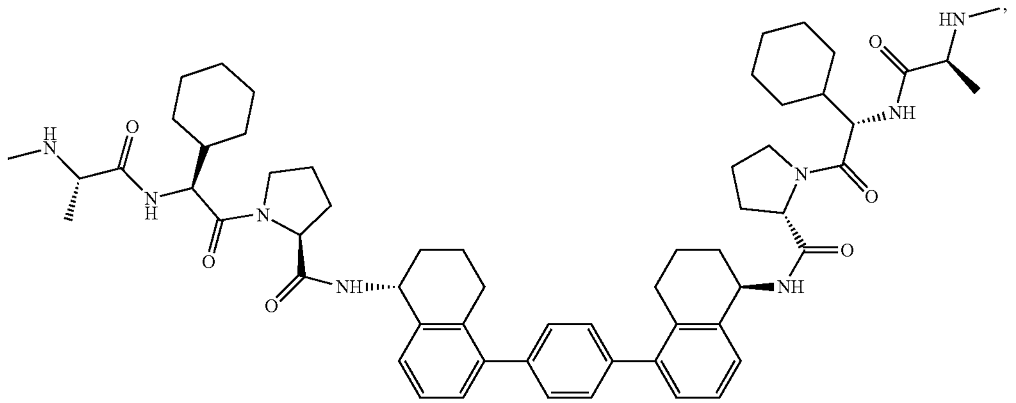
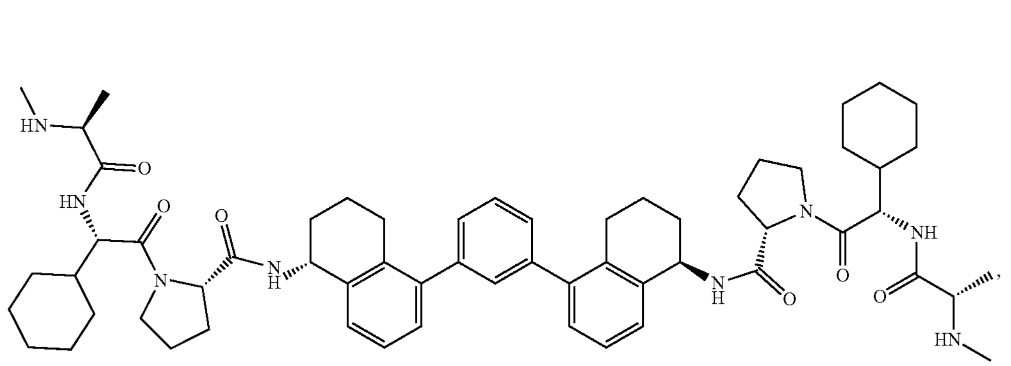

-continued
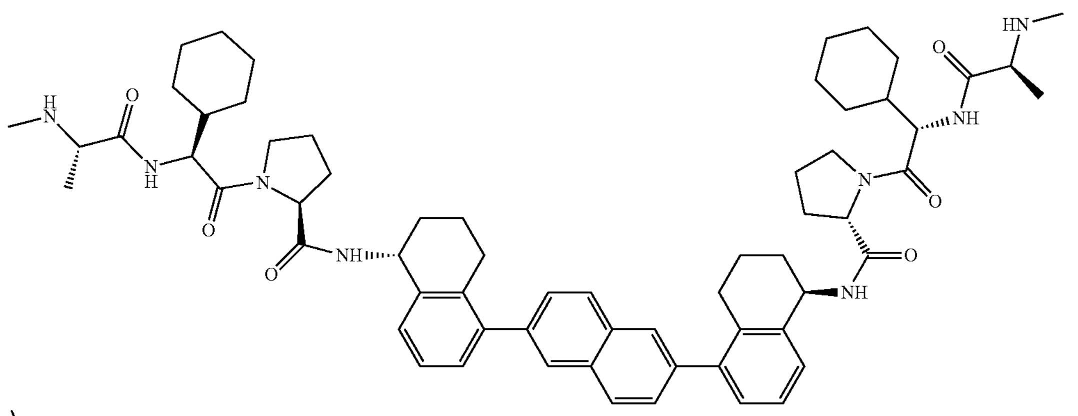
,
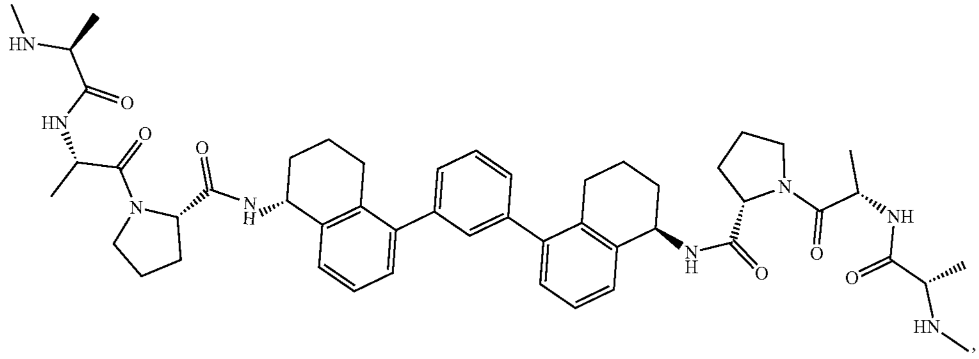
,
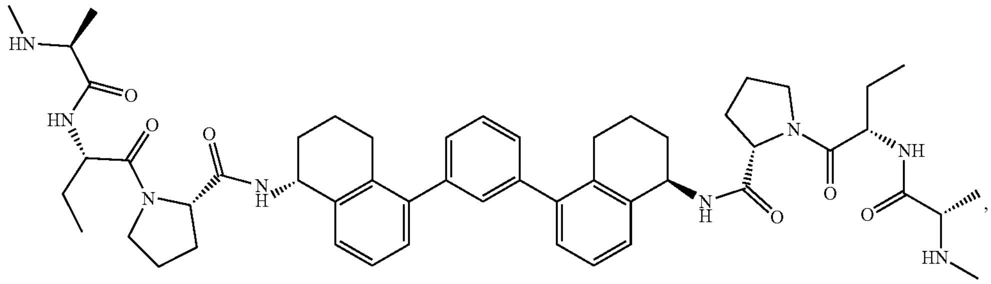 [SMILES: CC[C@H](NC(=O)[C@H](C)NC)C(=O)N1CCC[C@H]1C(=O)N[C@@H]1CCCc2c(-c3cccc(-c4cccc5c4CCC[C@H]5NC(=O)[C@@H]4CCCN4C(=O)[C@H](CC)NC(=O)[C@H](C)NC)c3)cccc21]
,
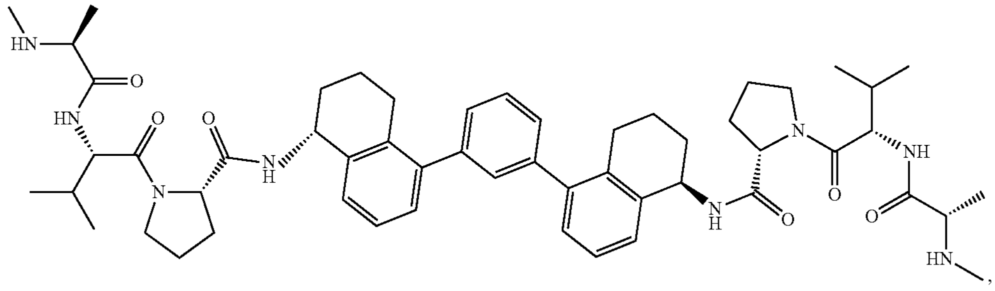
,

-continued
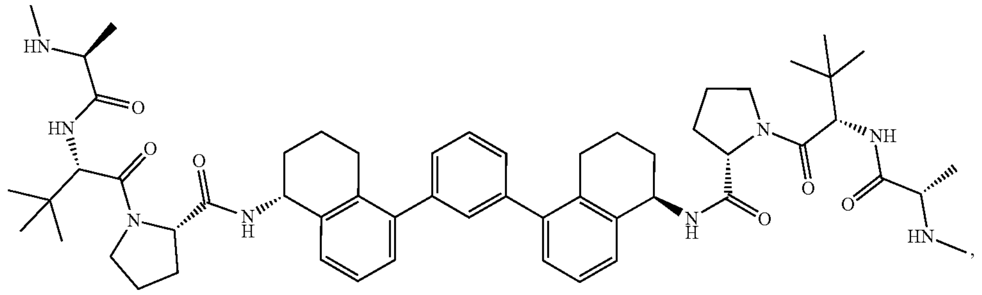
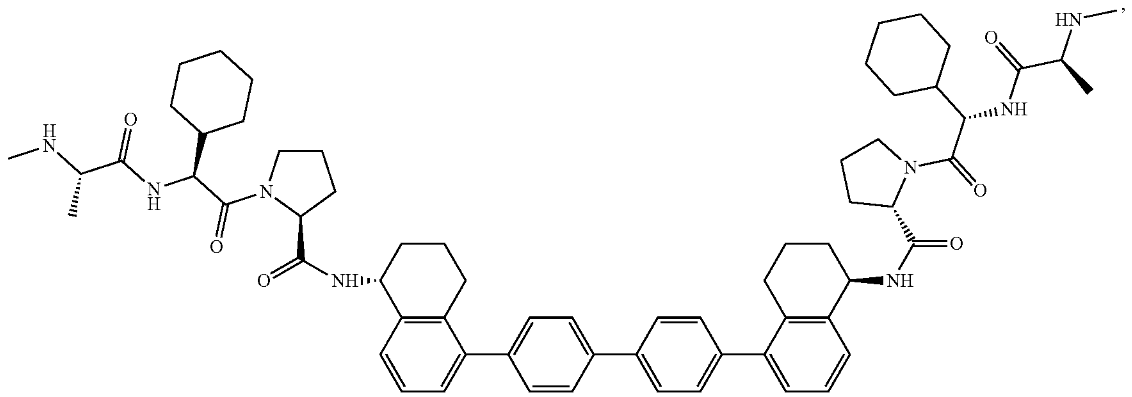
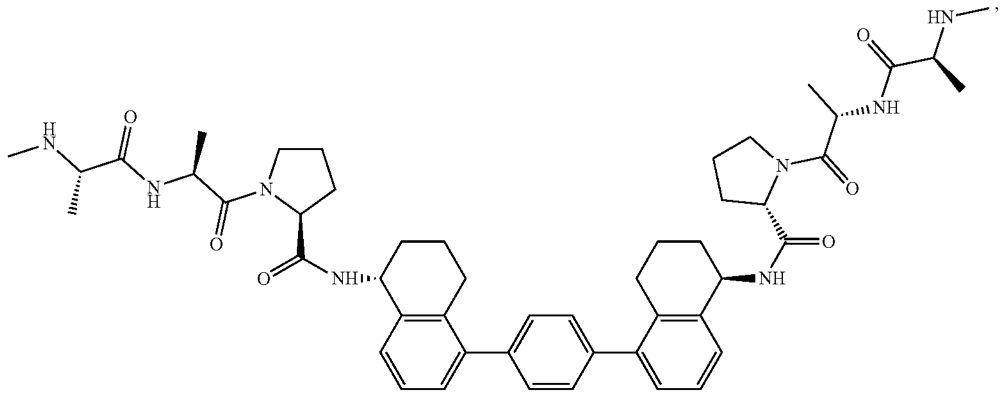
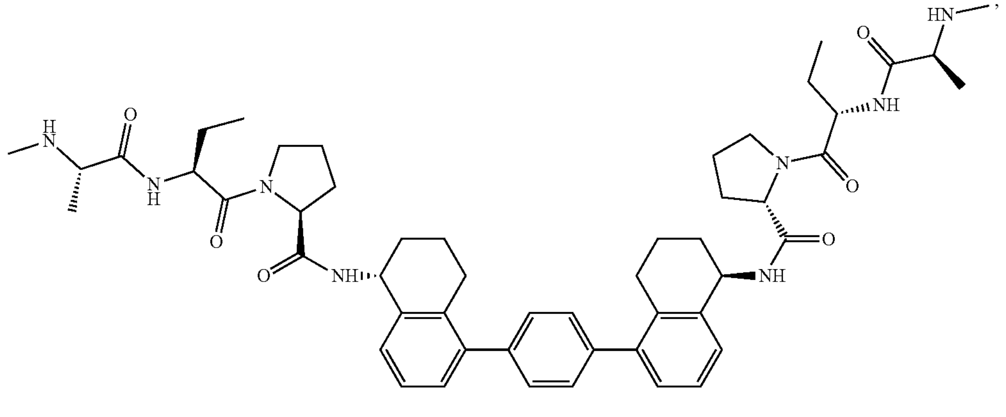

-continued
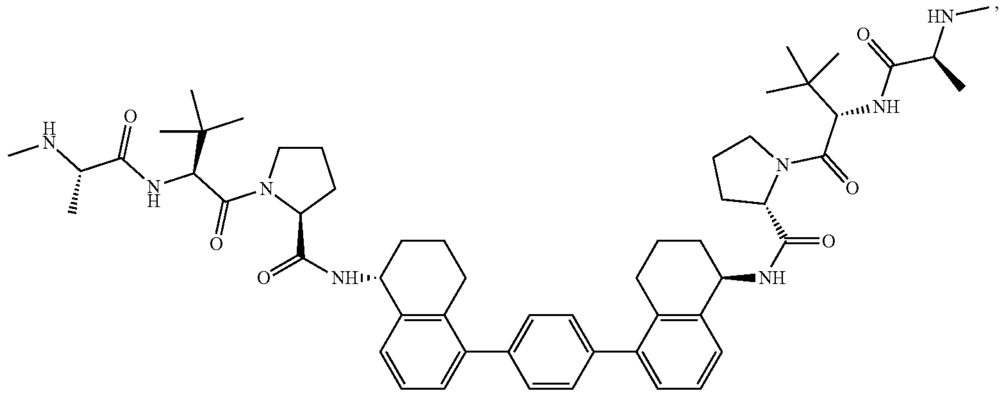
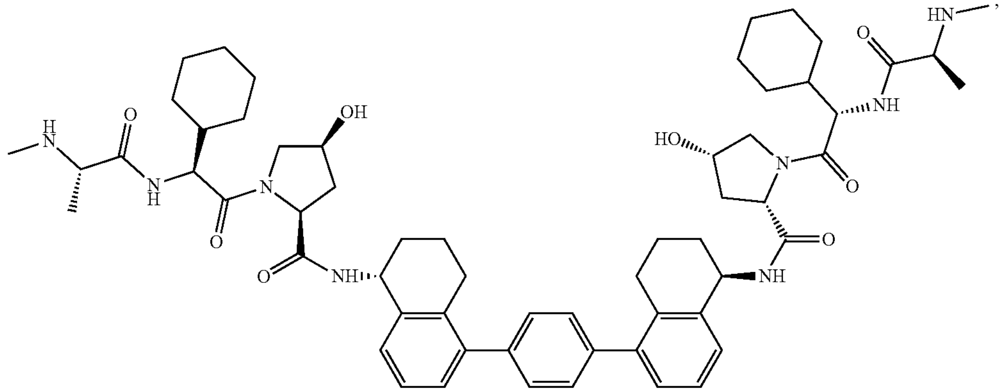
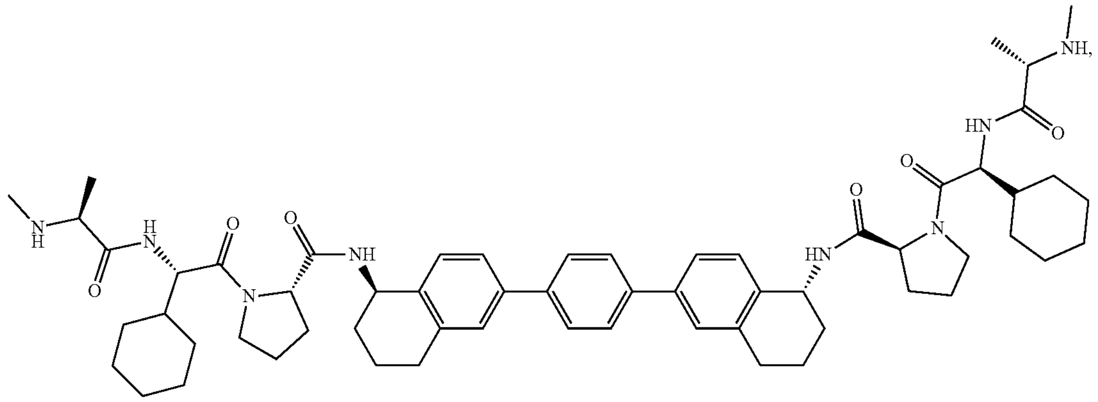
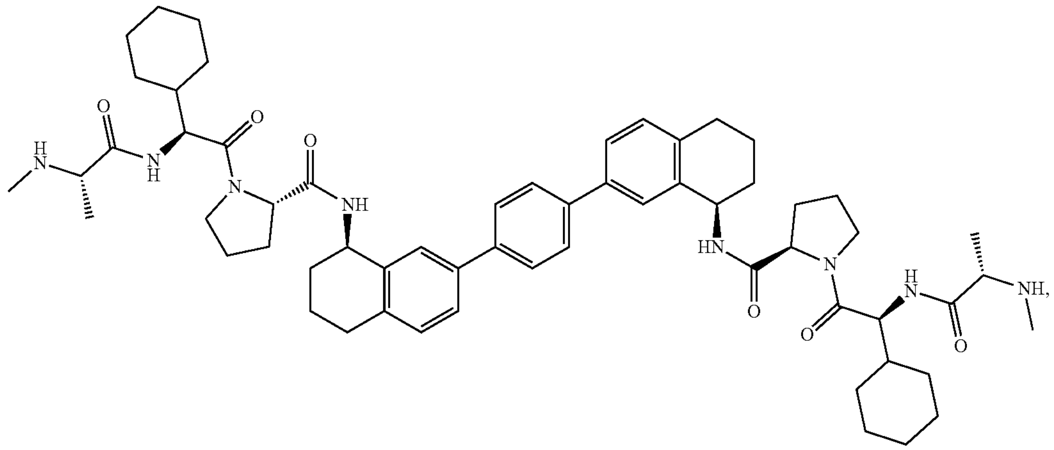

-continued
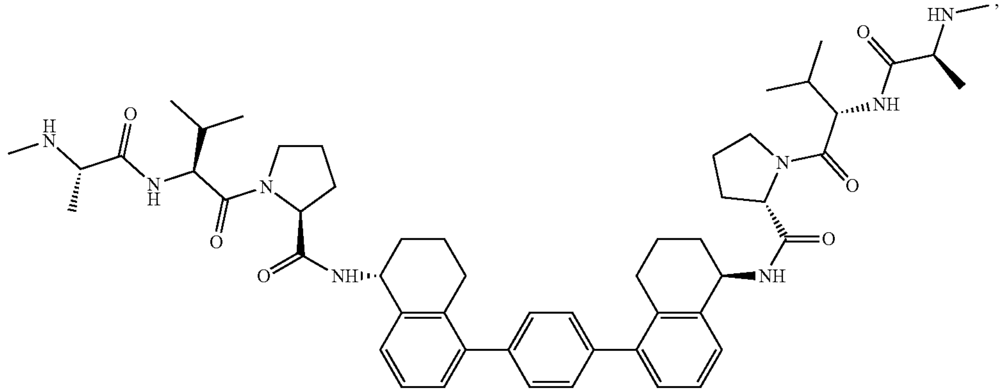
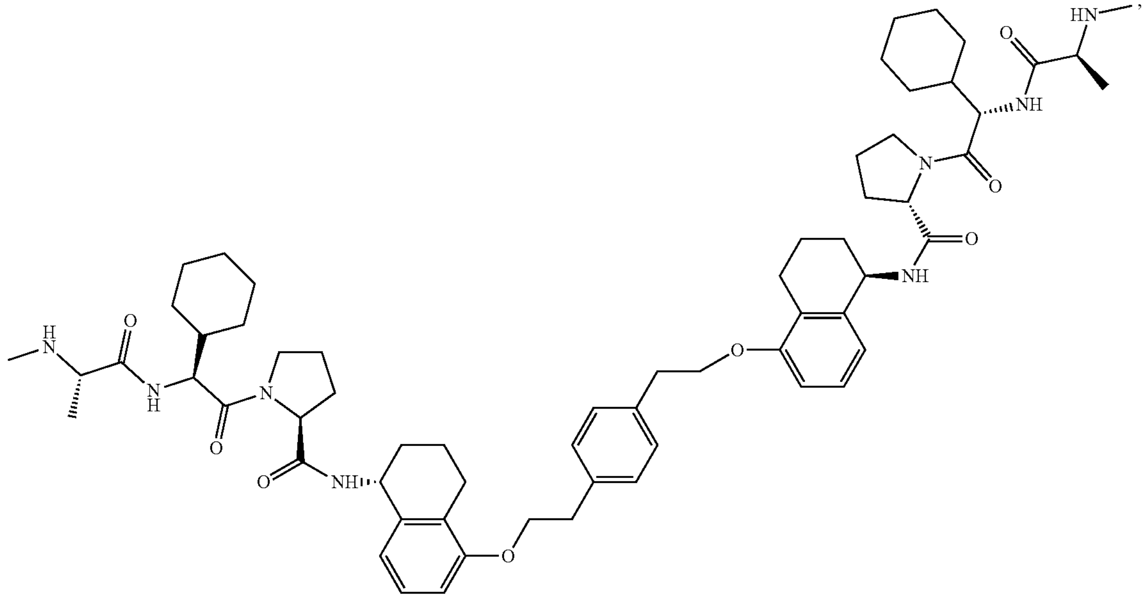
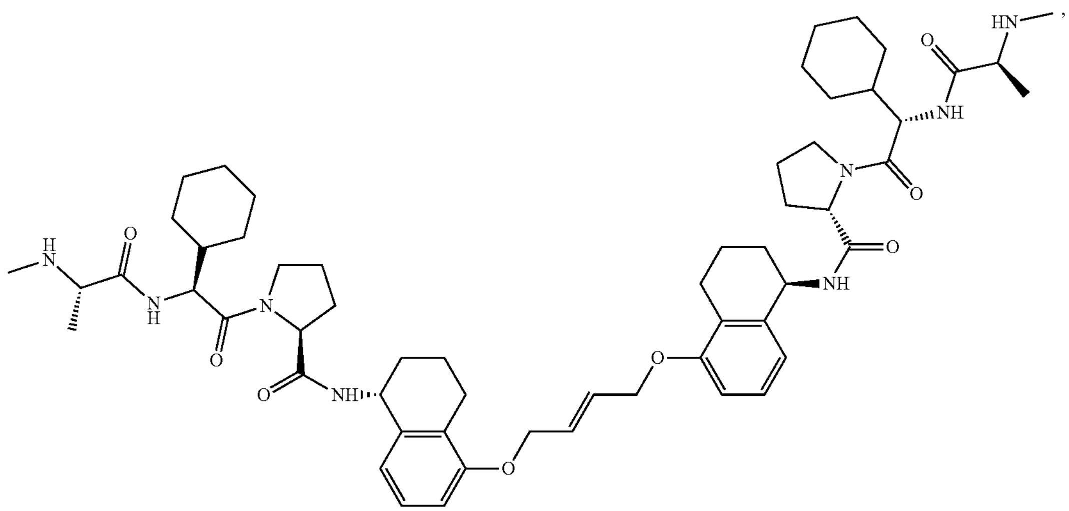

-continued
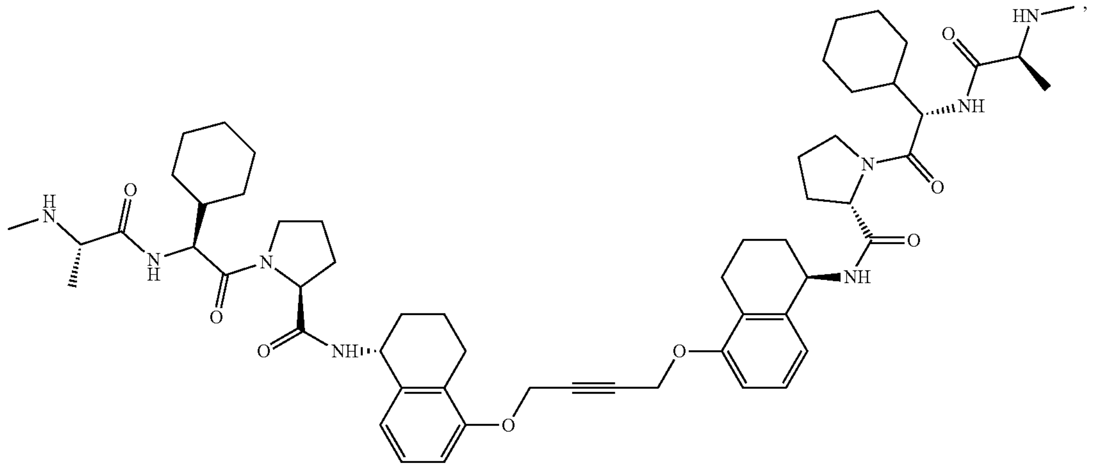
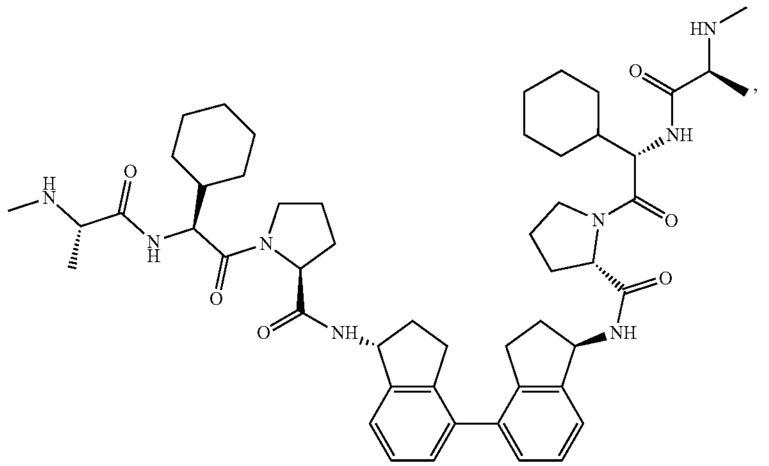
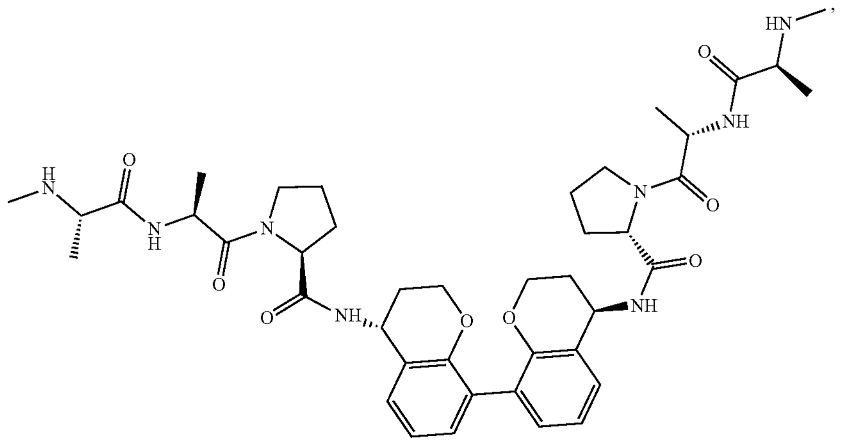

-continued
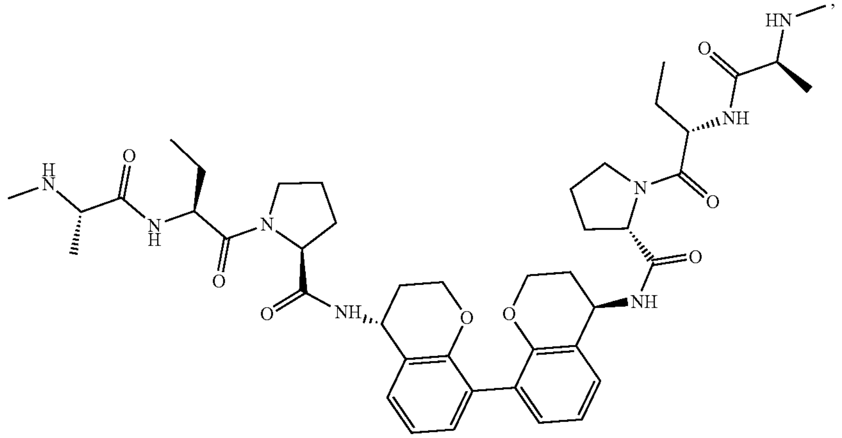
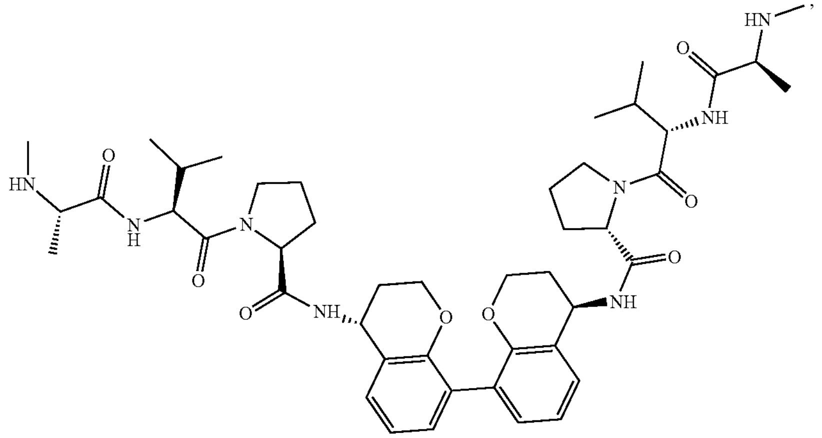
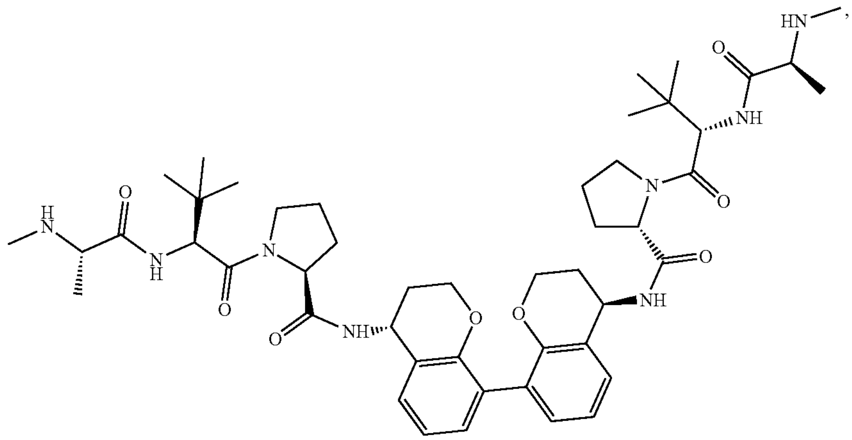

-continued
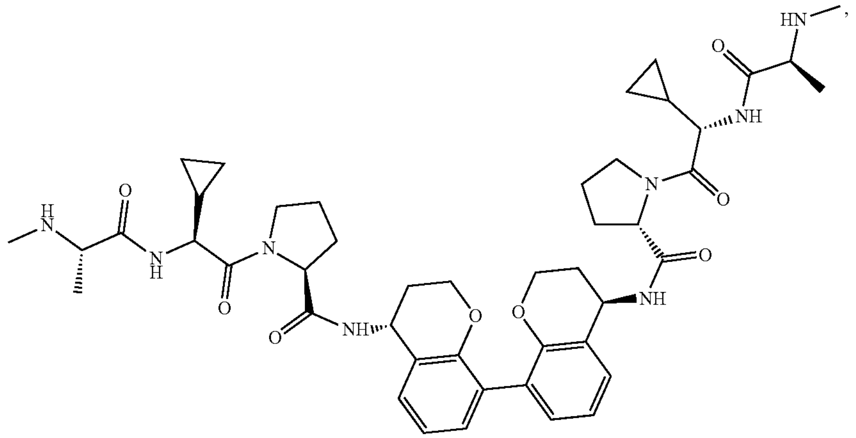
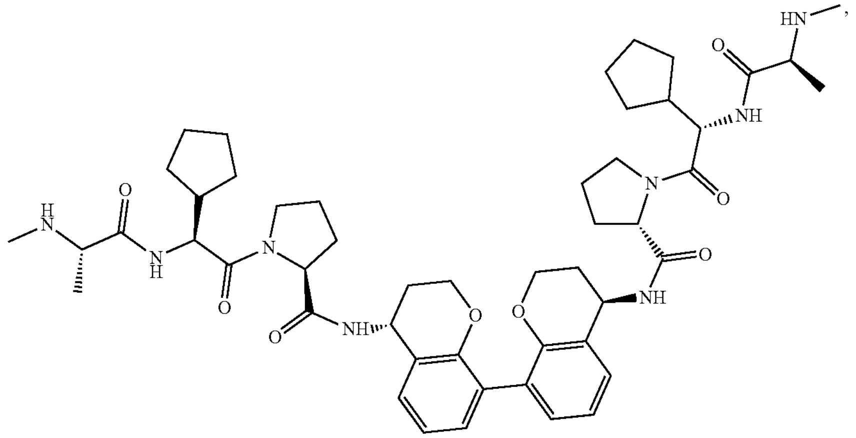
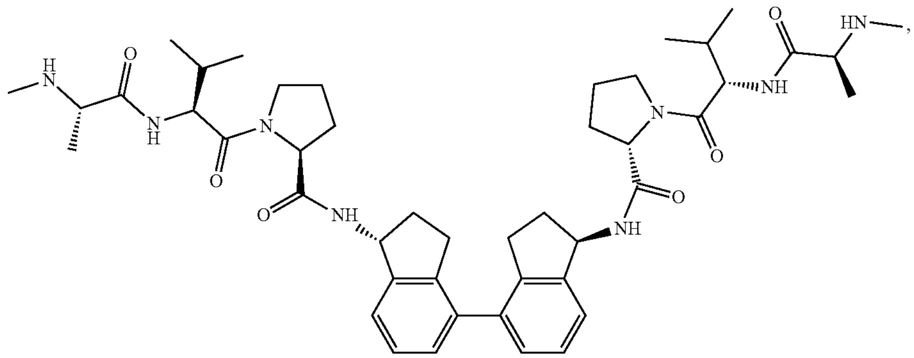
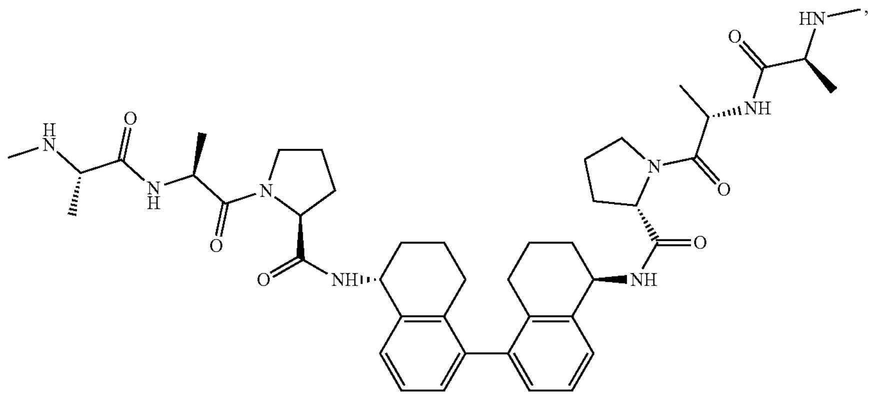

-continued
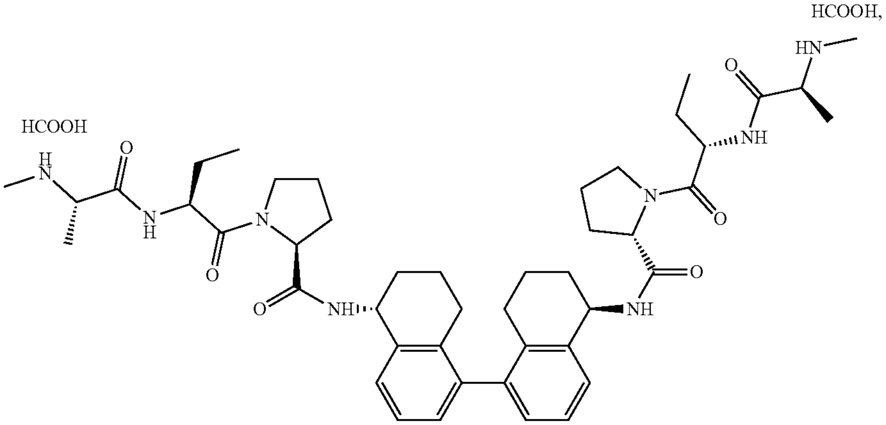
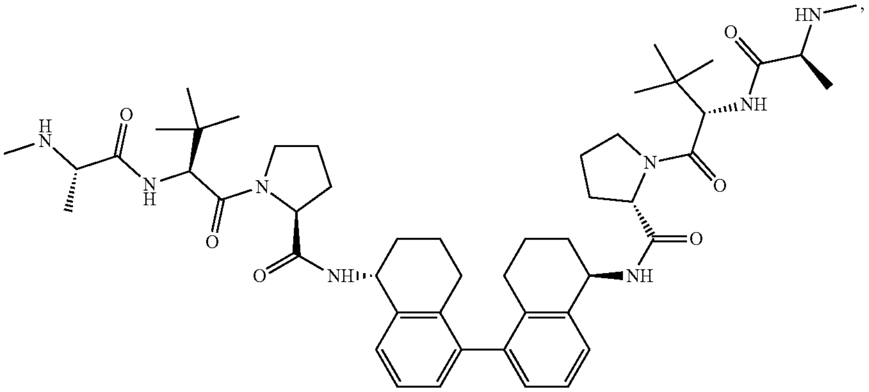
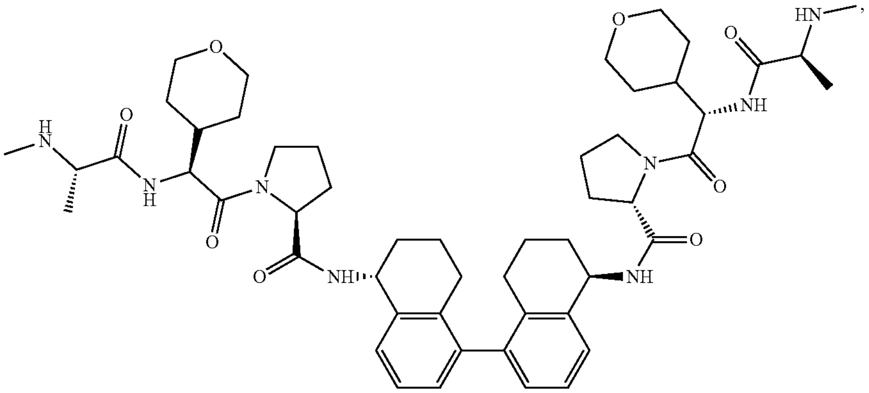
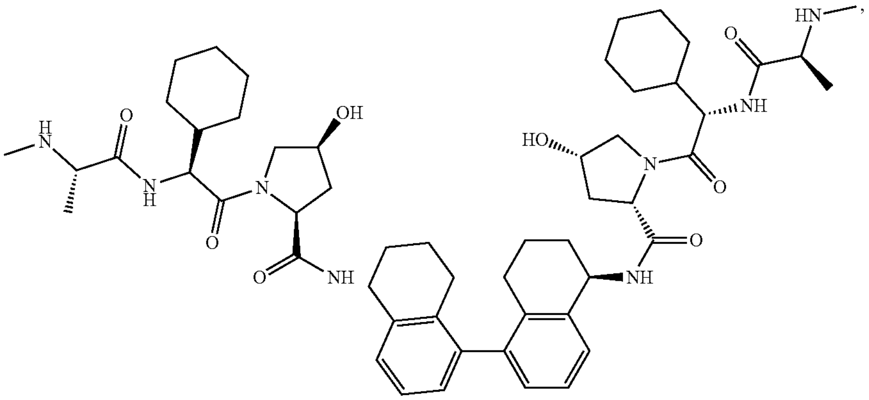

-continued
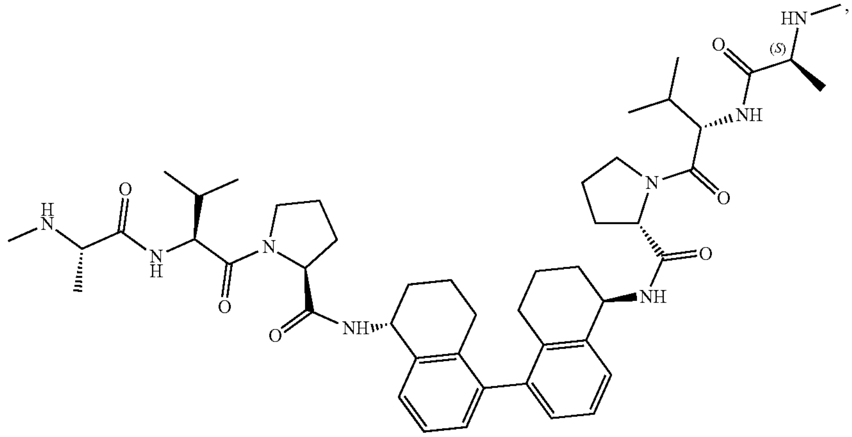
,
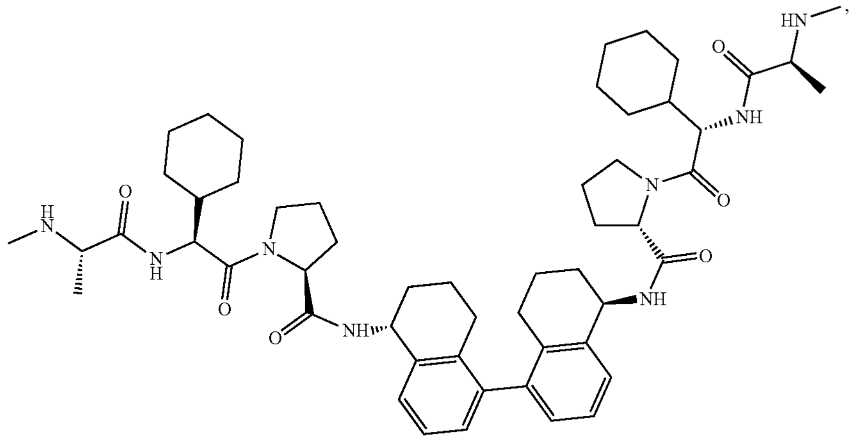
,
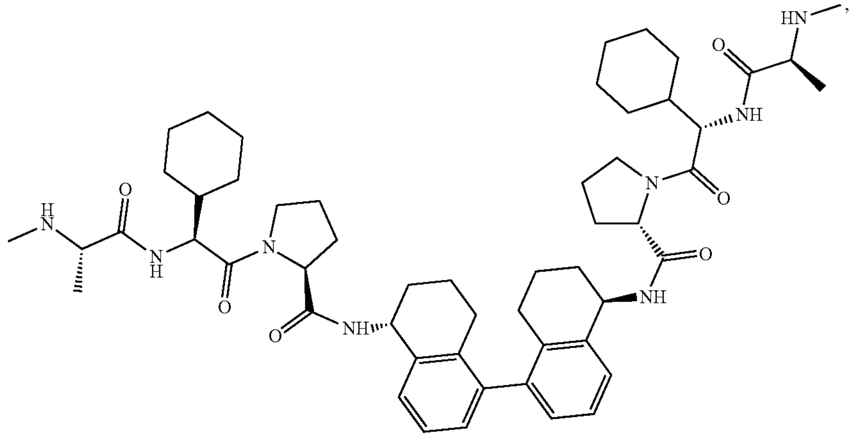
,

-continued
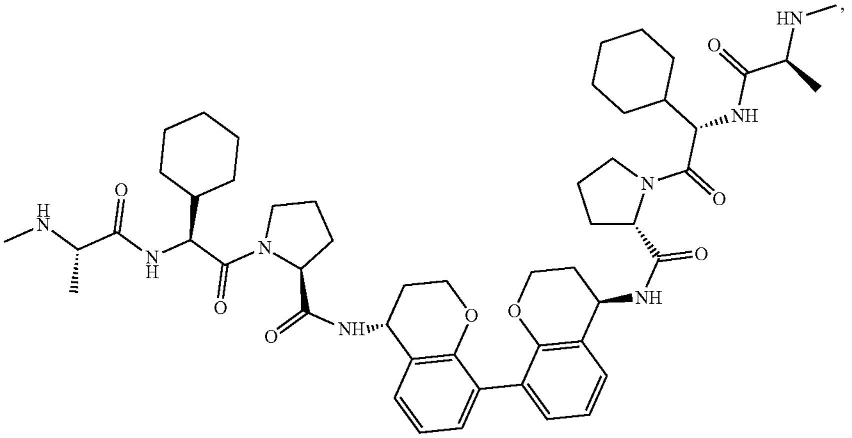
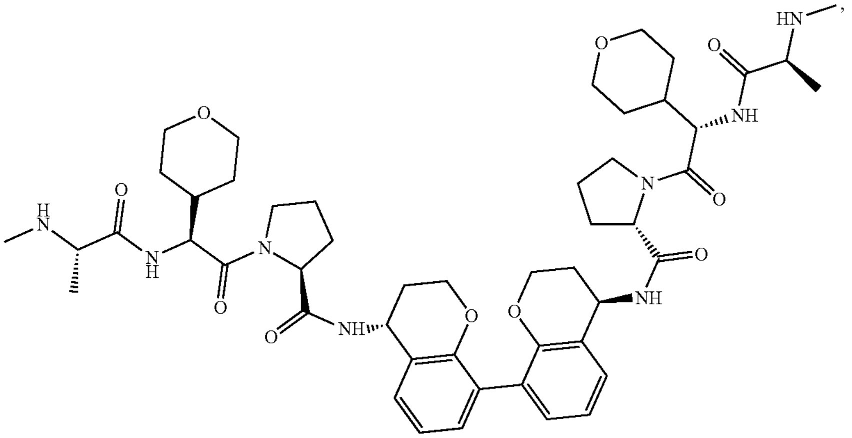
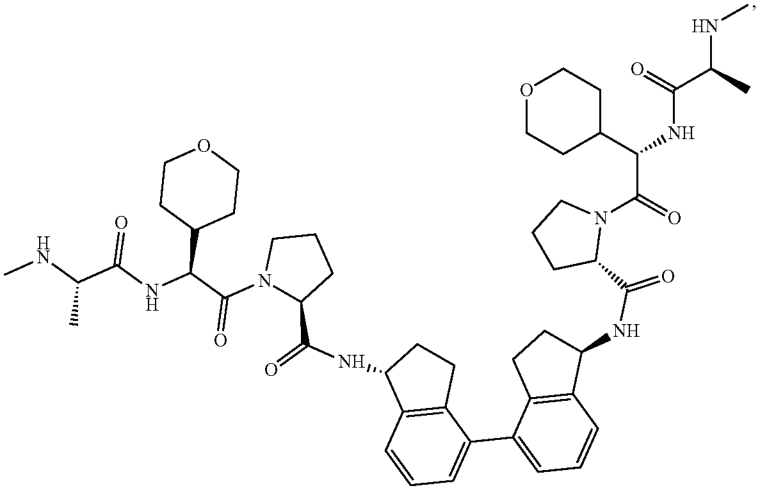
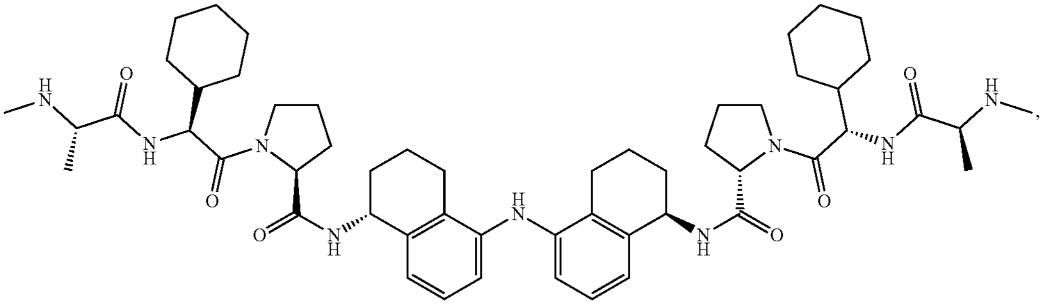

-continued
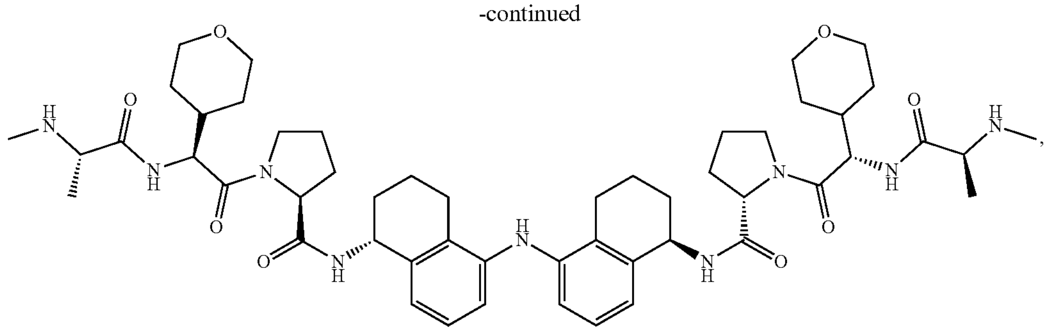
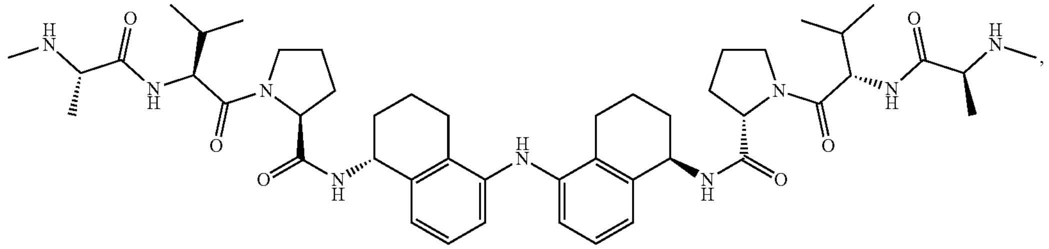
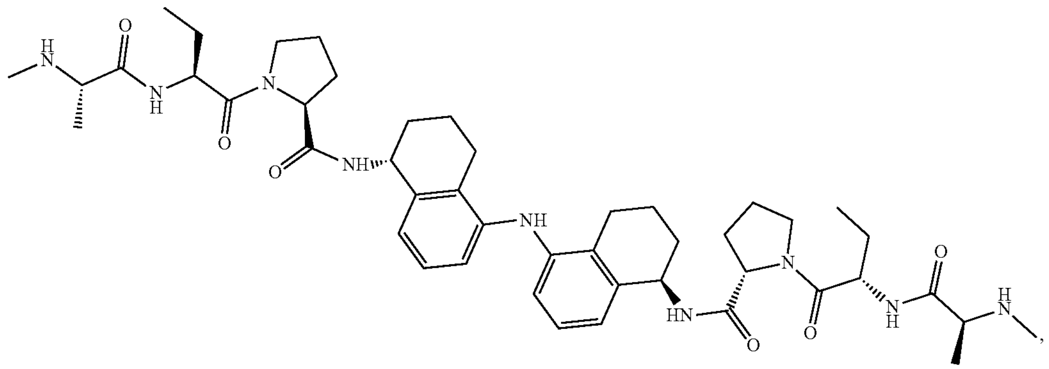
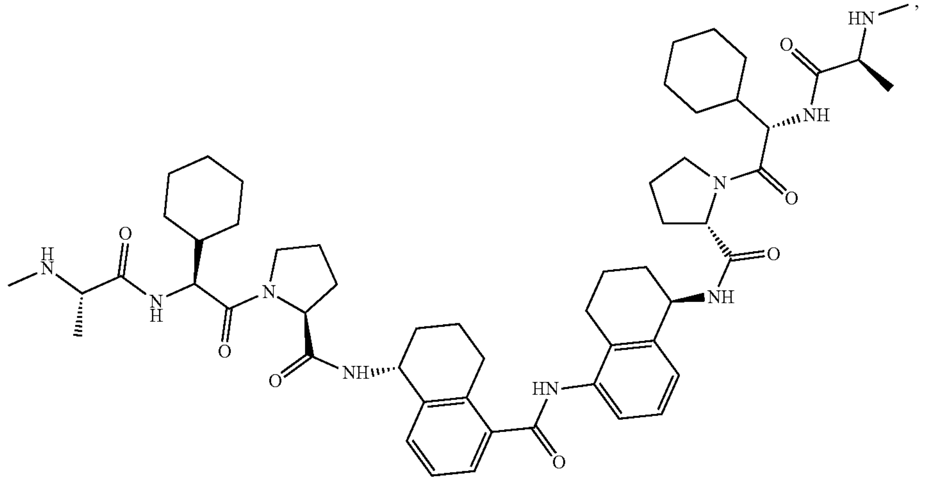

-continued
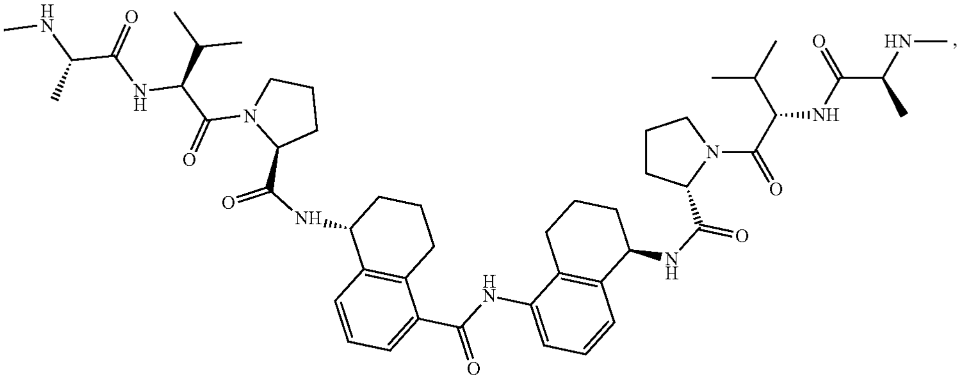
,
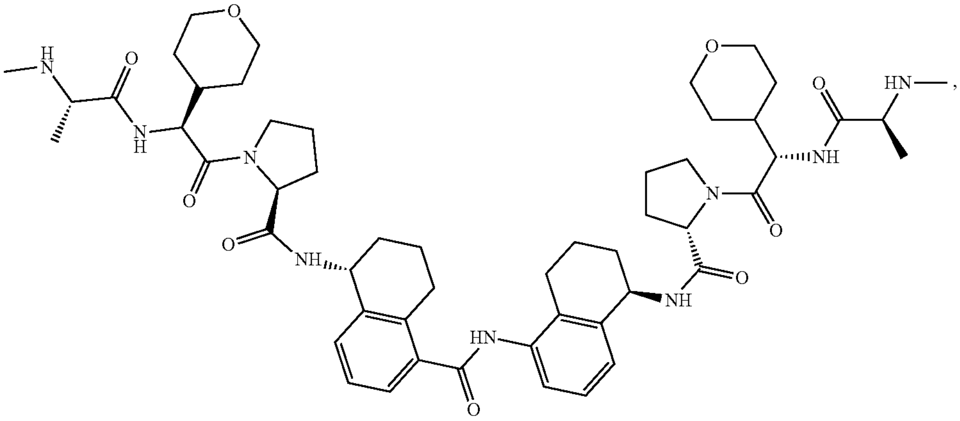
,
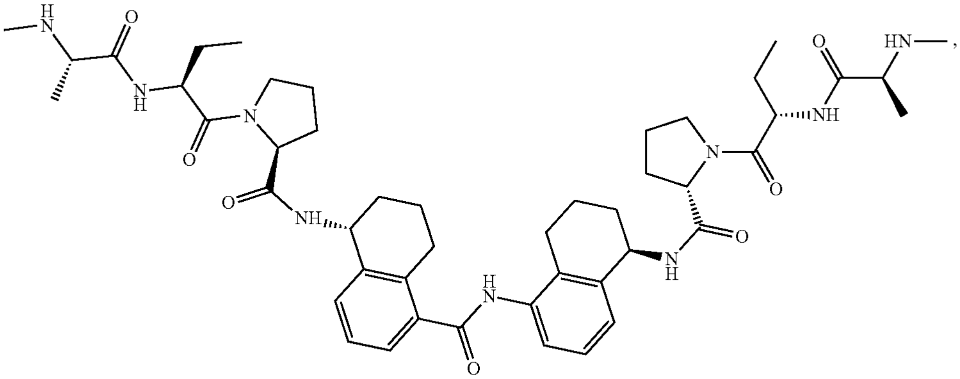
,
VII-D
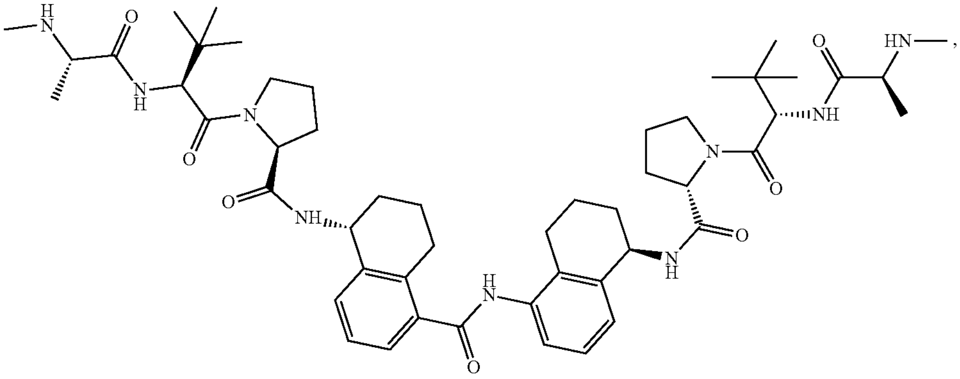
,

-continued
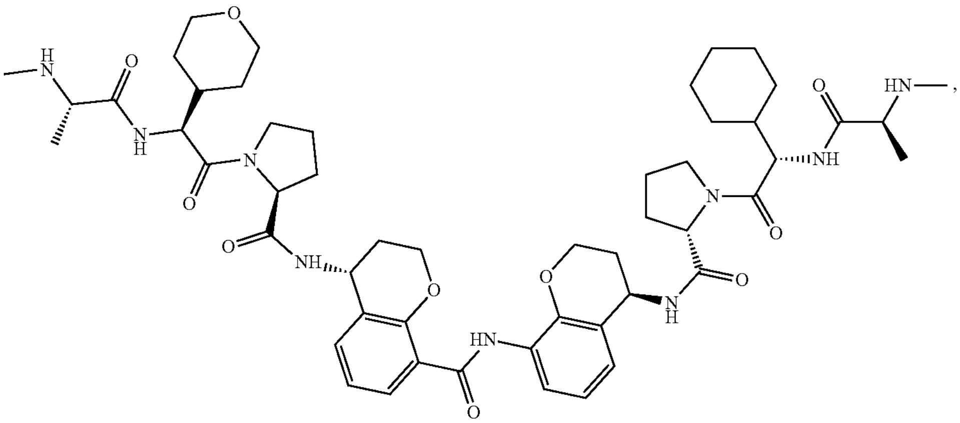
,
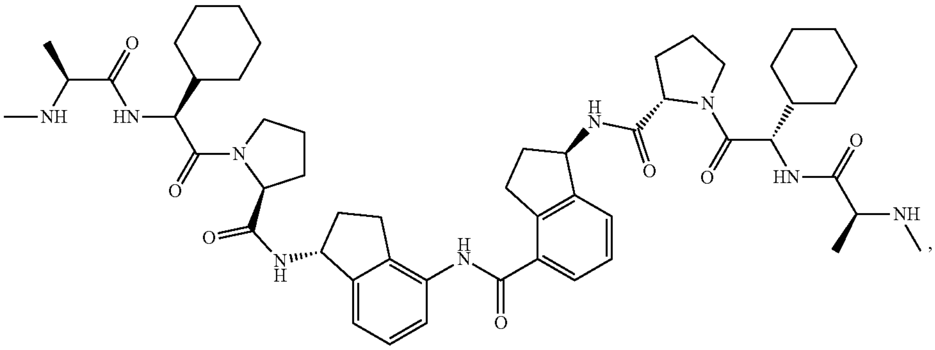
,
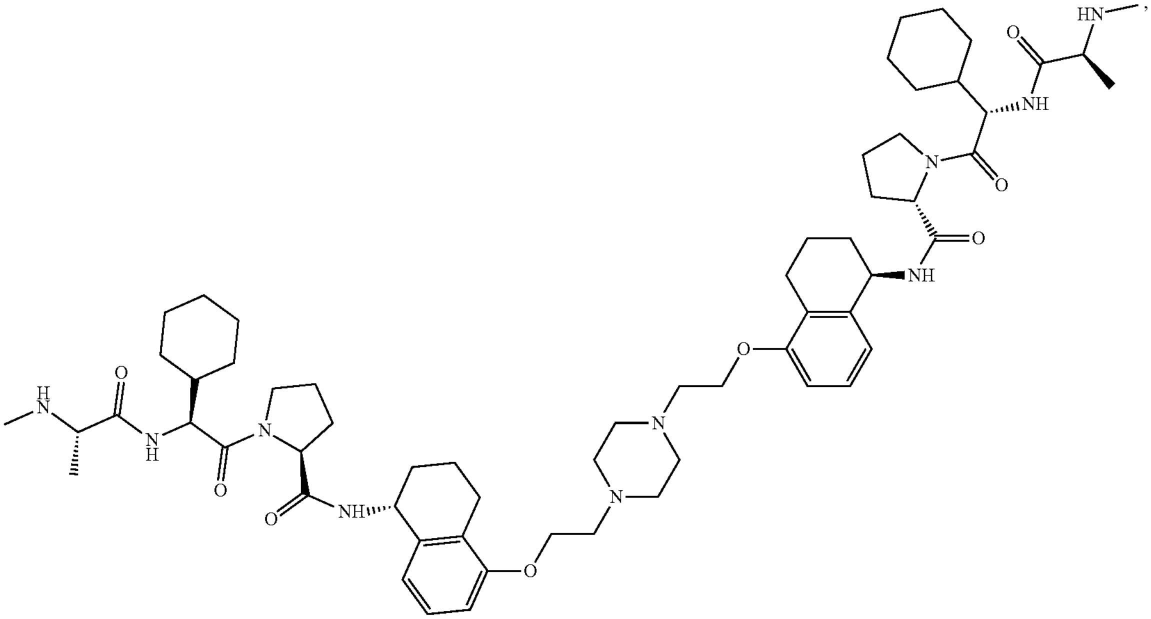
,
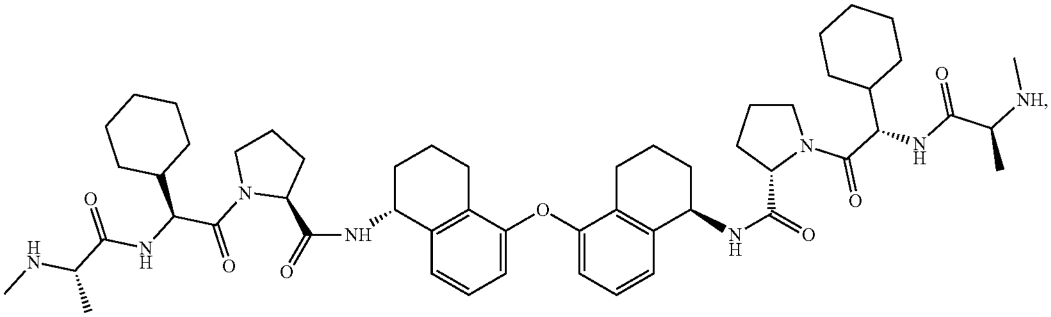
,

-continued
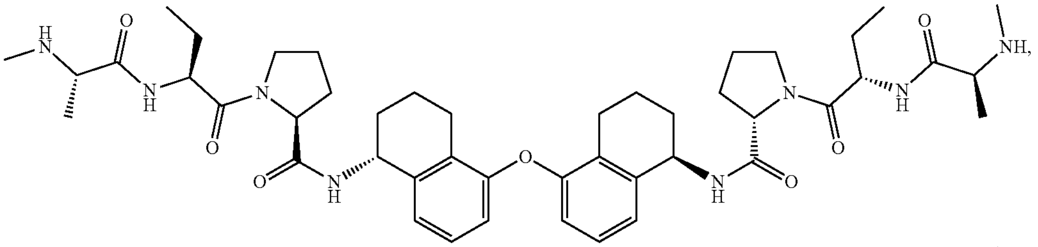
,
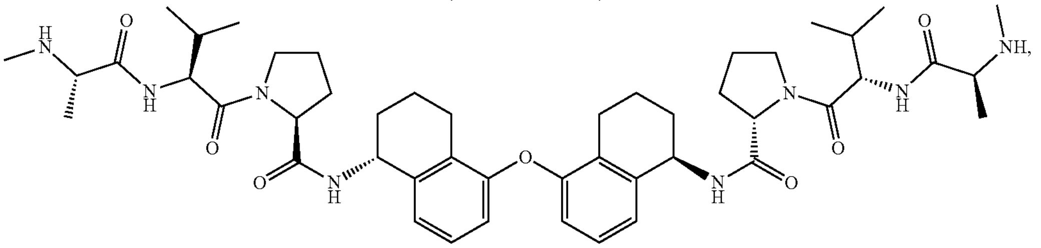
, and
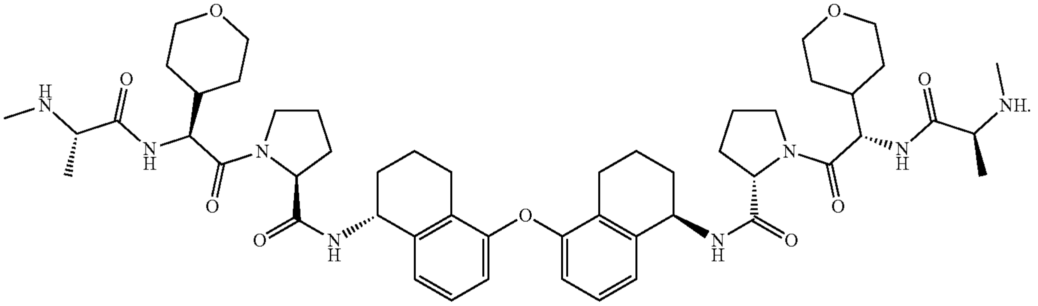
.
19. A composition comprising the compound of claim 1 and a pharmaceutically acceptable carrier.
* * * * *